United States Patent
Chahwan et al.

(10) Patent No.: US 12,214,008 B2
(45) Date of Patent: *Feb. 4, 2025

(54) PROTEIN INTERFACES

(71) Applicant: SyntheX, Inc., San Francisco, CA (US)

(72) Inventors: Charly Chahwan, San Francisco, CA (US); Maria Soloveychik, San Francisco, CA (US)

(73) Assignee: SyntheX, Inc., San Francisco, CA (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/171,841

(22) Filed: Feb. 9, 2021

(65) Prior Publication Data

US 2021/0252100 A1    Aug. 19, 2021

Related U.S. Application Data

(63) Continuation of application No. 16/215,432, filed on Dec. 10, 2018, now abandoned, which is a continuation of application No. 15/683,586, filed on Aug. 22, 2017, now Pat. No. 10,188,691, which is a continuation of application No. PCT/US2017/034870, filed on May 26, 2017.

(60) Provisional application No. 62/384,226, filed on Sep. 7, 2016, provisional application No. 62/342,840, filed on May 27, 2016.

(51) Int. Cl.
| | |
|---|---|
| A61K 38/02 | (2006.01) |
| A61K 38/00 | (2006.01) |
| A61K 39/00 | (2006.01) |
| A61K 45/06 | (2006.01) |
| C07K 5/11 | (2006.01) |
| C07K 7/06 | (2006.01) |
| C07K 7/08 | (2006.01) |
| C07K 14/00 | (2006.01) |
| C07K 16/30 | (2006.01) |

(52) U.S. Cl.
CPC .............. *A61K 38/02* (2013.01); *A61K 45/06* (2013.01); *C07K 5/1019* (2013.01); *C07K 7/06* (2013.01); *C07K 7/08* (2013.01); *C07K 14/00* (2013.01); *C07K 16/30* (2013.01); *A61K 38/00* (2013.01); *A61K 2039/585* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,925,523 A | 7/1999 | Dove et al. |
| 5,955,280 A | 9/1999 | Vidal et al. |
| 5,965,368 A | 10/1999 | Vidal et al. |
| 6,037,125 A | 3/2000 | Hasty |
| 6,057,104 A | 5/2000 | Hasty |
| 6,114,111 A | 9/2000 | Luo et al. |
| 6,200,759 B1 | 3/2001 | Dove et al. |
| 6,303,302 B1 | 10/2001 | Rupp et al. |
| 6,316,223 B1 | 11/2001 | Payan et al. |
| 6,332,897 B1 | 12/2001 | Weiner et al. |
| 6,500,636 B1 | 12/2002 | Hecht et al. |
| 6,599,705 B2 | 7/2003 | Rupp et al. |
| 6,610,473 B1 | 8/2003 | Butz et al. |
| 6,610,495 B1 | 8/2003 | Watt et al. |
| 6,790,607 B1 | 9/2004 | Edwards et al. |
| 7,033,768 B2 | 4/2006 | Vidal et al. |
| 7,105,341 B2 | 9/2006 | Kinsella |
| 7,208,571 B2 | 4/2007 | Kinsella |
| 7,252,952 B2 | 8/2007 | Lorenz et al. |
| 7,378,248 B2 | 5/2008 | Lorens et al. |
| 7,541,446 B2 | 6/2009 | Hillen et al. |
| 7,566,765 B2 | 7/2009 | Kinsella |
| 7,601,533 B2 | 10/2009 | Vidal et al. |
| 7,892,823 B2 | 2/2011 | Ezekiel |
| 8,597,949 B2 | 12/2013 | Connell et al. |
| 8,759,089 B2 | 6/2014 | Ezekiel |
| 9,040,462 B2 | 5/2015 | Lorens et al. |
| 9,150,897 B2 | 10/2015 | Kowalczykowski et al. |
| 9,198,914 B2 | 12/2015 | Connell et al. |
| 9,249,410 B2 | 2/2016 | Hill et al. |
| 9,273,100 B2 | 3/2016 | Hallen-Adams et al. |
| 9,408,816 B2 | 8/2016 | Adimoolam et al. |
| 9,518,097 B2 | 12/2016 | Hallen et al. |
| 10,188,691 B2 | 1/2019 | Chahwan et al. |

(Continued)

FOREIGN PATENT DOCUMENTS

| | | |
|---|---|---|
| AU | 716893 B2 | 3/2000 |
| AU | 735887 B2 | 7/2001 |

(Continued)

OTHER PUBLICATIONS

Stynen et al. (Microbiology and Molecular Biology Reviews 9.331-382, Jun. 2012 vol. 76 (2)).*

(Continued)

*Primary Examiner* — Julie Ha
*Assistant Examiner* — Tara L Martinez
(74) *Attorney, Agent, or Firm* — Wilson Sonsini Goodrich & Rosati

(57) ABSTRACT

The present disclosure provides methods to treat conditions, including cancer, using compounds that can target resistant cancer cells. The compounds can be used to sensitize resistant cancer cells or decrease the proliferation of cells. The compounds can target proteins in the DNA damage repair pathway leading to a decrease in DNA damage repair in target cells.

8 Claims, 26 Drawing Sheets
Specification includes a Sequence Listing.

(56) References Cited

U.S. PATENT DOCUMENTS

| | | |
|---|---|---|
| 2002/0086840 A1 | 7/2002 | Zarling et al. |
| 2002/0197627 A1 | 12/2002 | Vidal et al. |
| 2003/0068612 A1 | 4/2003 | Vidal et al. |
| 2003/0211495 A1 | 11/2003 | Hopkins et al. |
| 2003/0229004 A1 | 12/2003 | Zarling et al. |
| 2003/0235857 A1 | 12/2003 | Rupp et al. |
| 2004/0180325 A1 | 9/2004 | Edwards et al. |
| 2005/0053913 A1 | 3/2005 | Vidal et al. |
| 2006/0003391 A1 | 1/2006 | Ring et al. |
| 2006/0116316 A1 | 6/2006 | Kinsella et al. |
| 2006/0223089 A1 | 10/2006 | Vidal et al. |
| 2007/0105140 A1 | 5/2007 | Lorens et al. |
| 2007/0287677 A1 | 12/2007 | Kaneda |
| 2015/0306069 A1 | 10/2015 | Connell et al. |
| 2016/0281075 A1 | 9/2016 | Hallen-Adams et al. |
| 2017/0014360 A1 | 1/2017 | Connell et al. |
| 2017/0022494 A1 | 1/2017 | Hill et al. |
| 2018/0057483 A1 | 3/2018 | Zhu et al. |
| 2019/0216879 A1 | 7/2019 | Chahwan et al. |
| 2024/0287626 A1 | 8/2024 | Soloveychik et al. |

FOREIGN PATENT DOCUMENTS

| | | |
|---|---|---|
| AU | 745504 B2 | 3/2002 |
| AU | 2001283226 A1 | 2/2003 |
| AU | 762910 B2 | 7/2003 |
| AU | 2003265864 A8 | 3/2004 |
| AU | 775227 B2 | 7/2004 |
| AU | 783233 B2 | 10/2005 |
| AU | 2001245584 B2 | 2/2007 |
| AU | 2001247296 A8 | 4/2009 |
| CA | 2217545 A1 | 10/1996 |
| CA | 2272991 A1 | 5/1998 |
| CA | 2309754 A1 | 5/1999 |
| CA | 2310624 A1 | 5/1999 |
| CA | 2417135 A1 | 5/1999 |
| CA | 2386258 A1 | 4/2001 |
| CA | 2402111 A1 | 9/2001 |
| CA | 2402855 A1 | 9/2001 |
| CA | 2325447 C | 8/2007 |
| CA | 2317816 C | 2/2009 |
| CA | 2674084 C | 5/2013 |
| CA | 2376665 C | 2/2014 |
| CN | 1768142 A | 5/2006 |
| CN | 1905864 A | 1/2007 |
| CN | 101674820 B | 9/2013 |
| DE | 60120942 T2 | 2/2007 |
| DE | 69935313 T2 | 11/2007 |
| DE | 69935539 T2 | 12/2007 |
| DK | 2099442 T3 | 2/2015 |
| EP | 0942926 A2 | 9/1999 |
| EP | 1222261 A2 | 7/2002 |
| EP | 1263777 A2 | 12/2002 |
| EP | 1263951 A2 | 12/2002 |
| EP | 1049797 | 12/2004 |
| EP | 1032590 | 4/2005 |
| EP | 1575553 A2 | 9/2005 |
| EP | 1268842 B1 | 6/2006 |
| EP | 1731609 A1 | 12/2006 |
| EP | 0830459 B1 | 1/2007 |
| EP | 1053347 B1 | 2/2007 |
| EP | 1315958 B1 | 3/2007 |
| EP | 1810028 A2 | 7/2007 |
| EP | 2009442 A2 | 12/2008 |
| EP | 1200607 B1 | 2/2010 |
| EP | 2626067 A1 | 8/2013 |
| ES | 2284245 | 11/2007 |
| ES | 2529147 T3 | 2/2015 |
| JP | H11502717 A | 3/1999 |
| JP | 2001505418 A | 4/2001 |
| JP | 2002505072 A | 2/2002 |
| JP | 2003515314 A | 5/2003 |
| JP | 2003524371 A | 8/2003 |
| JP | 2004500805 A | 1/2004 |
| JP | 2004512001 A | 4/2004 |
| JP | 2004215624 A | 8/2004 |
| JP | 2005095613 A | 4/2005 |
| JP | 2007075107 A | 3/2007 |
| JP | 2008516979 A | 5/2008 |
| JP | 4440464 B2 | 3/2010 |
| JP | 2010514777 A | 5/2010 |
| JP | 2014139181 A | 7/2014 |
| JP | 5827706 B2 | 12/2015 |
| KR | 20090101362 A | 9/2009 |
| KR | 20120090100 A | 8/2012 |
| NZ | 578428 A | 3/2012 |
| PT | 2099442 E | 2/2015 |
| RU | 2009126655 A | 2/2011 |
| RU | 2446796 C2 | 4/2012 |
| RU | 2011148293 A | 6/2013 |
| SI | 2099442 T1 | 3/2015 |
| WO | WO-9632503 A1 | 10/1996 |
| WO | WO-9640721 A1 | 12/1996 |
| WO | WO-9807845 A1 | 2/1998 |
| WO | WO-9820030 A2 | 5/1998 |
| WO | WO-9925735 A1 | 5/1999 |
| WO | WO-9925865 A1 | 5/1999 |
| WO | WO-9935282 A1 | 7/1999 |
| WO | WO-9949294 A2 | 9/1999 |
| WO | WO-0042064 A1 | 7/2000 |
| WO | WO-0053630 A2 | 9/2000 |
| WO | WO-0075347 A2 | 12/2000 |
| WO | WO-0125420 A2 | 4/2001 |
| WO | WO-0166565 A9 | 9/2001 |
| WO | WO-0166787 A1 | 9/2001 |
| WO | WO-0168846 A2 | 9/2001 |
| WO | WO-02058738 A2 | 8/2002 |
| WO | WO-03013488 A2 | 2/2003 |
| WO | WO-2004019890 A2 | 3/2004 |
| WO | WO-2004074479 A1 | 9/2004 |
| WO | WO-2005095613 A1 | 10/2005 |
| WO | WO-2006052391 A2 | 5/2006 |
| WO | WO-2008082856 A1 | 7/2008 |
| WO | WO-2009018219 A2 | 2/2009 |
| WO | WO-2012019157 A2 | 2/2012 |
| WO | WO-2014085545 A1 | 6/2014 |
| WO | WO-2015138377 A1 | 9/2015 |
| WO | WO-2017205852 A2 | 11/2017 |

OTHER PUBLICATIONS

The Merriam-Webster dictionary (https://www.merriam-webster.com/dictionary/heterologous#:~:text=%3A%20derived%20from%20a%20different%20species accessed Jul. 21, 23).*

Rx Biosciences (https://rxbiosciences.com/our-services/phage-display/bacterial-display/ Sep. 22, 2015).*

EP17803737.0 Extended European Search Report dated Sep. 25, 2019.

Inoue et al. p53 Protein Transduction Therapy: Successful Targeting and Inhibition of Growth of the Bladder Cancer Cells. European Urology 49:161-168 (2006).

U.S. Appl. No. 15/683,586 Notice of Allowance dated Sep. 11, 2018.

U.S. Appl. No. 15/683,586 Office Action dated Jan. 10, 2018.

U.S. Appl. No. 15/683,586 Office Action dated Jun. 8, 2018.

U.S. Appl. No. 16/215,432 Office Action dated Nov. 10, 2020.

U.S. Appl. No. 16/215,432 Office Action dated Sep. 9, 2019.

Buchhop et al. Interaction of p53 with the human Rad51 protein. Nucleic Acids Res 25(19):3868-3874 (1997).

Budke et al. An optimized RAD51 inhibitor that disrupts homologous recombination without requiring Michael acceptor reactivity. J Med Chem 56:254-263 (2013).

Budke et al. RI-1: a chemical inhibitor of RAD51 that disrupts homologous recombination in human cells. Nucleic Acids Res 40:7347-7357 (2012).

Dunlop et al. Mechanistic insights into RAD51-associated protein 1 (RAD51AP1) action in homologous DNA repair. J Biol Chem 287(15):12343-12347 (2012).

Huang et al. Identification of specific inhibitors of human RAD51 recombinase using high-throughput screening. ACS Chem Biol 6:628-635 (2011).

(56) References Cited

OTHER PUBLICATIONS

Jerabek-Willemsen et al. Molecular interaction studies using microscale thermophoresis. Assay Drug Dev. Technol. 9:342-353 (2011).
Kovalenko et al. A novel nucleic acid-binding protein that interacts with human rad51 recombinase. Nucleic Acids Res 25(24):4946-4953 (1997).
Mason et al. The RAD51-stimulatory compound RS-1 can exploit the RAD51 overexpression that exists in cancer cells and tumors. Cancer Res. Jul. 1, 2014; 74(13): 3546-3555. Published online Apr. 2, 20141. doi: 10.1158/0008-5472.CAN-13-3220.
NCBI Reference Sequence: NP_594341.1 (2 pgs.) (Apr. 3, 2018).
NCBI Reference Sequence: XP_013017057.1 (2 pgs.) (Jul. 16, 2015).
PCT/US2017/034870 International Search Report and Written Opinion dated Dec. 11, 2017.
PCT/US2017/034870 Invitation to Pay Additional Fees dated Sep. 29, 2017.
Varshaysky. The N-end rule: functions, mysteries, uses. PNAS USA 93:12142-12149 (1996).
Zhu et al. A novel small molecule RAD51 inactivator overcomes imatinib-resistance in chronic myeloid leukaemia. EMBO Mol Med 5(3):353-365 (2013).
Ying. Synthesis of BRC4-like peptide and its interaction with RAD51 (231-260). Henan University of Technology, 2014. Retrieved Sep. 28, 2021 at: https://t.cnki.net/kcms/detail?v=3uoqlhG8C475KOm_zrgu4IQARvep2SAkbl4wwVeJ9RmnJRGnwiiNVvMG4_ewJd8c3MnYzhXsRgUXcAs0a-QEt5vvYByjvUmeuniplatform=NZKPT. Abstract with English translation. 6 pages.
Zhao et al. Research progresses on the interaction sites between BRC4 motif of BRCA2 and RAD51. Chinese Bulletin of Life Sciences, Issue 2, pp. 198-202 (2015). Retrieved Sep. 27, 2021 at: http://www.tzsti.com:85/Qikan/Article/Detail?id=663838456from=Qikan_Search_Index. English abstract only. 3 pages.
Adamovich et al. F-Box Protein-Mediated Resistance to PARP Inhibitor Therapy. Mol Cell. Jan. 17, 2019;73(2):195-196. doi: 10.1016/j.molcel.2018.12.019.
Cancer Types. NIH National Cancer Institute. Retrieved Aug. 2, 2019 at URL: https://www.cancer.gov/types. 8 pages.
Cervical Cancer: Chemotherapy. University of Rochester Medical Center. Health Encyclopedia online. Available Dec. 20, 2011. Retrieved Aug. 2, 2019 at URL: https://www.urmc.rochester.edu/encyclopedia/content.aspx?contenttypeid=34&contentid=17238-1. 6 pages.
Chen et al. The homologous recombination protein RAD51 is a promising therapeutic target for cervical carcinoma. Oncology Reports 38:767-774 (2017).
Chiu et al. DNA Repair Protein Rad51 Induces Tumor Growth and Metastasis in Esophageal Squamous Cell Carcinoma via a p38/Akt-Dependent Pathway. Ann Surg Oncol (2019). Published online Nov. 20, 2019. DOI: https://doi.org/10.1245/s10434-019-08043-x. 12 pages.
Connell et al. Pilot study examining tumor expression of RAD51 and clinical outcomes in human head cancers. Int. J. Oncol. 28(5):1113-1119 (May 2006).
D Amino Acid Peptides. Lifetein.com. Available May 12, 2012. Retrieved Aug. 2, 2019 at URL: https://www.lifetein.com/Peptide-Synthesis-D-Amino-Acid.html. 8 pages.
Expression of RAD51 in Cancer—Summary, The Human Protein Atlas (website). Accessed Nov. 1, 2020 at URL: https://http://www.proteinatlas.org/ENSG00000051180-RAD51/pathology. 3 pages.
Gachechiladze et al. RAD51 as a potential surrogate marker for DNA repair capacity in solid malignancies. Int J Cancer 141:1286-1294 (2017). Published online May 6, 2017.
Hannay et al. Rad51 overexpression contributes to chemoresistance in human soft tissue sarcoma cells: a role for p53/activator protein 2 transcriptional regulation. Mol Cancer Ther 6(5):1650-1660 (May 2007).
Hu et al. High expression of RAD51 promotes DNA damage repair and survival in KRAS-mutant lung cancer cells. BMB Rep. Feb. 2019; 52(2): 151-156. Epub Feb. 28, 2019. doi: 10.5483/BMBRep.2019.52.2.213.

Jiang et al. Network Analysis of RAD51 Proteins in Metazoa and the Evolutionary Relationships With Their Archaeal Homologs. Front Genet, vol. 9, Article 383 (Sep. 26, 2018). DOI: https://doi.org/10.3389/fgene.2018.00383. 9 pages.
Klein. The Consequences of Rad51 Overexpression for Normal and Tumor Cells. DNA Repair (Amst). May 3, 2008; 7(5): 686-693. Published online Feb. 1, 2008. doi: 10.1016/j.dnarep.2007.12.008.
Li et al. Overexpression of Rad51 Predicts Poor Prognosis in Colorectal Cancer: Our Experience with 54 Patients. PLoS ONE 12(1):e0167868 (Jan. 18, 2017). doi: 10.1371/journal.pone.0167868. 11 pages. Retraction in PLoS One. Nov. 1, 2018;13(11):e0206398. doi: 10.1371/journal.pone.0206398. eCollection 2018. One page.
Liu et al. RAD51 Mediates Resistance of Cancer Stem Cells to PARP Inhibition in Triple-Negative Breast Cancer. Clin Canc Res 23(2):514-522 (2017). Published online Dec. 29, 2016. Doi: 10.1158/1078-0432.CCR-15-1348.
Maacke et al. Autoantibodies in sera of pancreatic cancer patients identify recombination factor Rad51 as a tumour-associated antigen. J Cancer Res Clin Oncol 128:219-222 (2002). Published online Feb. 6, 2002. DOI: https://doi.org/10.1007/s00432-001-0321-2.
Maacke et al. DNA repair and recombination factor Rad51 is over-expressed in human pancreatic adenocarcinoma. Oncogene 19:2791-2795 (2000). DOI: https://doi.org/10.1038/sj.onc.1203578.
Martin et al. RAD51 Up-regulation Bypasses BRCA1 Function and Is a Common Feature of BRCA1-Deficient Breast Tumors. Cancer Res 67(20):9658-65 (Oct. 15, 2007).
Marzio et al. The F-Box Domain-Dependent Activity of EMI1 Regulates PARPi Sensitivity in Triple-Negative Breast Cancers. Mol Cell. Jan. 17, 2019;73(2):224-237.e6. Epub Dec. 13, 2018. doi: 10.1016/j.molcel.2018.11.003.
Milletti. Cell-penetrating peptides: classes, origin, and current landscape. Drug Discov Today. Aug. 2012;17(15-16):850-60.doi: 10.1016/j.drudis.2012.03.002. Epub Mar. 23, 2012.
Nagathihalli et al. RAD51 as a potential biomarker and therapeutic target for pancreatic cancer. Biochimica et Biophysica Acta 1816(2):209-218 (2011). Available online Jul. 23, 2011. DOI: 10.1016/j.bbcan.2011.07.004.
Qiao et al. High-level expression of Rad51 is an independent prognostic marker of survival in non-small-cell lung cancer patients. British Journal of Cancer 93:137-143 (2005). Published online Jun. 14, 2005.
Schild et al. Overexpression of RAD51 suppresses recombination defects: a possible mechanism to reverse genomic instability. Nucleic Acids Res. Mar. 2010; 38(4): 1061-1070. Published online Nov. 26, 2009. doi: 10.1093/nar/gkp1063.
Slupianek et al. BCR/ABL Regulates Mammalian RecA Homologs, Resulting in Drug Resistance. Molecular Cell 8:795-806 (Oct. 2001).
Tennstedt et al. RAD51 overexpression is a negative prognostic marker for colorectal adenocarcinoma. Int J Cancer 132:2118-2126 (2013). Published online Oct. 15, 2012.
Wiegmans et al. Rad51 supports triple negative breast cancer metastasis. Oncotarget 5(10):3261-3272 (Apr. 27, 2014). DOI: https://doi.org/10.18632/oncotarget.1923.
Woditschka et al. DNA Double-Strand Break Repair Genes and Oxidative Damage in Brain Metastasis of Breast Cancer. JNCI: Journal of the National Cancer Institute , vol. 106, Issue 7 (Jul. 2014). Published online Jun. 19, 2014. DOI: https://doi.org/10.1093/jnci/dju145. 13 pages.
Vidal et al. Prospects for drug screening using the reverse two-hybrid system. TIBTECH, vol. 17, pp. 374-381 (Sep. 1999).
Alberts et al. Molecular Biology of the Cell, Chapter 8 (Manipulating Proteins, DNA, and RNA), Section 4 (Analyzing protein structure and function), Subtitle "Protein-Protein Interactions Can Be Identified by Use of the Two-Hybrid System." 4th edition, New York: Garland Science (2002). 2 pages.
Young. Yeast Two-hybrid: So Many Interactions, (in) So Little Time . . . Biology of Reproduction, vol. 58, pp. 302-311 (1998).
EP23188944.5 Extended European Search Report dated Oct. 23, 2023.

* cited by examiner

TetR-Protein1 fusion at the *AscI* site:

Protein2-DOF1 Transcription Activation Domain fusion at the *PmeI* site:

FIGURE 8

SEQ ID NO.: 62

Cell Type      A549
Curve Type     DRC (Area under the curve vs conc)
Formula        Sigmoidal dose-response
Compound Name  Compound 10
IC50           4.7149E-006M

Various Compound sequence efficacy with SSP25s

| | Sequence | IC50 (M) | R² |
|---|---|---|---|
| Compound 1 | Ac-K(C6_5FAM)-QSLRLGLSRLARVKRLHPGARRRRRRRR-NH2 | 2.38E-08 | 0.91866 |
| Compound 3 | Ac-K(C6_5FAM)-QS-NMe-LRLGLSR-NMe-LAR-NMe-VKRLHPGARRRRRRRR-NH2 | 3.34E-08 | 0.831182 |
| Compound 4 | Ac-K(C6_5FAM)-QS-NMe-LRLGLSR-NMe-LAR-NMe-VKRLHPGC-NH2-InterDimer-Ac-CRRRRRRRR-NH2 | 5.26E-08 | 0.850437 |
| Compound 5 | Ac-K(C6_5FAM)-RRRRRRRKRLGVRLRVSRML-NH2 | 6.87E-06 | 0.999094 |
| Compound 7 | Ac-K(C6_5FAM)-RRRRRRRRLGMSRRF-NH2 | 8.23E-05 | 0.968636 |
| Compound 9 | Ac-K(C6_5FAM)-RRRRRRRKRLGLRLGVSRRV-NH2 | 1.02E-04 | 0.987984 |
| Compound 10 | Ac-kmmxrkrGkkxrrxrx-NH2 | 5.30E-06 | 0.99096 |
| Compound 11 | Ac-K(C6_5FAM)-RRRRRRRSLRLGLSRLARVKRLHPG-NH2 | 5.41E-05 | 0.956073 |
| Compound 13 | Ac-RRRRRRRKRLGVRLRVSRML-NH2 | 4.23E-05 | 0.984757 |
| Compound 14 | Ac-RQRIWFQNRRMKWKRLGVRLRVSRML-NH2 | 4.36E-05 | 0.984485 |
| Compound 19 | Ac-A(R8)KRLGVR(S5)RVSRML-NH2 | 1.87E-04 | 0.968038 |
| Compound 25 | Ac-kmmxrkrGkkxG:::(F®®4) | 1.09E-08 | 0.998139 |

FIGURE 17

Compound Optimization and Specificity with SSP25s

| | Sequence | IC50(M) | $R^2$ | Notes |
|---|---|---|---|---|
| Compound 5 | Ac-K(C6_5FAM)-RRRRRKRLGVRLRVSRML-NH2 | 6.87E-06 | 0.999094 | L-peptide with ployR |
| Compound 13 | Ac-RRRRRKRLGVRLRVSRML-NH2 | 4.21E-05 | 0.984757 | L-peptide with ployR |
| Compound 14 | Ac-RQKIWFQNRRMKWKKRLGVRLRVSRML-NH2 | 4.46E-05 | 0.984485 | L-peptide with penetratin |
| Compound 10 | Ac-lmrsvrlrvGlrkrrrrrr-NH2 | 5.30E-06 | 0.99096 | D-peptide with polyR |
| Compound 25 | Ac-lmrsvrlrvGlrkaG:::(cFφR4) via Isopeptide Bond to K in CFφR4 | 1.09E-05 | 0.998139 | D-peptide with cFφR4 |

FIG. 18

In-vivo A549 xenograft data
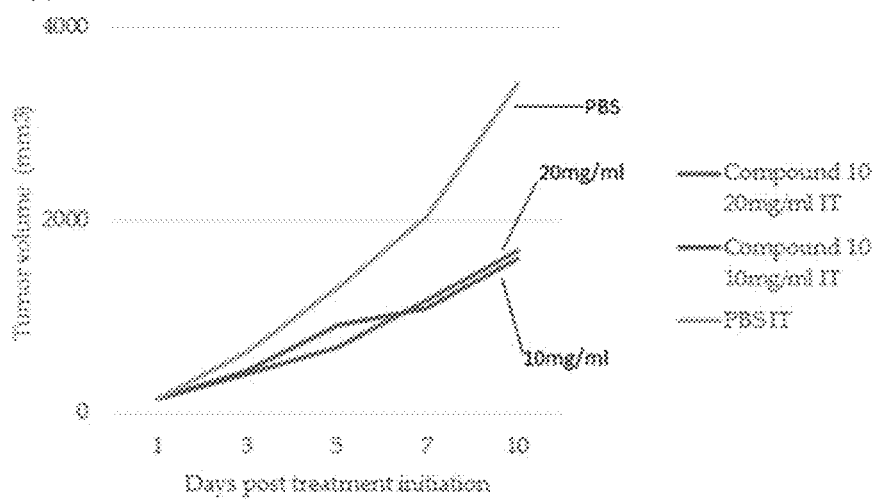
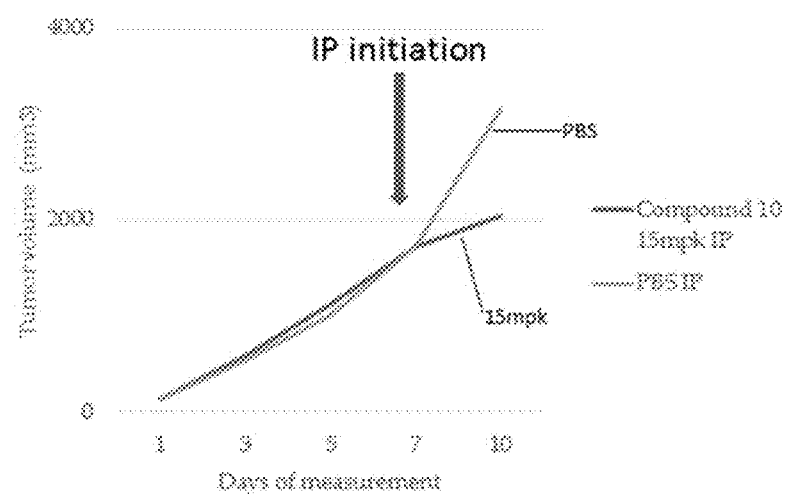
FIGURE 19

Compound 10 efficacy on various cell lines

| Cell Line | Tissue | IC50 (M) | $R^2$ |
|---|---|---|---|
| Calu3 | Lung adenocarcinoma | 1.50E-05 | 0.887633 |
| A549 | Lung epithelial carcinoma | 4.72E-06 | 0.995549 |
| NciH1975 | Non-small cell lung cancer adenocarcinoma | 8.42E-06 | 0.999948 |
| T98G | Glioblastoma multiforme | 9.70E-07 | 0.934034 |
| SSP25 | Intrahepaic cholangiocarcinoma | 8.84E-06 | 0.987454 |
| U2OS | Osteosarcoma | 7.48E-06 | 0.999692 |
| MDA_MB_231 | Breast adenocarcinoma | 2.80E-06 | 0.999708 |
| A375 | Malignant melanoma | 6.10E-06 | 0.992833 |

FIGURE 20

| Formula I | (T/K/R/Q)$_{1-3}$ – (L/I/V/F/M/W/Y) – (R/G/S) – (L/I/V/F/M/W/Y) |
|---|---|
| Formula II | (R/K) – (L) – (G) – (M/V) |
| Formula III | (R) – (L) – (G) – (V) – (M/V) – (L/I/V/F/M/A/W/Y) |
| Formula IV | (T/K/R/Q)$_{1-2}$– (R) – (L) – (G) – (V) – (M/V) – (L/I/V/F/M/A/W/Y) |

FIGURE 21

Binding of Compounds on a novel site of Rad51 – modelling on 1N0W PDB structure

Compound binding sites D187, Q202, Y205, Q206 highlighted in dark
BRCA2 peptide highlighted in gray

RAD51 Ortholog Sequence Alignment Correlation to SEQ ID NO.: 5 Binding

SEQUENCE LISTING

```
<160> NUMBER OF SEQ ID NOS: 144

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Gln Ser Leu Arg Leu Gly Leu Ser Arg Leu Ala Arg Val Lys Arg
1               5                   10                  15

Leu His Pro Gly Ala Arg Arg Arg Arg Arg Arg Arg Arg
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Gln Ser Leu Arg Leu Gly Gln Ser Arg Leu Ala Arg Val Lys Arg
1               5                   10                  15

Leu His Pro Gly Ala Arg Arg Arg Arg Arg Arg Arg Arg
            20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Lys Gln Ser Leu Arg Leu Gly Leu Ser Arg Leu Ala Arg Val Lys Arg
1               5                   10                  15

Leu His Pro Gly Ala Arg Arg Arg Arg Arg Arg Arg
            20                  25

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Gln Ser Asn Leu Arg Leu Gly Leu Ser Arg Leu Ala Arg Val Lys
1               5                   10                  15

Arg Leu His Pro Gly Cys Cys Arg Arg Arg Arg Arg Arg Arg
            20                  25                  30

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Arg Arg Arg Arg Arg Arg Arg Lys Arg Leu Gly Val Arg Leu Arg
1               5                   10                  15

Val Ser Arg Met Leu
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Arg Arg Arg Arg Arg Arg Arg Lys Arg Leu Gly Gln Arg Leu Arg
1               5                   10                  15

Gln Ser Arg Met Leu
            20

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Arg Arg Arg Arg Arg Arg Arg Arg Leu Gly Met Ser Arg Arg Phe
1               5                   10                  15

<210> SEQ ID NO 8

<400> SEQUENCE: 8
```

000

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Arg Arg Arg Arg Arg Arg Arg Lys Arg Leu Gly Leu Arg Leu Gly
1               5                   10                  15

Val Ser Arg Arg Val
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Met Arg Ser Val Arg Leu Arg Val Gly Leu Arg Lys Arg Arg Arg
1               5                   10                  15

Arg Arg Arg Arg
            20

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Arg Arg Arg Arg Arg Arg Arg Ser Leu Arg Leu Gly Leu Ser Arg
1               5                   10                  15

Leu Ala Arg Val Lys Arg Leu His Pro Gly
            20                  25

<210> SEQ ID NO 12

<400> SEQUENCE: 12

000

<210> SEQ ID NO 13
<211> LENGTH: 13
<212> TYPE: PRT
<213> ORGANISM: Human immunodeficiency virus 1

<400> SEQUENCE: 13

Gly Arg Lys Lys Arg Arg Gln Arg Arg Pro Pro Gln
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Arg Arg Arg Arg Arg Arg
1               5

<210> SEQ ID NO 15
<211> LENGTH: 18
<212> TYPE: PRT
<213> ORGANISM: Unknown
<220> FEATURE:
<223> OTHER INFORMATION: Description of Unknown:
      MAP sequence

<400> SEQUENCE: 15

Lys Leu Ala Leu Lys Leu Ala Leu Lys Ala Leu Lys Ala Ala Leu Lys
1               5                   10                  15

Leu Ala

<210> SEQ ID NO 16
<211> LENGTH: 27
<212> TYPE: PRT
<213> ORGANISM: Unknown
<220> FEATURE:
<223> OTHER INFORMATION: Description of Unknown:
      Transportan sequence

<400> SEQUENCE: 16

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 17
<211> LENGTH: 18
<212> TYPE: PRT
<213> ORGANISM: Unknown
<220> FEATURE:
<223> OTHER INFORMATION: Description of Unknown:
      Pegelin sequence

<400> SEQUENCE: 17

Arg Gly Gly Arg Leu Ser Tyr Ser Arg Arg Arg Phe Ser Thr Ser Thr
1               5                   10                  15

Gly Arg

<210> SEQ ID NO 18
<211> LENGTH: 16
<212> TYPE: PRT
<213> ORGANISM: Drosophila sp.

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Leu, Met or Val
<220> FEATURE:

```
<221> NAME/KEY: MOD_RES
<222> LOCATION: (7)..(7)
<223> OTHER INFORMATION: Arg, Leu or Lys
<220> FEATURE:
<221> NAME/KEY: MOD_RES
<222> LOCATION: (8)..(8)
<223> OTHER INFORMATION: Arg, Phe or Val

<400> SEQUENCE: 19

Arg Leu Gly Xaa Ser Arg Xaa Xaa
1               5

<210> SEQ ID NO 20
<211> LENGTH: 258
<212> TYPE: PRT
<213> ORGANISM: Vibrio cholerae

<400> SEQUENCE: 20

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
                20                  25                  30

Glu Ile Lys Gln Ser Gly Gly Leu Met Pro Arg Gly Gln Ser Glu Tyr
            35                  40                  45

Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220

Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 21
<211> LENGTH: 593
<212> TYPE: PRT
<213> ORGANISM: Salmonella enterica

<400> SEQUENCE: 21
```

```
Met Leu Ile Leu Asn Gly Phe Ser Ser Ala Thr Leu Ala Leu Ile Thr
1               5                   10                  15

Pro Pro Phe Leu Pro Lys Gly Gly Lys Ala Leu Ser Gln Ser Gly Pro
            20                  25                  30

Asp Gly Leu Ala Ser Ile Thr Leu Pro Leu Pro Ile Ser Ala Glu Arg
        35                  40                  45

Gly Phe Ala Pro Ala Leu Ala Leu His Tyr Ser Ser Gly Gly Gly Asn
    50                  55                  60

Gly Pro Phe Gly Val Gly Trp Ser Cys Ala Thr Met Ser Ile Ala Arg
65                  70                  75                  80

Arg Thr Ser His Gly Val Pro Gln Tyr Asn Asp Ser Asp Glu Phe Leu
                85                  90                  95

Gly Pro Asp Gly Glu Val Leu Val Gln Thr Leu Ser Thr Gly Asp Ala
            100                 105                 110

Pro Asn Pro Val Thr Cys Phe Ala Tyr Gly Asp Val Ser Phe Pro Gln
            115                 120                 125

Ser Tyr Thr Val Thr Arg Tyr Gln Pro Arg Thr Glu Ser Ser Phe Tyr
    130                 135                 140

Arg Leu Glu Tyr Trp Val Gly Asn Ser Asn Gly Asp Asp Phe Trp Leu
145                 150                 155                 160

Leu His Asp Ser Asn Gly Ile Leu His Leu Leu Gly Lys Thr Ala Ala
                165                 170                 175

Ala Arg Leu Ser Asp Pro Gln Ala Ala Ser His Thr Ala Gln Trp Leu
            180                 185                 190

Val Glu Glu Ser Val Thr Pro Ala Gly Glu His Ile Tyr Tyr Ser Tyr
    195                 200                 205

Leu Ala Glu Asn Gly Asp Asn Val Asp Leu Asn Gly Asn Glu Ala Gly
    210                 215                 220

Arg Asp Arg Ser Ala Met Arg Tyr Leu Ser Lys Val Gln Tyr Gly Asn
225                 230                 235                 240

Ala Thr Pro Ala Ala Asp Leu Tyr Leu Trp Thr Ser Ala Thr Pro Ala
            245                 250                 255

Val Gln Trp Leu Phe Thr Leu Val Phe Asp Tyr Gly Glu Arg Gly Val
    260                 265                 270

Asp Pro Gln Val Pro Pro Ala Phe Thr Ala Gln Asn Ser Trp Leu Ala
    275                 280                 285

Arg Gln Asp Pro Phe Ser Leu Tyr Asn Tyr Gly Phe Glu Ile Arg Leu
    290                 295                 300

His Arg Leu Cys Arg Gln Val Leu Met Phe His His Phe Pro Asp Glu
305                 310                 315                 320

Leu Gly Glu Ala Asp Thr Leu Val Ser Arg Leu Leu Glu Tyr Asp
            325                 330                 335

Glu Asn Pro Ile Leu Thr Gln Leu Cys Ala Ala Arg Thr Leu Ala Tyr
            340                 345                 350

Glu Gly Asp Gly Tyr Arg Arg Ala Pro Val Asn Asn Met Met Pro Pro
            355                 360                 365

Pro Pro Pro Pro Pro Pro Met Met Gly Gly Asn Ser Ser Arg Pro
    370                 375                 380

Lys Ser Lys Trp Ala Ile Val Glu Glu Ser Lys Gln Ile Gln Ala Leu
385                 390                 395                 400

Arg Tyr Tyr Ser Ala Gln Gly Tyr Ser Val Ile Asn Lys Tyr Leu Arg
                405                 410                 415

Gly Asp Asp Tyr Pro Glu Thr Gln Ala Lys Glu Thr Leu Leu Ser Arg
```

-continued

```
                420                 425                 430
Asp Tyr Leu Ser Thr Asn Glu Pro Ser Asp Glu Glu Phe Lys Asn Ala
            435                 440                 445

Met Ser Val Tyr Ile Asn Asp Ile Ala Glu Gly Leu Ser Ser Leu Pro
450                 455                 460

Glu Thr Asp His Arg Val Val Tyr Arg Gly Leu Lys Leu Asp Lys Pro
465                 470                 475                 480

Ala Leu Ser Asp Val Leu Lys Glu Tyr Thr Thr Ile Gly Asn Ile Ile
            485                 490                 495

Ile Asp Lys Ala Phe Met Ser Thr Ser Pro Asp Lys Ala Trp Ile Asn
            500                 505                 510

Asp Thr Ile Leu Asn Ile Tyr Leu Glu Lys Gly His Lys Gly Arg Ile
            515                 520                 525

Leu Gly Asp Val Ala His Phe Lys Gly Glu Ala Glu Met Leu Phe Pro
        530                 535                 540

Pro Asn Thr Lys Leu Lys Ile Glu Ser Ile Val Asn Cys Gly Ser Gln
545                 550                 555                 560

Asp Phe Ala Ser Gln Leu Ser Lys Leu Arg Leu Ser Asp Asp Ala Thr
                565                 570                 575

Ala Asp Thr Asn Arg Ile Lys Arg Ile Ile Asn Met Arg Val Leu Asn
            580                 585                 590

Ser
```

<210> SEQ ID NO 22
<211> LENGTH: 601
<212> TYPE: PRT
<213> ORGANISM: Mycoplasma pneumoniae

<400> SEQUENCE: 22

```
Met Ser Glu Asn Leu Tyr Phe Gln Gly His Met Pro Asn Pro Val Arg
1               5                   10                  15

Phe Val Tyr Arg Val Asp Leu Arg Ser Pro Glu Glu Ile Phe Glu His
                20                  25                  30

Gly Phe Ser Thr Leu Gly Asp Val Arg Asn Phe Phe Glu His Ile Leu
            35                  40                  45

Ser Thr Asn Phe Gly Arg Ser Tyr Phe Ile Ser Thr Ser Glu Thr Pro
        50                  55                  60

Thr Ala Ala Ile Arg Phe Gly Ser Trp Leu Arg Glu Tyr Val Pro
65                  70                  75                  80

Glu His Pro Arg Arg Ala Tyr Leu Tyr Glu Ile Arg Ala Asp Gln His
                85                  90                  95

Phe Tyr Asn Ala Arg Ala Thr Gly Glu Asn Leu Leu Asp Leu Met Arg
            100                 105                 110

Gln Arg Gln Val Val Phe Asp Ser Gly Asp Arg Glu Met Ala Gln Met
        115                 120                 125

Gly Ile Arg Ala Leu Arg Thr Ser Phe Ala Tyr Gln Arg Glu Trp Phe
    130                 135                 140

Thr Asp Gly Pro Ile Ala Ala Ala Asn Val Arg Ser Ala Trp Leu Val
145                 150                 155                 160

Asp Ala Val Pro Val Glu Pro Gly His Ala His Pro Ala Gly Arg
                165                 170                 175

Val Val Glu Thr Thr Arg Ile Asn Glu Pro Glu Met His Asn Pro His
            180                 185                 190

Tyr Gln Glu Leu Gln Thr Gln Ala Asn Asp Gln Pro Trp Leu Pro Thr
```

```
            195                 200                 205
Pro Gly Ile Ala Thr Pro Val His Leu Ser Ile Pro Gln Ala Ala Ser
210                 215                 220
Val Ala Asp Val Ser Glu Gly Thr Ser Ala Ser Leu Ser Phe Ala Cys
225                 230                 235                 240
Pro Asp Trp Ser Pro Ser Ser Asn Gly Glu Asn Pro Leu Asp Lys
            245                 250                 255
Cys Ile Ala Glu Lys Ile Asp Asn Tyr Asn Leu Gln Ser Leu Pro Gln
            260                 265                 270
Tyr Ala Ser Ser Val Lys Glu Leu Glu Asp Thr Pro Val Tyr Leu Arg
            275                 280                 285
Gly Ile Lys Thr Gln Lys Thr Phe Met Leu Gln Ala Asp Pro Gln Asn
            290                 295                 300
Asn Asn Val Phe Leu Val Glu Val Asn Pro Lys Gln Lys Ser Ser Phe
305                 310                 315                 320
Pro Gln Thr Ile Phe Phe Trp Asp Val Tyr Gln Arg Ile Cys Leu Lys
            325                 330                 335
Asp Leu Thr Gly Ala Gln Ile Ser Leu Ser Leu Thr Ala Phe Thr Thr
            340                 345                 350
Gln Tyr Ala Gly Gln Leu Lys Val His Leu Ser Val Ser Ala Val Asn
            355                 360                 365
Ala Val Asn Gln Lys Trp Lys Met Thr Pro Gln Asp Ile Ala Ile Thr
370                 375                 380
Gln Phe Arg Val Ser Ser Glu Leu Leu Gly Gln Thr Glu Asn Gly Leu
385                 390                 395                 400
Phe Trp Asn Thr Lys Ser Gly Gly Ser Gln His Asp Leu Tyr Val Cys
            405                 410                 415
Pro Leu Lys Asn Pro Pro Ser Asp Leu Glu Glu Leu Gln Ile Ile Val
            420                 425                 430
Asp Glu Cys Thr Thr His Ala Gln Phe Val Thr Met Arg Ala Ala Ser
            435                 440                 445
Thr Phe Phe Val Asp Val Gln Leu Gly Trp Tyr Trp Arg Gly Tyr Tyr
450                 455                 460
Tyr Thr Pro Gln Leu Ser Gly Trp Ser Tyr Gln Met Lys Thr Pro Asp
465                 470                 475                 480
Gly Gln Ile Phe Tyr Asp Leu Lys Thr Ser Lys Ile Phe Phe Val Gln
            485                 490                 495
Asp Asn Gln Asn Val Phe Phe Leu His Asn Lys Leu Asn Lys Gln Thr
            500                 505                 510
Gly Tyr Ser Trp Asp Trp Val Glu Trp Leu Lys His Asp Met Asn Glu
            515                 520                 525
Asp Lys Asp Glu Asn Phe Lys Trp Tyr Phe Ser Arg Asp Asp Leu Thr
            530                 535                 540
Ile Pro Ser Val Glu Gly Leu Asn Phe Arg His Ile Arg Cys Tyr Ala
545                 550                 555                 560
Asp Asn Gln Gln Leu Lys Val Ile Ile Ser Gly Ser Arg Trp Gly Gly
            565                 570                 575
Trp Tyr Ser Thr Tyr Asp Lys Val Glu Ser Asn Val Glu Asp Lys Ile
            580                 585                 590
Leu Val Lys Asp Gly Phe Asp Arg Phe
            595                 600
```

<210> SEQ ID NO 23

-continued

<211> LENGTH: 250
<212> TYPE: PRT
<213> ORGANISM: Streptococcus pyogenes

<400> SEQUENCE: 23

```
Met Leu Lys Lys Arg Tyr Gln Leu Ala Met Ile Leu Leu Ser Cys
1               5                   10                  15

Phe Ser Leu Val Trp Gln Thr Glu Gly Leu Val Glu Leu Phe Val Cys
            20                  25                  30

Glu His Tyr Glu Arg Ala Val Cys Glu Gly Thr Pro Ala Tyr Phe Thr
        35                  40                  45

Phe Ser Asp Gln Lys Gly Ala Glu Thr Leu Ile Lys Lys Arg Trp Gly
    50                  55                  60

Lys Gly Leu Val Tyr Pro Arg Ala Glu Gln Glu Ala Met Ala Ala Tyr
65                  70                  75                  80

Thr Cys Gln Gln Ala Gly Pro Ile Asn Thr Ser Leu Asp Lys Ala Lys
                85                  90                  95

Gly Lys Leu Ser Gln Leu Thr Pro Glu Leu Arg Asp Gln Val Ala Gln
            100                 105                 110

Leu Asp Ala Ala Thr His Arg Leu Val Ile Pro Trp Asn Ile Val Val
        115                 120                 125

Tyr Arg Tyr Val Tyr Glu Thr Phe Leu Arg Asp Ile Gly Val Ser His
    130                 135                 140

Ala Asp Leu Thr Ser Tyr Tyr Arg Asn His Gln Phe Asn Pro His Ile
145                 150                 155                 160

Leu Cys Lys Ile Lys Leu Gly Thr Arg Tyr Thr Lys His Ser Phe Met
                165                 170                 175

Ser Thr Thr Ala Leu Lys Asn Gly Ala Met Thr His Arg Pro Val Glu
            180                 185                 190

Val Arg Ile Cys Val Lys Lys Gly Ala Lys Ala Phe Val Glu Pro
        195                 200                 205

Tyr Ser Ala Val Pro Ser Glu Val Glu Leu Leu Phe Pro Arg Gly Cys
    210                 215                 220

Gln Leu Glu Val Val Gly Ala Tyr Val Ser Gln Asp His Lys Lys Leu
225                 230                 235                 240

His Ile Glu Ala Tyr Phe Lys Gly Ser Leu
                245                 250
```

<210> SEQ ID NO 24
<211> LENGTH: 264
<212> TYPE: PRT
<213> ORGANISM: Pseudomonas syringae

<400> SEQUENCE: 24

```
Met Asn Ile Asn Arg Gln Leu Pro Val Ser Gly Ser Glu Arg Leu Leu
1               5                   10                  15

Thr Pro Asp Val Gly Val Ser Arg Gln Ala Cys Ser Glu Arg His Tyr
            20                  25                  30

Ser Thr Gly Gln Asp Arg His Asp Phe Tyr Arg Phe Ala Ala Arg Leu
        35                  40                  45

His Val Asp Ala Gln Cys Phe Gly Leu Ser Ile Asp Asp Leu Met Asp
    50                  55                  60

Lys Phe Ser Asp Lys His Phe Arg Ala Glu His Pro Glu Tyr Arg Asp
65                  70                  75                  80

Val Tyr Pro Glu Glu Cys Ser Ala Ile Tyr Met His Thr Ala Gln Asp
                85                  90                  95
```

Tyr Ser Ser His Leu Val Arg Gly Glu Ile Gly Thr Pro Leu Tyr Arg
            100                 105                 110

Glu Val Asn Asn Tyr Leu Arg Leu Gln His Glu Asn Ser Gly Arg Glu
            115                 120                 125

Ala Glu Ile Asp Asn His Asp Glu Lys Leu Ser Pro His Ile Lys Met
130                 135                 140

Leu Ser Ser Ala Leu Asn Arg Leu Met Asp Val Ala Ala Phe Arg Gly
145                 150                 155                 160

Thr Val Tyr Arg Gly Ile Arg Gly Asp Leu Asp Thr Ile Ala Arg Leu
                165                 170                 175

Tyr His Leu Phe Asp Thr Gly Gly Arg Tyr Val Glu Pro Ala Phe Met
            180                 185                 190

Ser Thr Thr Arg Ile Lys Asp Ser Ala Gln Val Phe Glu Pro Gly Thr
            195                 200                 205

Pro Asn Asn Ile Ala Phe Gln Ile Ser Leu Lys Arg Gly Ala Asp Ile
            210                 215                 220

Ser Gly Ser Ser Gln Ala Pro Ser Glu Glu Glu Ile Met Leu Pro Met
225                 230                 235                 240

Met Ser Glu Phe Val Ile Glu His Ala Ser Ala Leu Ser Glu Gly Lys
                245                 250                 255

His Leu Phe Val Leu Ser Gln Ile
            260

<210> SEQ ID NO 25
<211> LENGTH: 601
<212> TYPE: PRT
<213> ORGANISM: Vibrio cholerae

<400> SEQUENCE: 25

Met Lys Thr Ile Ile Ser Leu Ile Phe Ile Met Phe Pro Leu Phe Val
1               5                   10                  15

Ser Ala His Asn Gly Asn Phe Tyr Arg Ala Asp Ser Arg Ser Pro Asn
            20                  25                  30

Glu Ile Lys Asp Leu Gly Gly Leu Tyr Pro Arg Gly Tyr Tyr Asp Phe
        35                  40                  45

Phe Glu Arg Gly Thr Pro Met Ser Ile Ser Leu Tyr Asp His Ala Arg
50                  55                  60

Gly Ala Pro Ser Gly Asn Thr Arg Tyr Asp Asp Gly Phe Val Ser Thr
65                  70                  75                  80

Thr Thr Asp Ile Asp Ser Ala His Glu Ile Gly Gln Asn Ile Leu Ser
                85                  90                  95

Gly Tyr Thr Glu Tyr Tyr Ile Tyr Leu Ile Ala Pro Ala Pro Asn Leu
            100                 105                 110

Leu Asp Val Asn Ala Val Leu Gly Arg Tyr Ser Pro His Pro Gln Glu
            115                 120                 125

Asn Glu Tyr Ser Ala Leu Gly Gly Ile Pro Trp Thr Gln Val Ile Gly
            130                 135                 140

Trp Tyr Val Val Asn Asn Gly Val Leu Asp Arg Asn Ile His Arg Asn
145                 150                 155                 160

Arg Gln Phe Arg Ala Asp Leu Phe Asn Asn Leu Ser Pro Ala Leu Pro
                165                 170                 175

Ser Glu Ser Tyr Gln Phe Ala Gly Phe Glu Pro Glu His Pro Ala Trp
            180                 185                 190

Arg Gln Glu Pro Trp Ile Asn Phe Ala Pro Pro Gly Cys Gly Arg Asn

```
                195                 200                 205
Val Arg Leu Thr Lys His Ile Asn Gln Gln Asp Cys Ser Asn Ser Gln
210                 215                 220

Glu Glu Leu Val Tyr Lys Lys Leu Gln Asp Leu Arg Thr Gln Phe Lys
225                 230                 235                 240

Val Asp Lys Lys Leu Lys Leu Val Asn Lys Thr Ser Ser Asn Asn Ile
                245                 250                 255

Ile Phe Pro Asn His Asp Phe Ile Arg Glu Trp Val Asp Leu Asp Gly
            260                 265                 270

Asn Gly Asp Leu Ser Tyr Cys Gly Phe Thr Val Asp Ser Asp Gly Ser
        275                 280                 285

Arg Lys Arg Ile Val Cys Ala His Asn Asn Gly Asn Phe Thr Tyr Ser
    290                 295                 300

Ser Ile Asn Ile Ser Leu Ser Asp Tyr Gly Trp Pro Lys Gly Gln Arg
305                 310                 315                 320

Phe Ile Asp Ala Asn Gly Asp Gly Leu Val Asp Tyr Cys Arg Val Gln
                325                 330                 335

Tyr Val Trp Thr His Leu Tyr Cys Ser Leu Ser Leu Pro Gly Gln Tyr
            340                 345                 350

Phe Ser Leu Asp Lys Asp Ala Gly Tyr Leu Asp Ala Gly Tyr Asn Asn
        355                 360                 365

Ser Arg Ala Trp Ala Lys Val Ile Gly Thr Asn Lys Tyr Ser Phe Cys
    370                 375                 380

Arg Leu Thr Ser Asn Gly Tyr Ile Cys Thr Asp Ile Asp Ser Tyr Ser
385                 390                 395                 400

Thr Ala Phe Lys Asp Asp Asp Gln Gly Trp Ala Asp Ser Arg Tyr Trp
                405                 410                 415

Met Asp Ile Asp Gly Asn Gly Asp Asp Tyr Cys Arg Leu Val Tyr
            420                 425                 430

Asn Trp Thr His Leu Arg Cys Asn Leu Gln Gly Lys Asp Gly Leu Trp
        435                 440                 445

Lys Arg Val Glu Ser Lys Tyr Leu Asp Gly Gly Tyr Pro Ser Leu Arg
    450                 455                 460

Phe Lys Ile Lys Met Thr Ser Asn Lys Asp Asn Tyr Cys Arg Ile Val
465                 470                 475                 480

Arg Asn His Arg Val Met Glu Cys Ala Tyr Val Ser Asp Asn Gly Glu
                485                 490                 495

Phe His Asn Tyr Ser Leu Asn Met Pro Phe Ser Leu Tyr Asn Lys Asn
            500                 505                 510

Asp Ile Gln Phe Ile Asp Ile Asp Gly Asp Asn Arg Asp Asp Ile Cys
        515                 520                 525

Arg Tyr Asn Ser Ala Pro Asn Thr Met Glu Cys Tyr Leu Asn Gln Asp
    530                 535                 540

Lys Ser Phe Ser Gln Asn Lys Leu Val Leu Tyr Leu Ser Ala Lys Pro
545                 550                 555                 560

Ile Ser Ser Leu Gly Ser Gly Ser Lys Ile Ile Arg Thr Phe Asn
                565                 570                 575

Ser Glu Lys Asn Ser Ser Ala Tyr Cys Tyr Asn Ala Gly Tyr Gly Thr
            580                 585                 590

Leu Arg Cys Asp Glu Phe Val Ile Tyr
        595                 600

<210> SEQ ID NO 26
```

```
<211> LENGTH: 476
<212> TYPE: PRT
<213> ORGANISM: Bacillus cereus

<400> SEQUENCE: 26

Met Lys Glu Ile Ile Arg Asn Leu Val Arg Leu Asp Val Arg Ser Asp
1               5                   10                  15

Val Asp Glu Asn Ser Lys Lys Thr Gln Glu Leu Val Glu Lys Leu Pro
            20                  25                  30

His Glu Val Leu Glu Leu Tyr Lys Asn Val Gly Gly Glu Ile Tyr Ile
        35                  40                  45

Thr Asp Lys Arg Leu Thr Gln His Glu Glu Leu Ser Asp Ser Ser His
    50                  55                  60

Lys Asp Met Phe Ile Val Ser Ser Glu Gly Lys Ser Phe Pro Leu Arg
65                  70                  75                  80

Glu His Phe Val Phe Ala Lys Gly Gly Lys Glu Pro Ser Leu Ile Ile
                85                  90                  95

His Ala Glu Asp Tyr Ala Ser His Leu Ser Ser Val Glu Val Tyr Tyr
            100                 105                 110

Glu Leu Gly Lys Ala Ile Ile Arg Asp Thr Phe Pro Leu Asn Gln Lys
        115                 120                 125

Glu Leu Gly Asn Pro Lys Phe Ile Asn Ala Ile Asn Glu Val Asn Gln
    130                 135                 140

Gln Lys Glu Gly Lys Gly Val Asn Ala Lys Ala Asp Glu Asp Gly Arg
145                 150                 155                 160

Asp Leu Leu Phe Gly Lys Glu Leu Lys Lys Asn Leu Glu His Gly Gln
                165                 170                 175

Leu Val Asp Leu Asp Leu Ile Ser Gly Asn Leu Ser Glu Phe Gln His
            180                 185                 190

Val Phe Ala Lys Ser Phe Ala Leu Tyr Tyr Glu Pro His Tyr Lys Glu
        195                 200                 205

Ala Leu Lys Ser Tyr Ala Pro Ala Leu Phe Asn Tyr Met Leu Glu Leu
    210                 215                 220

Asp Gln Met Arg Phe Lys Glu Ile Ser Asp Asp Val Lys Glu Lys Asn
225                 230                 235                 240

Lys Asn Val Leu Asp Phe Lys Trp Tyr Thr Arg Lys Ala Glu Ser Trp
                245                 250                 255

Gly Val Gln Thr Phe Lys Asn Trp Lys Glu Asn Leu Thr Ile Ser Glu
            260                 265                 270

Lys Asp Ile Ile Thr Gly Tyr Thr Gly Ser Lys Tyr Asp Pro Ile Asn
        275                 280                 285

Glu Tyr Leu Arg Lys Tyr Asp Gly Glu Ile Ile Pro Asn Ile Gly Gly
    290                 295                 300

Asp Leu Asp Lys Lys Ser Lys Lys Ala Leu Glu Lys Ile Glu Asn Gln
305                 310                 315                 320

Ile Lys Asn Leu Asp Ala Ala Leu Gln Lys Ser Lys Ile Thr Glu Asn
                325                 330                 335

Leu Ile Val Tyr Arg Arg Val Ser Glu Leu Gln Phe Gly Lys Lys Tyr
            340                 345                 350

Glu Asp Tyr Asn Leu Arg Gln Asn Gly Ile Ile Asn Glu Glu Lys Val
        355                 360                 365

Met Glu Leu Glu Ser Asn Phe Lys Gly Gln Thr Phe Ile Gln His Asn
    370                 375                 380

Tyr Met Ser Thr Ser Leu Val Gln Asp Pro His Gln Ser Tyr Ser Asn
```

```
               385                 390                 395                 400
Asp Arg Tyr Pro Ile Leu Leu Glu Ile Thr Ile Pro Glu Gly Val His
                    405                 410                 415

Gly Ala Tyr Ile Ala Asp Met Ser Glu Tyr Pro Gly Gln Tyr Glu Met
                    420                 425                 430

Leu Ile Asn Arg Gly Tyr Thr Phe Lys Tyr Asp Lys Phe Ser Ile Val
                    435                 440                 445

Lys Pro Thr Arg Glu Glu Asp Lys Gly Lys Glu Tyr Leu Lys Val Asn
                    450                 455                 460

Leu Ser Ile Tyr Leu Gly Asn Leu Asn Arg Glu Lys
465                 470                 475

<210> SEQ ID NO 27
<211> LENGTH: 487
<212> TYPE: PRT
<213> ORGANISM: Enterococcus faecalis V583

<400> SEQUENCE: 27

Met Ser Gln Leu Asn Lys Trp Gln Lys Glu Leu Gln Ala Leu Gln Lys
1               5                   10                  15

Ala Asn Tyr Gln Glu Thr Asp Asn Gln Leu Phe Asn Val Tyr Arg Gln
                20                  25                  30

Ser Leu Ile Asp Ile Lys Lys Arg Leu Lys Val Tyr Thr Glu Asn Ala
            35                  40                  45

Glu Ser Leu Ser Phe Ser Thr Arg Leu Glu Val Glu Arg Leu Phe Ser
        50                  55                  60

Val Ala Asp Glu Ile Asn Ala Ile Leu Gln Leu Asn Ser Pro Lys Val
65                  70                  75                  80

Glu Lys Thr Ile Lys Gly Tyr Ser Ala Lys Gln Ala Glu Gln Gly Tyr
                85                  90                  95

Tyr Gly Leu Trp Tyr Thr Leu Glu Gln Ser Gln Asn Ile Ala Leu Ser
                100                 105                 110

Met Pro Leu Ile Asn His Asp Tyr Ile Met Asn Leu Val Asn Ala Pro
            115                 120                 125

Val Ala Gly Lys Arg Leu Ser Lys Arg Leu Tyr Lys Tyr Arg Asp Glu
        130                 135                 140

Leu Ala Gln Asn Val Thr Asn Asn Ile Ile Thr Gly Leu Phe Glu Gly
145                 150                 155                 160

Lys Ser Tyr Ala Glu Ile Ala Arg Trp Ile Asn Glu Glu Thr Glu Ala
                165                 170                 175

Ser Tyr Lys Gln Ala Leu Arg Ile Ala Arg Thr Glu Ala Gly Arg Thr
                180                 185                 190

Gln Ser Val Thr Thr Gln Lys Gly Tyr Glu Glu Ala Lys Glu Leu Gly
            195                 200                 205

Ile Asn Ile Lys Lys Lys Trp Leu Ala Thr Ile Asp Lys His Thr Arg
210                 215                 220

Arg Thr His Gln Glu Leu Asp Gly Lys Glu Val Asp Val Asp Glu Glu
225                 230                 235                 240

Phe Thr Ile Arg Gly His Ser Ala Lys Gly Pro Arg Met Phe Gly Val
                245                 250                 255

Ala Ser Glu Asp Val Asn Cys Arg Cys Thr Thr Ile Glu Val Val Asp
                260                 265                 270

Gly Ile Ser Pro Glu Leu Arg Lys Asp Asn Glu Ser Lys Glu Met Ser
            275                 280                 285
```

```
Glu Phe Lys Ser Tyr Asp Glu Trp Tyr Ala Asp Arg Ile Arg Gln Asn
290                 295                 300

Glu Ser Lys Pro Lys Pro Asn Phe Thr Glu Leu Asp Phe Phe Gly Gln
305                 310                 315                 320

Ser Asp Leu Gln Asp Asp Ser Asp Lys Trp Val Ala Gly Leu Lys Pro
            325                 330                 335

Glu Gln Val Asn Ala Met Lys Asp Tyr Thr Ser Asp Ala Phe Ala Lys
                340                 345                 350

Met Asn Lys Ile Leu Arg Asn Glu Lys Tyr Asn Pro Arg Glu Lys Pro
            355                 360                 365

Tyr Leu Val Asn Ile Ile Gln Asn Leu Asp Asp Ala Ile Ser Lys Phe
370                 375                 380

Lys Leu Lys His Asp Ile Ile Thr Tyr Arg Gly Val Ser Ala Asn Glu
385                 390                 395                 400

Tyr Asp Ala Ile Leu Asn Gly Asn Val Phe Lys Glu Phe Lys Ser Thr
                405                 410                 415

Ser Ile Asn Lys Lys Val Ala Glu Asp Phe Leu Asn Phe Thr Ser Ala
            420                 425                 430

Asn Lys Asp Gly Arg Val Val Lys Phe Leu Ile Pro Lys Gly Thr Gln
            435                 440                 445

Gly Ala Tyr Ile Gly Thr Asn Ser Ser Met Lys Lys Glu Ser Glu Phe
450                 455                 460

Leu Leu Asn Arg Asn Leu Lys Tyr Thr Val Glu Ile Val Asp Asn Ile
465                 470                 475                 480

Leu Glu Val Thr Ile Leu Gly
                485

<210> SEQ ID NO 28
<211> LENGTH: 457
<212> TYPE: PRT
<213> ORGANISM: Pseudomonas aeruginosa

<400> SEQUENCE: 28

Met His Ile Gln Ser Ser Gln Gln Asn Pro Ser Phe Val Ala Glu Leu
1               5                   10                  15

Ser Gln Ala Val Ala Gly Arg Leu Gly Gln Val Glu Ala Arg Gln Val
                20                  25                  30

Ala Thr Pro Arg Glu Ala Gln Gln Leu Ala Gln Arg Gln Glu Ala Pro
            35                  40                  45

Lys Gly Glu Gly Leu Leu Ser Arg Leu Gly Ala Ala Leu Ala Arg Pro
50                  55                  60

Phe Val Ala Ile Ile Glu Trp Leu Gly Lys Leu Leu Gly Ser Arg Ala
65                  70                  75                  80

His Ala Ala Thr Gln Ala Pro Leu Ser Arg Gln Asp Ala Pro Pro Ala
                85                  90                  95

Ala Ser Leu Ser Ala Ala Glu Ile Lys Gln Met Met Leu Gln Lys Ala
                100                 105                 110

Leu Pro Leu Thr Leu Gly Gly Leu Gly Lys Ala Ser Glu Leu Ala Thr
            115                 120                 125

Leu Thr Ala Glu Arg Leu Ala Lys Asp His Thr Arg Leu Ala Ser Gly
            130                 135                 140

Asp Gly Ala Leu Arg Ser Leu Ala Thr Ala Leu Val Gly Ile Arg Asp
145                 150                 155                 160

Gly Ser Leu Ile Glu Ala Ser Arg Thr Gln Ala Ala Arg Leu Leu Glu
                165                 170                 175
```

```
Gln Ser Val Gly Gly Ile Ala Leu Gln Gln Trp Gly Thr Ala Gly Gly
                180                 185                 190

Ala Ala Ser Gln His Val Leu Ser Ala Ser Pro Glu Gln Leu Arg Glu
            195                 200                 205

Ile Ala Val Gln Leu His Ala Val Met Asp Lys Val Ala Leu Leu Arg
        210                 215                 220

His Ala Val Glu Ser Glu Val Lys Gly Glu Pro Val Asp Lys Ala Leu
225                 230                 235                 240

Ala Asp Gly Leu Val Glu His Phe Gly Leu Glu Ala Glu Gln Tyr Leu
                245                 250                 255

Gly Glu His Pro Asp Gly Pro Tyr Ser Asp Ala Glu Val Met Ala Leu
            260                 265                 270

Gly Leu Tyr Thr Asn Gly Glu Tyr Gln His Leu Asn Arg Ser Leu Arg
        275                 280                 285

Gln Gly Arg Glu Leu Asp Ala Gly Gln Ala Leu Ile Asp Arg Gly Met
290                 295                 300

Ser Ala Ala Phe Glu Lys Ser Gly Pro Ala Glu Gln Val Val Lys Thr
                310                 315                 320
305

Phe Arg Gly Thr Gln Gly Arg Asp Ala Phe Glu Ala Val Lys Glu Gly
            325                 330                 335

Gln Val Gly His Asp Ala Gly Tyr Leu Ser Thr Ser Arg Asp Pro Ser
        340                 345                 350

Val Ala Arg Ser Phe Ala Gly Leu Gly Thr Ile Thr Thr Leu Phe Gly
                355                 360                 365

Arg Ser Gly Ile Asp Val Ser Glu Ile Ser Ile Glu Gly Asp Glu Gln
            370                 375                 380

Glu Ile Leu Tyr Asp Lys Gly Thr Asp Met Arg Val Leu Leu Ser Ala
385                 390                 395                 400

Lys Asp Gly Gln Gly Val Thr Arg Arg Val Leu Glu Glu Ala Thr Leu
                405                 410                 415

Gly Glu Arg Ser Gly His Ser Glu Gly Leu Leu Asp Ala Leu Asp Leu
            420                 425                 430

Ala Thr Gly Thr Asp Arg Ser Gly Lys Pro Gln Glu Gln Asp Leu Arg
        435                 440                 445

Leu Arg Met Arg Gly Leu Asp Leu Ala
    450                 455

<210> SEQ ID NO 29
<211> LENGTH: 265
<212> TYPE: PRT
<213> ORGANISM: Unknown
<220> FEATURE:
<223> OTHER INFORMATION: Description of Unknown:
      CdtB toxin sequence

<400> SEQUENCE: 29

Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
        35                  40                  45

Gly Ala Asn Pro Leu Asp Ile Leu Met Ile Gln Glu Ala Gly Thr Leu
    50                  55                  60

Pro Arg Thr Ala Thr Pro Thr Gly Arg His Val Gln Gln Gly Gly Thr
```

65 70 75 80

Pro Ile Asp Glu Tyr Glu Trp Asn Leu Gly Thr Leu Ser Arg Pro Asp
85 90 95

Arg Val Phe Ile Tyr Tyr Ser Arg Val Asp Val Gly Ala Asn Arg Val
100 105 110

Asn Leu Ala Ile Val Ser Arg Met Gln Ala Glu Glu Val Ile Val Leu
115 120 125

Pro Pro Pro Thr Thr Val Ser Arg Pro Ile Ile Gly Ile Arg Asn Gly
130 135 140

Asn Asp Ala Phe Phe Asn Ile His Ala Leu Ala Asn Gly Gly Thr Asp
145 150 155 160

Val Gly Ala Ile Ile Thr Ala Val Asp Ala His Phe Ala Asn Met Pro
165 170 175

Gln Val Asn Trp Met Ile Ala Gly Asp Phe Asn Arg Asp Pro Ser Thr
180 185 190

Ile Thr Ser Thr Val Asp Arg Glu Leu Ala Asn Arg Ile Arg Val Val
195 200 205

Phe Pro Thr Ser Ala Thr Gln Ala Ser Gly Gly Thr Leu Asp Tyr Ala
210 215 220

Ile Thr Gly Asn Ser Asn Arg Gln Gln Thr Tyr Thr Pro Pro Leu Leu
225 230 235 240

Ala Ala Ile Leu Met Leu Ala Ser Leu Arg Ser His Ile Val Ser Asp
245 250 255

His Phe Pro Val Asn Phe Arg Lys Phe
260 265

<210> SEQ ID NO 30
<211> LENGTH: 560
<212> TYPE: PRT
<213> ORGANISM: Corynebacterium diphtheriae

<400> SEQUENCE: 30

Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

```
Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
            245                 250                 255

Glu Ser Pro Asn Lys Thr Val Ser Glu Glu Lys Ala Lys Gln Tyr Leu
        260                 265                 270

Glu Glu Phe His Gln Thr Ala Leu Glu His Pro Glu Leu Ser Glu Leu
    275                 280                 285

Lys Thr Val Thr Gly Thr Asn Pro Val Phe Ala Gly Ala Asn Tyr Ala
290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
            325                 330                 335

Ser Val Met Gly Ile Ala Asp Gly Ala Val His His Asn Thr Glu Glu
        340                 345                 350

Ile Val Ala Gln Ser Ile Ala Leu Ser Ser Leu Met Val Ala Gln Ala
    355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
            405                 410                 415

Asp Gly Tyr Ala Val Ser Trp Asn Thr Val Glu Asp Ser Ile Ile Arg
        420                 425                 430

Thr Gly Phe Gln Gly Glu Ser Gly His Asp Ile Lys Ile Thr Ala Glu
    435                 440                 445

Asn Thr Pro Leu Pro Ile Ala Gly Val Leu Leu Pro Thr Ile Pro Gly
450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
            485                 490                 495

Arg Pro Lys Ser Pro Val Tyr Val Gly Asn Gly Val His Ala Asn Leu
        500                 505                 510

His Val Ala Phe His Arg Ser Ser Glu Lys Ile His Ser Asn Glu
    515                 520                 525

Ile Ser Ser Asp Ser Ile Gly Val Leu Gly Tyr Gln Lys Thr Val Asp
530                 535                 540

His Thr Lys Val Asn Ser Lys Leu Ser Leu Phe Phe Glu Ile Lys Ser
545                 550                 555                 560

<210> SEQ ID NO 31
<211> LENGTH: 621
<212> TYPE: PRT
<213> ORGANISM: Unknown
<220> FEATURE:
<223> OTHER INFORMATION: Description of Unknown:
```

ExoU/VipB sequence

<400> SEQUENCE: 31

| | | | | | | | | | | | | | | |
|---|---|---|---|---|---|---|---|---|---|---|---|---|---|---|
| Met | Lys | Leu | Ala | Glu | Ile | Met | Thr | Lys | Ser | Arg | Lys | Leu | Lys | Arg | Asn |
| 1 | | | | 5 | | | | | 10 | | | | | 15 | |
| Leu | Leu | Glu | Ile | Ser | Lys | Thr | Glu | Ala | Gly | Gln | Tyr | Ser | Val | Ser | Ala |
| | | | 20 | | | | | 25 | | | | | 30 | | |
| Pro | Glu | His | Lys | Gly | Leu | Val | Leu | Ser | Gly | Gly | Ala | Lys | Gly | Ile | |
| | | 35 | | | | | 40 | | | | | 45 | | | |
| Ser | Tyr | Leu | Gly | Met | Ile | Gln | Ala | Leu | Gln | Glu | Arg | Gly | Lys | Ile | Lys |
| | 50 | | | | | 55 | | | | | 60 | | | | |
| Asn | Leu | Thr | His | Val | Ser | Gly | Ala | Ser | Ala | Gly | Ala | Met | Thr | Ala | Ser |
| 65 | | | | | 70 | | | | | 75 | | | | | 80 |
| Ile | Leu | Ala | Val | Gly | Met | Asp | Ile | Lys | Asp | Ile | Lys | Lys | Leu | Ile | Glu |
| | | | | 85 | | | | | 90 | | | | | 95 | |
| Gly | Leu | Asp | Ile | Thr | Lys | Leu | Leu | Asp | Asn | Ser | Gly | Val | Gly | Phe | Arg |
| | | | 100 | | | | | 105 | | | | | 110 | | |
| Ala | Arg | Gly | Asp | Arg | Phe | Arg | Asn | Ile | Leu | Asp | Val | Ile | Tyr | Met | Met |
| | | 115 | | | | | 120 | | | | | 125 | | | |
| Gln | Met | Lys | Lys | His | Leu | Glu | Ser | Val | Gln | Gln | Pro | Ile | Pro | Pro | Glu |
| | 130 | | | | | 135 | | | | | 140 | | | | |
| Gln | Gln | Met | Asn | Tyr | Gly | Ile | Leu | Lys | Gln | Lys | Ile | Ala | Leu | Tyr | Glu |
| 145 | | | | | 150 | | | | | 155 | | | | | 160 |
| Asp | Lys | Leu | Ser | Arg | Ala | Gly | Ile | Val | Ile | Asn | Asn | Val | Asp | Asp | Ile |
| | | | | 165 | | | | | 170 | | | | | 175 | |
| Ile | Asn | Leu | Thr | Lys | Ser | Val | Lys | Asp | Leu | Glu | Lys | Leu | Asp | Lys | Ala |
| | | | 180 | | | | | 185 | | | | | 190 | | |
| Leu | Asn | Ser | Ile | Pro | Thr | Glu | Leu | Lys | Gly | Ala | Lys | Gly | Glu | Gln | Leu |
| | | 195 | | | | | 200 | | | | | 205 | | | |
| Glu | Asn | Pro | Arg | Leu | Thr | Leu | Gly | Asp | Leu | Gly | Arg | Leu | Arg | Glu | Leu |
| | 210 | | | | | 215 | | | | | 220 | | | | |
| Leu | Pro | Glu | Glu | Asn | Lys | His | Leu | Ile | Lys | Asn | Leu | Ser | Val | Val | Val |
| 225 | | | | | 230 | | | | | 235 | | | | | 240 |
| Thr | Asn | Gln | Thr | Lys | His | Glu | Leu | Glu | Arg | Tyr | Ser | Glu | Asp | Thr | Thr |
| | | | | 245 | | | | | 250 | | | | | 255 | |
| Pro | Gln | Gln | Ser | Ile | Ala | Gln | Val | Val | Gln | Trp | Ser | Gly | Ala | His | Pro |
| | | | 260 | | | | | 265 | | | | | 270 | | |
| Val | Leu | Phe | Val | Pro | Gly | Arg | Asn | Ala | Lys | Gly | Glu | Tyr | Ile | Ala | Asp |
| | | 275 | | | | | 280 | | | | | 285 | | | |
| Gly | Gly | Ile | Leu | Asp | Asn | Met | Pro | Glu | Ile | Glu | Gly | Leu | Asp | Arg | Glu |
| | 290 | | | | | 295 | | | | | 300 | | | | |
| Glu | Val | Leu | Cys | Val | Lys | Ala | Glu | Ala | Gly | Thr | Ala | Phe | Glu | Asp | Arg |
| 305 | | | | | 310 | | | | | 315 | | | | | 320 |
| Val | Asn | Lys | Ala | Lys | Gln | Ser | Ala | Met | Glu | Ala | Ile | Ser | Trp | Phe | Lys |
| | | | | 325 | | | | | 330 | | | | | 335 | |
| Ala | Arg | Met | Asp | Ser | Leu | Val | Glu | Ala | Thr | Ile | Gly | Gly | Lys | Trp | Leu |
| | | | 340 | | | | | 345 | | | | | 350 | | |
| His | Ala | Thr | Ser | Ser | Val | Leu | Asn | Arg | Glu | Lys | Val | Tyr | Tyr | Asn | Ile |
| | | 355 | | | | | 360 | | | | | 365 | | | |
| Asp | Asn | Met | Ile | Tyr | Ile | Asn | Thr | Gly | Glu | Val | Thr | Thr | Asn | Thr | |
| | 370 | | | | | 375 | | | | | 380 | | | | |
| Ser | Pro | Thr | Pro | Glu | Gln | Arg | Ala | Arg | Ala | Val | Lys | Asn | Gly | Tyr | Asp |
| 385 | | | | | 390 | | | | | 395 | | | | | 400 |

```
Gln Thr Met Gln Leu Leu Asp Ser His Lys Gln Thr Phe Asp His Pro
                405                 410                 415
Leu Met Ala Ile Leu Tyr Ile Gly His Asp Lys Leu Lys Asp Ala Leu
            420                 425                 430
Ile Asp Glu Lys Ser Glu Lys Glu Ile Phe Glu Ala Ser Ala His Ala
        435                 440                 445
Gln Ala Ile Leu His Leu Gln Glu Gln Ile Val Lys Glu Met Asn Asp
    450                 455                 460
Gly Asp Tyr Ser Ser Val Gln Asn Tyr Leu Asp Gln Ile Glu Asp Ile
465                 470                 475                 480
Leu Thr Val Asp Ala Lys Met Asp Asp Ile Gln Lys Glu Lys Ala Phe
                485                 490                 495
Ala Leu Cys Ile Lys Gln Val Asn Phe Leu Ser Glu Gly Lys Leu Glu
            500                 505                 510
Thr Tyr Leu Asn Lys Val Glu Ala Glu Ala Lys Ala Ala Ala Glu Pro
        515                 520                 525
Ser Trp Ala Thr Lys Ile Leu Asn Leu Leu Trp Ala Pro Ile Glu Trp
    530                 535                 540
Val Val Ser Leu Phe Lys Gly Pro Ala Gln Asp Phe Lys Val Glu Val
545                 550                 555                 560
Gln Pro Glu Pro Val Lys Val Ser Thr Ser Glu Asn Gln Glu Thr Val
                565                 570                 575
Ser Asn Gln Lys Asp Ile Asn Pro Ala Val Glu Tyr Arg Lys Ile Ile
            580                 585                 590
Ala Glu Val Arg Arg Glu His Thr Asp Pro Ser Pro Ser Leu Gln Glu
        595                 600                 605
Lys Glu Arg Val Gly Leu Ser Thr Thr Phe Gly Gly His
610                 615                 620

<210> SEQ ID NO 32
<211> LENGTH: 211
<212> TYPE: PRT
<213> ORGANISM: Unknown
<220> FEATURE:
<223> OTHER INFORMATION: Description of Unknown:
      HopPtoE sequence

<400> SEQUENCE: 32

Met Asn Arg Val Ser Gly Ser Ser Ser Ala Thr Trp Gln Ala Val Asn
1               5                   10                  15
Asp Leu Val Glu Gln Val Ser Glu Arg Thr Thr Leu Ser Thr Thr Gly
            20                  25                  30
Tyr Gln Thr Ala Met Gly Arg Leu Asn Lys Pro Glu Lys Ser Asp Ala
        35                  40                  45
Asp Ala Leu Met Thr Met Arg Arg Ala Gln Gln Tyr Thr Asp Ser Ala
    50                  55                  60
Lys Arg Thr Tyr Ile Ser Glu Thr Leu Met Asn Leu Ala Asp Leu Gln
65                  70                  75                  80
Gln Arg Lys Ile Tyr Arg Thr Asn Ser Gly Asn Leu Arg Gly Ala Ile
                85                  90                  95
Glu Met Thr Pro Thr Gln Leu Thr Asp Cys Val Gln Lys Cys Arg Glu
            100                 105                 110
Glu Gly Phe Ser Asn Cys Asp Ile Gln Ala Leu Glu Ile Gly Leu His
        115                 120                 125
Leu Arg His Lys Leu Gly Ile Ser Asp Phe Thr Ile Tyr Ser Asn Arg
    130                 135                 140
```

-continued

Lys Leu Ser His Asn Tyr Val Val Ile His Pro Ser Asn Ala Phe Pro
145                 150                 155                 160

Lys Gly Ala Ile Val Asp Ser Trp Thr Gly Gln Gly Val Val Glu Leu
                165                 170                 175

Asp Phe Lys Thr Arg Leu Lys Phe Lys His Arg Glu Glu Asn Tyr Ala
            180                 185                 190

Val Asn Ala Asn Met His Glu Trp Ile Glu Arg Tyr Gly Gln Ala His
        195                 200                 205

Val Ile Asp
    210

<210> SEQ ID NO 33
<211> LENGTH: 204
<212> TYPE: PRT
<213> ORGANISM: Unknown
<220> FEATURE:
<223> OTHER INFORMATION: Description of Unknown:
      HopPtoF sequence

<400> SEQUENCE: 33

Met Gly Asn Ile Cys Gly Thr Ser Gly Ser Arg His Val Tyr Ser Pro
1               5                   10                  15

Ser His Thr Gln Arg Ile Thr Ser Ala Pro Ser Thr Ser Thr His Val
            20                  25                  30

Gly Gly Asp Thr Leu Thr Ser Ile His Gln Leu Ser His Ser Gln Arg
        35                  40                  45

Glu Gln Phe Leu Asn Met His Asp Pro Met Arg Val Met Gly Leu Asp
50                  55                  60

His Asp Thr Glu Leu Phe Arg Thr Thr Asp Ser Arg Tyr Ile Lys Asn
65                  70                  75                  80

Asp Lys Leu Ala Gly Asn Pro Gln Ser Met Ala Ser Ile Leu Met His
                85                  90                  95

Glu Glu Leu Arg Pro Asn Arg Phe Ala Ser His Thr Gly Ala Gln Pro
            100                 105                 110

His Glu Ala Arg Ala Tyr Val Pro Lys Arg Ile Lys Ala Thr Asp Leu
        115                 120                 125

Gly Val Pro Ser Leu Asn Val Met Thr Gly Ser Leu Ala Arg Asp Gly
    130                 135                 140

Ile Arg Ala Tyr Asp His Met Ser Asp Asn Gln Val Ser Val Lys Met
145                 150                 155                 160

Arg Leu Gly Asp Phe Leu Glu Arg Gly Gly Lys Val Tyr Ala Asp Ala
                165                 170                 175

Ser Ser Val Ala Asp Asp Gly Glu Thr Ser Gln Ala Leu Ile Val Thr
            180                 185                 190

Leu Pro Lys Gly Gln Lys Val Pro Val Glu Arg Val
        195                 200

<210> SEQ ID NO 34
<211> LENGTH: 493
<212> TYPE: PRT
<213> ORGANISM: Unknown
<220> FEATURE:
<223> OTHER INFORMATION: Description of Unknown:
      HopPtoG sequence

<400> SEQUENCE: 34

Met Gln Ile Lys Asn Ser His Leu Tyr Ser Ala Ser Arg Met Val Gln
1               5                   10                  15

```
Asn Thr Phe Asn Ala Ser Pro Lys Met Glu Val Thr Asn Ala Ile Ala
                20                  25                  30
Lys Asn Asn Glu Pro Ala Ala Leu Ser Ala Thr Gln Thr Ala Lys Thr
            35                  40                  45
His Glu Gly Asp Ser Lys Gly Gln Ser Ser Asn Asn Ser Lys Leu Pro
        50                  55                  60
Phe Arg Ala Met Arg Tyr Ala Ala Tyr Leu Ala Gly Ser Ala Tyr Leu
65                  70                  75                  80
Tyr Asp Lys Thr Ala Asn Asn Phe Phe Leu Ser Thr Thr Ser Leu His
                85                  90                  95
Asp Gly Lys Gly Gly Phe Thr Ser Asp Ala Arg Leu Asn Asp Ala Gln
            100                 105                 110
Asp Lys Ala Arg Lys Arg Tyr Gln Asn Asn His Ser Ser Thr Leu Glu
        115                 120                 125
Asn Lys Asn Ser Leu Leu Ser Pro Leu Arg Leu Cys Gly Glu Asn Gln
130                 135                 140
Phe Leu Thr Met Ile Asp Tyr Arg Ala Ala Thr Lys Ile Tyr Leu Ser
145                 150                 155                 160
Asp Leu Val Asp Thr Glu Gln Ala His Thr Ser Ile Leu Lys Asn Ile
                165                 170                 175
Met Cys Leu Lys Gly Glu Leu Thr Asn Glu Ala Ile Lys Lys Leu
            180                 185                 190
Asn Pro Glu Lys Thr Pro Lys Asp Tyr Asp Leu Thr Asn Ser Glu Ala
        195                 200                 205
Tyr Ile Ser Lys Asn Lys Tyr Ser Leu Thr Gly Val Lys Asn Glu Glu
        210                 215                 220
Thr Gly Ser Thr Gly Tyr Thr Ser Arg Ser Ile Thr Lys Pro Phe Val
225                 230                 235                 240
Glu Lys Gly Leu Lys His Phe Ile Lys Ala Thr His Gly Glu Lys Ala
                245                 250                 255
Leu Thr Pro Lys Gln Cys Met Glu Thr Leu Asp Asn Leu Leu Arg Lys
            260                 265                 270
Ser Ile Thr Leu Asn Ser Asp Ser Gln Phe Ala Ala Gly Gln Ala Leu
        275                 280                 285
Leu Val Phe Arg Gln Val Tyr Ala Gly Glu Asp Ala Trp Gly Asp Ala
        290                 295                 300
Glu Arg Val Ile Leu Lys Ser His Tyr Asn Arg Gly Thr Val Leu Gln
305                 310                 315                 320
Asp Glu Ala Asp Lys Ile Glu Leu Ser Arg Pro Phe Ser Glu Gln Asp
                325                 330                 335
Leu Ala Lys Asn Met Phe Lys Arg Asn Thr Ser Ile Ala Gly Pro Val
            340                 345                 350
Leu Tyr His Ala Tyr Ile Tyr Ile Gln Glu Lys Ile Phe Lys Leu Pro
        355                 360                 365
Pro Asp Lys Ile Glu Asp Leu Lys His Lys Ser Met Ala Asp Leu Lys
        370                 375                 380
Asn Leu Pro Leu Thr His Val Lys Leu Ser Asn Ser Gly Val Gly Phe
385                 390                 395                 400
Glu Asp Ala Ser Gly Leu Gly Asp Ser Phe Thr Ala Leu Asn Ala Thr
                405                 410                 415
Ser Cys Val Asn His Ala Arg Ile Met Ser Gly Glu Pro Pro Leu Ser
            420                 425                 430
```

```
Lys Asp Asp Val Val Ile Leu Ile Gly Cys Leu Asn Ala Val Tyr Asp
            435                 440                 445

Asn Ser Ser Gly Ile Arg His Ser Leu Arg Glu Ile Ala Arg Gly Cys
        450                 455                 460

Phe Val Gly Ala Gly Phe Thr Val Gln Asp Gly Asp Phe Tyr Lys
465                 470                 475                 480

Gln Ile Cys Lys Asn Ala Ser Lys Gln Phe Tyr Asn Gly
                485                 490

<210> SEQ ID NO 35
<211> LENGTH: 530
<212> TYPE: PRT
<213> ORGANISM: Vibrio cholerae

<400> SEQUENCE: 35

Met Phe Lys Ile Ser Val Ser Gln Gln Ala Asn Val Met Ser Thr Ser
1               5                   10                  15

Asp Thr Ala Gln Arg Ser Ser Leu Lys Ile Ser Ile Lys Ser Ile Cys
            20                  25                  30

Asn Lys Ser Leu Ser Lys Lys Leu His Thr Leu Ala Glu Lys Cys Arg
        35                  40                  45

Arg Phe Ser Gln Glu Leu Lys Glu His Thr Ala Ser Lys Lys Gln Ile
    50                  55                  60

Val Glu Gln Ala Thr Thr Thr Val Arg Glu Ser Ser Leu Thr Lys Ser
65                  70                  75                  80

Asp Ser Glu Leu Gly Ser Ser Arg Ser Leu Leu Thr Ser Asp Val Leu
                85                  90                  95

Ser Ser Ser Ser Ser His Glu Asp Leu Thr Ala Val Asn Leu Glu Asp
            100                 105                 110

Asn Asp Ser Val Phe Val Thr Ile Glu Ser Ser Ser Glu Leu Ile Val
        115                 120                 125

Lys Gln Asp Gly Ser Ile Pro Pro Ala Pro Pro Leu Pro Gly Asn Ile
    130                 135                 140

Pro Pro Ala Pro Pro Leu Pro Ser Ala Gly Asn Ile Pro Thr Ala Pro
145                 150                 155                 160

Gly Leu Pro Lys Gln Lys Ala Thr Thr Glu Ser Val Ala Gln Thr Ser
                165                 170                 175

Asp Asn Arg Ser Lys Leu Met Glu Glu Ile Arg Gln Gly Val Lys Leu
            180                 185                 190

Arg Ala Thr Pro Lys Ser Ser Thr Glu Lys Ser Ala Ser Asp Pro
        195                 200                 205

His Ser Lys Leu Met Lys Glu Leu Ile Asn His Gly Ala Lys Leu Lys
    210                 215                 220

Lys Val Ser Thr Ser Asp Ile Pro Val Pro Pro Leu Pro Ala Ala
225                 230                 235                 240

Phe Ala Ser Lys Pro Thr Asp Gly Arg Ser Ala Leu Leu Ser Glu Ile
                245                 250                 255

Ala Gly Phe Ser Lys Asp Arg Leu Arg Lys Ala Gly Ser Ser Glu Thr
            260                 265                 270

Leu Asn Val Ser Gln Pro Thr Val Ala Glu Ser Ser Ile Pro Glu Ala
        275                 280                 285

Tyr Asp Leu Leu Leu Ser Asp Glu Met Phe Asn Leu Ser Pro Lys Leu
    290                 295                 300

Ser Glu Thr Glu Leu Asn Thr Leu Ala Asp Ser Leu Ala Asp Tyr Leu
305                 310                 315                 320
```

```
Phe Lys Ala Ala Asp Ile Asp Trp Met Gln Val Ile Ala Glu Gln Thr
                325                 330                 335
Lys Gly Ser Thr Gln Ala Thr Ser Leu Lys Ser Gln Leu Glu Gln Ala
            340                 345                 350
Pro Glu Tyr Val Lys Ala Phe Cys Asp Glu Ile Leu Lys Phe Pro Asp
        355                 360                 365
Cys Tyr Lys Ser Ala Asp Val Ala Ser Pro Glu Ser Pro Lys Ala Gly
    370                 375                 380
Pro Ser Ser Val Ile Asp Val Ala Leu Lys Arg Leu Gln Ala Gly Arg
385                 390                 395                 400
Asn Arg Leu Phe Ser Thr Ile Asp Ala Lys Gly Thr Asn Glu Leu Lys
                405                 410                 415
Lys Gly Glu Ala Ile Leu Glu Ser Ala Ile Asn Ala Ala Arg Ser Val
            420                 425                 430
Met Thr Ala Glu Gln Lys Ser Ala Leu Leu Ser Ser Asn Val Lys Ser
        435                 440                 445
Ala Thr Phe Lys Val Phe Ser Glu Leu Pro Cys Met Glu Gly Phe Ala
    450                 455                 460
Glu Gln Asn Gly Lys Ala Ala Phe Asn Ala Leu Arg Leu Ala Phe Tyr
465                 470                 475                 480
Ser Ser Ile Gln Ser Gly Asp Thr Ala Gln Gln Asp Ile Ala Arg Phe
                485                 490                 495
Met Lys Glu Asn Leu Ala Thr Gly Phe Ser Gly Tyr Ser Tyr Leu Gly
            500                 505                 510
Leu Thr Ser Arg Val Ala Gln Leu Glu Ala Gln Leu Ala Ala Leu Thr
        515                 520                 525
Thr Lys
    530

<210> SEQ ID NO 36
<211> LENGTH: 288
<212> TYPE: PRT
<213> ORGANISM: Yersinia pestis

<400> SEQUENCE: 36

Met Ile Gly Pro Ile Ser Gln Ile Asn Ile Ser Gly Gly Leu Ser Glu
1               5                   10                  15
Lys Glu Thr Ser Ser Leu Ile Ser Asn Glu Leu Lys Asn Ile Ile
            20                  25                  30
Thr Gln Leu Glu Thr Asp Ile Ser Asp Gly Ser Trp Phe His Lys Asn
        35                  40                  45
Tyr Ser Arg Met Asp Val Glu Val Met Pro Ala Leu Val Ile Gln Ala
    50                  55                  60
Asn Asn Lys Tyr Pro Glu Met Asn Leu Asn Leu Val Thr Ser Pro Leu
65                  70                  75                  80
Asp Leu Ser Ile Glu Ile Lys Asn Val Ile Glu Asn Gly Val Arg Ser
                85                  90                  95
Ser Arg Phe Ile Ile Asn Met Gly Glu Gly Gly Ile His Phe Ser Val
            100                 105                 110
Ile Asp Tyr Lys His Ile Asn Gly Lys Thr Ser Leu Ile Leu Phe Glu
        115                 120                 125
Pro Ala Asn Phe Asn Ser Met Gly Pro Ala Met Leu Ala Ile Arg Thr
    130                 135                 140
Lys Thr Ala Ile Glu Arg Tyr Gln Leu Pro Asp Cys His Phe Ser Met
```

```
145                 150                 155                 160
Val Glu Met Asp Ile Gln Arg Ser Ser Glu Cys Gly Ile Phe Ser
                165                 170                 175

Phe Ala Leu Ala Lys Lys Leu Tyr Ile Glu Arg Asp Ser Leu Leu Lys
                180                 185                 190

Ile His Glu Asp Asn Ile Lys Gly Ile Leu Ser Asp Gly Glu Asn Pro
                195                 200                 205

Leu Pro His Asp Lys Leu Asp Pro Tyr Leu Pro Val Thr Phe Tyr Lys
            210                 215                 220

His Thr Gln Gly Lys Lys Arg Leu Asn Glu Tyr Leu Asn Thr Asn Pro
225                 230                 235                 240

Gln Gly Val Gly Thr Val Asn Lys Lys Asn Glu Thr Ile Val Asn
                245                 250                 255

Arg Phe Asp Asn Asn Lys Ser Ile Val Asp Gly Lys Glu Leu Ser Val
                260                 265                 270

Ser Val His Lys Lys Arg Ile Ala Glu Tyr Lys Thr Leu Leu Lys Val
                275                 280                 285
```

<210> SEQ ID NO 37
<211> LENGTH: 579
<212> TYPE: PRT
<213> ORGANISM: Unknown
<220> FEATURE:
<223> OTHER INFORMATION: Description of Unknown:
      AvrPtoB sequence

<400> SEQUENCE: 37

```
Met Ala Gly Ile Asn Gly Ala Gly Pro Ser Gly Ala Tyr Phe Val Gly
1               5                   10                  15

His Thr Asp Pro Glu Pro Ala Ser Gly Gly Ala His Gly Ser Ser Ser
                20                  25                  30

Gly Ala Ser Ser Asn Ser Pro Arg Leu Pro Ala Pro Pro Asp Ala
            35                  40                  45

Pro Ala Ser Gln Ala Arg Asp Arg Arg Glu Met Leu Leu Arg Ala Arg
50                  55                  60

Pro Leu Ser Arg Gln Thr Arg Glu Trp Val Ala Gln Gly Met Pro Pro
65                  70                  75                  80

Thr Ala Glu Ala Gly Val Pro Ile Arg Pro Gln Glu Ser Ala Glu Ala
                85                  90                  95

Ala Ala Pro Gln Ala Arg Ala Glu Glu Arg His Thr Pro Glu Ala Asp
                100                 105                 110

Ala Ala Ala Ser His Val Arg Thr Glu Gly Gly Arg Thr Pro Gln Ala
            115                 120                 125

Leu Ala Gly Thr Ser Pro Arg His Thr Gly Ala Val Pro His Ala Asn
            130                 135                 140

Arg Ile Val Gln Gln Leu Val Asp Ala Gly Ala Asp Leu Ala Gly Ile
145                 150                 155                 160

Asn Thr Met Ile Asp Asn Ala Met Arg Arg His Ala Ile Ala Leu Pro
                165                 170                 175

Ser Arg Thr Val Gln Ser Ile Leu Ile Glu His Phe Pro His Leu Leu
                180                 185                 190

Ala Gly Glu Leu Ile Ser Gly Ser Glu Leu Ala Thr Ala Phe Arg Ala
            195                 200                 205

Ala Leu Arg Arg Glu Val Arg Gln Gln Glu Ala Ser Ala Pro Pro Arg
    210                 215                 220
```

Thr Ala Ala Arg Ser Ser Val Arg Thr Pro Glu Arg Ser Thr Val Pro
225                 230                 235                 240

Pro Thr Ser Thr Glu Ser Ser Gly Ser Asn Gln Arg Thr Leu Leu
            245                 250                 255

Gly Arg Phe Ala Gly Leu Met Thr Pro Asn Gln Arg Pro Ser Ser
        260                 265                 270

Ala Ser Asn Ala Ser Ala Ser Gln Arg Pro Val Asp Arg Ser Pro Pro
    275                 280                 285

Arg Val Asn Gln Val Pro Thr Gly Ala Asn Arg Val Met Arg Asn
290                 295                 300

His Gly Asn Asn Glu Ala Asp Ala Ala Leu Gln Gly Leu Ala Gln Gln
305                 310                 315                 320

Gly Val Asp Met Glu Asp Leu Arg Ala Ala Leu Glu Arg His Ile Leu
                325                 330                 335

His Arg Arg Pro Ile Pro Met Asp Ile Ala Tyr Ala Leu Gln Gly Val
            340                 345                 350

Gly Ile Ala Pro Ser Ile Asp Thr Gly Glu Ser Leu Met Glu Asn Pro
        355                 360                 365

Leu Met Asn Leu Ser Val Ala Leu His Arg Ala Leu Gly Pro Arg Pro
370                 375                 380

Ala Arg Ala Gln Ala Pro Arg Pro Ala Val Pro Val Ala Pro Ala Thr
385                 390                 395                 400

Val Ser Arg Arg Pro Asp Ser Ala Arg Ala Thr Arg Leu Gln Val Ile
                405                 410                 415

Pro Ala Arg Glu Asp Tyr Glu Asn Asn Val Ala Tyr Gly Val Arg Leu
            420                 425                 430

Leu Ser Leu Asn Pro Gly Ala Gly Val Arg Glu Thr Val Ala Ala Phe
        435                 440                 445

Val Asn Asn Arg Tyr Glu Arg Gln Ala Val Val Ala Asp Ile Arg Ala
450                 455                 460

Ala Leu Asn Leu Ser Lys Gln Phe Asn Lys Leu Arg Thr Val Ser Lys
465                 470                 475                 480

Ala Asp Ala Ala Ser Asn Lys Pro Gly Phe Lys Asp Leu Ala Asp His
                485                 490                 495

Pro Asp Asp Ala Thr Gln Cys Leu Phe Gly Glu Leu Ser Leu Thr
            500                 505                 510

Ser Ser Val Gln Gln Val Ile Gly Leu Ala Gly Lys Ala Thr Asp Met
        515                 520                 525

Ser Glu Ser Tyr Ser Arg Glu Ala Asn Lys Asp Leu Val Phe Met Asp
530                 535                 540

Met Lys Lys Leu Ala Gln Phe Leu Ala Gly Lys Pro Glu His Pro Met
545                 550                 555                 560

Thr Arg Glu Thr Leu Asn Ala Glu Asn Ile Ala Lys Tyr Ala Phe Arg
                565                 570                 575

Ile Val Pro

<210> SEQ ID NO 38
<211> LENGTH: 1116
<212> TYPE: PRT
<213> ORGANISM: Unknown
<220> FEATURE:
<223> OTHER INFORMATION: Description of Unknown:
      SdbA sequence

<400> SEQUENCE: 38

-continued

```
Met His Lys Lys Tyr Asn Tyr Tyr Ser Leu Glu Lys Glu Lys Lys Thr
1               5                   10                  15

Phe Trp Gln His Ile Leu Asp Ile Leu Lys Ala Pro Phe Arg Leu Pro
            20                  25                  30

Gly Trp Val Val Ser Phe Phe Leu Ala Arg Asn Ile Thr His Val Ala
            35                  40                  45

Leu Asn Pro Asn Asn Ile Pro Gln Gln Arg Leu Ile His Leu Thr Lys
50                  55                  60

Thr Ser Asn Arg Pro Glu Asp Asp Ile Val Ile Asn Phe Lys Lys
65                  70                  75                  80

Arg Pro Pro His Lys Trp Phe Asn Asp Thr Leu Ile Lys Ile Ala Asn
                85                  90                  95

Thr Ile Ala Ala Leu Pro Phe Val Thr Pro Arg Leu Arg Thr Arg Leu
            100                 105                 110

His Tyr Asp Asn Glu Asn Asp Ile Asn His Val Asn Lys Leu Leu Ala
            115                 120                 125

Glu Ile Asp Ala Leu Val Gln Gly Lys Ser Lys Gln Lys Tyr Cys Lys
        130                 135                 140

Gly Arg Ala Phe Asp Trp Ser Lys Ile His Leu Lys Gly Leu Glu Phe
145                 150                 155                 160

Leu Asp Pro Lys Met Arg Gly Tyr Val Tyr Glu Gln Leu His Glu Lys
                165                 170                 175

Tyr Gly Tyr Val Ser Tyr Thr Thr Lys Arg Lys Pro Asn Ile Glu Phe
            180                 185                 190

Phe Thr Leu Lys Thr Pro Asp Gly Ser Glu Leu Asp Ser Val Gln Val
        195                 200                 205

Thr Gly Glu Asp Glu Lys Lys Pro Met Gly Glu Arg Lys Phe Ile
    210                 215                 220

Ile Thr Cys Ile Ala Arg Asp Gln Asn Phe Ile Asn Trp Ile Lys Asp
225                 230                 235                 240

Leu Asn Tyr Thr Ala Lys Asn Leu Gly Ala Thr Ala Ile Ser Phe Asn
                245                 250                 255

Tyr Arg Gly Val Asp Tyr Ser Arg Gly Leu Val Trp Thr Glu Asn Asn
            260                 265                 270

Leu Val Asp Asp Ile Leu Ala Gln Val Gln Arg Leu Ile Ser Leu Gly
        275                 280                 285

Ala Asp Pro Lys Asn Ile Cys Leu Asp Gly Met Cys Ile Gly Gly Ala
        290                 295                 300

Val Ala Thr Ile Ala Ala Ala Lys Leu His Glu Lys Gly Met Lys Val
305                 310                 315                 320

Lys Leu Asn Asn Glu Arg Ser Phe Thr Ser Leu Ser Ser Leu Val Phe
                325                 330                 335

Gly Phe Ile Val Pro Glu Leu Gln Thr Ala Asn Trp Trp Ser Pro Leu
            340                 345                 350

Thr Tyr Gly Arg Phe Leu Leu Ala Gly Val Val Tyr Ala Leu Leu Thr
        355                 360                 365

Pro Leu Ile Trp Leu Ala Gly Trp Pro Val Asp Val Thr Lys Ala Trp
    370                 375                 380

Asn Arg Ile Pro Ala Gln Asp Lys Met Tyr Ser Val Val Arg Asp Lys
385                 390                 395                 400

Asp Asn Gly Leu Tyr Asp Gly Val Ile His Asp His Phe Cys Ser Ile
                405                 410                 415

Ala Ser Leu Val Asp Ser Gln Ile Asn Ser Ile Leu Tyr Lys Leu Ser
```

```
                420             425             430
Thr Asp Gln Pro Leu Thr Glu Glu Lys Gln Ile Leu Cys Asp Asp
                435             440             445
Gln Phe Ser His His Phe Lys Pro Ser Gln Ser Val Leu Lys Asn Pro
    450             455             460
Lys Tyr Lys Gly Pro His Phe Ile Ser Arg Gln Asp Leu Val Ala Glu
465             470             475             480
Leu Gly His Arg Glu Glu Tyr Thr Asn His Asp Tyr Phe Leu Asp Arg
                485             490             495
Leu Arg Glu Lys Phe Gln Leu Asp Arg Ala Thr Arg Pro Val Ala Leu
                500             505             510
Ala Glu Asp Gly Glu Lys Asp Ile Asp Gly Ile Ser Ser Gln Leu Ser
                515             520             525
Asn Asn Lys Glu Arg Pro Leu Ile Ile Ala Ser Ser Gly Gly Thr Gly
                530             535             540
His Ile Ser Ala Thr His Gly Ile Ile Asn Asp Leu Gln Ser Lys Thr
545             550             555             560
Asp Asn Val Val Ile Thr Gln His His Ala Glu Leu Tyr Lys Asn Lys
                565             570             575
Pro Phe Ser Ile Thr Ser Val Leu Ile Arg Ile Gly Val Trp Phe Thr
                580             585             590
Ser Leu Pro Ile Leu Glu Asp Ile Leu Lys Gly Val Met Arg Phe Ile
                595             600             605
Gly Tyr Pro Val Leu Pro Ser Ser Ser Ile Phe Trp Asp Gln Met Ser
                610             615             620
Lys Ile Gln Gln Ser Glu Thr Lys Lys Glu Asn Gly Ile Glu Thr Gly
625             630             635             640
Arg Thr Arg Pro Tyr Val Asp Met Leu Leu Asp Ile Tyr Pro Glu Gly
                645             650             655
Tyr Glu Tyr Thr Ala Phe Asn Asn Ala Thr His Leu Thr Ser Ser Ile
                660             665             670
Glu Asp Ile Gln Thr Met Ile Ser Phe Lys Gly His Val Glu Glu Asp
                675             680             685
Asn Arg Asn Ile Val Tyr Gln Asn Ile Leu Gln Arg Leu Met His Ala
                690             695             700
Ala Lys Gln Asn Thr Pro Tyr Thr Arg Leu Ile Ser Thr Gln Ala Leu
705             710             715             720
Ser Leu Gly Ala Ile Cys Asp Ala Val Lys Tyr Tyr Asn Thr Val Phe
                725             730             735
Leu Pro Val Tyr Asn Ala Glu Arg Gly Thr Ser Tyr Gln Pro Ile Ala
                740             745             750
Ile Asp Gln Tyr Met Thr Asp Leu Pro Ser Leu Gly Cys Ile His Phe
                755             760             765
Met Asn Asn Leu Glu Glu Leu Thr Ser Glu Gln Arg Gln Leu Met Glu
                770             775             780
Ile His Ala Val Asn Met Ser Glu Pro Phe Lys Glu Ala His Phe Gly
785             790             795             800
Lys Glu Gln Gly Phe Lys Ala Val His Asn Ile Asp Pro Arg Asn Asn
                805             810             815
Pro Met Ile Arg Asn Ala Phe Lys Asp Pro Ser Leu Thr Lys Tyr Leu
                820             825             830
Asp Lys Thr Gln Ser Phe Asp Leu His Phe Asn Val Tyr Lys Lys Glu
                835             840             845
```

-continued

```
Lys Gln Asn Ala Leu Pro Val Leu Asn Gly Lys Glu Lys Ile Thr Ile
        850                 855                 860

Lys Pro His Ala Lys Ile Ala Ser Ile Met Ile Gly Ser Leu Ala Ala
865                 870                 875                 880

Asn Ala Ser Ala Asp Tyr Ala Lys Tyr Leu Leu Asn Gln Gly Tyr Glu
            885                 890                 895

His Ile Phe Leu Phe Gly Gly Leu Asn Asp Ser Ile Ala Ala Arg Ile
            900                 905                 910

Asp Gln Ile Ile Asn Ser Tyr Pro Ala Pro Thr Arg Asp Glu Ile Arg
        915                 920                 925

Lys Lys Ile Ile Leu Leu Gly Asn Gln Ser Asp Val Glu Met Ala Pro
        930                 935                 940

Ile Met Thr Arg Ser Asn Cys Val Val Ile Arg Gly Gly Leu Ser
945                 950                 955                 960

Val Met Glu Gln Met Ala Met Pro Ile Met Asp Asp Lys Ile Val Leu
            965                 970                 975

Leu His His Glu Asp Asn Glu Gly Pro Leu Thr Ser Gly Leu Ser
            980                 985                 990

Trp Glu Asp Gly Asn Ser Asp Lys Leu Ile Glu Tyr Leu Ser Glu Lys
        995                 1000                1005

Gly Ala Tyr Ala Lys Lys Thr Ser Pro Gly Leu Cys Ser Gly His
    1010                1015                1020

Leu His Glu Ala Glu Lys Ser Phe Glu Lys Lys Tyr His Gly Gln
    1025                1030                1035

Leu Lys Ser Thr Glu Thr Lys Lys Lys Val Asp Leu Thr Ile Pro
    1040                1045                1050

Gln Gln Glu Thr Tyr Ser Leu Lys Lys Glu Trp Asp Arg Lys Thr
    1055                1060                1065

Gly Tyr Thr Glu Ser Gly His Ile Leu Ser His Gln His Arg Phe
    1070                1075                1080

Phe Asn Thr Ile Pro Glu Val Arg Glu Pro Phe Cys Ser Lys Glu
    1085                1090                1095

Asp Leu His His Asn Glu Leu Ser Ser Gln Ser Leu Val Ser Val
    1100                1105                1110

Ser Ala Gly
    1115

<210> SEQ ID NO 39
<211> LENGTH: 965
<212> TYPE: PRT
<213> ORGANISM: Unknown
<220> FEATURE:
<223> OTHER INFORMATION: Description of Unknown:
      SidG sequence

<400> SEQUENCE: 39

Met Ser Arg Ser Lys Asp Glu Val Leu Glu Ala Asn Asp Ser Leu Phe
1               5                   10                  15

Gly Ile Thr Val Gln Thr Trp Gly Thr Asn Asp Arg Pro Ser Asn Gly
            20                  25                  30

Met Met Asn Phe Ala Asp Gln Phe Phe Gly Gly Asp Val Gly His
        35                  40                  45

Ala Ser Ile Asn Met Lys Leu Pro Val Thr Asp Lys Thr Lys Gln Trp
50                  55                  60

Ile Glu Lys Tyr Cys Tyr Ser Gln Thr Tyr Asp Gln Phe Lys Lys Val
```

```
                65                  70                  75                  80
Lys Gly Asn Glu Asp Lys Thr Tyr Glu Glu Tyr Leu Lys Thr Ala Lys
                    85                  90                  95

Arg Leu Ile Pro Val Glu Leu Lys Thr Gln Val Thr Arg Lys Ala Gln
                100                 105                 110

Tyr Asp Ser Asn Gly Asn Leu Val Thr Thr His Glu Lys Ala Tyr Glu
                115                 120                 125

Gln Ile Tyr Phe Asp Ile Asp Trp Ser Trp Trp Pro Gly Arg Leu Gln
        130                 135                 140

Asn Thr Glu Asp Asp Met Val Trp Glu Arg Glu Gly Lys His Phe Glu
145                 150                 155                 160

Tyr Asp Glu Lys Trp Lys Glu Tyr Leu Gln Pro Glu Gln Arg Val His
                165                 170                 175

Arg Gly Lys Leu Gly Ser Arg Lys Met Asp Tyr Ala Pro Thr Ser Ile
                180                 185                 190

Ile His Gln Arg Asp Ile Pro Thr Ser Glu Leu Glu Lys Ile Thr Arg
                195                 200                 205

Asp His Lys Ile His Thr Ile Glu Glu Lys Leu Asn Val Val Lys Leu
        210                 215                 220

Leu Gln Ser Lys Ile Asp Glu Met Pro His Thr Lys Met Ser Pro Ser
225                 230                 235                 240

Met Glu Leu Met Phe Lys Asn Leu Gly Ile Asn Val Glu Lys Leu Leu
                    245                 250                 255

Asp Glu Thr Lys Asp Asn Gly Val Asp Pro Thr Asn Leu Glu Ala Met
                260                 265                 270

Arg Glu Tyr Leu Thr Asn Arg Leu Thr Glu Arg Lys Leu Glu Leu Glu
            275                 280                 285

Thr Glu Leu Ser Glu Ala Lys Lys Glu Val Asp Ser Thr Gln Val Lys
        290                 295                 300

Asn Lys Val Glu Asp Val Tyr Tyr Asp Phe Glu Tyr Lys Leu Asn Gln
305                 310                 315                 320

Val Arg Lys Lys Met Glu Glu Val Asn Ser Gln Leu Glu Lys Met Asp
                325                 330                 335

Ser Leu Leu His Lys Leu Glu Gly Asn Thr Ser Gly Pro Ile Pro Tyr
                340                 345                 350

Thr Ala Glu Ile Asp Glu Leu Met Ser Val Leu Pro Phe Leu Lys Glu
            355                 360                 365

Glu Leu Glu Leu Glu Asn Gly Thr Leu Ser Pro Lys Ser Ile Glu Asn
        370                 375                 380

Leu Ile Asp His Ile Asp Glu Leu Lys Asn Glu Leu Ala Ser Lys Gln
385                 390                 395                 400

Glu Lys Lys Asn Glu Arg Asn Leu Asn Leu Ile Lys Lys Tyr Glu Glu
                405                 410                 415

Leu Cys Glu Gln Tyr Lys Asp Asp Glu Glu Gly Leu Glu Glu Ala Leu
                420                 425                 430

Trp Glu Glu Gly Ile Asp Val Glu Glu Val Asn Ser Ala Lys Lys Asp
            435                 440                 445

Ile Ser Lys Pro Ala Pro Glu Ile Gln Lys Leu Thr Asp Leu Gln Glu
        450                 455                 460

Gln Leu Arg Asn His Lys Glu Ser Gly Val Lys Leu Ser Ser Glu Leu
465                 470                 475                 480

Glu Glu Thr Leu Asn Ser Ser Val Lys Met Trp Lys Thr Lys Ile Asp
                485                 490                 495
```

```
Ser Pro Cys Gln Val Ile Ser Glu Ser Ser Lys Ala Leu Val Ser
            500                 505                 510

Lys Ile Asn Ser Thr Arg Pro Glu Leu Val Lys Glu Lys Glu Gln Leu
            515                 520                 525

Pro Glu Gln Glu Glu Ser Leu Ser Lys Glu Ala Lys Lys Ala Gln Glu
            530                 535                 540

Glu Leu Ile Lys Ile Gln Glu Phe Ser Gln Phe Tyr Ser Glu Asn Ser
545                 550                 555                 560

Ser Ala Tyr Met Val Ile Gly Leu Pro Pro His His Gln Val Ser Leu
                565                 570                 575

Pro Leu Ala Val Asn Gly Lys Arg Gly Leu His Pro Glu Ala Met Leu
            580                 585                 590

Lys Lys Met His Glu Leu Val Ala Gly Pro Glu Lys Lys Glu Phe Asn
            595                 600                 605

Leu His Thr Asn Asn Cys Ser Leu Thr Ser Ile Glu Val Leu Ser Ala
            610                 615                 620

Gly Ala Gln His Asp Pro Leu Leu His Ser Ile Met Gly Thr Arg Ala
625                 630                 635                 640

Leu Gly Phe Phe Gly Thr Pro Gln Gln Val Leu Glu Asn Ala Lys Leu
                645                 650                 655

Thr Ser Lys Thr Ile Asn Glu Gly Lys Lys Ser Asn Ile Phe Thr Pro
            660                 665                 670

Leu Val Thr Ala Ser Pro Leu Asp Arg Ala Leu Gly Tyr Ala Met Ser
            675                 680                 685

Ile Tyr Met Asp Pro Glu Ala Ser Lys Ala Lys Gln Asn Ala Gly Leu
            690                 695                 700

Ala Leu Gly Val Leu Val Gly Leu Ala Lys Thr Pro Gly Ile Ile Ile
705                 710                 715                 720

Gly Ser Leu Leu Asn Pro Lys Gln Gly Phe Asn Asp Ile Leu Asn Thr
                725                 730                 735

Leu Asn Leu Val Tyr Ser Arg Asn Ser Thr Gly Leu Lys Val Gly Leu
            740                 745                 750

Thr Leu Met Ala Leu Pro Ala Met Ile Val Leu Ala Pro Leu Ala Ala
            755                 760                 765

Ile Gln Lys Gly Val Glu Val Ile Ala Glu Thr Ile Ala Lys Pro Phe
            770                 775                 780

Lys Leu Ile Ala Asn Leu Phe Lys Gln Lys Pro Glu Ser Thr Asp Glu
785                 790                 795                 800

Ile Thr Val Ser Val Gly Ser Lys Val Ala Glu Lys Glu Gly Ser
                805                 810                 815

Tyr Ser Asn Thr Ala Leu Ala Gly Leu Val Asn Ser Lys Ile Lys Ser
                820                 825                 830

Lys Ile Asp Glu Asn Thr Ile Thr Val Glu Phe Gln Lys Ser Pro Gln
            835                 840                 845

Lys Met Ile Glu Glu Phe Glu Ser Gln Leu Lys Glu Asn Pro Gly Lys
            850                 855                 860

Val Val Leu Ser Glu Lys Ala His Asn Ala Val Leu Lys Phe Val
865                 870                 875                 880

Ser Lys Ser Asp Asp Glu Ala Leu Lys Gln Lys Phe Tyr Asp Cys Cys
            885                 890                 895

Asn Gln Ser Val Ala Arg Ser Gln Lys Phe Ala Pro Lys Thr Arg Asp
            900                 905                 910
```

```
Glu Ile Asp Glu Leu Val Glu Val Thr Ser Thr Asp Lys Thr Glu
            915                 920                 925

Leu Thr Thr Ser Pro Arg Gln Glu Pro Ser Met Ser Ser Thr Ile Asp
    930                 935                 940

Glu Glu Glu Asn Ile Asp Ser Glu His Gln Ile Glu Thr Gly Thr Glu
945                 950                 955                 960

Ser Thr Met Arg Ile
                965

<210> SEQ ID NO 40
<211> LENGTH: 665
<212> TYPE: PRT
<213> ORGANISM: Unknown
<220> FEATURE:
<223> OTHER INFORMATION: Description of Unknown:
      VpdA sequence

<400> SEQUENCE: 40

Met Lys Thr Lys Gln Glu Val Ser Gln Gln Asp Lys Leu Lys Asp Ser
1               5                   10                  15

Lys Ser Ser Thr Pro Leu Gln Thr Lys Glu Thr Trp Phe Ile Ser Asp
                20                  25                  30

Ala Leu Asn Ile Thr Phe Asp Pro Tyr Asp Phe Ser Ile Ser Val Thr
            35                  40                  45

Glu Gln Ala Pro Met Pro Tyr Arg Ile Val Phe Ser Gly Gly Gly Ser
    50                  55                  60

Arg Ile Leu Ala His Ile Gly Ala Leu Asp Glu Leu Thr Arg His Gly
65              70                  75                  80

Leu Lys Phe Thr Glu Phe Ser Gly Ser Ser Ala Gly Ala Met Val Ala
                85                  90                  95

Ala Phe Ala Tyr Leu Gly Tyr Asn Cys Ser Glu Ile Lys Gln Ile Ile
            100                 105                 110

Ser Trp Phe Asn Glu Asp Lys Leu Leu Asp Ser Pro Leu Ile Phe Asn
        115                 120                 125

Phe Asn Asn Ile Lys Gln Ile Phe Asn Lys Gly Gly Leu Ser Ser Ala
    130                 135                 140

Lys Leu Met Arg Gln Ala Ala Asn Tyr Val Ile Leu Lys Lys Val Met
145                 150                 155                 160

Asp Ile Ile Ser Asp Glu Lys Phe Lys Thr Arg Phe Ala Lys Phe Gln
                165                 170                 175

Asn Phe Leu Glu Glu Asn Ile Tyr Arg Cys Pro Glu Asn Ile Thr Phe
            180                 185                 190

Gln Thr Leu Ala Arg Ile Lys Glu Ile Cys Pro Glu Cys Glu Leu Gly
        195                 200                 205

Glu Lys Leu Phe Ile Thr Gly Thr Asn Leu Ser Thr Gln Lys His Glu
    210                 215                 220

Val Phe Ser Ile Asp Thr Thr Pro Ser Met Ala Leu Ala Asp Ala Ile
225                 230                 235                 240

Ile Ile Ser Ala Asn Leu Pro Ile Ala Phe Glu Arg Ile Cys Tyr Gln
                245                 250                 255

Gly Asn Val Tyr Ser Asp Gly Gly Ile Ser Asn Asn Leu Pro Ala His
            260                 265                 270

Cys Phe Ser Glu Lys Gly His Lys Thr Thr Phe Leu Lys His Lys Asp
        275                 280                 285

Asp Val Asp Phe Ser Val Leu Ala Leu Gln Phe Asp Asn Gly Leu Glu
    290                 295                 300
```

Glu Asn Ala Leu Tyr Ser Gln Asn Pro Ile Pro Lys Trp Ser Trp Leu
305                 310                 315                 320

Ser Asn Thr Phe Tyr Ser Leu Ile Thr Gly His Pro Asn Val Thr Glu
                325                 330                 335

Asn Trp Tyr Glu Asp Leu Gln Ile Leu Arg Arg His Ala His Gln Ser
            340                 345                 350

Ile Leu Ile Lys Thr Pro Thr Ile Ala Leu Thr Asn Leu Thr Ile Ser
        355                 360                 365

Gln Asp Thr Lys Lys Ala Leu Val Glu Ser Gly Arg Thr Ala Ala Lys
370                 375                 380

Thr Tyr Leu Glu Leu His Glu Phe Tyr Thr Asp Tyr Gly Asn Ile
385                 390                 395                 400

Arg His Asn Glu Cys Leu His Glu Lys Phe Gln Lys Pro Glu Glu Leu
                405                 410                 415

Leu Asp Tyr Cys Val Leu His Ser His Phe Glu Leu Leu Lys Lys Ile
            420                 425                 430

Lys Gln Ala Ile Ser Cys Ser Gln Tyr Leu Glu Lys Gly Tyr Lys His
        435                 440                 445

Tyr Leu Cys Glu Leu Cys Asp Asn Leu Leu Pro Pro Gln Leu Lys Cys
450                 455                 460

Pro Asn Glu Gly Ser Gly Thr Glu Gln Pro Glu Ile Lys Leu Glu Lys
465                 470                 475                 480

Asp Thr Ile Ile Cys Glu Lys Asn Asn Asn Ser Gly Leu Thr Phe Ser
                485                 490                 495

Met Thr Phe Phe Gly Val Pro Ser Pro Leu Val Lys Thr Leu Asn Gln
            500                 505                 510

Asp Ser Pro Glu Leu Lys Ile Lys Leu Phe Thr Gly Leu Tyr Pro Ile
        515                 520                 525

Leu Ile Gln Asn Trp Gln Asn Leu Cys Pro Val Ser Gly Ile Ser Gly
530                 535                 540

Ile Leu Asn Ser Ile Arg Met Ser Phe Val Glu Ile Ser Ser Thr Asp
545                 550                 555                 560

Thr Cys Ile Lys Thr Leu Ile Asp Lys Leu Asn Glu Ile Glu Ile Gly
                565                 570                 575

His Phe Leu Ile Phe Val Phe Lys Ala Ala Leu Lys Asn Tyr Asp Lys
            580                 585                 590

His Asp Phe Ile Leu Leu Lys Asn Leu Lys His Leu His His Ser
        595                 600                 605

Ile Glu Leu Ile Arg Asn Lys Pro Phe His Ser Asp Asp Arg Phe Tyr
610                 615                 620

Gly Gln Trp Ser Phe Glu Gly His Asp Pro Lys Arg Ile Leu Glu Phe
625                 630                 635                 640

Ile Lys Ser Asp Asp Ile Ser Gly Leu Met Thr Ile Leu Glu Asp Lys
                645                 650                 655

Lys Ala Leu Pro Asn Asn Lys Pro Asn
            660                 665

<210> SEQ ID NO 41
<211> LENGTH: 246
<212> TYPE: PRT
<213> ORGANISM: Legionella pneumophila

<400> SEQUENCE: 41

Met Val Ser Leu Glu His Ile Gln Lys Leu Ile Ser Glu Cys Arg Lys

```
1               5                   10                  15
Leu Gly Lys Asp Gly Leu Asp Asn Gly Thr Asn Gly Leu Ile Pro Glu
            20                  25                  30

Leu Glu Ile Asp Val Val Pro Pro Ser Ala Phe Leu Gly Val Gly Asn
        35                  40                  45

Asn Pro Ala Ile Phe Val Asn Ser Lys Thr Tyr Lys Leu Met Arg Thr
    50                  55                  60

Thr His Glu Lys Trp Val Glu Asn Lys Thr Ile Val Phe Lys Ser Tyr
65                  70                  75                  80

Leu Leu Ser Gln Pro Ala Ile Lys Ile Ile Gly Ala Ile Val His Glu
                85                  90                  95

Thr Gly His Ala Phe Asn Val Ala Ala Lys Ile Pro Asn Thr Glu Ala
            100                 105                 110

Asn Ala Cys Ile Phe Glu Ile Glu Val Leu Met Arg Leu Phe Gln Val
        115                 120                 125

Lys Ser Pro Leu Leu Leu Gly Cys Thr Glu Leu Asp Met Gln Ser Tyr
    130                 135                 140

Phe Lys Ser Arg Leu Thr Asp Tyr Asn Lys Cys Val Lys Asp Cys Gln
145                 150                 155                 160

Cys Leu Ala Glu Met Val Glu Phe Ile Thr His Gln Phe Lys Leu Asp
                165                 170                 175

Glu Val Ser Ile Ser Glu Lys Glu Asn Gln Ile Pro Leu Leu Ser Ile
            180                 185                 190

Ser Asn Lys Trp Pro Gly Leu Phe Ala Lys Lys Gln Ile Ala Pro Asp
        195                 200                 205

Met Asp Lys Leu Leu Thr Ser Pro Val Thr Ile Thr Pro Glu Val Lys
    210                 215                 220

Ile Leu Phe Tyr Gln Leu Val Lys Glu His Phe His Ser Pro Glu Thr
225                 230                 235                 240

Glu Ile Lys Leu Asp Ile
                245
```

<210> SEQ ID NO 42
<211> LENGTH: 644
<212> TYPE: PRT
<213> ORGANISM: Legionella pneumophila

<400> SEQUENCE: 42

```
Met Tyr Lys Ile Tyr Ser Tyr Leu Gly Trp Arg Ile Asp Met Lys Thr
1               5                   10                  15

Glu Asn Leu Pro Gln Ala Gly Gln Glu Ala Gln Ile Asp Lys Lys Ile
            20                  25                  30

His Phe Ile Trp Val Gly His Ile Met Pro Gln Lys Asn Ile Gln Val
        35                  40                  45

Val Ser Glu Trp Ala Glu Lys Asn Pro Gly Tyr Glu Thr Ile Ile Trp
    50                  55                  60

Val Asp Lys Lys Ile Ala Pro Ala Lys Glu Leu Asp Leu Phe Ile Leu
65                  70                  75                  80

Asp Met Lys Ser Lys Gly Ile Thr Val Lys Asp Ile Asn Glu Glu Gly
                85                  90                  95

Val Cys Arg Asp Ser Ile Arg His Glu Leu Asp Gln Glu Ser Pro Asn
            100                 105                 110

Tyr Gly Met Val Ser Asp Met Leu Arg Leu Asn Ile Leu Ala Ala Glu
        115                 120                 125
```

-continued

```
Gly Gly Ile Tyr Leu Asp Ser Asp Ile Leu Cys Ser Ala Pro Phe Pro
130                 135                 140

Asp Glu Ile Tyr Ala Pro Phe Gly Phe Leu Leu Ser Pro Trp Ser Gln
145                 150                 155                 160

Gly Ala Asn Asn Thr Leu Cys Asn Asp Ile Ile Leu Cys Ser Lys Gly
                165                 170                 175

Asn Gln Ile Ile Gln Gln Leu Ala Asp Ala Ile Glu Gln Ser Tyr Ile
            180                 185                 190

Ala Arg Asp Ser Phe Glu Phe Thr His Glu Tyr Ala Ser Met Lys Glu
        195                 200                 205

Thr Lys Gly Glu Arg Ile Ala Lys Thr Leu Gly Val Thr Gly Pro Gly
210                 215                 220

Phe Leu Phe His Gln Leu Lys Lys Met Gly Ile Leu Asn Asp Lys Ser
225                 230                 235                 240

Glu Met Glu Ala Ile His Trp Glu Leu Gln Asp Gln Arg Tyr Leu Ile
                245                 250                 255

Asp Gly Ser Val Lys Glu Pro Asp Tyr Phe Tyr Val Pro Gln Asn Asn
            260                 265                 270

Thr Asn Asp Ala Ser Trp Val Pro Ser Ile Lys Arg Pro Gly Ile Glu
        275                 280                 285

Asn Met Ser Phe Gln Glu Arg Leu Glu Asn Ala Val Gln Leu Ile Ala
290                 295                 300

Phe Asp Ile Gln Lys Thr Gly Leu Phe Asn Leu Asp His Tyr Ala Asn
305                 310                 315                 320

Glu Leu Lys Val Lys Gln Asn Ser Trp Cys Ile Ala Ala Glu Thr Ser
                325                 330                 335

Pro Glu Leu Lys Pro Asp Ser Tyr Leu Leu Ile Arg Pro Arg Asp Lys
            340                 345                 350

Thr Gly Glu Trp Thr Leu Tyr Tyr Val Asp Glu Asp Lys Lys Leu Asn
        355                 360                 365

Pro Val Thr Leu Pro Val Ile Lys Gly Ala Ile Lys Leu Ser Glu Val
370                 375                 380

Ser Asp Pro Leu Arg Lys Phe His Thr Leu Leu Ser Gln Val Ser Asp
385                 390                 395                 400

Pro Val Asn Pro Thr Ala His Glu Leu Lys Gln Ile Gly Arg Ala Leu
                405                 410                 415

Ile Glu Leu Lys Pro Arg Gln Asp Glu Trp His Cys Lys Asn Lys Trp
            420                 425                 430

Ser Gly Ala Glu Glu Ile Ala Gln Glu Leu Trp Gln Arg Ile Thr Ser
        435                 440                 445

Asn Glu Thr Leu Arg Ala Gln Ile Lys Gln Cys Phe Thr Gln Phe Glu
450                 455                 460

Ser Leu Lys Pro Arg Val Ala Glu Leu Gly Leu Thr Arg Ala Ser Gly
465                 470                 475                 480

Ala Gly Thr Glu Val Glu Ala His Glu Ser Thr Val Lys Glu Gln Glu
                485                 490                 495

Ile Ile Ser Gln Asn Thr Val Gly Glu Gly Thr Lys Glu Lys Asn
            500                 505                 510

Ser Val Gln Leu Ala Ser Glu Asn Ser Ser Asp Glu Lys Ile Lys Thr
        515                 520                 525

Ala His Asp Leu Ile Asp Glu Ile Ile Gln Asp Val Ile Gln Leu Asp
530                 535                 540

Gly Lys Leu Gly Leu Leu Gly Gly Asn Thr Arg Gln Leu Glu Asp Gly
```

```
                545                 550                 555                 560
Arg Val Ile Asn Ile Pro Asn Gly Ala Ala Met Ile Phe Asp Asp Tyr
                    565                 570                 575

Lys Lys Tyr Lys Gln Gly Glu Leu Thr Ala Glu Ser Ala Leu Glu Ser
                580                 585                 590

Met Ile Lys Ile Ala Lys Leu Ser Asn Gln Leu Asn Arg His Thr Phe
                595                 600                 605

Phe Asn Gln Arg Gln Pro Glu Thr Gly Gln Phe Tyr Lys Lys Val Ala
                610                 615                 620

Ala Ile Asp Leu Gln Thr Thr Ile Ala Ala Glu Tyr Asp Asn Asn His
625                 630                 635                 640

Gly Leu Arg Ile

<210> SEQ ID NO 43
<211> LENGTH: 219
<212> TYPE: PRT
<213> ORGANISM: Yersinia enterocolitica

<400> SEQUENCE: 43

Met Lys Ile Ser Ser Phe Ile Ser Thr Ser Leu Pro Leu Pro Thr Ser
1               5                   10                  15

Val Ser Gly Ser Ser Val Gly Glu Met Ser Gly Arg Ser Val Ser
                20                  25                  30

Gln Gln Thr Ser Asp Gln Tyr Ala Asn Asn Leu Ala Gly Arg Thr Glu
                35                  40                  45

Ser Pro Gln Gly Ser Ser Leu Ala Ser Arg Ile Ile Glu Arg Leu Ser
    50                  55                  60

Ser Val Ala His Ser Val Ile Gly Phe Ile Gln Arg Met Phe Ser Glu
65                  70                  75                  80

Gly Ser His Lys Pro Val Val Thr Pro Ala Pro Thr Pro Ala Gln Met
                    85                  90                  95

Pro Ser Pro Thr Ser Phe Ser Asp Ser Ile Lys Gln Leu Ala Ala Glu
                100                 105                 110

Thr Leu Pro Lys Tyr Met Gln Gln Leu Asn Ser Leu Asp Ala Glu Met
                115                 120                 125

Leu Gln Lys Asn His Asp Gln Phe Ala Thr Gly Ser Gly Pro Leu Arg
    130                 135                 140

Gly Ser Ile Thr Gln Cys Gln Gly Leu Met Gln Phe Cys Gly Gly Glu
145                 150                 155                 160

Leu Gln Ala Glu Ala Ser Ala Ile Leu Asn Thr Pro Val Cys Gly Ile
                165                 170                 175

Pro Phe Ser Gln Trp Gly Thr Ile Gly Gly Ala Ala Ser Ala Tyr Val
                180                 185                 190

Ala Ser Gly Val Asp Leu Thr Gln Ala Ala Asn Glu Ile Lys Gly Leu
                195                 200                 205

Ala Gln Gln Met Gln Lys Leu Leu Ser Leu Met
    210                 215

<210> SEQ ID NO 44
<211> LENGTH: 543
<212> TYPE: PRT
<213> ORGANISM: Salmonella typhimurium

<400> SEQUENCE: 44

Met Leu Lys Tyr Glu Glu Arg Lys Leu Asn Asn Leu Thr Leu Ser Ser
1               5                   10                  15
```

```
Phe Ser Lys Val Gly Val Ser Asn Asp Ala Arg Leu Tyr Ile Ala Lys
             20                  25                  30

Glu Asn Thr Asp Lys Ala Tyr Val Ala Pro Glu Lys Phe Ser Ser Lys
         35                  40                  45

Val Leu Thr Trp Leu Gly Lys Met Pro Leu Phe Lys Asn Thr Glu Val
 50                  55                  60

Val Gln Lys His Thr Glu Asn Ile Arg Val Gln Asp Gln Lys Ile Leu
 65                  70                  75                  80

Gln Thr Phe Leu His Ala Leu Thr Glu Lys Tyr Gly Glu Thr Ala Val
             85                  90                  95

Asn Asp Ala Leu Leu Met Ser Arg Ile Asn Met Asn Lys Pro Leu Thr
            100                 105                 110

Gln Arg Leu Ala Val Gln Ile Thr Glu Cys Val Lys Ala Ala Asp Glu
            115                 120                 125

Gly Phe Ile Asn Leu Ile Lys Ser Lys Asp Asn Val Gly Val Arg Asn
130                 135                 140

Ala Ala Leu Val Ile Lys Gly Gly Asp Thr Lys Val Ala Glu Lys Asn
145                 150                 155                 160

Asn Asp Val Gly Ala Glu Ser Lys Gln Pro Leu Leu Asp Ile Ala Leu
            165                 170                 175

Lys Gly Leu Lys Arg Thr Leu Pro Gln Leu Glu Gln Met Asp Gly Asn
            180                 185                 190

Ser Leu Arg Glu Asn Phe Gln Glu Met Ala Ser Gly Asn Gly Pro Leu
            195                 200                 205

Arg Ser Leu Met Thr Asn Leu Gln Asn Leu Asn Lys Ile Pro Glu Ala
            210                 215                 220

Lys Gln Leu Asn Asp Tyr Val Thr Thr Leu Thr Asn Ile Gln Val Gly
225                 230                 235                 240

Val Ala Arg Phe Ser Gln Trp Gly Thr Cys Gly Gly Glu Val Glu Arg
            245                 250                 255

Trp Val Asp Lys Ala Ser Thr His Glu Leu Thr Gln Ala Val Lys Lys
            260                 265                 270

Ile His Val Ile Ala Lys Glu Leu Lys Asn Val Thr Ala Glu Leu Glu
            275                 280                 285

Lys Ile Glu Ala Gly Ala Pro Met Pro Gln Thr Met Ser Gly Pro Thr
290                 295                 300

Leu Gly Leu Ala Arg Phe Ala Val Ser Ser Ile Pro Ile Asn Gln Gln
305                 310                 315                 320

Thr Gln Val Lys Leu Ser Asp Gly Met Pro Val Pro Val Asn Thr Leu
            325                 330                 335

Thr Phe Asp Gly Lys Pro Val Leu Ala Gly Ser Tyr Pro Lys Asn
            340                 345                 350

Thr Pro Asp Ala Leu Glu Ala His Met Lys Met Leu Leu Glu Lys Glu
            355                 360                 365

Cys Ser Cys Leu Val Val Leu Thr Ser Glu Asp Gln Met Gln Ala Lys
            370                 375                 380

Gln Leu Pro Pro Tyr Phe Arg Gly Ser Tyr Thr Phe Gly Glu Val His
385                 390                 395                 400

Thr Asn Ser Gln Lys Val Ser Ser Ala Ser Gln Gly Glu Ala Ile Asp
            405                 410                 415

Gln Tyr Asn Met Gln Leu Ser Cys Gly Glu Lys Arg Tyr Thr Ile Pro
            420                 425                 430
```

```
Val Leu His Val Lys Asn Trp Pro Asp His Gln Pro Leu Pro Ser Thr
        435                 440                 445

Asp Gln Leu Glu Tyr Leu Ala Asp Arg Val Lys Asn Ser Asn Gln Asn
450                 455                 460

Gly Ala Pro Gly Arg Ser Ser Asp Lys His Leu Pro Met Ile His
465                 470                 475                 480

Cys Leu Gly Gly Val Gly Arg Thr Gly Thr Met Ala Ala Leu Val
                485                 490                 495

Leu Lys Asp Asn Pro His Ser Asn Leu Glu Gln Val Arg Ala Asp Phe
                500                 505                 510

Arg Asp Ser Arg Asn Asn Arg Met Leu Glu Asp Ala Ser Gln Phe Val
            515                 520                 525

Gln Leu Lys Ala Met Gln Ala Gln Leu Leu Met Thr Thr Ala Ser
        530                 535                 540

<210> SEQ ID NO 45
<211> LENGTH: 240
<212> TYPE: PRT
<213> ORGANISM: Salmonella typhimurium

<400> SEQUENCE: 45

Met Thr Asn Ile Thr Leu Ser Thr Gln His Tyr Arg Ile His Arg Ser
1               5                   10                  15

Asp Val Glu Pro Val Lys Glu Lys Thr Thr Glu Lys Asp Ile Phe Ala
                20                  25                  30

Lys Ser Ile Thr Ala Val Arg Asn Ser Phe Ile Ser Leu Ser Thr Ser
            35                  40                  45

Leu Ser Asp Arg Phe Ser Leu His Gln Gln Thr Asp Ile Pro Thr Thr
50                  55                  60

His Phe His Arg Gly Asn Ala Ser Glu Gly Arg Ala Val Leu Thr Ser
65                  70                  75                  80

Lys Thr Val Lys Asp Phe Met Leu Gln Lys Leu Asn Ser Leu Asp Ile
                85                  90                  95

Lys Gly Asn Ala Ser Lys Asp Pro Ala Tyr Ala Arg Gln Thr Cys Glu
            100                 105                 110

Ala Ile Leu Ser Ala Val Tyr Ser Asn Asn Lys Asp Gln Cys Cys Lys
        115                 120                 125

Leu Leu Ile Ser Lys Gly Val Ser Ile Thr Pro Phe Leu Lys Glu Ile
    130                 135                 140

Gly Glu Ala Ala Gln Asn Ala Gly Leu Pro Gly Glu Ile Lys Asn Gly
145                 150                 155                 160

Val Phe Thr Pro Gly Gly Ala Gly Ala Asn Pro Phe Val Pro Leu
                165                 170                 175

Ile Ala Ser Ala Ser Ile Lys Tyr Pro His Met Phe Ile Asn His Asn
            180                 185                 190

Gln Gln Val Ser Phe Lys Ala Tyr Ala Glu Lys Ile Val Met Lys Glu
        195                 200                 205

Val Thr Pro Leu Phe Asn Lys Gly Thr Met Pro Thr Pro Gln Gln Phe
    210                 215                 220

Gln Leu Thr Ile Glu Asn Ile Ala Asn Lys Tyr Leu Gln Asn Ala Ser
225                 230                 235                 240

<210> SEQ ID NO 46
<211> LENGTH: 561
<212> TYPE: PRT
<213> ORGANISM: Salmonella typhimurium
```

<400> SEQUENCE: 46

```
Met Gln Ile Gln Ser Phe Tyr His Ser Ala Ser Leu Lys Thr Gln Glu
1               5                   10                  15

Ala Phe Lys Ser Leu Gln Lys Thr Leu Tyr Asn Gly Met Gln Ile Leu
            20                  25                  30

Ser Gly Gln Gly Lys Ala Pro Ala Lys Ala Pro Asp Ala Arg Pro Glu
        35                  40                  45

Ile Ile Val Leu Arg Glu Pro Gly Ala Thr Trp Gly Asn Tyr Leu Gln
50                  55                  60

His Gln Lys Ala Ser Asn His Ser Leu His Asn Leu Tyr Asn Leu Gln
65                  70                  75                  80

Arg Asp Leu Leu Thr Val Ala Ala Thr Val Leu Gly Lys Gln Asp Pro
                85                  90                  95

Val Leu Thr Ser Met Ala Asn Gln Met Glu Leu Ala Lys Val Lys Ala
            100                 105                 110

Asp Arg Pro Ala Thr Lys Gln Glu Ala Ala Ala Lys Ala Leu Lys
        115                 120                 125

Lys Asn Leu Ile Glu Leu Ile Ala Ala Arg Thr Gln Gln Asp Gly
130                 135                 140

Leu Pro Ala Lys Glu Ala His Arg Phe Ala Ala Val Ala Phe Arg Asp
145                 150                 155                 160

Ala Gln Val Lys Gln Leu Asn Asn Gln Pro Trp Gln Thr Ile Lys Asn
                165                 170                 175

Thr Leu Thr His Asn Gly His His Tyr Thr Asn Thr Gln Leu Pro Ala
            180                 185                 190

Ala Glu Met Lys Ile Gly Ala Lys Asp Ile Phe Pro Ser Ala Tyr Glu
        195                 200                 205

Gly Lys Gly Val Cys Ser Trp Asp Thr Lys Asn Ile His His Ala Asn
210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
                245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
        275                 280                 285

Leu Ala Gly Glu Ala Val Ser Leu Lys Leu Val Ser Val Gly Leu Leu
290                 295                 300

Thr Ala Ser Asn Ile Phe Gly Lys Glu Gly Thr Met Val Glu Asp Gln
305                 310                 315                 320

Met Arg Ala Trp Gln Ser Leu Thr Gln Pro Gly Lys Met Ile His Leu
                325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu
        355                 360                 365

Gly Phe Gly Leu Lys Ala Ser Asp Ser Tyr Asn Ala Glu Ala Leu His
370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
```

```
                    405                 410                 415
Thr Leu Ala Arg Gln Ile Lys Asp Ile Trp Lys Asn Asn Gln His His
            420                 425                 430

Lys Asp Gly Gly Glu Pro Tyr Lys Leu Ala Gln Arg Leu Ala Met Leu
            435                 440                 445

Ala His Glu Ile Asp Ala Val Pro Ala Trp Asn Cys Lys Ser Gly Lys
            450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
            485                 490                 495

Gly Gly Gln Lys Ile Phe Gln Lys Val Leu Leu Asn Ser Gly Asn Leu
            500                 505                 510

Glu Ile Gln Lys Gln Asn Thr Gly Gly Ala Gly Asn Lys Val Met Lys
            515                 520                 525

Asn Leu Ser Pro Glu Val Leu Asn Leu Ser Tyr Gln Lys Arg Val Gly
            530                 535                 540

Asp Glu Asn Ile Trp Gln Ser Val Lys Gly Ile Ser Ser Leu Ile Thr
545                 550                 555                 560

Ser

<210> SEQ ID NO 47
<211> LENGTH: 685
<212> TYPE: PRT
<213> ORGANISM: Salmonella typhimurium

<400> SEQUENCE: 47

Met Val Thr Ser Val Arg Thr Gln Pro Pro Val Ile Met Pro Gly Met
1               5                   10                  15

Gln Thr Glu Ile Lys Thr Gln Ala Thr Asn Leu Ala Ala Asn Leu Ser
            20                  25                  30

Ala Val Arg Glu Ser Ala Thr Thr Thr Leu Ser Gly Glu Ile Lys Gly
            35                  40                  45

Pro Gln Leu Glu Asp Phe Pro Ala Leu Ile Lys Gln Ala Ser Leu Asp
        50                  55                  60

Ala Leu Phe Lys Cys Gly Lys Asp Ala Glu Ala Leu Lys Glu Val Phe
65              70                  75                  80

Thr Asn Ser Asn Asn Val Ala Gly Lys Lys Ala Ile Met Glu Phe Ala
            85                  90                  95

Gly Leu Phe Arg Ser Ala Leu Asn Ala Thr Ser Asp Ser Pro Glu Ala
            100                 105                 110

Lys Thr Leu Leu Met Lys Val Gly Ala Glu Tyr Thr Ala Gln Ile Ile
            115                 120                 125

Lys Asp Gly Leu Lys Glu Lys Ser Ala Phe Gly Pro Trp Leu Pro Glu
        130                 135                 140

Thr Lys Lys Ala Glu Ala Lys Leu Glu Asn Leu Glu Lys Gln Leu Leu
145                 150                 155                 160

Asp Ile Ile Lys Asn Asn Thr Gly Gly Glu Leu Ser Lys Leu Ser Thr
            165                 170                 175

Asn Leu Val Met Gln Glu Val Met Pro Tyr Ile Ala Ser Cys Ile Glu
            180                 185                 190

His Asn Phe Gly Cys Thr Leu Asp Pro Leu Thr Arg Ser Asn Leu Thr
            195                 200                 205

His Leu Val Asp Lys Ala Ala Ala Lys Ala Val Glu Ala Leu Asp Met
```

```
            210                 215                 220

Cys His Gln Lys Leu Thr Gln Glu Gln Gly Thr Ser Val Gly Arg Glu
225                 230                 235                 240

Ala Arg His Leu Glu Met Gln Thr Leu Ile Pro Leu Leu Arg Asn
                245                 250                 255

Val Phe Ala Gln Ile Pro Ala Asp Lys Leu Pro Asp Pro Lys Ile Pro
                260                 265                 270

Glu Pro Ala Ala Gly Pro Val Pro Asp Gly Lys Lys Ala Glu Pro
            275                 280                 285

Thr Gly Ile Asn Ile Asn Ile Asn Ile Asp Ser Ser Asn His Ser Val
        290                 295                 300

Asp Asn Ser Lys His Ile Asn Asn Ser Arg Ser His Val Asp Asn Ser
305                 310                 315                 320

Gln Arg His Ile Asp Asn Ser Asn His Asp Asn Ser Arg Lys Thr Ile
                325                 330                 335

Asp Asn Ser Arg Thr Phe Ile Asp Asn Ser Gln Arg Asn Gly Glu Ser
            340                 345                 350

His His Ser Thr Asn Ser Ser Asn Val Ser His Ser His Ser Arg Val
            355                 360                 365

Asp Ser Thr Thr His Gln Thr Glu Thr Ala His Ser Ala Ser Thr Gly
370                 375                 380

Ala Ile Asp His Gly Ile Ala Gly Lys Ile Asp Val Thr Ala His Ala
385                 390                 395                 400

Thr Ala Glu Ala Val Thr Asn Ala Ser Ser Glu Ser Lys Asp Gly Lys
                405                 410                 415

Val Val Thr Ser Glu Lys Gly Thr Thr Gly Glu Thr Thr Ser Phe Asp
            420                 425                 430

Glu Val Asp Gly Val Thr Ser Lys Ser Ile Ile Gly Lys Pro Val Gln
            435                 440                 445

Ala Thr Val His Gly Val Asp Asp Asn Lys Gln Gln Ser Gln Thr Ala
        450                 455                 460

Glu Ile Val Asn Val Lys Pro Leu Ala Ser Gln Leu Ala Gly Val Glu
465                 470                 475                 480

Asn Val Lys Thr Asp Thr Leu Gln Ser Asp Thr Val Ile Thr Gly
                485                 490                 495

Asn Lys Ala Gly Thr Thr Asp Asn Asp Asn Ser Gln Thr Asp Lys Thr
            500                 505                 510

Gly Pro Phe Ser Gly Leu Lys Phe Lys Gln Asn Ser Phe Leu Ser Thr
            515                 520                 525

Val Pro Ser Val Thr Asn Met His Ser Met His Phe Asp Ala Arg Glu
        530                 535                 540

Thr Phe Leu Gly Val Ile Arg Lys Ala Leu Glu Pro Asp Thr Ser Thr
545                 550                 555                 560

Pro Phe Pro Val Arg Arg Ala Phe Asp Gly Leu Arg Ala Glu Ile Leu
                565                 570                 575

Pro Asn Asp Thr Ile Lys Ser Ala Ala Leu Lys Ala Gln Cys Ser Asp
            580                 585                 590

Ile Asp Lys His Pro Glu Leu Lys Ala Lys Met Glu Thr Leu Lys Glu
            595                 600                 605

Val Ile Thr His His Pro Gln Lys Glu Lys Leu Ala Glu Ile Ala Leu
        610                 615                 620

Gln Phe Ala Arg Glu Ala Gly Leu Thr Arg Leu Lys Gly Glu Thr Asp
625                 630                 635                 640
```

Tyr Val Leu Ser Asn Val Leu Asp Gly Leu Ile Gly Asp Gly Ser Trp
            645                 650                 655

Arg Ala Gly Pro Ala Tyr Glu Ser Tyr Leu Asn Lys Pro Gly Val Asp
            660                 665                 670

Arg Val Ile Thr Thr Val Asp Gly Leu His Met Gln Arg
            675                 680                 685

<210> SEQ ID NO 48
<211> LENGTH: 732
<212> TYPE: PRT
<213> ORGANISM: Yersinia pestis

<400> SEQUENCE: 48

Met Lys Ser Val Lys Ile Met Gly Thr Met Pro Pro Ser Ile Ser Leu
1               5                   10                  15

Ala Lys Ala His Glu Arg Ile Ser Gln His Trp Gln Asn Pro Val Gly
            20                  25                  30

Glu Leu Asn Ile Gly Gly Lys Arg Tyr Arg Ile Ile Asp Asn Gln Val
            35                  40                  45

Leu Arg Leu Asn Pro His Ser Gly Phe Ser Leu Phe Arg Glu Gly Val
50                  55                  60

Gly Lys Ile Phe Ser Gly Lys Met Phe Asn Phe Ser Ile Ala Arg Asn
65                  70                  75                  80

Leu Thr Asp Thr Leu His Ala Ala Gln Lys Thr Thr Ser Gln Glu Leu
            85                  90                  95

Arg Ser Asp Ile Pro Asn Ala Leu Ser Asn Leu Phe Gly Ala Lys Pro
            100                 105                 110

Gln Thr Glu Leu Pro Leu Gly Trp Lys Gly Glu Pro Leu Ser Gly Ala
            115                 120                 125

Pro Asp Leu Glu Gly Met Arg Val Ala Glu Thr Asp Lys Phe Ala Glu
            130                 135                 140

Gly Glu Ser His Ile Ser Ile Ile Glu Thr Lys Asp Lys Gln Arg Leu
145                 150                 155                 160

Val Ala Lys Ile Glu Arg Ser Ile Ala Glu Gly His Leu Phe Ala Glu
            165                 170                 175

Leu Glu Ala Tyr Lys His Ile Tyr Lys Thr Ala Gly Lys His Pro Asn
            180                 185                 190

Leu Ala Asn Val His Gly Met Ala Val Pro Tyr Gly Asn Arg Lys
            195                 200                 205

Glu Glu Ala Leu Leu Met Asp Glu Val Asp Gly Trp Arg Cys Ser Asp
            210                 215                 220

Thr Leu Arg Thr Leu Ala Asp Ser Trp Lys Gln Gly Lys Ile Asn Ser
225                 230                 235                 240

Glu Ala Tyr Trp Gly Thr Ile Lys Phe Ile Ala His Arg Leu Leu Asp
            245                 250                 255

Val Thr Asn His Leu Ala Lys Ala Gly Val His Asn Asp Ile Lys
            260                 265                 270

Pro Gly Asn Val Val Phe Asp Arg Ala Ser Gly Glu Pro Val Val Ile
            275                 280                 285

Asp Leu Gly Leu His Ser Arg Ser Gly Glu Gln Pro Lys Gly Phe Thr
            290                 295                 300

Glu Ser Phe Lys Ala Pro Glu Leu Gly Val Gly Asn Leu Gly Ala Ser
305                 310                 315                 320

Glu Lys Ser Asp Val Phe Leu Val Val Ser Thr Leu Leu His Cys Ile

```
                    325                 330                 335
Glu Gly Phe Glu Lys Asn Pro Glu Ile Lys Pro Asn Gln Gly Leu Arg
                340                 345                 350
Phe Ile Thr Ser Glu Pro Ala His Val Met Asp Glu Asn Gly Tyr Pro
                355                 360                 365
Ile His Arg Pro Gly Ile Ala Gly Val Glu Thr Ala Tyr Thr Arg Phe
                370                 375             380
Ile Thr Asp Ile Leu Gly Val Ser Ala Asp Ser Arg Pro Asp Ser Asn
385                 390                 395                 400
Glu Ala Arg Leu His Glu Phe Leu Ser Asp Gly Thr Ile Asp Glu Glu
                405                 410                 415
Ser Ala Lys Gln Ile Leu Lys Asp Thr Leu Thr Gly Glu Met Ser Pro
                420                 425                 430
Leu Ser Thr Asp Val Arg Arg Ile Thr Pro Lys Lys Leu Arg Glu Leu
                435                 440                 445
Ser Asp Leu Leu Arg Thr His Leu Ser Ser Ala Ala Thr Lys Gln Leu
450                 455                 460
Asp Met Gly Gly Val Leu Ser Asp Leu Asp Thr Met Leu Val Ala Leu
465                 470                 475             480
Asp Lys Ala Glu Arg Glu Gly Gly Val Asp Lys Asp Gln Leu Lys Ser
                485                 490                 495
Phe Asn Ser Leu Ile Leu Lys Thr Tyr Arg Val Ile Glu Asp Tyr Val
                500                 505                 510
Lys Gly Arg Glu Gly Asp Thr Lys Asn Ser Ser Thr Glu Val Ser Pro
                515                 520                 525
Tyr His Arg Ser Asn Phe Met Leu Ser Ile Val Glu Pro Ser Leu Gln
                530                 535                 540
Arg Ile Gln Lys His Leu Asp Gln Thr His Ser Phe Ser Asp Ile Gly
545                 550                 555                 560
Ser Leu Val Arg Ala His Lys His Leu Glu Thr Leu Leu Glu Val Leu
                565                 570                 575
Val Thr Leu Ser Gln Gln Gly Gln Pro Val Ser Ser Glu Thr Tyr Gly
                580                 585                 590
Phe Leu Asn Arg Leu Ala Glu Ala Lys Ile Thr Leu Ser Gln Gln Leu
                595                 600                 605
Asn Thr Leu Gln Gln Gln Gln Glu Ser Ala Lys Ala Gln Leu Ser Ile
                610                 615                 620
Leu Ile Asn Arg Ser Gly Ser Trp Ala Asp Val Ala Arg Gln Ser Leu
625                 630                 635                 640
Gln Arg Phe Asp Ser Thr Arg Pro Val Val Lys Phe Gly Thr Glu Gln
                645                 650                 655
Tyr Thr Ala Ile His Arg Gln Met Met Ala Ala His Ala Ile Thr
                660                 665                 670
Leu Gln Glu Val Ser Glu Phe Thr Asp Asp Met Arg Asn Phe Thr Val
                675                 680                 685
Asp Ser Ile Pro Leu Leu Ile Gln Leu Gly Arg Ser Ser Leu Met Asp
                690                 695             700
Glu His Leu Val Glu Gln Arg Glu Lys Leu Arg Glu Leu Thr Thr Ile
705                 710                 715                 720
Ala Glu Arg Leu Asn Arg Leu Glu Arg Glu Trp Met
                725                 730

<210> SEQ ID NO 49
```

```
<211> LENGTH: 529
<212> TYPE: PRT
<213> ORGANISM: Yersinia pestis

<400> SEQUENCE: 49

Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
            20                  25                  30

Val Lys Ser Lys Thr Glu Tyr Tyr Asn Ala Trp Ser Glu Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Glu Asn Asn Asn Leu Lys Ala Leu Pro Asp
        115                 120                 125

Leu Pro Pro Ser Leu Lys Lys Leu His Val Arg Glu Asn Asp Leu Thr
    130                 135                 140

Asp Leu Pro Glu Leu Pro Gln Ser Leu Glu Ser Leu Arg Val Asp Asn
145                 150                 155                 160

Asn Asn Leu Lys Ala Leu Ser Asp Leu Pro Pro Ser Leu Glu Tyr Leu
                165                 170                 175

Thr Ala Ser Ser Asn Lys Leu Glu Glu Leu Pro Glu Leu Gln Asn Leu
            180                 185                 190

Pro Phe Leu Ala Ala Ile Tyr Ala Asp Asn Asn Leu Leu Glu Thr Leu
        195                 200                 205

Pro Asp Leu Pro Pro Ser Leu Lys Lys Leu His Val Arg Glu Asn Asp
    210                 215                 220

Leu Thr Asp Leu Pro Glu Leu Pro Gln Ser Leu Glu Ser Leu Gln Val
225                 230                 235                 240

Asp Asn Asn Asn Leu Lys Ala Leu Ser Asp Leu Pro Pro Ser Leu Glu
                245                 250                 255

Tyr Leu Thr Ala Ser Ser Asn Lys Leu Glu Glu Leu Pro Glu Leu Gln
            260                 265                 270

Asn Leu Pro Phe Leu Ala Ala Ile Tyr Ala Asp Asn Asn Leu Leu Glu
        275                 280                 285

Thr Leu Pro Asp Leu Pro Pro His Leu Glu Ile Leu Val Ala Ser Tyr
    290                 295                 300

Asn Ser Leu Thr Glu Leu Pro Glu Leu Pro Gln Ser Leu Lys Ser Leu
305                 310                 315                 320

Arg Val Asp Asn Asn Leu Lys Ala Leu Ser Asp Leu Pro Ser
                325                 330                 335

Leu Glu Tyr Leu Thr Ala Ser Ser Asn Lys Leu Glu Glu Leu Pro Glu
            340                 345                 350

Leu Gln Asn Leu Pro Phe Leu Ala Ala Ile Tyr Ala Asp Asn Asn Leu
        355                 360                 365

Leu Glu Thr Leu Pro Asp Leu Pro Ser Leu Lys Lys Leu His Val
    370                 375                 380

Arg Glu Asn Asp Leu Thr Asp Leu Pro Glu Leu Pro Gln Ser Leu Thr
```

```
385                 390                 395                 400

Phe Leu Asp Val Ser Asp Asn Asn Ile Ser Gly Leu Ser Glu Leu Pro
                405                 410                 415

Pro Asn Leu Tyr Tyr Leu Asp Ala Ser Ser Asn Glu Ile Arg Ser Leu
            420                 425                 430

Cys Asp Leu Pro Pro Ser Leu Val Asp Leu Asn Val Lys Ser Asn Gln
        435                 440                 445

Leu Ser Glu Leu Pro Ala Leu Pro Pro His Leu Glu Arg Leu Ile Ala
    450                 455                 460

Ser Phe Asn Tyr Leu Ala Glu Val Pro Glu Leu Pro Gln Asn Leu Lys
465                 470                 475                 480

Gln Leu His Val Glu Gln Asn Ala Leu Arg Glu Phe Pro Asp Ile Pro
                485                 490                 495

Glu Ser Leu Glu Glu Leu Glu Met Asp Ser Glu Arg Val Val Asp Pro
            500                 505                 510

Tyr Glu Phe Ala His Glu Thr Thr Asp Lys Leu Glu Asp Asp Val Phe
        515                 520                 525

Glu

<210> SEQ ID NO 50
<211> LENGTH: 35
<212> TYPE: PRT
<213> ORGANISM: Unknown
<220> FEATURE:
<223> OTHER INFORMATION: Description of Unknown:
      Amatoxin sequence

<400> SEQUENCE: 50

Met Ser Asp Ile Asn Ala Thr Arg Leu Pro Ile Trp Gly Ile Gly Cys
1               5                   10                  15

Asn Pro Cys Val Gly Asp Asp Val Thr Thr Leu Leu Thr Arg Gly Glu
            20                  25                  30

Ala Leu Cys
        35

<210> SEQ ID NO 51
<211> LENGTH: 34
<212> TYPE: PRT
<213> ORGANISM: Amanita fuliginea

<400> SEQUENCE: 51

Met Ser Asp Ile Asn Ala Thr Arg Leu Pro Ala Trp Leu Val Asp Cys
1               5                   10                  15

Pro Cys Val Gly Asp Asp Val Asn Arg Leu Leu Thr Arg Gly Glu Ser
            20                  25                  30

Leu Cys

<210> SEQ ID NO 52
<211> LENGTH: 291
<212> TYPE: PRT
<213> ORGANISM: Ustilago maydis

<400> SEQUENCE: 52

Met Ile Lys Pro Glu Arg Ser Ile Leu Thr Ile Leu Ile Gly Ile Leu
1               5                   10                  15

Cys Leu Leu Ala Tyr Val Leu Ala Asn Gly Glu Pro His Asp Gly Asp
            20                  25                  30

Asn Glu Trp Ser Ser Tyr Cys Ser Asp Gln Gly Phe Arg Arg Ser Asp
```

```
            35                  40                  45
Asp Gly Leu Val Thr Thr Pro Asp Val Gly Gln Glu Ser Ile Gly Lys
 50                  55                  60

Asn Ser Ile Asn Gly Ser Glu Leu Val Asp Tyr Leu Gln Cys Leu Lys
65                  70                  75                  80

Val Arg Leu Asn Gly Gln Lys Gln Val Ser Asn Asp Gly Trp Leu
            85                  90                  95

Leu Leu Leu Val Gln Glu Pro Ser Val Asn Val Thr Gln Lys Ala Met
                100                 105                 110

Ser Glu Cys Asn Tyr Asn Val Ser Ser Gly His Lys Ala Gly Ser Tyr
            115                 120                 125

Ile Gln Val Thr Asn Thr Pro Ala Asp Tyr Lys Val Ile Ser Arg Arg
            130                 135                 140

Gly Ser Tyr Glu Gly Asp Gln Leu Pro Glu Asp Val Lys Pro Tyr Phe
145                 150                 155                 160

Gly Val Gln Lys Thr Ser Asp Tyr Arg Pro Ile Ser Lys Arg Ile Asn
                165                 170                 175

Pro Asn Leu Thr Leu Arg Gln Leu Ala Tyr Asn Phe Ala Ala Leu Asn
            180                 185                 190

Met Cys Ser Leu Trp Cys Asn Ser Cys Ile Ser Arg Ser Cys Pro Tyr
            195                 200                 205

Tyr Ile Ala Glu Leu Thr Val His Val Asn Asn Ile His His Gly Thr
210                 215                 220

Val Trp Leu His His Phe Cys Arg Asn Ala Ser Pro Gln Gly Gly Asn
225                 230                 235                 240

Leu Tyr Ser Thr Leu Thr Ile Ser His Lys Asp Thr Ala Tyr Tyr Val
                245                 250                 255

Gly Thr Gly Trp Trp Lys Val Arg Ser Thr Ala Ala Thr Asn Asp
            260                 265                 270

Val Ala Gly Asp Trp Tyr Pro Ala Ser Trp Asn Gln Tyr Trp Cys Gly
            275                 280                 285

Pro His Tyr
    290

<210> SEQ ID NO 53
<211> LENGTH: 219
<212> TYPE: PRT
<213> ORGANISM: Ustilago maydis

<400> SEQUENCE: 53

Met Leu Ile Phe Ser Val Leu Met Tyr Leu Gly Leu Leu Leu Ala Gly
1               5                   10                  15

Ala Ser Ala Leu Pro Asn Gly Leu Ser Pro Arg Asn Asn Ala Phe Cys
            20                  25                  30

Ala Gly Phe Gly Leu Ser Cys Lys Trp Glu Cys Trp Cys Thr Ala His
            35                  40                  45

Gly Thr Gly Asn Glu Leu Arg Tyr Ala Thr Ala Ala Gly Cys Gly Asp
    50                  55                  60

His Leu Ser Lys Ser Tyr Tyr Asp Ala Arg Ala Gly His Cys Leu Phe
65                  70                  75                  80

Ser Asp Asp Leu Arg Asn Gln Phe Tyr Ser His Cys Ser Ser Leu Asn
                85                  90                  95

Asn Asn Met Ser Cys Arg Ser Leu Ser Lys Arg Thr Ile Gln Asp Ser
            100                 105                 110
```

```
Ala Thr Asp Thr Val Asp Leu Gly Ala Glu Leu His Arg Asp Asp Pro
            115                 120                 125

Pro Pro Thr Ala Ser Asp Ile Gly Lys Arg Gly Lys Arg Pro Arg Pro
    130                 135                 140

Val Met Cys Gln Cys Val Asp Thr Thr Asn Gly Gly Val Arg Leu Asp
145                 150                 155                 160

Ala Val Thr Arg Ala Ala Cys Ser Ile Asp Ser Phe Ile Asp Gly Tyr
                165                 170                 175

Tyr Thr Glu Lys Asp Gly Phe Cys Arg Ala Lys Tyr Ser Trp Asp Leu
                180                 185                 190

Phe Thr Ser Gly Gln Phe Tyr Gln Ala Cys Leu Arg Tyr Ser His Ala
                195                 200                 205

Gly Thr Asn Cys Gln Pro Asp Pro Gln Tyr Glu
            210                 215
```

<210> SEQ ID NO 54
<211> LENGTH: 316
<212> TYPE: PRT
<213> ORGANISM: Saccharomyces cerevisiae

<400> SEQUENCE: 54

```
Met Thr Lys Pro Thr Gln Val Leu Val Arg Ser Val Ser Ile Leu Phe
1               5                   10                  15

Phe Ile Thr Leu Leu His Leu Val Ala Leu Asn Asp Val Ala Gly
            20                  25                  30

Pro Ala Glu Thr Ala Pro Val Ser Leu Leu Pro Arg Glu Ala Pro Trp
            35                  40                  45

Tyr Asp Lys Ile Trp Glu Val Lys Asp Trp Leu Leu Gln Arg Ala Thr
    50                  55                  60

Asp Gly Asn Trp Gly Lys Ser Ile Thr Trp Gly Ser Phe Val Ala Ser
65                  70                  75                  80

Asp Ala Gly Val Val Ile Phe Gly Ile Asn Val Cys Lys Asn Cys Val
                85                  90                  95

Gly Glu Arg Lys Asp Asp Ile Ser Thr Asp Cys Gly Lys Gln Thr Leu
            100                 105                 110

Ala Leu Leu Val Ser Ile Phe Val Ala Val Thr Ser Gly His His Leu
            115                 120                 125

Ile Trp Gly Gly Asn Arg Pro Val Ser Gln Ser Asp Pro Asn Gly Ala
            130                 135                 140

Thr Val Ala Arg Arg Asp Ile Ser Thr Val Ala Asp Gly Asp Ile Pro
145                 150                 155                 160

Leu Asp Phe Ser Ala Leu Asn Asp Ile Leu Asn Glu His Gly Ile Ser
                165                 170                 175

Ile Leu Pro Ala Asn Ala Ser Gln Tyr Val Lys Arg Ser Asp Thr Ala
            180                 185                 190

Glu His Thr Thr Ser Phe Val Val Thr Asn Asn Tyr Thr Ser Leu His
            195                 200                 205

Thr Asp Leu Ile His His Gly Asn Gly Thr Tyr Thr Thr Phe Thr Thr
    210                 215                 220

Pro His Ile Pro Ala Val Ala Lys Arg Tyr Val Tyr Pro Met Cys Glu
225                 230                 235                 240

His Gly Ile Lys Ala Ser Tyr Cys Met Ala Leu Asn Asp Ala Met Val
                245                 250                 255

Ser Ala Asn Gly Asn Leu Tyr Gly Leu Ala Glu Lys Leu Phe Ser Glu
            260                 265                 270
```

```
Asp Glu Gly Gln Trp Glu Thr Asn Tyr Tyr Lys Leu Tyr Trp Ser Thr
            275                 280                 285

Gly Gln Trp Ile Met Ser Met Lys Phe Ile Glu Glu Ser Ile Asp Asn
290                 295                 300

Ala Asn Asn Asp Phe Glu Gly Cys Asp Thr Gly His
305                 310                 315

<210> SEQ ID NO 55
<211> LENGTH: 296
<212> TYPE: PRT
<213> ORGANISM: Saccharomyces cerevisiae

<400> SEQUENCE: 55

Met Gly His Leu Ala Ile Leu Phe Ser Ile Ile Ala Val Leu Asn Ile
1               5                   10                  15

Ala Thr Ala Val Ala Ser Ser Asp Ser Ile Tyr Leu Lys Gly His Arg
            20                  25                  30

Val Gly Gln Asp Ile Asp Ser Leu Tyr Arg Val Tyr Asp Asn Gly Thr
        35                  40                  45

Met Tyr Pro Val Thr Phe Asn Glu Trp Leu Asn Asp Leu Thr Gly Met
    50                  55                  60

Asn Asp Leu Ala Thr Asn Asn Ala Thr Ile Leu Lys Arg Asp Ser Ser
65                  70                  75                  80

Asp Val Ser Cys Val Thr Glu Thr Cys Gln Tyr Val Asp Tyr His Val
                85                  90                  95

Asp Asp Glu Gly Val Ile Thr Ile Asp Ile Ser Thr Tyr Arg Ile Pro
            100                 105                 110

Val Glu Trp Asp Ser Gly Ser Ala Gly Asn Ala Ser Tyr Gly Val Ser
        115                 120                 125

Lys Arg Asp Thr Lys Tyr Glu Thr Phe Cys Lys Lys Ile Cys Gly
130                 135                 140

Ile Asn Val Ser Gly Phe Cys Asn Ala Tyr Asp Phe Ala Val His Ala
145                 150                 155                 160

Phe Asp Phe Gly Gly Ser Val Tyr Asn Pro Val Ser Gly Ile Thr Asp
                165                 170                 175

Arg Ile Lys Glu Ala Thr Lys Arg Asp Lys Thr Glu Cys Leu Gly Tyr
            180                 185                 190

Glu Leu Asp His Val Arg Ile Asp Pro Ala Val Asp Trp Ser Ile Ser
        195                 200                 205

Ile Ser Thr Trp Lys Gln Gly Ser Ala Asn Cys Asp Thr Gln Ala Ser
    210                 215                 220

Ala Asp Ser Leu Lys Cys Ala Ala Gln Lys Ala Leu Glu Ser Glu His
225                 230                 235                 240

Asn His Gln Lys Thr Ala Phe Cys Ile His Leu Asp Asn Gly Gly Ser
                245                 250                 255

Phe Asn Leu Asp Ile Arg Leu Ile Ser Glu Leu Ser Phe Ser Lys Tyr
            260                 265                 270

Asn Pro Trp Ala Leu Pro Cys Pro Lys Tyr Lys Gly Ser Asn Ser Trp
        275                 280                 285

Gln Val Val Ser Asp Cys Phe Gln
    290                 295

<210> SEQ ID NO 56
<211> LENGTH: 708
<212> TYPE: PRT
```

<213> ORGANISM: Saccharomyces cerevisiae

<400> SEQUENCE: 56

Met Pro Arg Phe Ala Ile Ile Phe Ala Leu Leu Ile Ala Tyr Ser Leu
1               5                   10                  15

Phe Leu Ser Thr Leu Phe Thr Gly Ser Ile Pro Asp Arg Ala Asn Thr
            20                  25                  30

Val Thr Ser Asn Ala Pro Cys Gln Val Val Ile Trp Asp Trp Ile Arg
        35                  40                  45

Thr Arg Arg Ile Cys Asn Cys Cys Ser Arg Leu Cys Tyr Ser Leu Leu
    50                  55                  60

Gly Arg Ser Asn Leu Ser Arg Thr Ala Lys Arg Gly Val Cys Thr Ile
65                  70                  75                  80

Ala Gly Ala Val Leu Ala Thr Ala Val Ile Val Ala Ala Val Leu
            85                  90                  95

Val Gly Lys Ser Ser Gly Ser Ala Thr Lys Arg Gly Leu Thr Lys Thr
            100                 105                 110

Ile Ser Val Leu Asn His Thr Ile Pro Phe Thr Asp His Ile Leu Asn
            115                 120                 125

Gly Gln Thr Leu Ser Asn Gly Thr Gly Ser Asn Phe Val Thr Ile Gly
            130                 135                 140

Phe Ser Gly Tyr Ala Val His Ala Thr Ile Lys Arg Ala Ser Thr Thr
145                 150                 155                 160

Asp Ile Ile Ser Trp Val Ile Pro Glu Ser Met Glu Pro Thr Leu Ala
                165                 170                 175

Arg Val Ala Ser Tyr Val Ser Ser Ser Ile Asn Leu Ala Ala Val
            180                 185                 190

Pro Asp Thr Gly Gly Asn Ala Ser Ala Leu Ser Phe Gln Asn Ala Val
            195                 200                 205

Gln Glu Phe Ala Thr Ser Trp Val Ser Met Thr Tyr Asp Gln Ser Tyr
    210                 215                 220

Gly Asp Leu Arg Asn Val Ala Asn Asp Glu Gly Gly Glu Glu Ile Leu
225                 230                 235                 240

Ile Leu Met Arg Lys Arg Ser Tyr Arg Ile Ser Phe Gln Val Ile Glu
                245                 250                 255

Thr Gly Ser Thr Ala Leu Leu Leu Arg Thr Arg Arg Val Val Ser Gln
            260                 265                 270

Leu Ile Thr Met Thr Tyr Leu Val Thr Val Gln Ala Arg Val Gly Ile
            275                 280                 285

Gln Ile Gly Asp Ile Phe Gln His Tyr Gly Gly Ile Asp Asn Tyr Val
    290                 295                 300

Met Thr Ser Ile Ser Val Leu Arg Thr Leu Glu Asp Lys Ala Phe His
305                 310                 315                 320

Glu Asn Lys Leu Leu Ile Val Arg Glu Pro Pro Asn Lys Ser Asn Gln
                325                 330                 335

Asp Ala Asn Gln Ser Tyr Arg Leu Arg Pro Phe Ser Ala Asn Asp Leu
            340                 345                 350

Ile Gln Asn Leu Lys Ser Val Asp Ile Gly Phe Leu Ala Phe Cys Ser
            355                 360                 365

Phe Phe Asp Lys Tyr Ala His Tyr Pro Glu Ile Ile Met Met Lys Ile
            370                 375                 380

Thr Ile Phe Ile Ser Lys Gly Asn Leu Trp Ser Ile Ile Tyr Val Ile
385                 390                 395                 400

```
Gln Ala Arg Tyr Val Arg Lys Arg Val Met Lys Val Arg Gly Gln Met
                405                 410                 415
Pro Gly Gly Leu Leu Thr Asn Met Glu Ser Leu Leu Asn Ile Val Ser
            420                 425                 430
Thr Pro Asn Leu Asn Ile Ser Glu Phe His Ile Gln Thr His Ser Met
        435                 440                 445
Ser Gln Ser Lys Pro Met Tyr Phe Gln Lys Gln Cys Tyr Ser Ser Gln
    450                 455                 460
Asn Asn Ile Ile Tyr Ile Tyr Asn Ser Ile His Ile Thr Cys Gly Ala
465                 470                 475                 480
Val Tyr Val Ile Val His Asp Val Arg Thr Pro Ser Val Phe Val Leu
                485                 490                 495
Ile Glu Leu Arg Asn Cys Lys Pro Leu Lys Asn Ser Trp Cys Glu Thr
            500                 505                 510
Thr Lys Thr Ser Pro Arg Asp Thr Lys Ile Lys Lys Asn Glu Tyr Asn
        515                 520                 525
Glu Thr Val Cys Arg Arg Ala Gly Ala Leu Leu Asp Gly Arg Val Arg
    530                 535                 540
Thr Ile Arg Phe Leu Met Met Arg Thr His Trp Ser Arg Val Lys Gly
545                 550                 555                 560
Val Ser Cys Asn Thr Ala Asn Arg Leu Ser Arg Phe Cys Asn His Val
                565                 570                 575
Val Ser Tyr Tyr Pro Ser Gln Asn Ala Thr Ile His Leu Leu Pro Thr
            580                 585                 590
Ser Leu Arg Ala Glu Ser Leu Glu Gln Gln Tyr Thr Thr Arg Pro Leu
        595                 600                 605
Ser Ser Ser Asn Asn Arg Phe Cys Cys Leu Lys Ser Ile Phe Ile Asn
    610                 615                 620
Asn Cys Lys Lys Ala Cys Glu Ser Pro Ser Leu Val Ser Cys Asn Leu
625                 630                 635                 640
Gln Gln Thr Ala Glu Leu Leu Met Val Tyr Tyr Leu Tyr Ile Cys Glu
                645                 650                 655
Ala Cys Tyr Val Ser Arg Asn His Asp Leu Leu Ser Lys Gln Cys Met
            660                 665                 670
Ser Thr Val Arg Ala Val Tyr Val Ala Arg Met Arg Leu Pro Lys Phe
        675                 680                 685
Arg Ser Thr Phe Pro Cys Met Pro Arg Leu Cys Trp Leu Val Asn Gly
    690                 695                 700
Val Val Val Val
705

<210> SEQ ID NO 57
<211> LENGTH: 768
<212> TYPE: PRT
<213> ORGANISM: Bacillus anthracis

<400> SEQUENCE: 57

Met His Val Lys Glu Lys Glu Lys Asn Lys Asp Glu Asn Lys Arg Lys
1               5                   10                  15
Asp Glu Glu Arg Asn Lys Thr Gln Glu Glu His Leu Lys Glu Ile Met
            20                  25                  30
Lys His Ile Val Lys Ile Glu Val Lys Gly Glu Glu Ala Val Lys Lys
        35                  40                  45
Glu Ala Ala Glu Lys Leu Leu Glu Lys Val Pro Ser Asp Val Leu Glu
    50                  55                  60
```

```
Met Tyr Lys Ala Ile Gly Gly Lys Ile Tyr Ile Val Asp Gly Asp Ile
 65                  70                  75                  80

Thr Lys His Ile Ser Leu Glu Ala Leu Ser Glu Asp Lys Lys Lys Ile
                 85                  90                  95

Lys Asp Ile Tyr Gly Lys Asp Ala Leu Leu His Glu His Tyr Val Tyr
                100                 105                 110

Ala Lys Glu Gly Tyr Glu Pro Val Leu Val Ile Gln Ser Ser Glu Asp
            115                 120                 125

Tyr Val Glu Asn Thr Glu Lys Ala Leu Asn Val Tyr Tyr Glu Ile Gly
        130                 135                 140

Lys Ile Leu Ser Arg Asp Ile Leu Ser Lys Ile Asn Gln Pro Tyr Gln
145                 150                 155                 160

Lys Phe Leu Asp Val Leu Asn Thr Ile Lys Asn Ala Ser Asp Ser Asp
                165                 170                 175

Gly Gln Asp Leu Leu Phe Thr Asn Gln Leu Lys Glu His Pro Thr Asp
                180                 185                 190

Phe Ser Val Glu Phe Leu Glu Gln Asn Ser Asn Glu Val Gln Glu Val
            195                 200                 205

Phe Ala Lys Ala Phe Ala Tyr Tyr Ile Glu Pro Gln His Arg Asp Val
        210                 215                 220

Leu Gln Leu Tyr Ala Pro Glu Ala Phe Asn Tyr Met Asp Lys Phe Asn
225                 230                 235                 240

Glu Gln Glu Ile Asn Leu Ser Leu Glu Glu Leu Lys Asp Gln Arg Met
                245                 250                 255

Leu Ser Arg Tyr Glu Lys Trp Glu Lys Ile Lys Gln His Tyr Gln His
                260                 265                 270

Trp Ser Asp Ser Leu Ser Glu Glu Gly Arg Gly Leu Leu Lys Lys Leu
            275                 280                 285

Gln Ile Pro Ile Glu Pro Lys Lys Asp Asp Ile Ile His Ser Leu Ser
        290                 295                 300

Gln Glu Glu Lys Glu Leu Leu Lys Arg Ile Gln Ile Asp Ser Ser Asp
305                 310                 315                 320

Phe Leu Ser Thr Glu Glu Lys Glu Phe Leu Lys Lys Leu Gln Ile Asp
                325                 330                 335

Ile Arg Asp Ser Leu Ser Glu Glu Lys Glu Leu Leu Asn Arg Ile
                340                 345                 350

Gln Val Asp Ser Ser Asn Pro Leu Ser Glu Lys Glu Lys Glu Phe Leu
            355                 360                 365

Lys Lys Leu Lys Leu Asp Ile Gln Pro Tyr Asp Ile Asn Gln Arg Leu
        370                 375                 380

Gln Asp Thr Gly Gly Leu Ile Asp Ser Pro Ser Ile Asn Leu Asp Val
385                 390                 395                 400

Arg Lys Gln Tyr Lys Arg Asp Ile Gln Asn Ile Asp Ala Leu Leu His
                405                 410                 415

Gln Ser Ile Gly Ser Thr Leu Tyr Asn Lys Ile Tyr Leu Tyr Glu Asn
                420                 425                 430

Met Asn Ile Asn Asn Leu Thr Ala Thr Leu Gly Ala Asp Leu Val Asp
            435                 440                 445

Ser Thr Asp Asn Thr Lys Ile Asn Arg Gly Ile Phe Asn Glu Phe Lys
        450                 455                 460

Lys Asn Phe Lys Tyr Ser Ile Ser Ser Asn Tyr Met Ile Val Asp Ile
465                 470                 475                 480
```

-continued

```
Asn Glu Arg Pro Ala Leu Asp Asn Glu Arg Leu Lys Trp Arg Ile Gln
                485                 490                 495

Leu Ser Pro Asp Thr Arg Ala Gly Tyr Leu Glu Asn Gly Lys Leu Ile
            500                 505                 510

Leu Gln Arg Asn Ile Gly Leu Glu Ile Lys Asp Val Gln Ile Ile Lys
        515                 520                 525

Gln Ser Glu Lys Glu Tyr Ile Arg Ile Asp Ala Lys Val Val Pro Lys
    530                 535                 540

Ser Lys Ile Asp Thr Lys Ile Gln Glu Ala Gln Leu Asn Ile Asn Gln
545                 550                 555                 560

Glu Trp Asn Lys Ala Leu Gly Leu Pro Lys Tyr Thr Lys Leu Ile Thr
                565                 570                 575

Phe Asn Val His Asn Arg Tyr Ala Ser Asn Ile Val Glu Ser Ala Tyr
            580                 585                 590

Leu Ile Leu Asn Glu Trp Lys Asn Asn Ile Gln Ser Asp Leu Ile Lys
        595                 600                 605

Lys Val Thr Asn Tyr Leu Val Asp Gly Asn Gly Arg Phe Val Phe Thr
    610                 615                 620

Asp Ile Thr Leu Pro Asn Ile Ala Glu Gln Tyr Thr His Gln Asp Glu
625                 630                 635                 640

Ile Tyr Glu Gln Val His Ser Lys Gly Leu Tyr Val Pro Glu Ser Arg
                645                 650                 655

Ser Ile Leu Leu His Gly Pro Ser Lys Gly Val Glu Leu Arg Asn Asp
            660                 665                 670

Ser Glu Gly Phe Ile His Glu Phe Gly His Ala Val Asp Asp Tyr Ala
        675                 680                 685

Gly Tyr Leu Leu Asp Lys Asn Gln Ser Asp Leu Val Thr Asn Ser Lys
    690                 695                 700

Lys Phe Ile Asp Ile Phe Lys Glu Glu Gly Ser Asn Leu Thr Ser Tyr
705                 710                 715                 720

Gly Arg Thr Asn Glu Ala Glu Phe Phe Ala Glu Ala Phe Arg Leu Met
                725                 730                 735

His Ser Thr Asp His Ala Glu Arg Leu Lys Val Gln Lys Asn Ala Pro
            740                 745                 750

Lys Thr Phe Gln Phe Ile Asn Asp Gln Ile Lys Phe Ile Ile Asn Ser
        755                 760                 765

<210> SEQ ID NO 58
<211> LENGTH: 319
<212> TYPE: PRT
<213> ORGANISM: Unknown
<220> FEATURE:
<223> OTHER INFORMATION: Description of Unknown:
      Shiga Toxin sequence

<400> SEQUENCE: 58

Met Lys Cys Ile Leu Leu Lys Trp Val Leu Cys Leu Leu Leu Gly Phe
1               5                   10                  15

Ser Ser Val Ser Tyr Ser Arg Glu Phe Thr Ile Asp Phe Ser Thr Gln
            20                  25                  30

Gln Ser Tyr Val Ser Ser Leu Asn Ser Ile Arg Thr Glu Ile Ser Thr
        35                  40                  45

Pro Leu Glu His Ile Ser Gln Gly Thr Thr Ser Val Ser Val Ile Asn
    50                  55                  60

His Thr Pro Pro Gly Ser Tyr Phe Ala Val Asp Ile Arg Gly Leu Asp
65                  70                  75                  80
```

Val Tyr Gln Ala Arg Phe Asp His Leu Arg Leu Ile Ile Glu Gln Asn
                85                  90                  95

Asn Leu Tyr Val Ala Gly Phe Val Asn Thr Ala Thr Asn Thr Phe Tyr
            100                 105                 110

Arg Phe Ser Asp Phe Ala His Ile Ser Val Pro Gly Val Thr Thr Val
        115                 120                 125

Ser Met Thr Thr Asp Ser Ser Tyr Thr Thr Leu Gln Arg Val Ala Ala
    130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
    210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Glu Ser Gln Pro Glu Cys Gln Ile Thr Gly Asp Arg
        275                 280                 285

Pro Val Ile Lys Ile Asn Asn Thr Leu Trp Glu Ser Asn Thr Ala Ala
    290                 295                 300

Ala Phe Leu Asn Arg Lys Ser Gln Ser Leu Tyr Thr Thr Gly Glu
305                 310                 315

<210> SEQ ID NO 59
<211> LENGTH: 565
<212> TYPE: PRT
<213> ORGANISM: Ricinus communis

<400> SEQUENCE: 59

Met Tyr Ala Val Ala Thr Trp Leu Cys Phe Gly Ser Thr Ser Gly Trp
1               5                   10                  15

Ser Phe Thr Leu Glu Asp Asn Asn Ile Phe Pro Lys Gln Tyr Pro Ile
            20                  25                  30

Ile Asn Phe Thr Thr Ala Gly Ala Thr Val Gln Ser Tyr Thr Asn Phe
        35                  40                  45

Ile Arg Ala Val Arg Gly Arg Leu Thr Thr Gly Ala Asp Val Arg His
    50                  55                  60

Asp Ile Pro Val Leu Pro Asn Arg Val Gly Leu Pro Ile Asn Gln Arg
65                  70                  75                  80

Phe Ile Leu Val Glu Leu Ser Asn His Ala Glu Leu Ser Val Thr Leu
                85                  90                  95

Ala Leu Asp Val Thr Asn Ala Tyr Val Val Gly Tyr Arg Ala Gly Asn
            100                 105                 110

Ser Ala Tyr Phe Phe His Pro Asp Asn Gln Glu Asp Ala Glu Ala Ile
        115                 120                 125

Thr His Leu Phe Thr Asp Val Gln Asn Arg Tyr Thr Phe Ala Phe Gly

```
            130                 135                 140
Gly Asn Tyr Asp Arg Leu Glu Gln Leu Ala Gly Asn Leu Arg Glu Asn
145                 150                 155                 160

Ile Glu Leu Gly Asn Gly Pro Leu Glu Glu Ala Ile Ser Ala Leu Tyr
                165                 170                 175

Tyr Tyr Ser Thr Gly Gly Thr Gln Leu Pro Thr Leu Ala Arg Ser Phe
            180                 185                 190

Ile Ile Cys Ile Gln Met Ile Ser Glu Ala Ala Arg Phe Gln Tyr Ile
            195                 200                 205

Glu Gly Glu Met Arg Thr Arg Ile Arg Tyr Asn Arg Arg Ser Ala Pro
210                 215                 220

Asp Pro Ser Val Ile Thr Leu Glu Asn Ser Trp Gly Arg Leu Ser Thr
225                 230                 235                 240

Ala Ile Gln Glu Ser Asn Gln Gly Ala Phe Ala Ser Pro Ile Gln Leu
                245                 250                 255

Gln Arg Arg Asn Gly Ser Lys Phe Ser Val Tyr Asp Val Ser Ile Leu
                260                 265                 270

Ile Pro Ile Ile Ala Leu Met Val Tyr Arg Cys Ala Pro Pro Pro Ser
            275                 280                 285

Ser Gln Phe Ser Leu Leu Ile Arg Pro Val Val Pro Asn Phe Asn Ala
    290                 295                 300

Asp Val Cys Met Asp Pro Glu Pro Ile Val Arg Ile Val Gly Arg Asn
305                 310                 315                 320

Gly Leu Cys Val Asp Val Arg Asp Gly Arg Phe His Asn Gly Asn Ala
                325                 330                 335

Ile Gln Leu Trp Pro Cys Lys Ser Asn Thr Asp Ala Asn Gln Leu Trp
            340                 345                 350

Thr Leu Lys Arg Asp Asn Thr Ile Arg Ser Asn Gly Lys Cys Leu Thr
            355                 360                 365

Thr Tyr Gly Tyr Ser Pro Gly Val Tyr Val Met Ile Tyr Asp Cys Asn
    370                 375                 380

Thr Ala Ala Thr Asp Ala Thr Arg Trp Gln Ile Trp Asp Asn Gly Thr
385                 390                 395                 400

Ile Ile Asn Pro Arg Ser Ser Leu Val Leu Ala Ala Thr Ser Gly Asn
                405                 410                 415

Ser Gly Thr Thr Leu Thr Val Gln Thr Asn Ile Tyr Ala Val Ser Gln
            420                 425                 430

Gly Trp Leu Pro Thr Asn Asn Thr Gln Pro Phe Val Thr Thr Ile Val
            435                 440                 445

Gly Leu Tyr Gly Leu Cys Leu Gln Ala Asn Ser Gly Gln Val Trp Ile
    450                 455                 460

Glu Asp Cys Ser Ser Glu Lys Ala Glu Gln Gln Trp Ala Leu Tyr Ala
465                 470                 475                 480

Asp Gly Ser Ile Arg Pro Gln Gln Asn Arg Asp Asn Cys Leu Thr Ser
                485                 490                 495

Asp Ser Asn Ile Arg Glu Thr Val Val Lys Ile Leu Ser Cys Gly Pro
            500                 505                 510

Ala Ser Ser Gly Gln Arg Trp Met Phe Lys Asn Asp Gly Thr Ile Leu
            515                 520                 525

Asn Leu Tyr Ser Gly Leu Val Leu Asp Val Arg Arg Ser Asp Pro Ser
    530                 535                 540

Leu Lys Gln Ile Ile Leu Tyr Pro Leu His Gly Asp Pro Asn Gln Ile
545                 550                 555                 560
```

Trp Leu Pro Leu Phe
            565

<210> SEQ ID NO 60
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(72)

<400> SEQUENCE: 60 aag ggt gac gct gaa aga tgg gtt tct ggt cca ggc gcg cca ctt cta    48
Lys Gly Asp Ala Glu Arg Trp Val Ser Gly Pro Gly Ala Pro Leu Leu
1               5                   10                  15 aat aag cga att tct tat gat tta tgatttttat tattaaataa gttata       98
Asn Lys Arg Ile Ser Tyr Asp Leu
            20

<210> SEQ ID NO 61
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(111)

<400> SEQUENCE: 61 gag cag aag cta atc tca gag gag gac ctg ttt aaa cca gga ggc ggt    48
Glu Gln Lys Leu Ile Ser Glu Glu Asp Leu Phe Lys Pro Gly Gly Gly
1               5                   10                  15 tct ggt cca ggt act gaa gac gct gaa gct gtt gct ttg ggt ttg ggt    96
Ser Gly Pro Gly Thr Glu Asp Ala Glu Ala Val Ala Leu Gly Leu Gly
            20                  25                  30 ttg tct gac ttc cca t                                              112
Leu Ser Asp Phe Pro
        35

<210> SEQ ID NO 62
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (33)..(62)
<223> OTHER INFORMATION: a, c, t, g, unknown or other
<220> FEATURE:
<221> NAME/KEY: CDS
<222> LOCATION: (69)..(113)

<400> SEQUENCE: 62
aacgtcaagg agaaaaaact ataatggtta atnnnnnnnn nnnnnnnnnn nnnnnnnnnn    60 nntaatag aca agc tac gtt gaa aca aga acc cgc ctc ctt tca gaa ctc   110
         Thr Ser Tyr Val Glu Thr Arg Thr Arg Leu Leu Ser Glu Leu
           1               5                   10 act t                                                              114
Thr
15

<210> SEQ ID NO 63
<211> LENGTH: 7737
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cgagctcggt | acccgtcttc | 420 |
| tgtcccagtt | accgaatcta | agggcactac | caccaaagaa | acaggtgtta | ctaccaaaca | 480 |
| aaccacagcc | aacccaagtc | taccgtctc | cacagtcgtc | ccagtttcat | cctctgcttc | 540 |
| ttctcattcc | gttgtcatca | acagtaacgg | tgctaacgtc | gtcgttccag | gtgctttagg | 600 |
| tttggctggt | gttgctatgt | tattcttata | acggtggtg | tttgacacat | ccgccttctt | 660 |
| aatgctttct | ttcagtatta | tgttattttt | ttgttattcg | tttttcactt | ctaggctttt | 720 |
| tgacagacta | gccccgttat | accaccatct | tgtgggaaa | gccctaaat | tgccctgagc | 780 |
| agtatcgttt | catgtctagt | ctctttaaag | atgtttctta | cacttctcct | atgcacatat | 840 |
| attaattaaa | gtccaatgct | agtagagaag | ggggtaaca | cccctccgcg | ctcttttccg | 900 |
| atttttttct | aaaccgtgga | atatttcgga | tatcctttg | ttgtttccgg | gtgtacaata | 960 |
| tggacttcct | ctttttctggc | aaccaaaccc | atacatcggg | attcctataa | taccttcgtt | 1020 |
| ggtctcccta | acatgtaggt | ggcggagggg | agatatacaa | tagaacagat | accagacaag | 1080 |
| acataatggg | ctaaacaaga | ctacaccaat | tacactgcct | cattgatggt | ggtacataac | 1140 |
| gaactaatac | tgtagcccta | gacttgatag | ccatcatcat | atcgaagttt | cactacccct | 1200 |
| tttccattg | ccatctattg | aagtaataat | aggcgcatgc | aacttctttt | ctttttttt | 1260 |
| cttttctctc | tcccccgttg | ttgtctcacc | atatccgcaa | tgacaaaaaa | atgatggaag | 1320 |
| acactaaagg | aaaaaattaa | cgacaaagac | agcaccaaca | gatgtcgttg | ttccagagct | 1380 |
| gatgaggggt | atctcgaagc | acacgaaact | ttttccttcc | ttcattcacg | cacactactc | 1440 |
| tctaatgagc | aacggtatac | ggccttcctt | ccagttactt | gaatttgaaa | taaaaaaaag | 1500 |
| tttgctgtct | tgctatcaag | tataaataga | cctgcaatta | ttaatctttt | gtttcctcgt | 1560 |
| cattgttctc | gttcccttc | ttccttgttt | cttttctgc | acaatatttc | aagctatacc | 1620 |
| aagcatacaa | tcaactccaa | gctttgcaaa | gatgggtca | aaggccgagc | taatcccaga | 1680 |
| gcccctaaa | aaaagagaa | aggtcgagct | gggaactgcg | gcagagtacc | cgtatgatgt | 1740 |
| accggactat | gccggaggta | tgtctagatt | ggacaagtct | aaggttatca | actctgcttt | 1800 |
| ggaattgttg | aacgaagttg | gtatcgaagg | tttgactact | agaaagttgg | ctcaaaagtt | 1860 |
| gggtgttgaa | caaccaactt | tgtactggca | cgttaagaac | aagagagctt | tgttggacgc | 1920 |
| tttggctatc | gaaatgttgg | acagacacca | cactcacttc | tgtccattgg | aaggtgaatc | 1980 |
| ttggcaagac | ttcttgagaa | acaacgctaa | gtctttcaga | tgtgctttgt | tgtctcacag | 2040 |

```
agacggtgct aaggttcact tgggtactag accaactgaa aagcaatacg aaactttgga    2100
aaaccaattg gctttcttgt gtcaacaagg tttctctttg gaaaacgctt tgtacgcttt    2160
gtctgctgtt ggtcacttca ctttgggttg tgttttggaa gaccaagaac accaagttgc    2220
taaggaagaa agagaaactc caactactga ctctatgcca ccattgttga dacaagctat    2280
cgaattgttc gaccaccaag gtgctgaacc agctttcttg ttcggtttgg aattgatcat    2340
ctgtggtttg gaaaagcaat tgaagtgtga atctggttct gggcaaccat ctttgagatc    2400
tgaatacgaa tacccagttt tctctcacgt tcaagctggt atgttctctc cagaattgag    2460
aactttcact aagggtgacg ctgaaagatg ggtttctggt ccaggcgcgc cacttctaaa    2520
taagcgaatt tcttatgatt tatgattttt attattaaat aagttataaa aaaaataagt    2580
gtatacaaat tttaaagtga ctcttaggtt ttaaaacgaa aattcttatt cttgagtaac    2640
tctttcctgt aggtcaggtt gctttctcag gtatagcatg aggtcgctct tattgaccac    2700
acctctaccg gcagatctgt acaatcttga tccggagctt ttcttttttt gccgattaag    2760
aattaattcg gtcgaaaaaa gaaaaggaga gggccaagag ggagggcatt ggtgactatt    2820
gagcacgtga gtatacgtga ttaagcacac aaaggcagct tggagtatgt ctgttattaa    2880
tttcacaggt agttctggtc cattggtgaa agtttgcggc ttgcagagca cagaggccgc    2940
agaatgtgct ctagattccg atgctgactt gctgggtatt atatgtgtgc ccaatagaaa    3000
gagaacaatt gacccggtta ttgcaaggaa aatttcaagt cttgtaaaag catataaaaa    3060
tagttcaggc actccgaaat acttggttgg cgtgtttcgt aatcaaccta aggaggatgt    3120
tttggctctg gtcaatgatt acggcattga tatcgtccaa ctgcatggag atgagtcgtg    3180
gcaagaatac caagagttcc tcggtttgcc agttattaaa agactcgtat tccaaaaga    3240
ctgcaacata ctactcagtg cagcttcaca gaaacctcat tcgtttattc ccttgtttga    3300
ttcagaagca ggtgggacag gtgaactttt ggattggaac tcgatttctg actgggttgg    3360
aaggcaagag agccccgaaa gcttacattt tatgttagct ggtggactga cgccagaaaa    3420
tgttggtgat gcgcttagat taaatggcgt tattggtgtt gatgtaagcg gaggtgtgga    3480
gacaaatggt gtaaaagact ctaacaaaat agcaaatttc gtcaaaaatg ctaagaaata    3540
ggttattact gagtagtatt tatttaagta ttgtttgtgc acttgcctgc ggtgtgaaat    3600
accgcacaga tgcgtaagga atatttcgga tatccttttg ttgtttccgg gtgtacaata    3660
tggacttcct cttttctggc aaccaaaccc atacatcggg attcctataa taccttcgtt    3720
ggtctcccta acatgtaggt ggcggagggg agatatacaa tagaacagat accagacaag    3780
acataatggg ctaaacaaga ctacaccaat tacactgcct cattgatggt ggtacataac    3840
gaactaatac tgtagcccta gacttgatag ccatcatcat atcgaagttt cactaccctt    3900
tttccatttg ccatctattg aagtaataat aggcgcatgc aacttctttt cttttttttt    3960
cttttctctc tccccgttg ttgtctcacc atatccgcaa tgacaaaaaa atgatggaag    4020
acactaaagg aaaaaattaa cgacaaagac agcaccaaca gatgtcgttg ttccagagct    4080
gatgaggggt atctcgaagc acacgaaact ttttccttcc ttcattcacg cacactactc    4140
tctaatgagc aacggtatac ggccttcctt ccagttactt gaatttgaaa taaaaaaaag    4200
tttgctgtct tgctatcaag tataaataga cctgcaatta ttaatctttt gtttcctcgt    4260
cattgttctc gttcccttc ttccttgttt ctttttctgc acaatatttc aagctatacc    4320
aagcatacaa tcaactccaa gctttgcaaa gatggggtca aaggccgagc taatcccaga    4380
```

| | |
|---|---|
| gccccctaaa aaaaagagaa aggtcgagct gggaactgcg gcagaggagc agaagctgat | 4440 |
| ctcagaggag gacctgttta aaccaggagg cggttctggt ccaggtactg aagacgctga | 4500 |
| agctgttgct ttgggtttgg gtttgtctga cttcccatct gctggtaagg ctgttttgga | 4560 |
| cgacgaagac tctttcgttt ggccagctgc ttctttcgac atgggtgctt gttgggctgg | 4620 |
| tgctggtttc gctgacccag acccagcttg tatcttcttg aacttgccat gagcccatct | 4680 |
| tttttttgga cctaaattct tcatgaaaat atattacgag gcttattca gaagctttgg | 4740 |
| acttcttcgc cagaggtttg gtcaagtctc caatcaaggt tgtcggcttg tctaccttgc | 4800 |
| cagaaattta cgaaaagatg aaaagggtc aaatcgttgg tagatacgtt gttgacactt | 4860 |
| ctaaataagc gaatttctta tgatttatga tttttattat taaataagtt ataaaaaaaa | 4920 |
| taagtgtata caaattttaa agtgactctt aggttttaaa acgaaaattc ttattcttga | 4980 |
| gtaactcttt cctgtaggtc aggttgcttt ctcaggtata gcatgaggtc gctcttattg | 5040 |
| accacacctc taccgccgg tcgaaattcc cctaccctat gaacatattc cattttgtaa | 5100 |
| tttcgtgtcg cgttgcgtgt aaaacatcct ctcattcaag acagggtttt ctaaaagcaa | 5160 |
| taggggtagt ttaataattc ttatataatc atcatataca ctattttag ttcttaattc | 5220 |
| tttaatacaa acttattaat gtgctctcca ttgatctctt aatcaggagg cgatatatac | 5280 |
| cggaagcggt gtacttttct tcacctctta ctcaactatg ttgatgtgca agtttaacca | 5340 |
| ctcgtcgata ttatctattg ctataacgaa aactttattc gagttcacag tgaaaaactt | 5400 |
| cagcacattt atggaagatc taagcaaaat ggagaacgcc agtagatgcg aacaacaaac | 5460 |
| tttatcaaat ttgaaatacc actgctttga taagctatag cttggcgtaa tcatggtcat | 5520 |
| agctgtttcc tgtgtgaaat tgttatccgc tcacaattcc acacaacata cgagccggaa | 5580 |
| gcataaagtg taaagcctgg ggtgcctaat gagtgagcta actcacatta attgcgttgc | 5640 |
| gctcactgcc cgctttccag tcgggaaacc tgtcgtgcca gctgcattaa tgaatcggcc | 5700 |
| aacgcgcggg gagaggcggt ttgcgtattg gcgctcttc cgcttcctcg ctcactgact | 5760 |
| cgctgcgctc ggtcgttcgg ctgcggcgag cggtatcagc tcactcaaag gcggtaatac | 5820 |
| ggttatccac agaatcaggg gataacgcag gaaagaacat gtgagcaaaa ggccagcaaa | 5880 |
| aggccaggaa ccgtaaaaag gccgcgttgc tggcgttttt ccataggctc cgcccccctg | 5940 |
| acgagcatca aaaaatcga cgctcaagtc agaggtggcg aaacccgaca ggactataaa | 6000 |
| gataccaggc gtttccccct ggaagctccc tcgtgcgctc tcctgttccg accctgccgc | 6060 |
| ttaccggata cctgtccgcc tttctccctt cgggaagcgt ggcgctttct catagctcac | 6120 |
| gctgtaggta tctcagttcg gtgtaggtcg ttcgctccaa gctgggctgt gtgcacgaac | 6180 |
| cccccgttca gcccgaccgc tgcgccttat ccggtaacta tcgtcttgag tccaacccgg | 6240 |
| taagacacga cttatcgcca ctggcagcag ccactggtaa caggattagc agagcgaggt | 6300 |
| atgtaggcgg tgctacagag ttcttgaagt ggtggcctaa ctacggctac actagaagaa | 6360 |
| cagtatttgg tatctgcgct ctgctgaagc cagttacctt cggaaaaaga gttggtagct | 6420 |
| cttgatccgg caaacaaacc accgctggta gcggtggttt ttttgtttgc aagcagcaga | 6480 |
| ttacgcgcag aaaaaaagga tctcaagaag atcctttgat cttttctacg ggtctgacg | 6540 |
| ctcagtggaa cgaaaactca cgttaaggga ttttggtcat gagattatca aaaaggatct | 6600 |
| tcacctagat ccttttaaat taaaaatgaa gttttaaatc aatctaaagt atatatgagt | 6660 |
| aaacttggtc tgacagttac caatgcttaa tcagtgaggc acctatctca gcgatctgtc | 6720 |
| tatttcgttc atccatagtt gcctgactcc ccgtcgtgta gataactacg atacgggagg | 6780 |

-continued

```
gcttaccatc tggccccagt gctgcaatga taccgcgaga cccacgctca ccggctccag    6840
atttatcagc aataaaccag ccagccggaa gggccgagcg cagaagtggt cctgcaactt    6900
tatccgcctc catccagtct attaattgtt gccgggaagc tagagtaagt agttcgccag    6960
ttaatagttt gcgcaacgtt gttgccattg ctacaggcat cgtggtgtca cgctcgtcgt    7020
ttggtatggc ttcattcagc tccggttccc aacgatcaag gcgagttaca tgatccccca    7080
tgttgtgcaa aaaagcggtt agctccttcg gtcctccgat cgttgtcaga agtaagttgg    7140
ccgcagtgtt atcactcatg gttatggcag cactgcataa ttctcttact gtcatgccat    7200
ccgtaagatg cttttctgtg actggtgagt actcaaccaa gtcattctga aatagtgta    7260 tgcggcgacc gagttgctct tgcccggcgt caatacggga taataccgcg ccacatagca    7320
gaactttaaa agtgctcatc attggaaaac gttcttcggg gcgaaaactc tcaaggatct    7380
taccgctgtt gagatccagt tcgatgtaac ccactcgtgc acccaactga tcttcagcat    7440
cttttacttt caccagcgtt tctgggtgag caaaaacagg aaggcaaaat gccgcaaaaa    7500
agggaataag ggcgacacgg aaatgttgaa tactcatact cttcctttt caatattatt     7560 gaagcattta tcagggttat tgtctcatga gcggatacat atttgaatgt atttagaaaa    7620
ataaacaaat aggggttccg cgcacatttc cccgaaaagt gccacctgac gtctaagaaa    7680
ccattattat catgacatta acctataaaa ataggcgtat cacgaggccc tttcgtc       7737
```

<210> SEQ ID NO 64
<211> LENGTH: 10004
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1458)..(2224)
<223> OTHER INFORMATION: a, c, t, g, unknown or other
<220> FEATURE:
<221> NAME/KEY: modified_base
<222> LOCATION: (2945)..(2974)
<223> OTHER INFORMATION: a, c, t, g, unknown or other

<400> SEQUENCE: 64

```
tgcatgcctg caggtcgaga tccgggatcg aagaaatgat ggtaaatgaa ataggaaatc      60
aaggagcatg aaggcaaaag acaaatataa gggtcgaacg aaaaataaag tgaaaagtgt    120
tgatatgatg tatttggctt tgcggcgccg aaaaaacgag tttacgcaat tgcacaatca    180
tgctgactct gtggcggacc cgcgctcttg ccggcccggc gataacgctg ggcgtgaggc    240
tgtgcccggc ggagtttttt gcgcctgcat tttccaaggt ttaccctgcg ctaaggggcg    300
agattggaga agcaataaga atgccggttg gggttgcgat gatgacgacc acgacaactg    360
gtgtcattat ttaagttgcc gaaagaacct gagtgcattt gcaacatgag tatactagaa    420
gaatgagcca agacttgcga gacgcgagtt tgccggtggt gcgaacaata gagcgaccat    480
gaccttgaag gtgagacgcg cataaccgct agagtacttt gaagaggaaa cagcaatagg    540
gttgctacca gtataaatag acaggtacat acaacactgg aaatggttgt ctgtttgagt    600
acgctttcaa ttcatttggg tgtgcacttt attatgttac aatatggaag ggaactttac    660
acttctccta tgcacatata ttaatcataa gttgaattcg acaggttatc agcaacaaca    720
cagtcatatc cattctcaat tagctctacc acagtgtgtg aaccaatgta tccagcacca    780
cctgtaacca aaacaatttt acctcgatcg agtttaccac tccctatcag tgatagagaa    840
```

```
aagttaaagt cgagtttacc actccctatc agtgatagag aacagtcaaa gtcgagttta      900
ccactcccta tcagtgatag agaaaagtta aagtcgagtt taccactccc tatcagtgat      960
agagaaaagt taaagtcgag tttaccactc cctatcagtg atagagaaca gtcaaagtcg     1020
agtttaccac tccctatcag tgatagagaa ttgtgaaagt cgagtttacc actccctatc     1080
agtgatagag aaaagtccaa gtcgagctcg gtaccctatg gcatgcatgt ggatgataat     1140
gcgattagtt ttttagcctt atttctgggg taattaatca gcgaagcgat gattttgat      1200 ctattaacag atatataaat ggaaaagctg cataaccact ttaactaata ctttcaacat     1260
tttcagtttg tattacttct tattcaaatg tcataaaagt atcaacaaaa aattgttaat     1320
atacctctat actttaacgt caaggagaaa aaactataat gcaaaatct cattcagaag      1380 aagtgattgt acctgagttc aattctagcg caaaggaatt accaagacca ttggccgaaa     1440
agtgcccgag cggtgctnnn nnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn     1560
nnnnnnnnnn nnnnnnnnnn nnnnnnnnnn nnnnnnnnnn nnnnnnnnnn nnnnnnnnnn     1620
nnnnnnnnnn nnnnnnnnnn nnnnnnnnnn nnnnnnnnnn nnnnnnnnnn nnnnnnnnnn     1680
nnnnnnnnnn nnnnnnnnnn nnnnnnnnnn nnnnnnnnnn nnnnnnnnnn nnnnnnnnnn     1740
nnnnnnnnnn nnnnnnnnnn nnnnnnnnnn nnnnnnnnnn nnnnnnnnnn nnnnnnnnnn     1800
nnnnnnnnnn nnnnnnnnnn nnnnnnnnnn nnnnnnnnnn nnnnnnnnnn nnnnnnnnnn     1860
nnnnnnnnnn nnnnnnnnnn nnnnnnnnnn nnnnnnnnnn nnnnnnnnnn nnnnnnnnnn     1920
nnnnnnnnnn nnnnnnnnnn nnnnnnnnnn nnnnnnnnnn nnnnnnnnnn nnnnnnnnnn     1980
nnnnnnnnnn nnnnnnnnnn nnnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn     2100
nnnnnnnnnn nnnnnnnnnn nnnnnnnnnn nnnnnnnnnn nnnnnnnnnn nnnnnnnnnn     2160
nnnnnnnnnn nnnnnnnnnn nnnnnnnnnn nnnnnnnnnn nnnnnnnnnn nnnnnnnnnn     2220
nnnntaatag catcatgtaa ttagttatgt cacgcttaca ttcacgccct ccccccacat      2280
ccgctctaac cgaaaaggaa ggagttagac aacctgaagt ctaggtccct atttattttt     2340
ttatagttat gttagtatta agaacgttat ttatatttca aattttcctt tttttttctgt    2400 acagacgcgt gtacgcatgt aacattatac tgaaaacctt gcttgagaag gttttgggac     2460
gctcgaaggc tttaatttga tacggattag aagccgccga gcgggcgaca gccctccgac     2520
ggaagactct cctccgtgcg tcctcgtctt caccggtcgc gttcctgaaa cgcagatgtg     2580
cctcgcgccg cactgctccg aacaataaag attctacaat actagctttt atggttatga     2640
agaggaaaaa ttggcagtaa cctggccca caaaccttca aattaacgaa tcaaattaac      2700
aaccatagga tgataatgcg attagttttt tagccttatt tctggggtaa ttaatcagcg     2760
aagcgatgat ttttgatcta ttaacagata tataaatgga aaagctgcat aaccacttta    2820
actaatactt tcaacatttt cagtttgtat tacttcttat tcaaatgtca taaaagtatc     2880
aacaaaaaat tgttaatata cctctatact ttaacgtcaa ggagaaaaaa ctataatggt     2940
taatnnnnnn nnnnnnnnnn nnnnnnnnnn nnnntaatag acaagctacg ttgaaacaag     3000
aacccgcctc ctttcagaac tcacttacgg tacattagcg atgactacga cttcattact     3060 cttttttttca gaaaattttta atcaatattc atttattcta cgaacagtct ccttcacctt   3120
agtttctttc tctgctcctt tgaaactatt attgtatttg gtacatttta gagaaaataa     3180
```

```
aacatatata gaacaatgag aaggtacgta atttcttagc taattatttg taatcaatta    3240
agcgtcttcc tttagcaaag cgtctctctt ttcagcaact ctttgagctc ttctgtcacg    3300
agcagctctg ttcttcaatc ttctagcttc agcttcttcg ttcaaagcct tttcacgttg    3360
agcatcagcc ttagcttgaa taatgtgttc aaccaaagct ctcttgtgct tgaaggcgtt    3420
acccttggat tccttgtaca aaacgtggta caaatgcttg tcaatcttac cagcgtcacg    3480
gtacttggcc aataatcttc tcaagacacg taatcttctg atccagacga cttgggatgg    3540
taaacgagct tctctagtac cctttctctt accgtaacca ctgtgacgac cttctctctt    3600
ggattgagca tgggctctag ttctagattt agagtggaca gtaacggcct tcttgacgat    3660
ggttccgttc ttgaccaatt ttctaatggc atttctagag ttggcttggg caatttcaga    3720
agtttcgttt gggtctaacc aaacctttct cttaccaaca ccgacaacag aagcggcaag    3780
tctcttttga gtacgcaagt tagccctgtg aaaaaaagtt tttgcagatt tatttgcata    3840
ttgatgttag taaagttgct tcatttttaa aatcctgaaa cctaacagta aagagcatat    3900
tcgcaaaggt taatgaatta ctttatctat caatcgaatt aacgcttgca ggaacagaca    3960
cgtaccattg ctgcgataat tctatagttt gtaataaacg cggcaattcg tacaagcttg    4020
aaatttatct gaggttcttc tatggatgtt gctaccaact atgcgaccac cggatgctgt    4080
atcctcaatt ttttccttta tctatttctc tccaaaggat gacattcata acatatttaa    4140
agataaatct tgtgaaaggt tcaaaattta gtatcactgt taaacataca ttttcctcta    4200
atttattggt gactttttat tcgatttggt gaaaagatct atcaagtagc actagcgtat    4260
aaatgtacta ttagtatccc gatgtagata cagtaagctt tggacttctt cgccagaggt    4320
ttggtcaagt ctccaatcaa ggttgtcggc ttgtctacct tgccagaaat ttacgaaaag    4380
atggaaaagg tcaaatcgt tggtagatac gttgttgaca cttctaaata agcgaatttc    4440
ttatgattta tgattttat tattaaataa gttataaaaa aataagtgt atacaaattt    4500 taaagtgact cttaggtttt aaaacgaaaa ttcttattct tgagtaactc tttcctgtag    4560
gtcaggttgc tttctcaggt atagcatgag gtcgctctta ttgaccacac ctctaccggc    4620
cggtcgaaat tcccctaccc tatgaacata ttccattttg taatttcgtg tcgtttctat    4680
tatgaatttc atttataaag tttatgtaca aatatcataa aaaaagagaa tcttttttaag    4740 caaggatttt cttaacttct tcggcgacag catcaccgac ttcggtggta ctgttggaac    4800
cacctaaatc accagttctg atacctgcat ccaaaacctt tttaactgca tcttcaatgg    4860
ccttaccttc ttcaggcaag ttcaatgaca atttcaacat cattgcagca gacaagatag    4920
tggcgatagg gttgacctta ttctttggca aatctggagc agaaccgtgg catggttcgt    4980
acaaaccaaa tgcggtgttc ttgtctggca aagaggccaa ggacgcagat ggcaacaaac    5040
ccaaggaacc tgggataacg gaggcttcat cggagatgat atcaccaaac atgttgctgg    5100
tgattataat accatttagg tgggttgggt tcttaactag gatcatggcg gcagaatcaa    5160
tcaattgatg ttgaaccttc aatgtaggaa attcgttctt gatggtttcc tccacagttt    5220
ttctccataa tcttgaagag gccaaaacat tagctttatc caaggaccaa ataggcaatg    5280
gtggctcatg ttgtagggcc atgaaagcgg ccattcttgt gattctttgc acttctggaa    5340
cggtgtattg ttcactatcc caagcgacac catcaccatc gtcttccttt ctcttaccaa    5400
agtaaatacc tcccactaat tctctgacaa caacgaagtc agtacctta gcaaattgtg    5460 gcttgattgg agataagtct aaaagagagt cggatgcaaa gttacatggt cttaagttgg    5520
cgtacaattg aagttcttta cggatttta gtaaaccttg ttcaggtcta acactacctg    5580
```

```
tacccattt aggaccaccc acagcaccta acaaaacggc atcagccttc ttggaggctt    5640
ccagcgcctc atctggaagt gggacacctg tagcttcgat agcagcacca ccaattaaat    5700
gattttcgaa atcgaacttg acattggaac gaacatcaga aatagcttta agaaccttaa    5760
tggcttcggc tgtgatttct tgaccaacgt ggtcacctgg caaaacgacg atcttcttag    5820
gggcagacat tagaatggta tatccttgaa atatatatat atattgctga aatgtaaaag    5880
gtaagaaaag ttagaaagta agacgattgc taaccaccta ttggaaaaaa caataggtcc    5940
ttaaataata ttgtcaactt caagtattgt gatgcaagca tttagtcatg aacgcttctc    6000
tattctatat gaaaagccgg ttccggcgct ctcacctttc cttttctcc caattttca     6060 gttgaaaaag gtatatgcgt caggcgacct ctgaaattaa caaaaattt ccagtcatcg     6120 aatttgattc tgtgcgatag cgcccctgtg tgttctcgtt atgttgagga aaaaataat    6180 ggttgctaag agattcgaac tcttgcatct tacgatacct gagtattccc acagttgggg    6240
gatctcgact ctagctagag gatcaattcg taatcatgtc atagctgttt cctgtgtgaa    6300
attgttatcc gctcacaatt ccacacaaca tacgagccgg aagcataaag tgtaaagcct    6360
ggggtgccta atgagtgagc taactcacat taattgcgtt gcgctcactg cccgcttcc    6420 agtcgggaaa cctgtcgtgc cagctgataa cttcgtataa tgtatgctat acgaagttat    6480
taggtctgaa gaggagttta cgtccagcca agctagcttg gctgcaggtc gagcggccgc    6540
gatccggaac ccttaatata acttcgtata atgtatgcta tacgaagtta tcagctgcat    6600
taatgaatcg gccaacgcgc ggggagaggc ggtttgcgta ttgggcgctc ttccgcttcc    6660
tcgctcactg actcgctgcg ctcggtcgtt cggctgcggc gagcggtatc agctcactca    6720
aaggcggtaa tacggttatc cacagaatca ggggataacg caggaaagaa catgtgagca    6780
aaaggccagc aaaaggccag gaaccgtaaa aaggccgcgt tgctggcgtt tttccatagg    6840
ctccgccccc ctgacgagca tcacaaaaat cgacgctcaa gtcagaggtg gcgaaacccg    6900
acaggactat aaagatacca ggcgtttccc cctggaagct ccctcgtgcg ctctcctgtt    6960
ccgaccctgc cgcttaccgg atacctgtcc gcctttctcc cttcgggaag cgtggcgctt    7020
tctcatagct cacgctgtag gtatctcagt tcggtgtagg tcgttcgctc caagctgggc    7080
tgtgtgcacg aaccccccgt tcagcccgac cgctgcgcct tatccggtaa ctatcgtctt    7140
gagtccaacc cggtaagaca cgacttatcg ccactggcag cagccactgg taacaggatt    7200
agcagagcga ggtatgtagg cggtgctaca gagttcttga agtggtggcc taactacggc    7260
tacactagaa gaacagtatt tggtatctgc gctctgctga gccagttac cttcggaaaa     7320 agagttggta gctcttgatc cggcaaacaa accaccgctg gtagcggtgg ttttttgtt     7380 tgcaagcagc agattacgcg cagaaaaaaa ggatctcaag aagatccttt gatcttttct    7440
acggggtctg acgctcagtg gaacgaaaac tcacgttaag ggattttggt catgagatta    7500
tcaaaaagga tcttcaccta gatccttta aattaaaaat gaagttttaa atcaatctaa     7560
agtatatatg agtaaacttg gtctgacagt taccaatgct taatcagtga ggcacctatc    7620
tcagcgatct gtctatttcg ttcatccata gttgcctgac tccccgtcgt gtagataact    7680
acgatacggg agggcttacc atctggcccc agtgctgcaa tgataccgcg agacccacgc    7740
tcaccggctc cagatttatc agcaataaac cagccagccg aagggccga gcgcagaagt     7800 ggtcctgcaa cttatccgc ctccatccag tctattaatt gttgccggga agctagagta    7860
agtagttcgc cagttaatag tttgcgcaac gttgttgcca ttgctacagg catcgtggtg    7920
```

```
tcacgctcgt cgtttggtat ggcttcattc agctccggtt cccaacgatc aaggcgagtt    7980
acatgatccc ccatgttgtg caaaaaagcg gttagctcct tcggtcctcc gatcgttgtc    8040
agaagtaagt tggccgcagt gttatcactc atggttatgg cagcactgca taattctctt    8100
actgtcatgc catccgtaag atgcttttct gtgactggtg agtactcaac caagtcattc    8160
tgagaatagt gtatgcggcg accgagttgc tcttgcccgg cgtcaatacg ggataatacc    8220
gcgccacata gcagaacttt aaaagtgctc atcattggaa aacgttcttc ggggcgaaaa    8280
ctctcaagga tcttaccgct gttgagatcc agttcgatgt aacccactcg tgcacccaac    8340
tgatcttcag catcttttac tttcaccagc gtttctgggt gagcaaaaac aggaaggcaa    8400
aatgccgcaa aaaagggaat aagggcgaca cggaaatgtt gaatactcat actcttcctt    8460
tttcaatatt attgaagcat ttatcagggt tattgtctca tgagcggata catatttgaa    8520
tgtatttaga aaaataaaca aataggggtt ccgcgcacat ttccccgaaa agtgccacct    8580
gacgtctaag aaaccattat tatcatgaca ttaacctata aaaataggcg tatcacgagg    8640
cccttttcgtc tcgcgcgttt cggtgatgac ggtgaaaacc tctgacacat gcagctcccg    8700
gagacggtca cagcttgtct gtaagcggat gccgggagca gacaagcccg tcagggcgcg    8760
tcagcgggtg ttggcgggtg tcggggctgg cttaactatg cggcatcaga gcagattgta    8820
ctgagagtgc accataacgc atttaagcat aaacacgcac tatgccgttc ttctcatgta    8880
tatatatata caggcaacac gcagatatag gtgcgacgtg aacagtgagc tgtatgtgcg    8940
cagctcgcgt tgcattttcg gaagcgctcg ttttcggaaa cgctttgaag ttcctattcc    9000
gaagttccta ttctctagct agaaagtata ggaacttcag agcgcttttg aaaaccaaaa    9060
gcgctctgaa gacgcacttt caaaaaacca aaaacgcacc ggactgtaac gagctactaa    9120
aatattgcga ataccgcttc cacaaacatt gctcaaaagt atctctttgc tatatatctc    9180
tgtgctatat ccctatataa cctacccatc cacctttcgc tccttgaact tgcatctaaa    9240
ctcgacctct acatttttta tgtttatctc tagtattact ctttagacaa aaaaattgta    9300
gtaagaacta ttcatagagt gaatcgaaaa caatacgaaa atgtaaacat ttcctatacg    9360
tagtatatag agacaaaata gaagaaaccg ttcataattt tctgaccaat gaagaatcat    9420
caacgctatc actttctgtt cacaaagtat gcgcaatcca catcggtata gaatataatc    9480
ggggatgcct ttatcttgaa aaaatgcacc cgcagcttcg ctagtaatca gtaaacgcgg    9540
gaagtggagt caggcttttt ttatggaaga gaaaatagac accaaagtag ccttcttcta    9600
accttaacgg acctacagtg caaaaagtta tcaagagact gcattataga gcgcacaaag    9660
gagaaaaaaa gtaatctaag atgctttgtt agaaaaatag cgctctcggg atgcattttt    9720
gtagaacaaa aaagaagtat agattctttg ttggtaaaat agcgctctcg cgttgcattt    9780
ctgttctgta aaaatgcagc tcagattctt tgtttgaaaa attagcgctc tcgcgttgca    9840
tttttgtttt acaaaaatga agcacagatt cttcgttggt aaaatagcgc tttcgcgttg    9900
catttctgtt ctgtaaaaat gcagctcaga ttctttgttt gaaaaattag cgctctcgcg    9960
ttgcattttt gttctacaaa atgaagcaca gatgcttcgt tgct                    10004
```

<210> SEQ ID NO 65
<211> LENGTH: 7781
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
cggtgcgggc ctcttcgcta ttacgccaga tccttttgtt gtttccgggt gtacaatatg      60
gacttcctct tttctggcaa ccaaacccat acatcgggat tcctataata ccttcgttgg     120
tctccctaac atgtaggtgg cggaggggag atatacaata gaacagatac cagacaagac     180
ataatgggct aaacaagact acaccaatta cactgcctca ttgatggtgg tacataacga     240
actaatactg tagccctaga cttgatagcc atcatcatat cgaagtttca ctacccttt     300
tccatttgcc atctattgaa gtaataatag gcgcatgcaa cttcttttct ttttttttct     360
tttctctctc ccccgttgtt gtctcaccat atccgcaatg acaaaaaaat gatggaagac     420
actaaaggaa aaaattaacg acaaagacag caccaacaga tgtcgttgtt ccagagctga     480
tgaggggtat ctcgaagcac acgaaacttt ttccttcctt cattcacgca cactactctc     540
taatgagcaa cggtatacgg ccttccttcc agttacttga atttgaaata aaaaaaagtt     600
tgctgtcttg ctatcaagta taaatagacc tgcaattatt aatcttttgt ttcctcgtca     660
ttgttctcgt tcccttcctt ccttgtttct ttttctgcac aatatttcaa gctataccaa     720
gcatacaatc aactccaagc tttgcaaaga tggggtcaaa ggccgagcta atcccagagc     780
cccctaaaaa aaagagaaag gtcgagctgg gaactgcggc agagtacccg tatgatgtac     840
cggactatgc cggaggtatg tctagattgg acaagtctaa ggttatcaac tctgctttgg     900
aattgttgaa cgaagttggt atcgaaggtt tgactactag aaagttggct caaaagttgg     960
gtgttgaaca accaactttg tactggcacg ttaagaacaa gagagctttg ttggacgctt    1020
tggctatcga aatgttggac agacaccaca ctcacttctg tccattggaa ggtgaatctt    1080
ggcaagactt cttgagaaac aacgctaagt cttttcagatg tgctttgttg tctcacagag    1140
acggtgctaa ggttcacttg ggtactagac caactgaaaa gcaatacgaa actttggaaa    1200
accaattggc tttcttgtgt caacaaggtt tctctttgga aaacgctttg tacgctttgt    1260
ctgctgttgg tcacttcact ttgggttgtg ttttggaaga ccaagaacac caagttgcta    1320
aggaagaaag agaaactcca actactgact ctatgccacc attgttgaga caagctatcg    1380
aattgttcga ccaccaaggt gctgaaccag cttttcttgtt cggtttggaa ttgatcatct    1440
gtggtttgga aaagcaattg aagtgtgaat ctggttctgg gcaaccatct ttgagatctg    1500
aatacgaata cccagttttc tctcacgttc aagctggtat gttctctcca gaattgagaa    1560
ctttcactaa gggtgacgct gaaagatggg tttctggtcc aggtactgaa gacgctgaag    1620
ctgttgcttt gggttttgggt ttgtctgact cccatctgc tggtaaggct gttttggacg    1680
acgaagactc tttcgtttgg ccagctgctt cttcgacat gggtgcttgt tgggctggtg    1740
ctggtttcgc tgacccagac ccagcttgta tcttcttgaa cttgccatga gcccatcttt    1800
ttttttggacc taaattcttc atgaaaatat attacgaggg cttattcaga agctttggac    1860
ttcttcgctt gcagccaagc taattccggg cgaatttctt atgatttatg attttattat    1920
ttaaataagt tataaaaaaa ataagtgtat acaaatttta aagtgactct taggttttaa    1980
aacgaaaatt cttattcttg agtaactctt tcctgtaggt caggttgctt tctcaggtat    2040
agcatgaggt cgctcttatt gaccacacct ctaccggcat gcaagcttgg cgtaatcatg    2100
gtcatagctg tttcctgtgt gaaattgtta tccgctcaca attccacaca acatacgagc    2160
cggaagcata aagtgtaaag cctggggtgc ctaatgagtg agctaactca cattaattgc    2220
gttgcgctca ctgcccgctt tccagtcggg aaacctgtcg tgccagctgc attaatgaat    2280
cggccaacgc gcggggagag gcggtttgcg tattgggcgc tcttccgctt cctcgctcac    2340
```

```
tgactcgctg cgctcggtcg ttcggctgcg gcgagcggta tcagctcact caaaggcggt    2400
aatacggtta tccacagaat caggggataa cgcaggaaag aacatgtgag caaaaggcca    2460
gcaaaaggcc aggaaccgta aaaaggccgc gttgctggcg ttttcccata ggctccgccc    2520
ccctgacgag catcacaaaa atcgacgctc aagtcagagg tggcgaaacc cgacaggact    2580
ataaagatac caggcgtttc ccctggaag ctccctcgtg cgctctcctg ttccgaccct     2640
gccgcttacc ggatacctgt ccgcctttct cccttcggga agcgtggcgc tttctcatag    2700
ctcacgctgt aggtatctca gttcggtgta ggtcgttcgc tccaagctgg gctgtgtgca    2760 cgaaccccc gttcagcccg accgctgcgc cttatccggt aactatcgtc ttgagtccaa     2820
cccggtaaga cacgacttat cgccactggc agcagccact ggtaacagga ttagcagagc    2880
gaggtatgta ggcggtgcta cagagttctt gaagtggtgg cctaactacg gctacactag    2940
aagaacagta tttggtatct gcgctctgct gaagccagtt accttcggaa aaagagttgg    3000
tagctcttga tccggcaaac aaaccaccgc tggtagcggt ggttttttg tttgcaagca     3060 gcagattacg cgcagaaaaa aaggatctca agaagatcct ttgatctttt ctacggggtc    3120
tgacgctcag tggaacgaaa actcacgtta agggattttg gtcatgagat tatcaaaaag    3180
gatcttcacc tagatccttt taaattaaaa atgaagtttt aaatcaatct aaagtatata    3240
tgagtaacct gaggctatgg cagggcctgc cgccccgacg ttggctgcga gccctgggcc    3300
ttcacccgaa cttgggggt ggggtgggga aaggaagaa acgcgggcgt attggcccca     3360
atggggtctc ggtggggtat cgacagagtg ccagccctgg gaccgaaccc cgcgtttatg    3420
aacaaacgac ccaacaccgt gcgttttatt ctgtcttttt attgccgtca tagcgcgggt    3480
tccttccggt attgtctcct tccgtgtttc agttagcctc ccctagggt gggcgaagaa     3540 ctccagcatg agatccccgc gctggaggat catccagccg gcgtcccgga aaacgattcc    3600
gaagcccaac ctttcataga aggcggcggt ggaatcgaaa tctcgtgatg gcaggttggg    3660
cgtcgcttgg tcggtcattt cgaaccccag agtcccgctc agaagaactc gtcaagaagg    3720
cgatagaagg cgatgcgctg cgaatcggga gcggcgatac cgtaaagcac gaggaagcgg    3780
tcagcccatt cgccgccaag ctcttcagca atatcacggg tagccaacgc tatgtcctga    3840
tagcggtccg ccacacccag ccggccacag tcgatgaatc cagaaaagcg gccattttcc    3900
accatgatat tcggcaagca ggcatcgcca tgagtcacga cgagatcctc gccgtcgggc    3960
atgctcgcct tgagcctggc gaacagttcg gctggcgcga ccctgatg ctcttcgtcc      4020 agatcatcct gatcgacaag accggcttcc atccgagtac gtgctcgctc gatgcgatgt    4080
ttcgcttggt ggtcgaatgg gcaggtagcc ggatcaagcg tatgcagccg ccgcattgca    4140
tcagccatga tggatacttt ctcggcagga gcaaggtgag atgacaggag atcctgcccc    4200
ggcacttcgc ccaatagcag ccagtccctt cccgcttcag tgacaacgtc gagcacagct    4260
gcgcaaggaa cgcccgtcgt ggccagccac gatagccgcg ctgcctcgtc ttgcagttca    4320
ttcagggcac cggacaggtc ggtcttgaca aaaagaaccg ggcgcccctg cgctgacagc    4380
cggaacacgg cggcatcaga gcagccgatt gtctgttgtg cccagtcata gccgaatagc    4440
ctctccaccc aagcggccgg agaacctgcg tgcaatccat cttgttcaat catactcttc    4500 cttttcaat attattgaag catttatcag ggttattgtc tcatgagcgg atacatattt     4560
gaatgtattt agaaaaataa acaaataggg gttccgcgca catttccccg aaaagtgcca    4620
cctgaacgaa gcatctgtgc ttcattttgt agaacaaaaa tgcaacgcga gagcgctaat    4680
```

-continued

```
ttttcaaaca aagaatctga gctgcatttt tacagaacag aaatgcaacg cgaaagcgct      4740
attttaccaa cgaagaatct gtgcttcatt tttgtaaaac aaaaatgcaa cgcgagagcg      4800
ctaatttttc aaacaaagaa tctgagctgc attttacag aacagaaatg caacgcgaga      4860
gcgctatttt accaacaaag aatctatact tcttttttgt tctacaaaaa tgcatcccga      4920
gagcgctatt tttctaacaa agcatcttag attactttt ttctcctttg tgcgctctat      4980
aatgcagtct cttgataact ttttgcactg taggtccgtt aaggttagaa gaaggctact      5040
ttggtgtcta ttttctcttc cataaaaaaa gcctgactcc acttcccgcg tttactgatt      5100
actagcgaag ctgcgggtgc atttttcaa gataaaggca tccccgatta tattctatac      5160
cgatgtggat tgcgcatact ttgtgaacag aaagtgatag cgttgatgat tcttcattgg      5220
tcagaaaatt atgaacggtt tcttctattt tgtctctata tactacgtat aggaaatgtt      5280
tacattttcg tattgttttc gattcactct atgaatagtt cttactacaa ttttttttgtc     5340 taaagagtaa tactagagat aaacataaaa aatgtagagg tcgagtttag atgcaagttc      5400
aaggagcgaa aggtggatgg gtaggttata tagggatata gcacagagat atatagcaaa      5460
gagatacttt tgagcaatgt tgtggaagc ggtattcgca atattttagt agctcgttac       5520
agtccggtgc gttttggtt ttttgaaagt gcgtcttcag agcgcttttg gttttcaaaa       5580
gcgctctgaa gttcctatac tttctagaga ataggaactt cggaatagga acttcaaagc      5640
gtttccgaaa cgagcgctt ccgaaaatgc aacgcgagct gcgcacatac agctcactgt       5700
tcacgtcgca cctatatctg cgtgttgcct gtatatatat atacatgaga agaacggcat      5760
agtgcgtgtt tatgcttaaa tgcgtactta tatgcgtcta tttatgtagg atgaaaggta     5820
gtctagtacc tcctgtgata ttatcccatt ccatgcgggg tatcgtatgc ttccttcagc     5880
actacccttt agctgttcta tatgctgcca ctcctcaatt ggattagtct catccttcaa     5940
tgctatcatt tccttgtgata ttggatcata ctaagaaacc attattatca tgacattaac    6000
ctataaaaat aggcgtatca cgaggccctt tcgtctcgcg cgtttcggtg atgacggtga    6060
aaacctctga cacatgcagc tcccggagac ggtcacagct tgtctgtaag cggatgccgg    6120
gagcagacaa gcccgtcagg gcgcgtcagc gggtgttggc gggtgtcggg gctggcttaa    6180
ctatgcggca tcagagcaga ttgtactgag agtgcaccat agatcaacga cattactata    6240 tataataat aggaagcatt taatagaaca gcatcgtaat atatgtgtac tttgcagtta    6300
tgacgccaga tggcagtagt ggaagatatt ctttattgaa aaatagcttg tcaccttacg    6360
tacaatcttg atccggagct tttctttttt tgccgattaa gaattaattc ggtcgaaaaa    6420
agaaaaggag agggccaaga gggagggcat tggtgactat tgagcacgtg agtatacgtg    6480
attaagcaca caaaggcagc ttggagtatg tctgttatta atttcacagg tagttctggt    6540
ccattggtga agtttgcgg cttgcagagc acagaggccg cagaatgtgc tctagattcc     6600
gatgctgact tgctgggtat tatatgtgtg cccaatagaa agagaacaat tgacccggtt    6660
attgcaagga aatttcaag tcttgtaaaa gcatataaaa atagttcagg cactccgaaa     6720
tacttggttg gcgtgtttcg taatcaacct aaggaggatg ttttggctct ggtcaatgat    6780
tacggcatta atatcgtcca actgcatgga gatgagtcgt ggcaagaata ccaagagttc    6840
ctcggtttgc cagttattaa aagactcgta tttccaaaag actgcaacat actactcagt    6900
gcagcttcac agaaacctca ttcgtttatt cccttgtttg attcagaagc aggtgggaca    6960
ggtgaacttt tggattggaa ctcgatttct gactgggttg gaaggcaaga gagccccgaa    7020
agcttacatt ttatgttagc tggtggactg acgccagaaa atgttggtga tgcgcttaga    7080
```

```
ttaaatggcg ttattggtgt tgatgtaagc ggaggtgtgg agacaaatgg tgtaaaagac    7140
tctaacaaaa tagcaaattt cgtcaaaaat gctaagaaat aggttattac tgagtagtat    7200
ttatttaagt attgtttgtg cacttgccga tctatgcggt gtgaaatacc gcacagatgc    7260
gtaaggagaa ataccgcat caggaaattg taagcgttaa tattttgtta aaattcgcgt     7320 taaattttg ttaaatcagc tcattttta accataggc cgaaatcggc aaaatcccctt     7380 ataaatcaaa agaatagacc gagatagggt tgagtgttgt tccagtttgg aacaagagtc    7440
cactattaaa gaacgtggac tccaacgtca aagggcgaaa aaccgtctat cagggcgatg    7500
gcccactacg tgaaccatca ccctaatcaa gttttttggg gtcgaggtgc cgtaaagcac    7560
taaatcggaa ccctaaaggg agcccccgat ttagagcttg acggggaaag ccggcgaacg    7620
tggcgagaaa ggaagggaag aaagcgaaag gagcgggcgc tagggcgctg gcaagtgtag    7680
cggtcacgct gcgcgtaacc accacacccg ccgcgcttaa tgcgccgcta cagggcgcgt    7740
ccattcgcca ttcaggctgc gcaactgttg ggaagggcga t                        7781
```

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Arg Arg Arg Arg Arg Arg Lys Arg Leu Gly Val Arg Leu Arg Val
1               5                   10                  15

Ser Arg Met Leu
            20

<210> SEQ ID NO 67
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Gln Lys Ile Trp Phe Gln Asn Arg Arg Met Lys Trp Lys Lys Arg
1               5                   10                  15

Leu Gly Val Arg Leu Arg Val Ser Arg Met Leu
            20                  25

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-2-(7'-octenyl)alanine
<220> FEATURE:
<221> NAME/KEY: MISC_FEATURE
<222> LOCATION: (2)..(9)
<223> OTHER INFORMATION: Crosslink between residues
<220> FEATURE:
<221> NAME/KEY: MOD_RES
<222> LOCATION: (9)..(9)
<223> OTHER INFORMATION: 2-(4'-pentenyl)alanine

```
<400> SEQUENCE: 68

Ala Ala Lys Arg Leu Gly Val Arg Ala Arg Val Ser Arg Met Leu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Met Arg Ser Val Arg Leu Arg Val Gly Leu Arg Lys Ala Gly
1               5                   10                  15

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Thr, Lys, Arg or Gln
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (4)..(4)
<223> OTHER INFORMATION: Leu, Ile, Val, Phe, Met, Trp or Tyr
<220> FEATURE:
<221> NAME/KEY: MOD_RES
<222> LOCATION: (5)..(5)
<223> OTHER INFORMATION: Arg, Gly or Ser
<220> FEATURE:
<221> NAME/KEY: MOD_RES
<222> LOCATION: (6)..(6)
<223> OTHER INFORMATION: Leu, Ile, Val, Phe, Met, Trp or Tyr

<400> SEQUENCE: 70

Xaa Xaa Xaa Xaa Xaa Xaa
1               5

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (4)..(4)
<223> OTHER INFORMATION: Met or Val

<400> SEQUENCE: 71

Xaa Leu Gly Xaa
1

<210> SEQ ID NO 72
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Met or Val
<220> FEATURE:
<221> NAME/KEY: MOD_RES
<222> LOCATION: (6)..(6)
<223> OTHER INFORMATION: Leu, Ile, Val, Phe, Met, Ala, Trp or Tyr

<400> SEQUENCE: 72

Arg Leu Gly Val Xaa Xaa
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Thr, Lys, Arg or Gln
<220> FEATURE:
<221> NAME/KEY: MISC_FEATURE
<222> LOCATION: (1)..(2)
<223> OTHER INFORMATION: This region may encompass 1-2 residues
<220> FEATURE:
<221> NAME/KEY: MOD_RES
<222> LOCATION: (7)..(7)
<223> OTHER INFORMATION: Met or Val
<220> FEATURE:
<221> NAME/KEY: MOD_RES
<222> LOCATION: (8)..(8)
<223> OTHER INFORMATION: Leu, Ile, Val, Phe, Met, Ala, Trp or Tyr

<400> SEQUENCE: 73

Xaa Xaa Arg Leu Gly Val Xaa Xaa
1               5

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78
```

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82
<211> LENGTH: 339
<212> TYPE: PRT
<213> ORGANISM: Homo sapiens

<400> SEQUENCE: 82

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

-continued

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 83
<211> LENGTH: 730
<212> TYPE: PRT
<213> ORGANISM: Amanita bisporigera

<400> SEQUENCE: 83

Met Pro Pro Thr Pro Trp Ala Pro His Ser Tyr Pro Pro Thr Arg Arg
1               5                   10                  15

Ser Asp His Val Asp Val Tyr Gln Ser Ala Ser Arg Gly Glu Val Pro
            20                  25                  30

Val Pro Asp Pro Tyr Gln Trp Leu Glu Glu Asn Ser Asn Glu Val Asp
        35                  40                  45

Glu Trp Thr Thr Ala Gln Thr Ala Phe Thr Gln Gly Tyr Leu Asp Lys
    50                  55                  60

Asn Ala Asp Arg Gln Lys Leu Glu Glu Lys Phe Arg Ala Ser Lys Asp
65                  70                  75                  80

Tyr Val Lys Phe Ser Ala Pro Thr Leu Leu Asp Ser Gly His Trp Tyr
                85                  90                  95

Trp Phe Tyr Asn Ser Gly Val Gln Ser Gln Ala Val Leu Tyr Arg Ser
            100                 105                 110

Lys Lys Pro Val Leu Pro Asp Phe Gln Arg Gly Thr Arg Lys Val Gly
        115                 120                 125

Glu Val Tyr Phe Asp Pro Asn Val Leu Ser Ala Asp Gly Thr Ala Ile
    130                 135                 140

Met Gly Thr Cys Arg Phe Ser Pro Ser Gly Glu Tyr Phe Ala Tyr Ala
145                 150                 155                 160

Val Ser His Leu Gly Val Asp Tyr Phe Thr Ile Tyr Val Arg Pro Thr
                165                 170                 175

Ser Ser Ser Leu Ser Gln Ala Pro Glu Ala Glu Gly Gly Asp Gly Arg
            180                 185                 190

Leu Ser Asp Gly Val Lys Trp Cys Lys Phe Thr Thr Ile Thr Trp Thr
        195                 200                 205

Lys Asp Ser Lys Gly Phe Leu Tyr Gln Arg Tyr Pro Ala Arg Glu Ser
    210                 215                 220

Leu Val Ala Lys Asp Arg Asp Lys Asp Ala Met Val Cys Tyr His Arg
225                 230                 235                 240

Val Gly Thr Thr Gln Leu Glu Asp Ile Ile Val Gln Gln Asp Lys Glu
                245                 250                 255

Asn Pro Asp Trp Thr Tyr Gly Asp Ala Ser Glu Asp Gly Lys Tyr
            260                 265                 270

```
Ile Tyr Leu Val Val Tyr Lys Asp Ala Ser Lys Gln Asn Leu Leu Trp
            275                 280                 285

Val Ala Glu Phe Asp Lys Asp Gly Val Lys Pro Glu Ile Pro Trp Arg
    290                 295                 300

Lys Val Ile Asn Glu Phe Gly Asp Tyr His Val Ile Thr Asn His
305                 310                 315                 320

Gly Ser Leu Ile Tyr Val Lys Thr Asn Val Asn Ala Pro Gln Tyr Lys
                325                 330                 335

Val Val Thr Ile Asp Leu Ser Thr Gly Glu Pro Glu Ile Arg Asp Phe
                340                 345                 350

Ile Pro Glu Gln Lys Asp Ala Lys Leu Thr Gln Val Lys Cys Val Asn
            355                 360                 365

Lys Gly Tyr Phe Val Ala Ile Tyr Lys Arg Asn Val Lys Asp Glu Ile
    370                 375                 380

Tyr Leu Tyr Ser Lys Ala Gly Asp Gln Leu Ser Arg Leu Ala Ser Asp
385                 390                 395                 400

Phe Ile Gly Val Ala Ser Ile Thr Asn Arg Glu Lys Gln Pro His Ser
                405                 410                 415

Phe Leu Thr Phe Ser Gly Phe Asn Thr Pro Gly Thr Ile Ser Arg Tyr
                420                 425                 430

Asp Phe Thr Ala Pro Asp Thr Gln Arg Leu Ser Ile Leu Arg Thr Thr
            435                 440                 445

Lys Leu Asn Gly Leu Asn Ala Asp Phe Glu Ser Thr Gln Val Trp
    450                 455                 460

Tyr Lys Ser Lys Asp Gly Thr Lys Val Pro Met Phe Ile Val Arg His
465                 470                 475                 480

Lys Ser Thr Lys Phe Asp Gly Thr Ala Pro Ala Ile Gln Asn Gly Tyr
                485                 490                 495

Gly Gly Phe Ala Ile Thr Ala Asp Pro Phe Phe Ser Pro Ile Met Leu
                500                 505                 510

Thr Phe Met Gln Thr Tyr Gly Ala Ile Leu Ala Val Pro Asn Ile Arg
            515                 520                 525

Gly Gly Gly Glu Phe Gly Gly Glu Trp His Lys Ala Gly Arg Arg Glu
    530                 535                 540

Thr Lys Gly Asn Thr Phe Asp Asp Phe Ile Ala Ala Gln Phe Leu
545                 550                 555                 560

Val Lys Asn Lys Tyr Ala Ala Pro Gly Lys Val Ala Ile Thr Gly Ala
                565                 570                 575

Ser Asn Gly Gly Phe Leu Val Cys Gly Ser Val Arg Ala Pro Glu
            580                 585                 590

Gly Thr Phe Gly Ala Ala Val Ser Glu Gly Gly Val Ala Asp Leu Leu
    595                 600                 605

Lys Phe Asn Lys Phe Thr Gly Gly Met Ala Trp Thr Ser Glu Tyr Gly
610                 615                 620

Asn Pro Phe Ile Lys Glu Asp Phe Asp Phe Val Gln Ala Leu Ser Pro
625                 630                 635                 640

Val His Asn Val Pro Lys Asp Arg Val Leu Pro Ala Thr Leu Leu Met
                645                 650                 655

Thr Asn Ala Gly Asp Asp Arg Val Val Pro Met His Ser Leu Lys Phe
            660                 665                 670

Val Ala Asn Leu Gln Tyr Asn Val Pro Gln Asn Pro His Pro Leu Leu
    675                 680                 685

Ile Arg Val Asp Lys Ser Trp Leu Gly His Gly Phe Gly Lys Thr Thr
```

```
                  690                 695                 700
Asp Lys His Thr Lys Asp Ala Ala Asp Lys Trp Ser Phe Val Ala Gln
705                 710                 715                 720

Ser Leu Gly Leu Glu Trp Lys Thr Val Asp
                725                 730

<210> SEQ ID NO 84
<211> LENGTH: 730
<212> TYPE: PRT
<213> ORGANISM: Galerina marginata

<400> SEQUENCE: 84

Met Ser Ser Val Thr Trp Ala Pro Gly Asn Tyr Pro Ser Thr Arg Arg
1               5                   10                  15

Ser Asp His Val Asp Thr Tyr Gln Ser Ala Ser Lys Gly Glu Val Pro
                20                  25                  30

Val Pro Asp Pro Tyr Gln Trp Leu Glu Glu Ser Thr Asp Glu Val Asp
            35                  40                  45

Lys Trp Thr Thr Ala Gln Ala Asp Leu Ala Gln Ser Tyr Leu Asp Gln
50                  55                  60

Asn Ala Asp Ile Gln Lys Leu Ala Glu Lys Phe Arg Ala Ser Arg Asn
65                  70                  75                  80

Tyr Ala Lys Phe Ser Ala Pro Thr Leu Leu Asp Asp Gly His Trp Tyr
                85                  90                  95

Trp Phe Tyr Asn Arg Gly Leu Gln Ser Gln Ser Val Leu Tyr Arg Ser
                100                 105                 110

Asn Glu Pro Ala Leu Pro Asp Phe Ser Asn Gly Asp Asp Asn Val Gly
            115                 120                 125

Asp Val Phe Phe Asp Pro Asn Val Leu Ala Thr Asp Gly Ser Ala Gly
130                 135                 140

Met Val Leu Cys Lys Phe Ser Pro Asp Gly Lys Phe Phe Ala Tyr Ala
145                 150                 155                 160

Val Ser His Leu Gly Gly Asp Tyr Ser Thr Ile Tyr Ile Arg Ser Thr
                165                 170                 175

Ser Ser Pro Leu Ser Gln Ala Ser Ala Val Gln Gly Thr Asp Gly Arg
            180                 185                 190

Leu Ser Asp Glu Val Lys Trp Phe Lys Phe Ser Thr Ile Ile Trp Thr
            195                 200                 205

Lys Asp Ser Lys Gly Phe Leu Tyr Gln Arg Tyr Pro Ala Arg Glu Arg
210                 215                 220

His Glu Gly Thr Arg Ser Asp Arg Asn Ala Met Met Cys Tyr His Lys
225                 230                 235                 240

Val Gly Thr Thr Gln Glu Glu Asp Ile Ile Val Tyr Gln Asp Asn Glu
                245                 250                 255

His Pro Glu Trp Ile Tyr Gly Ala Asp Thr Ser Glu Asp Gly Lys Tyr
            260                 265                 270

Leu Tyr Leu Tyr Gln Phe Lys Asp Thr Ser Lys Lys Asn Leu Leu Trp
            275                 280                 285

Val Ala Glu Leu Asn Glu Asp Gly Val Lys Ser Gly Ile Gln Trp Arg
290                 295                 300

Lys Val Val Asn Glu Tyr Val Ala Asp Tyr Asn Val Ile Thr Asn His
305                 310                 315                 320

Gly Ser Leu Val Tyr Ile Lys Thr Asn Leu Asn Ala Pro Gln Tyr Lys
                325                 330                 335
```

Val Ile Thr Ile Asp Leu Ser Lys Asp Glu Pro Glu Ile Arg Asp Phe
            340                 345                 350

Ile Pro Glu Glu Lys Asp Ala Lys Leu Ala Gln Val Asn Cys Ala Asn
355                 360                 365

Glu Glu Tyr Phe Val Ala Ile Tyr Lys Arg Asn Val Lys Asp Glu Ile
        370                 375                 380

Tyr Leu Tyr Ser Lys Ala Gly Val Gln Leu Thr Arg Leu Ala Pro Asp
385                 390                 395                 400

Phe Val Gly Ala Ala Ser Ile Ala Asn Arg Gln Lys Gln Thr His Phe
                405                 410                 415

Phe Leu Thr Leu Ser Gly Phe Asn Thr Pro Gly Thr Ile Ala Arg Tyr
            420                 425                 430

Asp Phe Thr Ala Pro Glu Thr Gln Arg Phe Ser Ile Leu Arg Thr Thr
        435                 440                 445

Lys Val Asn Glu Leu Asp Pro Asp Asp Phe Glu Ser Thr Gln Val Trp
450                 455                 460

Tyr Glu Ser Lys Asp Gly Thr Lys Ile Pro Met Phe Ile Val Arg His
465                 470                 475                 480

Lys Ser Thr Lys Phe Asp Gly Thr Ala Ala Ile Gln Tyr Gly Tyr
                485                 490                 495

Gly Gly Phe Ala Thr Ser Ala Asp Pro Phe Phe Ser Pro Ile Ile Leu
            500                 505                 510

Thr Phe Leu Gln Thr Tyr Gly Ala Ile Phe Ala Val Pro Ser Ile Arg
        515                 520                 525

Gly Gly Gly Glu Phe Gly Glu Glu Trp His Lys Gly Gly Arg Arg Glu
530                 535                 540

Thr Lys Val Asn Thr Phe Asp Asp Phe Ile Ala Ala Ala Gln Phe Leu
545                 550                 555                 560

Val Lys Asn Lys Tyr Ala Ala Pro Gly Lys Val Ala Ile Asn Gly Ala
                565                 570                 575

Ser Asn Gly Gly Leu Leu Val Met Gly Ser Ile Val Arg Ala Pro Glu
            580                 585                 590

Gly Thr Phe Gly Ala Ala Val Pro Glu Gly Gly Val Ala Asp Leu Leu
        595                 600                 605

Lys Phe His Lys Phe Thr Gly Gly Gln Ala Trp Ile Ser Glu Tyr Gly
610                 615                 620

Asn Pro Ser Ile Pro Glu Glu Phe Asp Tyr Ile Tyr Pro Leu Ser Pro
625                 630                 635                 640

Val His Asn Val Arg Thr Asp Lys Val Met Pro Ala Thr Leu Ile Thr
                645                 650                 655

Val Asn Ile Gly Asp Gly Arg Val Val Pro Met His Ser Phe Lys Phe
            660                 665                 670

Ile Ala Thr Leu Gln His Asn Val Pro Gln Asn Pro His Pro Leu Leu
        675                 680                 685

Ile Lys Ile Asp Lys Ser Trp Leu Gly His Gly Met Gly Lys Pro Thr
690                 695                 700

Asp Lys Asn Val Lys Asp Ala Ala Asp Lys Trp Gly Phe Ile Ala Arg
705                 710                 715                 720

Ala Leu Gly Leu Glu Leu Lys Thr Val Glu
                725                 730

<210> SEQ ID NO 85
<211> LENGTH: 29
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 85

Lys Gln Ser Leu Arg Leu Gly Leu Ser Arg Leu Ala Arg Val Lys Arg
1               5                   10                  15

Leu His Pro Gly Ala Arg Arg Arg Arg Arg Arg Arg
            20                  25

<210> SEQ ID NO 86
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 86

Lys Gln Ser Leu Arg Leu Gly Gln Ser Arg Leu Ala Arg Val Lys Arg
1               5                   10                  15

Leu His Pro Gly Ala Arg Arg Arg Arg Arg Arg Arg
            20                  25

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<221> NAME/KEY: MOD_RES
<222> LOCATION: (4)..(4)
<223> OTHER INFORMATION: NMe-Leu
<220> FEATURE:
<221> NAME/KEY: MOD_RES
<222> LOCATION: (11)..(11)
<223> OTHER INFORMATION: NMe-Leu
<220> FEATURE:
<221> NAME/KEY: MOD_RES
<222> LOCATION: (14)..(14)
<223> OTHER INFORMATION: NMe-Val
<220> FEATURE:
<223> OTHER INFORMATION: C-term NH2

<400> SEQUENCE: 87

Lys Gln Ser Leu Arg Leu Gly Leu Ser Arg Leu Ala Arg Val Lys Arg
1               5                   10                  15

Leu His Pro Gly Cys
         20

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 88

Cys Arg Arg Arg Arg Arg Arg Arg
1               5

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 89

Lys Arg Arg Arg Arg Arg Arg Arg Lys Arg Leu Gly Val Arg Leu Arg
1               5                   10                  15

Val Ser Arg Met Leu
         20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 90

Lys Arg Arg Arg Arg Arg Arg Arg Lys Arg Leu Gly Gln Arg Leu Arg
1               5                   10                  15

Gln Ser Arg Met Leu
         20

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 91

Lys Arg Arg Arg Arg Arg Arg Arg Arg Leu Gly Met Ser Arg Arg Phe
1               5                   10                  15

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 92

Lys Arg Arg Arg Arg Arg Arg Arg Lys Arg Leu Gly Leu Arg Leu Gly
1               5                   10                  15

Val Ser Arg Arg Val
            20

<210> SEQ ID NO 93
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<223> OTHER INFORMATION: C-term NH2

<400> SEQUENCE: 93

Lys Arg Arg Arg Arg Arg Arg Arg Ser Leu Arg Leu Gly Leu Ser Arg
1               5                   10                  15

Leu Ala Arg Val Lys Arg Leu His Pro Gly
            20                  25

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 94

```
Arg Arg Arg Arg Arg Arg Arg Lys Arg Leu Gly Val Arg Leu Arg Val
1               5                   10                  15

Ser Arg Met Leu
            20

<210> SEQ ID NO 95
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 95

Arg Gln Lys Ile Trp Phe Gln Asn Arg Arg Met Lys Trp Lys Lys Arg
1               5                   10                  15

Leu Gly Val Arg Leu Arg Val Ser Arg Met Leu
            20                  25

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: D-2-(7'-octenyl)alanine
<220> FEATURE:
<221> NAME/KEY: MISC_FEATURE
<222> LOCATION: (2)..(9)
<223> OTHER INFORMATION: Crosslink between residues
<220> FEATURE:
<221> NAME/KEY: MOD_RES
<222> LOCATION: (9)..(9)
<223> OTHER INFORMATION: 2-(4'-pentenyl)alanine
<220> FEATURE:
<223> OTHER INFORMATION: C-term NH2

<400> SEQUENCE: 96

Ala Ala Lys Arg Leu Gly Val Arg Ala Arg Val Ser Arg Met Leu
1               5                   10                  15

<210> SEQ ID NO 97
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Gly Asp Ala Glu Arg Trp Val Ser Gly Pro Gly Ala Pro Leu Leu
1               5                   10                  15

Asn Lys Arg Ile Ser Tyr Asp Leu
            20

<210> SEQ ID NO 98
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 98

Glu Gln Lys Leu Ile Ser Glu Glu Asp Leu Phe Lys Pro Gly Gly Gly
1               5                   10                  15

Ser Gly Pro Gly Thr Glu Asp Ala Glu Ala Val Ala Leu Gly Leu Gly
            20                  25                  30

Leu Ser Asp Phe Pro
        35

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Ser Tyr Val Glu Thr Arg Thr Arg Leu Leu Ser Glu Leu Thr
1               5                   10                  15

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Ac
<220> FEATURE:
<221> NAME/KEY: MOD_RES
<222> LOCATION: (1)..(1)
<223> OTHER INFORMATION: Lys-(C6-5FAM)
<220> FEATURE:
<221> NAME/KEY: MOD_RES
<222> LOCATION: (4)..(4)
<223> OTHER INFORMATION: NMe-Leu
<220> FEATURE:
<221> NAME/KEY: MOD_RES
<222> LOCATION: (11)..(11)
<223> OTHER INFORMATION: NMe-Leu
<220> FEATURE:
<221> NAME/KEY: MOD_RES
<222> LOCATION: (14)..(14)
<223> OTHER INFORMATION: NMe-Val
<220> FEATURE:
<223> OTHER INFORMATION: C-term NH2

<400> SEQUENCE: 100

Lys Gln Ser Leu Arg Leu Gly Leu Ser Arg Leu Ala Arg Val Lys Arg
1               5                   10                  15

Leu His Pro Gly Ala Arg Arg Arg Arg Arg Arg Arg
            20                  25

<210> SEQ ID NO 101
<211> LENGTH: 87
<212> TYPE: PRT
<213> ORGANISM: Homo sapiens

<400> SEQUENCE: 101

Tyr Ile Asp Thr Glu Gly Thr Phe Arg Pro Glu Arg Leu Leu Ala Val
1               5                   10                  15

Ala Glu Arg Tyr Gly Leu Ser Gly Ser Asp Val Leu Asp Asn Val Ala
```

```
                20                  25                  30

Tyr Ala Arg Ala Phe Asn Thr Asp His Gln Thr Gln Leu Leu Tyr Gln
            35                  40                  45

Ala Ser Ala Met Met Val Glu Ser Arg Tyr Ala Leu Leu Ile Val Asp
        50                  55                  60

Ser Ala Thr Ala Leu Tyr Arg Thr Asp Tyr Ser Gly Arg Gly Glu Leu
65                  70                  75                  80

Ser Ala Arg Gln Met His Leu
                85

<210> SEQ ID NO 102
<211> LENGTH: 87
<212> TYPE: PRT
<213> ORGANISM: Gallus gallus

<400> SEQUENCE: 102

Tyr Ile Asp Thr Glu Gly Thr Phe Arg Pro Glu Arg Leu Leu Ala Val
1               5                   10                  15

Ala Glu Arg Tyr Gly Leu Ser Gly Ser Asp Val Leu Asp Asn Val Ala
            20                  25                  30

Tyr Ala Arg Gly Phe Asn Thr Asp His Gln Thr Gln Leu Leu Tyr Gln
        35                  40                  45

Ala Ser Ala Met Met Ala Glu Ser Arg Tyr Ala Leu Leu Ile Val Asp
    50                  55                  60

Ser Ala Thr Ala Leu Tyr Arg Thr Asp Tyr Ser Gly Arg Gly Glu Leu
65                  70                  75                  80

Ser Ala Arg Gln Met His Leu
                85

<210> SEQ ID NO 103
<211> LENGTH: 87
<212> TYPE: PRT
<213> ORGANISM: Danio rerio

<400> SEQUENCE: 103

Tyr Ile Asp Thr Glu Gly Thr Phe Arg Pro Glu Arg Leu Leu Ala Val
1               5                   10                  15

Ala Glu Arg Tyr Gly Leu Val Gly Ser Asp Val Leu Asp Asn Val Ala
            20                  25                  30

Tyr Ala Arg Ala Phe Asn Thr Asp His Gln Thr Gln Leu Leu Tyr Gln
        35                  40                  45

Ala Ser Ala Met Met Thr Glu Ser Arg Tyr Ala Leu Leu Ile Val Asp
    50                  55                  60

Ser Ala Thr Ala Leu Tyr Arg Thr Asp Tyr Ser Gly Arg Gly Glu Leu
65                  70                  75                  80

Ser Ala Arg Gln Gly His Leu
                85

<210> SEQ ID NO 104
<211> LENGTH: 87
<212> TYPE: PRT
<213> ORGANISM: Xenopus laevis

<400> SEQUENCE: 104

Tyr Ile Asp Thr Glu Gly Thr Phe Arg Pro Glu Arg Leu Leu Ala Val
1               5                   10                  15

Ala Glu Arg Tyr Gly Leu Ser Gly Ser Asp Val Leu Asp Asn Val Ala
            20                  25                  30
```

Tyr Ala Arg Ala Phe Asn Thr Asp His Gln Thr Gln Leu Leu Tyr Gln
                35                  40                  45

Ala Ser Ala Met Met Ala Glu Ser Arg Tyr Ala Leu Leu Ile Val Asp
    50                  55                  60

Ser Ala Thr Ala Leu Tyr Arg Thr Asp Tyr Ser Gly Arg Gly Glu Leu
65                  70                  75                  80

Ser Ala Arg Gln Met His Leu
                85

<210> SEQ ID NO 105
<211> LENGTH: 87
<212> TYPE: PRT
<213> ORGANISM: Ustilago maydis

<400> SEQUENCE: 105

Tyr Ile Asp Thr Glu Asn Thr Phe Arg Pro Thr Arg Leu Leu Ala Val
1               5                   10                  15

Ala Glu Arg Phe Gly Leu Asn Gly Glu Val Leu Asp Asn Val Ala
    20                  25                  30

Tyr Ala Arg Ala Tyr Asn Ala Asp His Gln Leu Gln Leu Leu Met Gln
                35                  40                  45

Ala Ser Ala Met Met Ala Glu Ser Arg Phe Ser Leu Leu Ile Val Asp
    50                  55                  60

Ser Leu Thr Ser Leu Tyr Arg Thr Asp Phe Ser Gly Arg Gly Glu Leu
65                  70                  75                  80

Ser Ala Arg Gln Met His Leu
                85

<210> SEQ ID NO 106
<211> LENGTH: 87
<212> TYPE: PRT
<213> ORGANISM: Schizosaccharomyces pombe

<400> SEQUENCE: 106

Tyr Ile Asp Thr Glu Gly Thr Phe Arg Pro Val Arg Leu Leu Ala Val
1               5                   10                  15

Ala Asp Arg Tyr Gly Leu Asn Gly Glu Val Leu Asp Asn Val Ala
    20                  25                  30

Tyr Ala Arg Ala Tyr Asn Ala Asp His Gln Leu Glu Leu Leu Gln Gln
                35                  40                  45

Ala Ala Asn Met Met Ser Glu Ser Arg Phe Ser Leu Leu Val Val Asp
    50                  55                  60

Ser Cys Thr Ala Leu Tyr Arg Thr Asp Phe Ser Gly Arg Gly Glu Leu
65                  70                  75                  80

Ser Ala Arg Gln Met His Leu
                85

<210> SEQ ID NO 107
<211> LENGTH: 87
<212> TYPE: PRT
<213> ORGANISM: Schizosaccharomyces japonicus

<400> SEQUENCE: 107

Tyr Ile Asp Thr Glu Gly Thr Phe Arg Pro Val Arg Leu Leu Ala Val
1               5                   10                  15

Ala Glu Arg Tyr Gly Leu Asn Gly Glu Val Leu Asp Asn Val Ala
    20                  25                  30

```
Tyr Ala Arg Ala Tyr Asn Ala Asp His Gln Leu Glu Leu Gln Gln
            35                  40                  45

Ala Ala Asn Met Met Ala Glu Ser Arg Phe Ser Leu Leu Val Val Asp
 50                  55                  60

Ser Cys Thr Ala Leu Tyr Arg Thr Asp Phe Ser Gly Arg Gly Glu Leu
 65                  70                  75                  80

Ser Ala Arg Gln Met His Leu
                85
```

<210> SEQ ID NO 108
<211> LENGTH: 87
<212> TYPE: PRT
<213> ORGANISM: Pichia membranifaciens

<400> SEQUENCE: 108

```
Phe Ile Asp Thr Glu Ser Thr Phe Arg Pro Ile Arg Ile Val Pro Ile
 1               5                  10                  15

Ala Arg Arg Phe Gly Leu Asp Glu His Glu Ala Met Glu Asn Ile Ala
            20                  25                  30

Tyr Ala Arg Ala Tyr Asn Ala Asp His Gln Leu Gln Leu Leu Asn Gln
            35                  40                  45

Ala Ala Gln Met Met Ala Gln Ser Arg Phe Ser Leu Leu Val Val Asp
 50                  55                  60

Ser Ile Met Ala Leu Tyr Arg Thr Asp Tyr Ser Gly Arg Gly Glu Leu
 65                  70                  75                  80

Ser Ala Arg Gln Met His Val
                85
```

<210> SEQ ID NO 109
<211> LENGTH: 87
<212> TYPE: PRT
<213> ORGANISM: Pichia kudriavzevii

<400> SEQUENCE: 109

```
Phe Ile Asp Thr Glu Ser Thr Phe Arg Pro Val Arg Ile Val Pro Ile
 1               5                  10                  15

Ala Arg Arg Phe Gly Leu Asp Glu Arg Glu Ala Met Glu Asn Ile Ala
            20                  25                  30

Tyr Ala Arg Ala Tyr Asn Ala Asp His Gln Leu Gln Leu Leu Asn Gln
            35                  40                  45

Ala Ala Gln Met Met Ala Gln Ser Arg Phe Ser Leu Leu Ile Val Asp
 50                  55                  60

Ser Ile Met Ala Leu Tyr Arg Thr Asp Tyr Ser Gly Arg Gly Glu Leu
 65                  70                  75                  80

Ser Ala Arg Gln Met His Val
                85
```

<210> SEQ ID NO 110
<211> LENGTH: 87
<212> TYPE: PRT
<213> ORGANISM: Arthrobotrys oligospora

<400> SEQUENCE: 110

```
Tyr Ile Asp Thr Glu Gly Thr Phe Arg Pro Val Arg Leu Leu Ala Val
 1               5                  10                  15

Ala Gln Arg Tyr Gly Leu Asn Gly Glu Glu Val Leu Asp Asn Val Ala
            20                  25                  30

Tyr Ala Arg Ala Tyr Asn Ser Asp His Gln Leu Gln Leu Leu Asn Met
```

```
                35                  40                  45

Ala Ala Gln Met Met Thr Glu Thr Arg Phe Ser Leu Leu Ile Val Asp
         50                  55                  60

Ser Ala Thr Ser Leu Tyr Arg Thr Asp Phe Ser Gly Arg Gly Asp Leu
 65                  70                  75                  80

Ser Ala Arg Gln Met His Leu
                 85

<210> SEQ ID NO 111
<211> LENGTH: 87
<212> TYPE: PRT
<213> ORGANISM: Dactylellina haptotyla

<400> SEQUENCE: 111

Tyr Ile Asp Thr Glu Gly Thr Phe Arg Pro Val Arg Leu Val Ser Ile
  1               5                  10                  15

Ala Gln Arg Tyr Gly Leu Asn Pro Glu Asp Cys Leu Asp Asn Val Ala
                 20                  25                  30

Tyr Ala Arg Ala Tyr Asn Ala Glu His Gln Phe Gln Leu Leu Asn His
             35                  40                  45

Ala Ala Gln Met Met Ser Glu Ser Arg Phe Ser Cys Leu Ile Val Asp
         50                  55                  60

Ser Ile Met Ser Leu Tyr Arg Thr Asp Tyr Ser Gly Arg Ala Glu Leu
 65                  70                  75                  80

Ser Ala Arg Gln Thr His Val
                 85

<210> SEQ ID NO 112
<211> LENGTH: 87
<212> TYPE: PRT
<213> ORGANISM: Millerozyma farinose

<400> SEQUENCE: 112

Tyr Ile Asp Thr Glu Gly Thr Phe Arg Pro Val Arg Leu Val Ser Ile
  1               5                  10                  15

Ala Gln Arg Tyr Gly Leu Asn Pro Asp Asp Cys Leu Asp Asn Val Ala
                 20                  25                  30

Tyr Ala Arg Ala Tyr Asn Ala Asp His Gln Phe Gln Leu Leu Asn Leu
             35                  40                  45

Ala Ala Gln Met Met Ala Glu Ser Arg Phe Ser Leu Leu Ile Val Asp
         50                  55                  60

Ser Ile Met Ser Leu Tyr Arg Thr Asp Tyr Ser Gly Arg Gly Glu Leu
 65                  70                  75                  80

Ser Ala Arg Gln Ser His Val
                 85

<210> SEQ ID NO 113
<211> LENGTH: 87
<212> TYPE: PRT
<213> ORGANISM: Debaryomyces hansenii

<400> SEQUENCE: 113

Tyr Ile Asp Thr Glu Gly Thr Phe Arg Pro Val Arg Leu Val Ser Ile
  1               5                  10                  15

Ala Gln Arg Tyr Gly Leu Asn Pro Glu Asp Cys Leu Asp Asn Val Ala
                 20                  25                  30

Tyr Ala Arg Ala Tyr Asn Ala Glu His Gln Phe Gln Leu Leu Asn His
             35                  40                  45
```

```
Ala Ala Gln Met Met Ser Glu Ser Arg Phe Ser Cys Leu Ile Val Asp
 50                  55                  60

Ser Ile Met Ser Leu Tyr Arg Thr Asp Tyr Ser Gly Arg Ala Glu Leu
 65                  70                  75                  80

Ser Ala Arg Gln Thr His Val
                 85

<210> SEQ ID NO 114
<211> LENGTH: 87
<212> TYPE: PRT
<213> ORGANISM: Ogataea parapolymorpha

<400> SEQUENCE: 114

Tyr Ile Asp Thr Glu Gly Thr Phe Arg Pro Ile Arg Leu Val Ala Ile
  1               5                  10                  15

Ala Arg Arg Phe Gly Leu Asp Glu Asn Glu Thr Leu Asp Asn Val Ala
                 20                  25                  30

Tyr Ala Arg Ala Tyr Asn Ala Asp His Gln Leu Gln Leu Leu His Gln
             35                  40                  45

Ala Ala Ser Met Met Thr Glu Ser Arg Phe Ser Leu Leu Ile Val Asp
 50                  55                  60

Ser Ile Met Ala Leu Tyr Arg Thr Asp Tyr Ser Gly Arg Gly Glu Leu
 65                  70                  75                  80

Ser Ala Arg Gln Met His Val
                 85

<210> SEQ ID NO 115
<211> LENGTH: 87
<212> TYPE: PRT
<213> ORGANISM: Komagataella phaffii

<400> SEQUENCE: 115

Tyr Ile Asp Thr Glu Gly Thr Phe Arg Pro Ile Arg Leu Val Ser Ile
  1               5                  10                  15

Ala Lys Arg Tyr Gly Leu Asn Glu Asp Asp Thr Leu Asp Asn Val Ala
                 20                  25                  30

Tyr Ala Arg Ala Tyr Asn Ala Asp His Gln Leu Gln Leu Leu Asn Gln
             35                  40                  45

Ala Ala Ala Met Met Ser Glu Ser Arg Phe Ser Leu Leu Ile Val Asp
 50                  55                  60

Ser Ile Met Ala Leu Tyr Arg Thr Asp Phe Ser Gly Arg Gly Glu Leu
 65                  70                  75                  80

Ser Ala Arg Gln Met His Val
                 85

<210> SEQ ID NO 116
<211> LENGTH: 87
<212> TYPE: PRT
<213> ORGANISM: Aspergillus clavatus

<400> SEQUENCE: 116

Tyr Ile Asp Thr Glu Gly Thr Phe Arg Pro Val Arg Leu Leu Ala Val
  1               5                  10                  15

Ala Gln Arg Tyr Gly Leu Val Gly Glu Glu Val Leu Asp Asn Val Ala
                 20                  25                  30

Tyr Ala Arg Ala Tyr Asn Ser Asp His Gln Leu Gln Leu Leu Asn Gln
             35                  40                  45
```

```
Ala Ser Gln Met Met Cys Glu Thr Arg Phe Ser Leu Leu Val Val Asp
     50                  55                  60

Ser Ala Thr Ser Leu Tyr Arg Thr Asp Phe Asn Gly Arg Gly Glu Leu
 65                  70                  75                  80

Ser Ser Arg Gln Thr His Leu
                 85
```

<210> SEQ ID NO 117
<211> LENGTH: 87
<212> TYPE: PRT
<213> ORGANISM: Pneumocystis jirovecii

<400> SEQUENCE: 117

```
Tyr Ile Asp Thr Glu Gly Thr Phe Arg Pro Thr Arg Leu Leu Ala Val
 1               5                  10                  15

Ala Asp Arg Tyr Gly Leu Asn Gly Glu Glu Val Leu Asp Asn Val Ala
                 20                  25                  30

Tyr Ala Arg Ala Tyr Asn Ala Asp His Gln Leu Gln Leu Leu Gly Gln
             35                  40                  45

Ala Ala Asn Met Met Ala Glu Ser Arg Phe Ser Leu Leu Ile Val Asp
     50                  55                  60

Ser Ala Thr Ser Leu Tyr Arg Thr Asp Phe Ala Gly Arg Gly Glu Leu
 65                  70                  75                  80

Ser Ala Arg Gln Met His Leu
                 85
```

<210> SEQ ID NO 118
<211> LENGTH: 87
<212> TYPE: PRT
<213> ORGANISM: Yarrowia lipolytica

<400> SEQUENCE: 118

```
Tyr Ile Asp Thr Glu Gly Thr Phe Arg Pro Glu Arg Leu His Gln Ile
 1               5                  10                  15

Ala Arg Arg Tyr Gly Leu Asn Gly Asp Glu Val Leu Asp Asn Val Ala
                 20                  25                  30

Tyr Ala Arg Ala His Asn Ser Asp His Gln Met Gln Leu Leu Gln Met
             35                  40                  45

Ala Ala Asn Met Met Thr Lys Ser Arg Phe Ser Cys Leu Ile Val Asp
     50                  55                  60

Ser Ile Met Ala Leu Tyr Arg Thr Asp Tyr Ala Gly Arg Gly Glu Leu
 65                  70                  75                  80

Ser Ala Arg Gln Thr His Val
                 85
```

<210> SEQ ID NO 119
<211> LENGTH: 87
<212> TYPE: PRT
<213> ORGANISM: Candida albicans

<400> SEQUENCE: 119

```
Tyr Ile Asp Thr Glu Gly Thr Phe Arg Pro Asn Arg Leu Val Ser Ile
 1               5                  10                  15

Ala Gln Arg Tyr Gly Leu Asn Pro Asn Asp Cys Leu Asp Asn Val Ala
                 20                  25                  30

Tyr Ala Arg Ala Tyr Asn Ala Glu His Gln Leu Asn Leu Leu Asn Ile
             35                  40                  45

Ala Ala Glu Met Met Ala Glu Ser Arg Phe Ser Leu Leu Ile Val Asp
```

```
                    50                  55                  60

Ser Ile Met Ser Leu Tyr Arg Thr Asp Tyr Ala Gly Arg Gly Glu Leu
 65                  70                  75                  80

Ser Ala Arg Gln Thr His Val
                85

<210> SEQ ID NO 120
<211> LENGTH: 87
<212> TYPE: PRT
<213> ORGANISM: Wickerhamomyces ciferrii

<400> SEQUENCE: 120

Tyr Ile Asp Thr Glu Gly Thr Phe Arg Pro Val Arg Leu Val Ser Ile
  1               5                  10                  15

Ala Arg Arg Tyr Gly Leu Asn Glu Asp Asp Ala Leu Asp Asn Val Ala
                 20                  25                  30

Tyr Ala Arg Ala Tyr Asn Ala Asp His Gln Leu Gln Leu Leu Asn Gln
             35                  40                  45

Ala Ala Ala Met Met Ser Glu Ser Arg Phe Ser Leu Leu Ile Val Asp
         50                  55                  60

Ser Ile Met Ala Leu Tyr Arg Thr Asp Phe Ala Gly Arg Gly Glu Leu
 65                  70                  75                  80

Ser Ala Arg Gln Met His Val
                85

<210> SEQ ID NO 121
<211> LENGTH: 87
<212> TYPE: PRT
<213> ORGANISM: Cyberlindnera fabianii

<400> SEQUENCE: 121

Tyr Ile Asp Thr Glu Gly Thr Phe Arg Pro Val Arg Leu Val Ser Ile
  1               5                  10                  15

Ala Arg Arg Tyr Gly Leu Asn Glu Asp Asp Ala Leu Asp Asn Val Ala
                 20                  25                  30

Tyr Ala Arg Ala Tyr Asn Ala Asp His Gln Leu Ser Leu Leu Asn Gln
             35                  40                  45

Ala Ala Ala Met Met Ser Glu Ser Arg Phe Ser Leu Leu Ile Val Asp
         50                  55                  60

Ser Ile Met Ala Leu Tyr Arg Thr Asp Phe Ala Gly Arg Gly Glu Leu
 65                  70                  75                  80

Ser Ala Arg Gln Met His Val
                85

<210> SEQ ID NO 122
<211> LENGTH: 87
<212> TYPE: PRT
<213> ORGANISM: Candida dubliniensis

<400> SEQUENCE: 122

Tyr Ile Asp Thr Glu Gly Thr Phe Arg Pro Asn Arg Leu Val Ser Ile
  1               5                  10                  15

Ala Gln Arg Tyr Gly Leu Asn Pro Asn Asp Cys Leu Asp Asn Val Ala
                 20                  25                  30

Tyr Ala Arg Ala Tyr Asn Ala Glu His Gln Leu Asn Leu Leu Asn Ile
             35                  40                  45

Ala Ser Gln Met Met Ala Glu Ser Arg Phe Ser Leu Leu Ile Val Asp
         50                  55                  60
```

Ser Ile Met Ser Leu Tyr Arg Thr Asp Tyr Ala Gly Arg Gly Glu Leu
65                  70                  75                  80

Ser Ala Arg Gln Thr His Val
                85

<210> SEQ ID NO 123
<211> LENGTH: 87
<212> TYPE: PRT
<213> ORGANISM: Lodderomyces elongisporus

<400> SEQUENCE: 123

Tyr Ile Asp Thr Glu Gly Thr Phe Arg Pro Asn Arg Leu Val Ser Ile
1               5                   10                  15

Ala Glu Arg Tyr Gly Leu Asn Ala Asn Asp Cys Leu Asp Asn Val Ala
                20                  25                  30

Tyr Ala Arg Ala Tyr Asn Ala Glu His Gln Leu Asn Leu Leu Asn Leu
            35                  40                  45

Ala Ala Glu Met Met Ala Glu Ser Arg Phe Ser Leu Leu Ile Val Asp
        50                  55                  60

Ser Ile Met Ser Leu Tyr Arg Thr Asp Tyr Ala Gly Arg Gly Glu Leu
65                  70                  75                  80

Ser Ala Arg Gln Thr Ser Val
                85

<210> SEQ ID NO 124
<211> LENGTH: 87
<212> TYPE: PRT
<213> ORGANISM: Candida maltosa

<400> SEQUENCE: 124

Tyr Ile Asp Thr Glu Gly Thr Phe Arg Pro Asn Arg Leu Ile Ser Ile
1               5                   10                  15

Ala Glu Arg Tyr Gly Leu Asn Pro Asn Asp Cys Leu Asp Asn Val Ala
                20                  25                  30

Tyr Ala Arg Ala Tyr Asn Ala Glu His Gln Leu Asn Leu Leu Asn Val
            35                  40                  45

Ala Ala Gln Met Met Ala Glu Ser Arg Phe Ser Leu Leu Ile Val Asp
        50                  55                  60

Ser Ile Met Ser Leu Tyr Arg Thr Asp Tyr Ala Gly Arg Gly Glu Leu
65                  70                  75                  80

Ser Ala Arg Gln Thr His Val
                85

<210> SEQ ID NO 125
<211> LENGTH: 87
<212> TYPE: PRT
<213> ORGANISM: Candida tropicalis

<400> SEQUENCE: 125

Tyr Ile Asp Thr Glu Gly Thr Phe Arg Pro Asn Arg Leu Ile Ser Ile
1               5                   10                  15

Ala Glu Arg Tyr Gly Leu Asn Ala Asn Asp Cys Leu Asp Asn Val Ala
                20                  25                  30

Tyr Ala Arg Ala Tyr Asn Ala Glu His Gln Leu Asn Leu Leu Asn Ile
            35                  40                  45

Ala Ala Gln Met Met Ala Glu Ser Arg Phe Ser Leu Leu Ile Val Asp
        50                  55                  60

Ser Ile Met Ser Leu Tyr Arg Thr Asp Tyr Ala Gly Arg Gly Glu Leu
65                  70                  75                  80

Ser Ala Arg Gln Thr His Val
                85

<210> SEQ ID NO 126
<211> LENGTH: 87
<212> TYPE: PRT
<213> ORGANISM: Zygosaccharomyces bailii

<400> SEQUENCE: 126

Tyr Ile Asp Thr Glu Gly Thr Phe Arg Pro Val Arg Leu Val Ser Ile
1               5                   10                  15

Ala Gln Arg Phe Gly Leu Asp Pro Asp Ala Leu Asn Asn Val Ala
            20                  25                  30

Tyr Ala Arg Ala Tyr Asn Ala Asp His Gln Ile Arg Leu Leu Asp Ala
        35                  40                  45

Ala Ala Gln Met Met Ser Glu Ser Arg Phe Ser Leu Val Val Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
                85

<210> SEQ ID NO 127
<211> LENGTH: 87
<212> TYPE: PRT
<213> ORGANISM: Lachancea mirantina

<400> SEQUENCE: 127

Tyr Ile Asp Thr Glu Gly Thr Phe Arg Pro Ile Arg Leu Val Ser Ile
1               5                   10                  15

Ala Gln Arg Phe Gly Leu Asp Pro Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

<210> SEQ ID NO 128
<211> LENGTH: 87
<212> TYPE: PRT
<213> ORGANISM: Candida glabrata

<400> SEQUENCE: 128

Tyr Ile Asp Thr Glu Gly Thr Phe Arg Pro Val Arg Leu Val Ser Ile
1               5                   10                  15

Ala Gln Arg Phe Gly Leu Asp Pro Asp Ala Leu Asn Asn Val Ala
            20                  25                  30

Tyr Ala Arg Ala Tyr Asn Ala Asp His Gln Met Arg Leu Leu Asp Ala
        35                  40                  45

Ala Ala Gln Met Met Ser Glu Ser Arg Phe Ser Leu Ile Val Val Asp
    50                  55                  60

Ser Val Met Ala Leu Tyr Arg Thr Asp Phe Ser Gly Arg Gly Glu Leu

```
                65                  70                  75                  80

Ser Ala Arg Gln Met His Leu
                85

<210> SEQ ID NO 129
<211> LENGTH: 87
<212> TYPE: PRT
<213> ORGANISM: Kazachstania saulgeensis

<400> SEQUENCE: 129

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Lys Leu Leu Asp Ala
        35                  40                  45

Ala Ala Gln Met Met Ser Glu Ser Arg Phe Ser Leu Ile Val Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
                85

<210> SEQ ID NO 130
<211> LENGTH: 87
<212> TYPE: PRT
<213> ORGANISM: Naumovozyma dairenensis

<400> SEQUENCE: 130

Tyr Ile Asp Thr Glu Gly Thr Phe Arg Pro Val Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Lys Leu Leu Asp Ala
        35                  40                  45

Ala Ser Gln Met Met Ser Glu Ser Arg Phe Ser Leu Ile Ile Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
                85

<210> SEQ ID NO 131
<211> LENGTH: 87
<212> TYPE: PRT
<213> ORGANISM: Kluyveromyces lactis

<400> SEQUENCE: 131

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Lys Leu Leu Asp Ala
        35                  40                  45

Ala Ala Gln Met Met Ser Glu Ser Arg Phe Ser Leu Ile Ile Val Asp
    50                  55                  60

Ser Ile Met Ala Leu Tyr Arg Thr Asp Phe Ser Gly Arg Gly Glu Leu
65                  70                  75                  80
```

Ser Ala Arg Gln Met His Leu
                85

<210> SEQ ID NO 132
<211> LENGTH: 87
<212> TYPE: PRT
<213> ORGANISM: Kluyveromyces dobzhanskii

<400> SEQUENCE: 132

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Lys Leu Leu Asp Ala
        35                  40                  45

Ala Ala Gln Met Met Ser Glu Ser Arg Phe Ser Leu Ile Ile Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

<210> SEQ ID NO 133
<211> LENGTH: 87
<212> TYPE: PRT
<213> ORGANISM: Zygosaccharomyces rouxii

<400> SEQUENCE: 133

Tyr Ile Asp Thr Glu Gly Thr Phe Arg Pro Val Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Ile Arg Leu Leu Asp Ala
        35                  40                  45

Ala Ala Gln Met Met Ser Glu Ser Arg Phe Ser Leu Val Val Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
                85

<210> SEQ ID NO 134
<211> LENGTH: 87
<212> TYPE: PRT
<213> ORGANISM: Naumovozyma castelli

<400> SEQUENCE: 134

Tyr Ile Asp Thr Glu Gly Thr Phe Arg Pro Val Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Ile Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
            85

<210> SEQ ID NO 135
<211> LENGTH: 87
<212> TYPE: PRT
<213> ORGANISM: Torulaspora delbrueckii

<400> SEQUENCE: 135

Tyr Ile Asp Thr Glu Gly Thr Phe Arg Pro Val Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Ile Arg Leu Leu Asp Ala
        35                  40                  45

Ala Ala Gln Met Met Ser Glu Ser Arg Phe Ser Leu Ile Val Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
            85

<210> SEQ ID NO 136
<211> LENGTH: 87
<212> TYPE: PRT
<213> ORGANISM: Lachancea dasiensis

<400> SEQUENCE: 136

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Ile Met Ala Leu Tyr Arg Thr Asp Phe Ala Gly Arg Gly Glu Leu
65                  70                  75                  80

Ser Ala Arg Gln Met His Leu
            85

<210> SEQ ID NO 137
<211> LENGTH: 87
<212> TYPE: PRT
<213> ORGANISM: Kazachstania africana

<400> SEQUENCE: 137

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Ile Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu

<210> SEQ ID NO 138
<211> LENGTH: 87
<212> TYPE: PRT
<213> ORGANISM: Eremothecium sinecaudum

<400> SEQUENCE: 138

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

<210> SEQ ID NO 139
<211> LENGTH: 87
<212> TYPE: PRT
<213> ORGANISM: Ashbya aceri

<400> SEQUENCE: 139

Tyr Ile Asp Thr Glu Gly Thr Phe Arg Pro Ile Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

<210> SEQ ID NO 140
<211> LENGTH: 87
<212> TYPE: PRT
<213> ORGANISM: Vanderwaltozyma polyspora

<400> SEQUENCE: 140

Tyr Ile Asp Thr Glu Gly Thr Phe Arg Pro Val Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Ile Arg Leu Leu Asp Ala
        35                  40                  45

Ala Ala Gln Met Met Ser Glu Ser Arg Phe Ser Leu Ile Val Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
                85

<210> SEQ ID NO 141
<211> LENGTH: 87
<212> TYPE: PRT
<213> ORGANISM: Eremothecium gossypii

<400> SEQUENCE: 141

Tyr Ile Asp Thr Glu Gly Thr Phe Arg Pro Ile Arg Leu Val Ser Ile
1               5                   10                  15

Ala Gln Arg Phe Gly Leu Asp Pro Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

<210> SEQ ID NO 142
<211> LENGTH: 87
<212> TYPE: PRT
<213> ORGANISM: Lachancea nothofagi

<400> SEQUENCE: 142

Tyr Ile Asp Thr Glu Gly Thr Phe Arg Pro Ile Arg Leu Val Ser Ile
1               5                   10                  15

Ala Gln Arg Phe Gly Leu Asp Pro Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Val Ile Val Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

<210> SEQ ID NO 143
<211> LENGTH: 87
<212> TYPE: PRT
<213> ORGANISM: Eremothecium cymbalariae

<400> SEQUENCE: 143

Tyr Ile Asp Thr Glu Gly Thr Phe Arg Pro Ile Arg Leu Val Ser Ile
1               5                   10                  15

Ala Gln Arg Phe Gly Leu Asp Pro Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Ile Met Ala Leu Tyr Arg Thr Asp Phe Ser Gly Arg Gly Glu Leu
65                  70                  75                  80

Ser Ala Arg Gln Met His Leu
                85

```
<210> SEQ ID NO 144
<211> LENGTH: 87
<212> TYPE: PRT
<213> ORGANISM: Saccharomyces cerevisiae

<400> SEQUENCE: 144

Tyr Ile Asp Thr Glu Gly Thr Phe Arg Pro Val Arg Leu Val Ser Ile
1               5                   10                  15

Ala Gln Arg Phe Gly Leu Asp Pro Asp Asp Ala Leu Asn Asn Val Ala
            20                  25                  30

Tyr Ala Arg Ala Tyr Asn Ala Asp His Gln Leu Arg Leu Leu Asp Ala
        35                  40                  45

Ala Ala Gln Met Met Ser Glu Ser Arg Phe Ser Leu Ile Val Val Asp
    50                  55                  60

Ser Val Met Ala Leu Tyr Arg Thr Asp Phe Ser Gly Arg Gly Glu Leu
65                  70                  75                  80

Ser Ala Arg Gln Met His Leu
                85
```

PROTEIN INTERFACES

CROSS-REFERENCE

This application is a continuation of U.S. patent application Ser. No. 16/215,432, filed Dec. 10, 2018, which is a continuation of U.S. patent application Ser. No. 15/683,586, filed Aug. 22, 2017, now U.S. Pat. No. 10,188,691, which is a continuation of PCT Application No. PCT/US17/34870, filed on May 26, 2017, which claims the benefit of U.S. Provisional Appl. No. 62/342,840, filed on May 27, 2016, and Provisional Application No. 62/384,226, filed on Sep. 7, 2016. All of these applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 8, 2021, is named 50607_701_303_SL.txt and is 264,764 bytes in size.

BACKGROUND

Cancer, an uncontrolled proliferation of cells, is a multifactorial disease characterized by tumor formation, growth, and in some instances, metastasis. Current cancer therapies include chemotherapy and targeted therapies, which attempt to destroy cancer cells via apoptosis, necrosis, or proliferative inhibition. Deoxyribonucleic acid (DNA) repair pathways are frequently overexpressed in cancer cells, and can be essential to the proliferation of chemotherapy-resistant cancers. Thus, compounds that can attenuate aberrant DNA damage repair pathway signaling could be beneficial to cancer patients. However, such signaling pathways in DNA repair and cancer frequently involve protein-protein interactions as critical regulatory steps, making the traditional enzyme active-site inhibitor-based drug development scheme challenging. Accordingly, there is need for development of methods and compositions that target protein-protein interactions in cancer and DNA repair.

SUMMARY

The present disclosure is directed to methods, compositions, and techniques for the identification and production of protein-protein interaction inhibitors as well as methods, compositions, and techniques for using protein-protein interaction inhibitors.

In one aspect, the invention relates to a non-naturally occurring compound which interacts with RAD51AP1's binding site on human RAD51. In one embodiment the compound interacts with at least one of residues 202, 205, and 206 of human RAD51. In one embodiment, the compound further interacts with residue 187 of human RAD51. In another embodiment, the compound has a binding constant to RAD51 with a Kd value of $10^{-4}$ M or less. In another embodiment, the compound comprises a polypeptide. In one embodiment, the polypeptide comprises non-naturally occurring amino acids. In another embodiment, the polypeptide comprises both (L)- and (D)-amino acids. In another embodiment, the polypeptide comprises at least one (D)-amino acid. In another embodiment the compound comprises an amino acid sequence according to formula I, or an invert thereof, wherein any one or more of the amino acids are optionally non-natural amino acids or (D)-amino acids. In another embodiment, the compound comprises an amino acid sequence according to any one of formulas II-IV, or an invert thereof, wherein any one or more of the amino acids are optionally non-natural amino acids or (D)-amino acids. In another embodiment, the compound comprises an amino acid sequence according to SEQ ID NO.: 1, SEQ ID NO.: 5, SEQ ID NO.: 10, SEQ ID NO.: 66, or SEQ ID NO.: 67, wherein any one or more of the amino acids are optionally non-natural amino acids or (D)-amino acids. In another embodiment, the compound is compound 1, compound 5, compound 10, compound 13, or compound 14. In another embodiment, the polypeptide is not an antibody. In another embodiment, the polypeptide consists of fewer than 30 amino acid residues. In another embodiment, the polypeptide consists of 60 or fewer amino acid residues. In another embodiment, the polypeptide consists of fewer than 30 amino acid residues. In another embodiment, the polypeptide consists of fewer than 20, fewer than 15, or fewer than 10 amino acid residues. In another embodiment, the polypeptide further comprises a cell-penetrating peptide sequence. In another embodiment, the compound displays at least one of the following characteristics upon binding to RAD51 in a cell: (a) inhibition of assembly of RAD51 monomers on DNA; (b) inhibition of cellular homologous recombination; (c) lack of inhibition of RAD51 ATPase activity; or (d) lowering of RAD51 affinity for Ca2+.

In another aspect, the invention relates to a method of inducing cell death, wherein the method comprises contacting the cell with a polypeptide that binds to a eukaryotic recombinase in a cell, wherein the binding of the polypeptide to the eukaryotic recombinase in inhibits binding of the eukaryotic recombinase to a protein in the cell, wherein the cell exhibits an increase in intracellular free calcium concentration upon binding of the polypeptide to the eukaryotic recombinase. In one embodiment, the polypeptide comprises an amino acid sequence according to formula I or an invert thereof. In another embodiment, the eukaryotic recombinase is RAD51. In another embodiment, the protein is BRCA2. In another embodiment, the protein is RAD51AP1. In another embodiment the cell death is apoptotic cell death. In another embodiment, the binding of the polypeptide to a eukaryotic recombinase in the cell sensitizes the cell to a chemotherapeutic. In another embodiment, the method further comprises administering a chemotherapeutic agent. In another embodiment, the chemotherapeutic agent is PD-L1, an anti-PD1 agent, or a PARP inhibitor. In another embodiment, the eukaryotic cell is a cancer cell. In another embodiment, the cell is a human cell. In another embodiment, the polypeptide induces death of the cell at a rate at least 10-fold greater than in the absence of the polypeptide. In another embodiment, the polypeptide induces death of a cancer cell at a rate greater than that of a non-cancerous cell. In another embodiment, the polypeptide induces death of a cancer cell at a rate at least 10-fold greater than a non-cancerous cell. In another embodiment, the polypeptide induces death of a cancer cell dependent on elevated RAD51 activity at a rate greater than that of a non-cancerous cell.

In a further aspect, the invention relates to a method of treating a condition associated with aberrant RAD51 activity, comprising administering to a subject in need thereof a therapeutically effective amount of a polypeptide which interacts with RAD51AP1's binding site on human RAD51. In one embodiment the compound interacts with at least one of residues 202, 205, and 206 of human RAD51. In one embodiment, the compound further interacts with residue 187 of human RAD51. In another embodiment, the compound has a binding constant to RAD51 with a Kd value of $10^{-4}$ M or less. In another embodiment, the compound comprises a polypeptide. In another embodiment, the polypeptide comprises non-naturally occurring amino acids. In another embodiment, the polypeptide comprises both (L)- and (D)-amino acids. In another embodiment, the polypeptide comprises at least one (D)-amino acid. In another embodiment the compound comprises an amino acid sequence according to formula I, or an invert thereof, wherein any one or more of the amino acids are optionally non-natural amino acids or (D)-amino acids. In another embodiment, the compound comprises an amino acid sequence according to any one of formulas II-IV, or an invert thereof, wherein any one or more of the amino acids are optionally non-natural amino acids or (D)-amino acids. In another embodiment, the compound comprises an amino acid sequence according to SEQ ID NO.: 1, SEQ ID NO.: 5, SEQ ID NO.: 10, SEQ ID NO.: 66, or SEQ ID NO.: 67, wherein any one or more of the amino acids are optionally non-natural amino acids or (D)-amino acids. In another embodiment, the compound is compound 1, compound 5, compound 10, compound 13, or compound 14. In another embodiment, the polypeptide is not an antibody. In another embodiment, the polypeptide consists of fewer than 30 amino acid residues. In another embodiment, the peptide consists of 60 or fewer amino acid residues. In another embodiment, the polypeptide consists of fewer than 20, fewer than 15, or fewer than 10 amino acid residues. In another embodiment, the polypeptide further comprises a cell-penetrating peptide sequence. In another embodiment, the compound displays at least one of the following characteristics upon binding to RAD51 in a cell: (a) inhibition of assembly of RAD51 monomers on DNA; (b) inhibition of cellular homologous recombination; (c) lack of inhibition of RAD51 ATPase activity; or (d) lowering of RAD51 affinity for Ca2+. In another embodiment, the condition is Bloom's syndrome. In another embodiment, the condition is Bloom's syndrome, Fanconi Anemia, Werner's syndrome, or Nijmegen Breakage syndrome.

In yet a further aspect, the invention relates to a method of reducing drug resistance in a cell, comprising contacting the cell with a polypeptide that binds RADAP1's binding site on human RAD51. In one embodiment the compound interacts with at least one of residues 202, 205, and 206 of human RAD51. In one embodiment, the compound further interacts with residue 187 of human RAD51. In another embodiment, the compound has a binding constant to RAD51 with a Kd value of $10^{-4}$ M or less. In another embodiment, the compound comprises a polypeptide. In another embodiment, the polypeptide comprises non-naturally occurring amino acids. In another embodiment, the polypeptide comprises both (L)- and (D)-amino acids. In another embodiment, the polypeptide comprises at least one (D)-amino acid. In another embodiment the compound comprises an amino acid sequence according to formula I, or an invert thereof, wherein any one or more of the amino acids are optionally non-natural amino acids or (D)-amino acids. In another embodiment, the compound comprises an amino acid sequence according to any one of formulas II-IV, or an invert thereof, wherein any one or more of the amino acids are optionally non-natural amino acids or (D)-amino acids. In another embodiment, the compound comprises an amino acid sequence according to SEQ ID NO.: 1, SEQ ID NO.: 5, SEQ ID NO.: 10, SEQ ID NO.: 66, or SEQ ID NO.: 67, wherein any one or more of the amino acids are optionally non-natural amino acids or (D)-amino acids. In another embodiment, the compound is compound 1, compound 5, compound 10, compound 13, or compound 14. In another embodiment, the polypeptide is not an antibody. In another embodiment, the polypeptide consists of fewer than 30 amino acid residues. In another embodiment, the polypeptide consists of 60 or fewer amino acid residues. In another embodiment, the polypeptide consists of fewer than 20, fewer than 15, or fewer than 10 amino acid residues. In another embodiment, the polypeptide further comprises a cell-penetrating peptide sequence. In another embodiment, the compound displays at least one of the following characteristics upon binding to RAD51 in a cell: (a) inhibition of assembly of RAD51 monomers on DNA; (b) inhibition of cellular homologous recombination; (c) lack of inhibition of RAD51 ATPase activity; or (d) lowering of RAD51 affinity for Ca2+. In another embodiment, the drug is PD-L1, an anti-PD1 agent, or a PARP inhibitor. In another embodiment, the drug is melphalan, doxorubicin, adriamycin, etoposide, camptothecins, mitomycin C, cisplatin, temozolomide, oxaliplatin, carboplatin, or gemcitabine.

In still yet a further aspect, the invention relates to a method for detecting an interaction between a first test protein and a second test protein in a host cell, comprising: a) expressing in the host cell a first fusion protein comprising the first test protein and a DNA-binding moiety; b) expressing in the host cell a second fusion protein comprising the second test protein and a gene activating moiety; and c) expressing in the host cell a death agent, wherein the cytotoxic reporter is activated by a promoter DNA sequence specific for the DNA binding moiety, wherein interaction between the first protein and the second protein causes the gene activating moiety to activate expression of the cytotoxic reporter. In one embodiment, the host cell comprises more than one cytotoxic reporter activated by the promoter DNA sequence specific for the DNA-binding moiety. In another embodiment, the host cell comprises: a) genomic DNA encoding the first fusion protein and genomic DNA encoding the second fusion protein; and b) plasmid DNA encoding the cytotoxic reporter. In another embodiment, the DNA binding moiety is derived from LexA, cI, Glucocorticoid receptor, TetR, or Ume6. In another embodiment, the gene activating moiety is derived from GAL4, B42, VP16 or Dof1. In another embodiment, the cytotoxic reporter is a ribosomally-encoded xenobiotic agent, a ribosomally-encoded poison, a ribosomally-encoded endogenous or exogenous gene that results in severe growth defects upon mild overexpression, a ribosomally-encoded recombinase that excises an essential gene for viability, a limiting factor involved in the synthesis of a toxic secondary metabolite, or any combination thereof. In another embodiment, the cytotoxic reporter is Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Ricin Toxin, or any combination thereof. In another embodiment, the host cell is fungal or bacterial. In another embodiment, the method further comprises expressing a test gene in the host cell comprising a DNA sequence that encodes a randomized polypeptide library. In another embodiment, the randomized polypeptide library comprises polypeptides 60 or fewer amino acids in length. In another embodiment, the randomized polypeptide library comprises polypeptides 30 or fewer amino acids in length. In another embodiment, the randomized polypeptide library comprises polypeptides 20 or fewer amino acids in length. In another embodiment, the test gene comprises a 3'UTR of a short protein. In another embodiment, the 3'UTR is the 3'UTR of sORF1. In another embodiment, the DNA sequence that encodes a randomized polypeptide library encodes a common N-terminal sequence of Methionine-Valine-Asparagine. In another embodiment, the DNA sequence that encodes a randomized polypeptide library encodes a common N-terminal stabilization sequence. In another embodiment, polypeptides encoded by the randomized peptide library are processed into cyclic peptides in the host cell. In another embodiment, polypeptides encoded by the randomized peptide library are processed into cyclic peptides in the host cell by POPB from *G. marginata* or *A. bisporigera*.

In a further aspect, the invention relates to a plasmid vector comprising the nucleotide sequence of SEQ ID NO.: 63. In one embodiment, the plasmid vector has a DNA sequence encoding a first polypeptide inserted in frame with TetR-DBD, and a DNA sequence encoding a second polypeptide inserted in frame with Dof1-AD.

In a further aspect, the invention relates to a host cell, comprising the nucleotide sequence of SEQ ID NO.: 63, or a host cell comprising the nucleotide sequence of SEQ ID NO.: 63 wherein a DNA sequence encoding a first polypeptide is inserted in frame with TetR-DBD, and wherein a DNA sequence encoding a second polypeptide is inserted in frame with Dof1-AD.

In a further aspect, the invention relates to a library of plasmid vectors, each plasmid vector comprising: a) a DNA sequence encoding a different peptide sequence operably linked to a first switchable promoter; and b) a DNA sequence encoding a cytotoxic reporter under control of a second switchable promoter. In one embodiment, the different peptide sequences encode a common N-terminal stabilization sequence. In another embodiment, the DNA sequence encoding a different peptide sequence further encodes a 3'UTR. In another embodiment, the different peptide sequence is 60 or fewer amino acids in length. In another embodiment, the different peptide sequence is 30 or fewer amino acids in length. In another embodiment, the different peptide sequence is 20 or fewer amino acids in length. In another embodiment, the N-terminal stabilization sequence is M-V-A. In another embodiment, the 3'UTR is derived from sORF1. In another embodiment, the different peptide sequences are random. In another embodiment, the different peptide sequences are pre-enriched for binding to a target.

In a further aspect, the invention relates to a library of host cells, each comprising 0 or 1 copy of the plasmid vectors of the plasmid vector library described above.

In a further aspect, the invention relates to a host cell, expressing: a) a first fusion protein comprising a DNA-binding moiety; b) a second fusion protein comprising a gene activating moiety; c) a cytotoxic reporter, wherein the expression of the cytotoxic reporter is under control of a DNA-binding sequence specific for the DNA-binding moiety; and d) an mRNA comprising a nucleotide sequence encoding a polypeptide of 60 or fewer amino acids, wherein the mRNA comprises a 3'UTR 3' to the polypeptide, and wherein the polypeptide encodes an N-terminal sequence for peptide stabilization. In one embodiment, the host cell is fungal or bacterial. In another embodiment, the host cell is a haploid yeast cell. In another embodiment, the host cell is a diploid yeast cell. In another embodiment, the diploid yeast cell is produced by mating a first host cell comprising DNA sequences encoding the first chimeric gene and the second chimeric gene, to a second host cell comprising DNA sequences encoding the cytotoxic reporter and the mRNA comprising a nucleotide sequence encoding a polypeptide. In another embodiment, the host cell is mammalian.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

Each patent, publication, and non-patent literature cited in the application is hereby incorporated by reference in its entirety as if each was incorporated by reference individually.

BRIEF DESCRIPTION OF THE FIGURES

The novel features of the disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings of which:

FIG. 8 is a sequence for the protein-protein integration plasmid (In the first section of FIG. 8, SEQ ID NO: 60 is disclosed as the top nucleotide sequence and SEQ ID NO: 97 is disclosed as the coded protein. In the second section of FIG. 8, SEQ ID NO: 61 is disclosed as the top nucleotide sequence and SEQ ID NO: 98 is disclosed as the coded protein).

FIG. 17 shows the full chemical structure of exemplary compounds according to the invention, alongside measurements of their cell-death IC50 on SSP-25 cells. FIG. 17 discloses SEQ ID NOS 85, 100, 87-89 and 91-96, respectively, in order of appearance.

FIG. 18 shows exemplary compounds according to the invention showing the relative insensitivity of cell-death IC50s to which cell-penetrating peptides are utilized. FIG. 18 discloses SEQ ID NOS 89 and 94-95, respectively, in order of appearance.

FIG. 19 shows the effect of Compound 10 administered intratumorally and intraperitoneally in an in vivo athymic mouse A549 xenograft model.

FIG. 20 shows IC50s of compound 10 in vitro against immortalized cell lines originating from diverse tumor types.

FIG. 21 shows exemplary markush structures encompassing RAD51-interacting compounds as described herein. FIG. 21 discloses SEQ ID NOS 70-73, respectively, in order of appearance.

FIG. 23 discloses SEQ ID NOS 101-144, respectively, in order of appearance.

DETAILED DESCRIPTION

Figure 1:
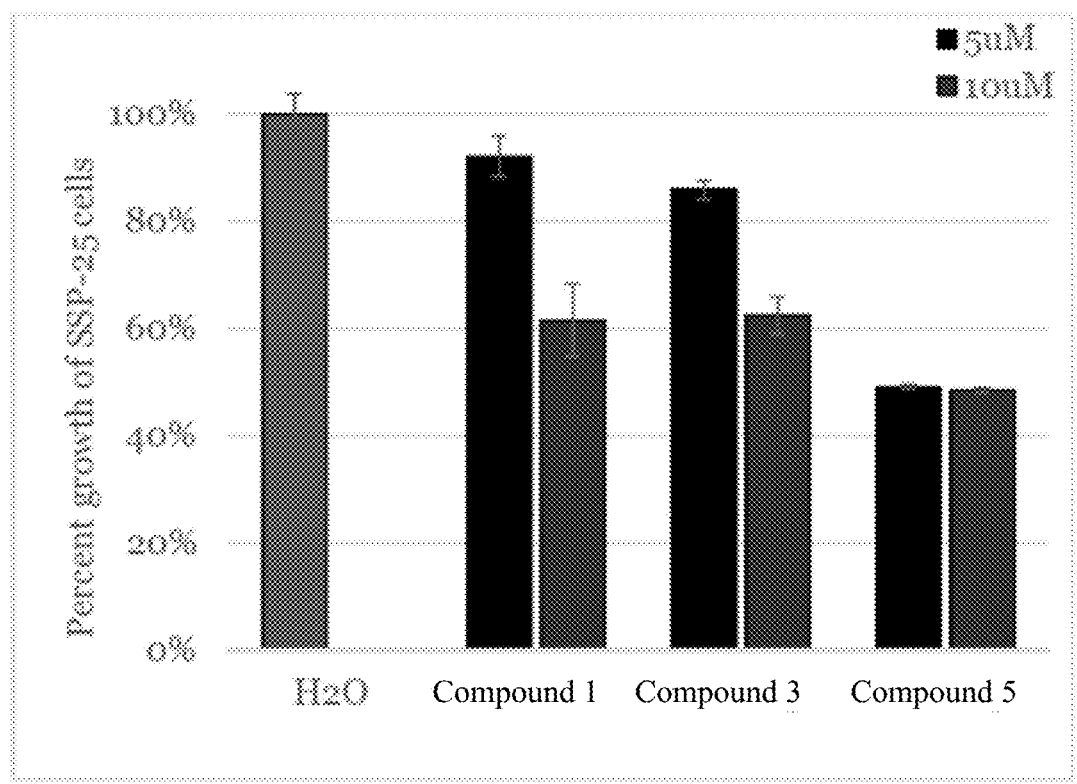
FIG. 1 depicts the effect of Compounds 1, 3, and 5 on SSP-25 cells.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides methods for the treatment of cancer using compounds that can bind to proteins involved in the homologous recombination DNA repair pathway. The present compounds can decrease the rate of cellular proliferation in cancer cells, and avoid affecting those cells that do not overexpress proteins specific to the DNA repair pathway. The present compounds can further sensitize cells to chemotherapy, and sensitize those cells that have developed resistance to therapeutics. The compounds disclosed herein can display specificity toward cancer cells harboring specific transcriptional signatures.

Cancer is a collection of related diseases characterized by uncontrolled proliferation of cells with the potential to metastasize throughout the body. Cancer can be classified into five broad categories including, for example, carcinomas, sarcomas, lymphomas, leukemias, and adenomas. Carcinomas can arise from cells that cover internal and external parts of the body such as the lung, breast, and colon. Sarcomas can arise from cells that are located in bone, cartilage, fat, connective tissue, muscle, and other supportive tissues. Lymphomas can arise in the lymph nodes and immune system tissues. Leukemias can arise in the bone marrow and accumulate in the bloodstream. Adenomas can arise in the thyroid, the pituitary gland, the adrenal gland, and other glandular tissues.

Although different cancers can develop in virtually any of the body's tissues, the basic processes that cause cancer can be similar in all forms of the disease. Cancer begins when a cell breaks free from the normal restraints on cell division and begins to grow and divide abnormally. Genetic mutations in the cell can preclude the ability of the cell to control cell division or initiate apoptosis, and can result in uncontrolled growth and division of cells.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, c-MYC, EGFR, HER2, K-Ras, PDGFR, Raf kinase, and VEGF. Tumor suppressor genes that can be mutated in cancer include, for example, BRCA1, BRCA2, cyclin-dependent kinase inhibitor 1C, PTEN, p16, p27, p53, p73, and Retinoblastoma protein (pRb).

DNA Damage and Cancer.

DNA damage can occur as a result of, for example, UV radiation, IR radiation, X-rays, reactive oxygen species, depurination, depyrimidination, single-strand breaks, double-strand breaks, cytosine deamination, O6-methylguanines, base alkylation, cross-linking of DNA, replication errors, or free radicals. Chemical compounds can also cause DNA damage by causing bulky adducts, interstrand cross-links, intrastrand crosslinks, intercalation between DNA strands, or DNA alkylation. Compounds that can cause DNA damage include, for example, actinomycin-D, benzo[a]pyrenes, cisplatin, daunorubicin, ethidium bromide, nitrogen mustards, methyl methanesulphonate (MMS), N-ethyl-N-nitrosourea (ENU), N-nitroso-N-methylurea (NMU), or psoralens.

Mutations or precocious expression of the DNA damage repair pathway can be found in cancer. Genes that can be affected in the DNA damage repair pathway include, for example, ATM, ATRX, BRCA1, BRCA2, ERCC1, FANCB, FANCF, FEN1, HMGA1, HMGA1, MDC1, MGMT, MLH1, MSH2, MSH4, Mre11A, NBS1, NEIL1, PARP1, PARP2, PMS2, RAD51, RAD52, RAD54, RAD51AP1, WRN, or XPF.

BRCA1 and BRCA2 are tumor suppressors that are involved in the cellular DNA damage repair pathway. Both BRCA1 and BRCA2 can interact with RAD51, a eukaryotic recombinase involved in DNA repair. Germline mutations in BRCA1 or BRCA2 can predispose individuals to various cancers including, for example, breast, ovarian, prostate, lung, and liver cancers. Tumors with BRCA2 mutations can exhibit loss of heterozygosity of the wild-type allele.

BRCA1 can combine with other tumor suppressors, DNA damage sensors, and signal transducers to form a large multi-subunit protein complex known as the BRCA1-associated genome surveillance complex (BASC). BRCA1 can also associate with RNA polymerase II and histone deacetylase complexes. Thus, BRCA1 can play a role in transcription, DNA repair of double-stranded breaks, and recombination. BRCA1 has cell-cycle dependent localization and can be found in, for the example, the nucleus, cytoplasm, or endoplasmic reticulum.

BRCA2 can maintain genome stability, and both BRCA1 and BRCA2 can specifically regulate the homologous recombination pathway for double-strand DNA repair. The BRCA2 protein contains about seven copies of a 70 amino acid motif known as the BRC motif, which can mediate binding to the RAD51 recombinase. RAD51 can perform certain biochemical activities required for homologous recombination and DNA repair, for example, promotion of joint molecule formation and DNA strand exchange between homologous DNA molecules. As a prerequisite for these functions, RAD51 can bind to DNA to form highly ordered nucleoprotein filaments in which the DNA is encased within a protein sheath. RAD51AP1 is a RAD51 accessory protein that can stimulates joint molecule formation through the combination of structure-specific DNA binding and physical contact with RAD51. RAD51AP1 can protect cells from the adverse effects of DNA double-strand break-inducing agents.

Direct and specific interactions between the BRC3 or BRC4 repeats in BRCA2 and RAD51 can sequester RAD51 in a form that is ready to be localized to sites of DNA damage, and thus become activated for DNA repair. Lack of functional BRCA2, or overexpression of BRCA2, can perturb RAD51 function by, for example, preventing RAD51 from localizing to sites of DNA damage. These damaged sites, which can contain double-strand breaks formed at stalled or broken replication forks, or double-strand breaks induced by exogenous agents, can provide the signal for activation of the mammalian SOS repair response. Activation can involve the posttranslational modification of RAD51 or occur via interactions with other repair proteins.

The BRC motifs of BRCA2 can bind monomeric or oligomeric forms of RAD51 in a cell cycle-dependent manner and in response to DNA damage. BRCA2 protein can be directly involved in the nuclear transport of RAD51. For example, the pancreatic adenocarcinoma cell line CAPAN-1 is defective in BRCA2, which can lead to impaired nuclear transportation of RAD51 in CAPAN-1. Thus, RAD51 can require BRCA2 for nuclear translocation and proper homologous recombination processes.

Double-strand DNA breaks can be caused by, for example, natural and medical radiation and other environmental exposures. Double-strand DNA breaks can also occur when chromosomes exchange genetic material during meiosis and during repair of DNA crosslinks. By repairing DNA, BRCA1 and BRCA1 play a role in maintaining the stability of the human genome and reducing the likelihood of dangerous gene rearrangements that can lead to malignancies.

Cancer treatments using chemotherapy or radiotherapy can target and disrupt the function of the DNA of tumor cells by inducing adducts or DNA double-strand or single-strand breaks. Cancer cells can overcome these therapies by developing resistance mechanisms, which can either be induced or intrinsic to the cancer cells. A high level of homologous recombination can be present in cancer cells due to the overexpression of RAD51. This overexpression of RAD51 can be seen in, for example, breast cancer, pancreatic, NSCLC, mCRPC, AML, ICC, and CML. In these cancer cells, the overexpression of RAD51 can provide cancer resistance by promoting the repair of double strand breaks induced by chemotherapy. Thus, the compounds of the present invention can interfere with the activity of RAD51, or other proteins involved in the DNA damage repair pathway, to resensitize cancer cells to chemotherapy, or to potentiate the effect of chemotherapy.

Two-Hybrid System.

Two-hybrid screening can be used to identify and characterize protein-protein interactions. The two-hybrid system was initially developed using yeast as a host organism. However, bacterial two-hybrid systems can also be used to characterize protein-protein interactions. The present disclosure provides a system that can use a unified yeast and bacterial two-hybrid system in which a single bait expression plasmid is used in both organismal contexts. Additionally, an extensive series of leucine zipper fusion proteins of known affinities can be generated to compare the efficiency of interaction detection using both systems. The yeast system can produce a quantitative readout over a dynamic range. "Auto-activation" by baits can be less prevalent in the bacterial system. In addition, modified expression vectors disclosed herein can be used for expression of a protein of interest in both yeast and bacteria.

As used herein, "reporter gene" refers to a gene whose expression can be assayed. Such genes include, for example, LacZ, β-glucuronidase (GUS), amino acid biosynthetic genes, the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available.

A "promoter" is a DNA sequence located proximal to the start of transcription at the 5' end of an operably linked transcribed sequence. The promoter can contain one or more regulatory elements or modules, which interact in modulating transcription of the operably linked gene. Promoters can come be switchable or constitutive. Switchable promoters allow for reversible induction or repression of operably linked target genes upon administration of an agent. Examples of switchable promoters include but are not limited to the TetO operator and the alcohol dehydrogenase I (alcA) gene promoter. Examples of constitutive promoters include the human beta-actin gene promoter.

"Operably linked" describes two macromolecular elements arranged such that modulating the activity of the first element induces an effect on the second element. In this manner, modulation of the activity of a promoter element can be used to alter or regulate the expression of an operably-linked coding sequence. For example, the transcription of a coding sequence that is operably-linked to a promoter element is induced by factors that activate the promoter's activity; transcription of a coding sequence that is operably-linked to a promoter element is inhibited by factors that repress the promoter's activity. Thus, a promoter region is operably-linked to the coding sequence of a protein if transcription of such coding sequence activity is influenced by the activity of the promoter.

"In frame" as used herein throughout, refers to the proper positioning of a desired sequence of nucleotides within a DNA fragment or coding sequence operably linked to a promoter sequence that results in optimal transcription or translation.

"Fusion construct" refers to recombinant genes that encode fusion proteins.

A "fusion protein" is a hybrid protein, i.e., a protein that has been constructed to contain domains from at least two different proteins. As used herein, a fusion protein is a hybrid protein that possesses (a) transcriptional regulatory domain from a transcriptional regulatory protein, or (b) a DNA binding domain from a DNA binding protein linked to a heterologous protein to be assayed for interaction. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain. In other words, the two domains are heterologous to each other.

The transcriptional regulatory domain of the fusion protein can either activate or repress transcription of target genes, depending on the native biological activity of the domain. The bait proteins of the invention are also fusion proteins encoded by a fusion gene that can contain a protein of interest operably linked to a DNA binding moiety.

The term "fusion protein gene" refers to a DNA sequence which encodes a fusion protein. A fusion protein gene can further provide transcriptional and translational regulatory elements for the transcriptional and translational control thereof.

"Expression" is the process by which the information encoded within a gene is revealed. If the gene encodes a protein, then expression involves both transcription of the DNA into mRNA, the processing of mRNA (if necessary) into a mature mRNA product, and translation of the mature mRNA into protein.

A nucleic acid molecule, such as a DNA or gene is said to be "capable of expressing" a polypeptide if the molecule contains the coding sequences for the polypeptide and the expression control sequences that, in the appropriate host environment, provide the ability to transcribe, process and translate the genetic information contained in the DNA into a protein product, and if such expression control sequences are operably-linked to the nucleotide sequence that encodes the polypeptide.

As used herein, a "cloning vehicle" is any entity that is capable of delivering a nucleic acid sequence into a host cell for cloning purposes. Examples of cloning vehicles include plasmids or phage genomes. A plasmid that can replicate autonomously in the host cell is especially desired. Alternatively, a nucleic acid molecule that can insert (integrate) into the host cell's chromosomal DNA is useful, especially a molecule that inserts into the host cell's chromosomal DNA in a stable manner, that is, a manner that allows such molecule to be inherited by daughter cells.

A "host cell" as described herein can be a bacterial, fungal, or mammalian cell. Examples of bacterial host cells are *E. coli* and *B. subtilis* Examples of fungal cells are *S. cerevisiae* and *S. pombe*. Non-limiting examples of mammalian cells are immortalized mammalian cell lines, such as HEK293, A549, HeLa, or CHO cells, or isolated patient primary tissue cells that have been genetically immortalized (such as by transfection with hTERT).

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle can further contain a marker suitable for use in the identification of cells transformed with the cloning vehicle. For example, a marker gene can be a gene that confers resistance to a specific antibiotic on a host cell.

The word "vector" can be used interchangeably with "cloning vehicle".

As used herein, an "expression vehicle" is a vehicle or vector similar to the cloning vehicle but is especially designed to provide an environment that allows the expression of the cloned gene after transformation into the host. One manner of providing such an environment is to include transcriptional and translational regulatory sequences on such expression vehicles, such transcriptional and translational regulatory sequences being capable of being operably linked to the cloned gene. Another manner of providing such an environment is to provide a cloning site or sites on such vehicle, wherein a desired cloned gene and a desired expression regulatory element can be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and can additionally contain transcriptional elements such as enhancer elements, termination sequences, tissue-specificity elements, or translational initiation and termination sites.

A "host" refers to any organism that is the recipient of a cloning or expression vehicle. The host may be a yeast cell or a cultured animal cell such as a mammalian or insect cell. The yeast host may be *Saccharomyces cerevisiae*.

A "binding moiety" or a "DNA-binding moiety" is a stretch of amino acids that is capable of directing specific polypeptide binding to a particular DNA sequence (i.e., a "protein binding site"). Also referred to herein as a DNA binding domain, these proteins can be homodimers or monomers that bind DNA in a sequence specific manner. Exemplary DNA binding domains of the invention include LexA, cI, glucocorticoid receptor binding domains, and the Ume6 domain.

A "gene activating moiety" is a stretch of amino acids that is capable of weakly inducing the expression of a gene to whose control region it is bound (one example is an activation domain from a transcription factor). As used herein, "weakly" is meant below the level of activation effected by GAL4 activation region II and is preferably at or below the level of activation effected by the B42 activation domain. Levels of activation can be measured using any downstream reporter gene system and comparing, in parallel assays, the level of expression stimulated by the GAL4 region II-polypeptide with the level of expression stimulated by the polypeptide to be tested.

Screening of Protein-Protein Interaction Inhibitors.

The large and broad surfaces that form the contact interface between two proteins can be potential targets of canonical small molecule inhibitors. However, the large and broad surfaces can have size limitations, and evolved resistance can occur readily. The specificity of antibodies can be combined with cell permeability in the form of short peptides, for example, peptides of less than 25 residues. Screening for short peptide blockers of protein-protein interaction (PPIs) can be performed using technologies such as phage display or mRNA display; however, these screens are performed in vitro and can require the purification of one of the interacting proteins of interest. Upon selection of a peptide sequence with affinity toward one of the proteins, secondary screens can be performed to validate that the peptide interferes with the binding interface of the second protein. This secondary screening can further rely upon the proper folding of the proteins and the replication of intracellular biophysical conditions in the assays.

A method of the invention can involve the intracellular selection of potent peptide disruptors of PPIs. A model organism, for example, *Saccharomyces cerevisiae*, can be employed, and the coexpression of a PPI of interest with a test gene comprising a DNA sequence that encodes randomized peptide library can allow the selection of unbiased peptides that interfere with a PPI using stringent selection mechanisms. The method can begin with a permutation of a yeast two-hybrid system that can rely on the reconstitution of a transcription factor that requires an interaction between a first test protein fused to a DNA binding domain (DBD) and a second test protein fused to a transcription activation domain (AD) or gene activating moiety.

An efficient interaction between the two proteins of interest can direct RNA polymerase to a specific genomic site, and allow for the expression of a genetic element. The genetic element can be, for example, a gene that encodes a protein that enables an organism to grown on selection media. The selection media can be specific to, for example, ADE2, URA3, TRP1, $KAN^R$, or $NAT^R$. Markers that can detect when an interaction is no longer present, for example, disrupted by an external object, can be referred to as counter-selection markers, such as the URA3 gene, and can be poor or leaky (easily masked by the selection of mutants that escape the selection). This leakiness of the selection marker can lead to a high false positive rate.

A method of the invention can combine a strong negative selection marker with the intracellular stabilization of the production of short peptides to screen for blockers of PPIs. An inducible two-hybrid approach can be employed, which can drive the expression of any one or combination of several cytotoxic reporters (death agents). A method of the invention involving induced expression of a combination of cytotoxic reporters in a two-hybrid system can allow for a multiplicative effect in lowering the false-positive rate of the two-hybrid assay, as all of the cytotoxic reporters must simultaneously be "leaky" to allow for an induced cell to survive, The cytotoxic reporters can be, for example:

TABLE 1

| | | |
|---|---|---|
| Cholera toxin (CtxA) | SEQ ID NO.: 20 | MVKIIFVFFIFLSSFSYANDDKLYRADSRPPDEIKQSGGLMPRG QSEYFDRGTQMNINLYDHARGTQTGFVRHDDGYVSTSISLRS AHLVGQTILSGHSTYYIYVIATAPNMFNVNDVLGAYSPHPDE QEVSALGGIPYSQIYGWYRVHFGVLDEQLHRNRGYRDRYYS NLDIAPAADGYGLAGFPPEHRAWREEPWIHHAPPGCGNAPRS SMSNTCDEKTQSLGVKFLDEYQSKVKRQIFSGYQSDIDTHNRI KDEL |
| SpvB toxin (*Salmonella enterica*) | SEQ ID NO.: 21 | MLILNGFSSATLALITPPFLPKGGKALSQSGPDGLASITLPLPIS AERGFAPALALHYSSGGGNGPFGVGWSCATMSIARRTSHGVP QYNDSDEFLGPDGEVLVQTLSTGDAPNPVTCFAYGDVSFPQS YTVTRYQPRTESSFYRLEYWVGNSNGDDFWLLHDSNGILHLL GKTAAARLSDPQAASHTAQWLVEESVTPAGEHIYYSYLAENG DNVDLNGNEAGRDRSAMRYLSKVQYGNATPAADLYLWTSA TPAVQWLFTLVFDYGERGVDPQVPPAFTAQNSWLARQDPFSL YNYGFEIRLHRLCRQVLMFHHFPDELGEADTLVSRLLLEYDE NPILTQLCAARTLAYEGDGYRRAPVNNMMPPPPPPPPMMGG NSSRPKSKWAIVEESKQIQALRYYSAQGYSVINKYLRGDDYP ETQAKETLLSRDYLSTNEPSDEEFKNAMSVYINDIAEGLSSLPE TDHRVVYRGLKLDKPALSDVLKEYTTIGNIIIDKAFMSTSPDK AWINDTILNIYLEKGHKGRILGDVAHFKGEAEMLFPPNTKLKI ESIVNCGSQDFASQLSKLRLSDDATADTNRIKRIINMRVLNS |
| CARDS toxin (*Mycoplasma pneumoniae*) | SEQ ID NO.: 22 | MSENLYFQGHMPNPVRFVYRVDLRSPEEIFEHGFSTLGDVRN FFEHILSTNFGRSYFISTSETPTAAIRFFGSWLREYVPEHPRRAY LYEIRADQHFYNARATGENLLDLMRQRQVVFDSGDREMAQ MGIRALRTSFAYQREWFTDGPIAAANVRSAWLVDAVPVEPG HAHHPAGRVVETTRINEPEMHNPHYQELQTQANDQPWLPTP GIATPVHLSIPQAASVADVSEGTSASLSFACPDWSPPSSNGENP LDKCIAEKIDNYNLQSLPQYASSVKELEDTPVYLRGIKTQKTF MLQADPQNNNVFLVEVNPKQKSSFPQTIFFWDVYQRICLKDL TGAQISLSLTAFTTQYAGQLKVHLSVSAVNAVNQKWKMTPQ DIAITQFRVSSELLGQTENGLFWNTKSGGSQHDLYVCPLKNPP SDLEELQIIVDECTTHAQFVTMRAASTFFVDVQLGWYWRGY YYTPQLSGWSYQMKTPDGQIFYDLKTSKIFFVQDNQNVFFLH NKLNKQTGYSWDWVEWLKHDMNEDKDENFKWYFSRDDLTI PSVEGLNFRHIRCYADNQQLKVIISGSRWGGWYSTYDKVESN VEDKILVKDGFDRF |
| SpyA Toxin (*Streptococcus pyogenes*) | SEQ ID NO.: 23 | MLKKRYQLAMILLLSCFSLVWQTEGLVELFVCEHYERAVCEG TPAYFTFSDQKGAETLIKKRWGKGLVYPRAEQEAMAAYTCQ QAGPINTSLDKAKGKLSQLTPELRDQVAQLDAATHRLVIPWN IVVYRYVYETFLRDIGVSHADLTSYYRNHQFNPHILCKIKLGT RYTKHSFMSTTALKNGAMTHRPVEVRICVKKGAKAAFVEPY SAVPSEVELLFPRGCQLEVVGAYVSQDHKKLHIEAYFKGSL |

TABLE 1-continued

| | | |
|---|---|---|
| HopU1 (Pseudomonas syringae) | SEQ ID NO.: 24 | MNINRQLPVSGSERLLTPDVGVSRQACSERHYSTGQDRHDFY RFAARLHVDAQCFGLSIDDLMDKFSDKHFRAEHPEYRDVYPE ECSAIYMHTAQDYSSHLVRGEIGTPLYREVNNYLRLQHENSG REAEIDNHDEKLSPHIKMLSSALNRLMDVAAFRGTVYRGIRG DLDTIARLYHLFDTGGRYVEPAFMSTTRIKDSAQVFEPGTPNN IAFQISLKRGADISGSSQAPSEEEIMLPMMSEFVIEHASALSEGK HLFVLSQI |
| Chelt toxin | SEQ ID NO.: 25 | MKTIISLIFIMFPLFVSAHNGNFYRADSRSPNEIKDLGGLYPRG YYDFFERGTPMSISLYDHARGAPSGNTRYDDGFVSTTTDIDSA HEIGQNILSGYTEYYIYLIAPAPNLLDVNAVLGRYSPHPQENE YSALGGIPWTQVIGWYVVNNGVLDRNIHRNRQFRADLFNNLS PALPSESYQFAGFEPEHPAWRQEPWINFAPPGCGRNVRLTKHI NQQDCSNSQEELVYKKLQDLRTQFKVDKKLKLVNKTSSNNII FPNHDFIREWVDLDGNGDLSYCGFTVDSDGSRKRIVCAHNNG NFTYSSINISLSDYGWPKGQRFIDANGDGLVDYCRVQYVWTH LYCSLSLPGQYFSLDKDAGYLDAGYNNSRAWAKVIGTNKYS FCRLTSNGYICTDIDSYSTAFKDDDQGWADSRYWMDIDGNG GDDYCRLVYNWTHLRCNLQGKDGLWKRVESKYLDGGYPSL RFKIKMTSNKDNYCRIVRNHRVMECAYVSDNGEFHNYSLNM PFSLYNKNDIQFIDIDGDNRDDICRYNSAPNTMECYLNQDKSF SQNKLVLYLSAKPISSLGSGSSKIIRTFNSEKNSSAYCYNAGYG TLRCDEFVIY |
| Certhrax toxin | SEQ TABLE 1-continued

| | | |
|---|---|---|
| | | WNTVEDSIIRTGFQGESGHDIKITAENTPLPIAGVLLPTIPGKLD<br>VNKSKTHISVNGRKIRMRCRAIDGDVTFCRPKSPVYVGNGVH<br>ANLHVAFHRSSSEKIHSNEISSDSIGVLGYQKTVDHTKVNSKL<br>SLFFEIKS |
| ExoU/VipB | SEQ ID<br>NO.: 31 | MKLAEIMTKSRKLKRNLLEISKTEAGQYSVSAPEHKGLVLSG<br>GGAKGISYLGMIQALQERGKIKNLTHVSGASAGAMTASILAV<br>GMDIKDIKKLIEGLDITKLLDNSGVGFRARGDRFRNILDVIYM<br>MQMKKHLESVQQPIPPEQQMNYGILKQKIALYEDKLSRAGIVI<br>NNVDDIINLTKSVKDLEKLDKALNSIPTELKGAKGEQLENPRL<br>TLGDLGRLRELLPEENKHLIKNLSVVVTNQTKHELERYSEDTT<br>PQQSIAQVVQWSGAHPVLFVPGRNAKGEYIADGGILDNMPEI<br>EGLDREEVLCVKAEAGTAFEDRVNKAKQSAMEAISWFKARM<br>DSLVEATIGGKWLHATSSVLNREKVYYNIDNMIYINTGEVTTT<br>NTSPTPEQRARAVKNGYDQTMQLLDSHKQTFDHPLMAILYIG<br>HDKLKDALIDEKSEKEIFEASAHAQAILHLQEQIVKEMNDGD<br>YSSVQNYLDQIEDILTVDAKMDDIQKEKAFALCIKQVNFLSEG<br>KLETYLNKVEAEAKAAAEPSWATKILNLLWAPIEWVVSLFKG<br>PAQDFKVEVQPEPVKVSTSENQETVSNQKDINPAVEYRKIIAE<br>VRREHTDPSPSLQEKERVGLSTTFGGH |
| HopPtoE | SEQ ID<br>NO.: 32 | MNRVSGSSSATWQAVNDLVEQVSERTTLSTTGYQTAMGRLN<br>KPEKSDADALMTMRRAQQYTDSAKRTYISETLMNLADLQQR<br>KIYRTNSGNLRGAIEMTPTQLTDCVQKCREEGFSNCDIQALEI<br>GLHLRHKLGISDFTIYSNRKLSHNYVVIHPSNAFPKGAIVDSW<br>TGQGVVELDFKTRLKFKHREENYAVNANMHEWIERYGQAH<br>VID |
| HopPtoF | SEQ ID<br>NO.: 33 | MGNICGTSGSRHVYSPSHTQRITSAPSTSTHVGGDTLTSIHQLS<br>HSQREQFLNMHDPMRVMGLDHDTELFRTTDSRYIKNDKLAG<br>NPQSMASILMHEELRPNRFASHTGAQPHEARAYVPKRIKATD<br>LGVPSLNVMTGSLARDGIRAYDHMSDNQVSVKMRLGDFLER<br>GGKVYADASSVADDGETSQALIVTLPKGQKVPVERV |
| HopPtoG | SEQ ID<br>NO.: 34 | MQIKNSHLYSASRMVQNTFNASPKMEVTNAIAKNNEPAALSA<br>TQTAKTHEGDSKGQSSNNSKLPFRAMRYAAYLAGSAYLYDK<br>TANNFFLSTTSLHDGKGGFTSDARLNDAQDKARKRYQNNHS<br>STLENKNSLLSPLRLCGENQFLTMIDYRAATKIYLSDLVDTEQ<br>AHTSILKNIMCLKGELTNEEAIKKLNPEKTPKDYDLTNSEAYIS<br>KNKYSLTGVKNEETGSTGYTSRSITKPFVEKGLKHFIKATHGE<br>KALTPKQCMETLDNLLRKSITLNSDSQFAAGQALLVFRQVYA<br>GEDAWGDAERVILKSHYNRGTVLQDEADKIELSRPFSEQDLA<br>KNMFKRNTSIAGPVLYHAYIYIQEKIFKLPPDKIEDLKHKSMA<br>DLKNLPLTHVKLSNSGVGFEDASGLGDSFTALNATSCVNHAR<br>IMSGEPPLSKDDVVILIGCLNAVYDNSSGIRHSLREIARGCFVG<br>AGFTVQDGDDFYKQICKNASKQFYNG |
| VopF | SEQ ID<br>NO.: 35 | MFKISVSQQANVMSTSDTAQRSSLKISIKSICNKSLSKKLHTLA<br>EKCRRFSQELKEHTASKKQIVEQATTTVRESSLTKSDSELGSS<br>RSLLTSDVLSSSSSHEDLTAVNLEDNDSVFVTIESSSELIVKQD<br>GSIPPAPPLPGNIPPAPPLPSAGNIPTAPGLPKQKATTESVAQTS<br>DNRSKLMEEIRQGVKLRATPKSSSTEKSASDPHSKLMKELINH<br>GAKLKKVSTSDIPVPPPLPAAFASKPTDGRSALLSEIAGFSKDR<br>LRKAGSSETLNVSQPTVAESSIPEAYDLLLSDEMFNLSPKLSET<br>ELNTLADSLADYLFKAADIDWMQVIAEQTKGSTQATSLKSQL<br>EQAPEYVKAFCDEILKFPDCYKSADVASPESPKAGPSSVIDVA<br>LKRLQAGRNRLFSTIDAKGTNELKKGEAILESAINAARSVMTA<br>EQKSALLSSNVKSATFKVFSELPCMEGFAEQNGKAAFNALRL<br>AFYSSIQSGDTAQQDIARFMKENLATGFSGYSYLGLTSRVAQL<br>EAQLAALTTK |
| YopJ | SEQ ID<br>NO.: 36 | MIGPISQINISGGLSEKETSSLISNEELKNIITQLETDISDGSWFH<br>KNYSRMDVEVMPALVIQANNKYPEMNLNLVTSPLDLSIEIKN<br>VIENGVRSSRFIINMGEGGIHFSVIDYKHINGKTSLILFEPANFN<br>SMGPAMLAIRTKTAIERYQLPDCHFSMVEMDIQRSSSECGIFSF<br>ALAKKLYIERDSLLKIHEDNIKGILSDGENPLPHDKLDPYLPVT<br>FYKHTQGKKRLNEYLNTNPQGVGTVVNKKNETIVNRFDNNK<br>SIVDGKELSVSVHKKRIAEYKTLLKV |
| AvrPtoB | SEQ ID<br>NO.: 37 | MAGINGAGPSGAYFVGHTDPEPASGGAHGSSSGASSSNSPRLP<br>APPDAPASQARDRREMLLRARPLSRQTREWVAQGMPPTAEA<br>GVPIRPQESAEAAAPQARAEERHTPEADAAASHVRTEGGRTP<br>QALAGTSPRHTGAVPHANRIVQQLVDAGADLAGINTMIDNA<br>MRRHAIALPSRTVQSILIEHFPHLLAGELISGSELATAFRAALR<br>REVRQQEASAPPRTAARSSVRTPERSTVPPTSTESSSGSNQRTL<br>LGRFAGLMTPNQRRPSSASNASASQRPVDRSPPRVNQVPTGA<br>NRVVMRNHGNNEADAALQGLAQQGVDMEDLRAALERHILH<br>RRPIPMDIAYALQGVGIAPSIDTGESLMENPLMNLSVALHRAL<br>GPRPARAQAPRPAVPVAPATVSRRPDSARATRLQVIPAREDYE<br>NNVAYGVRLLSLNPGAGVRETVAAFVNNRYERQAVVADIRA |

TABLE 1-continued

| | | |
|---|---|---|
| | | ALNLSKQFNKLRTVSKADAASNKPGFKDLADHPDDATQCLF GEELSLTSSVQQVIGLAGKATDMSESYSREANKDLVFMDMK KLAQFLAGKPEHPMTRETLNAENIAKYAFRIVP |
| SdbA | SEQ ID NO.: 38 | MHKKYNYYSLEKEKKTFWQHILDILKAPFRLPGWVVSFFLAR NITHVALNPNNIPQQRLIHLTKTSNRPEDDIVVINFKKRPPHKW FNDTLIKIANTIAALPFVTPRLRTRLHYDNENDINHVNKLLAEI DALVQGKSKQKYCKGRAFDWSKIHLKGLEFLDPKMRGYVYE QLHEKYGVSYTTKRKPNIEFFTLKTPDGSELDSVQVTGEDEE KKPMGERKFIITCIARDQNFINWIKDLNYTAKNLGATAISFNY RGVDYSRGLVWTENNLVDDILAQVQRLISLGADPKNICLDGM CIGGAVATIAAAKLHEKGMKVKLNNERSFTSLSSLVFGFIVPE LQTANWWSPLTYGRFLLAGVVYALLTPLIWLAGWPVDVTKA WNRIPAQDKMYSVVRDKDNGLYDGVIHDHFCSIASLVDSQIN SILYKLSTDQPLTEEEKQILCDDQFSHHFKPSQSVLKNPKYKGP HFISRQDLVAELGHREEYTNHDYFLDRLREKFQLDRATRPVA LAEDGEKDIDGISSQLSNNKERPLIIASSGGTGHISATHGIINDL QSKTDNVVITQHHAELYKNKPFSITSVLIRIGVWFTSLPILEDIL KGVMRFIGYPVLPSSSIFWDQMSKIQQSETKKENGIETGRTRP YVDMLLDIYPEGYEYTAFNNATHLTSSIEDIQTMISFKGHVEE DNRNIVYQNILQRLMHAAKQNTPYTRLISTQALSLGAICDAV KYYNTVFLPVYNAERGTSYQPIAIDQYMTDLPSLGCIHFMNN LEELTSEQRQLMEIHAVNMSEPFKEAHFGKEQGFKAVHNIDP RNNPMIRNAFKDPSLTKYLDKTQSFDLHFNVYKKEKQNALPV LNGKEKITIKPHAKIASIMIGSLAANASADYAKYLLNQGYEHIF LFGGLNDSIAARIDQIINSYPAPTRDEIRKKIILLGNQSDVEMAP IMTRSNCVVIRGGGLSVMEQMAMPIMDDKIVLLHHEDNEEGP LTSGLSWEDGNSDKLIEYLSEKGAYAKKTSPGLCSGHLHEAE KSFEKKYHGQLKSTETKKKVDLTIPQQETYSLKKEWDRKTGY TESGHILSHQHRFFNTIPEVREPFCSKEDLHHNELSSQSLVSVS AG |
| SidG | SEQ ID NO.: 39 | MSRSKDEVLEANDSLFGITVQTWGTNDRPSNGMMNFADQQF FGGDVGHASINMKLPVTDKTKQWIEKYCYSQTYDQFKKVKG NEDKTYEEYLKTAKRLIPVELKTQVTRKAQYDSNGNLVTTHE KAYEQIYFDIDWSWWPGRLQNTEDDMVWEREGKHFEYDEK WKEYLQPEQRVHRGKLGSRKMDYAPTSIIHQRDIPTSELEKIT RDHKIHTIEEKLNVVKLLQSKIDEMPHTKMSPSMELMFKNLGI NVEKLLDETKDNGVDPTNLEAMREYLTNRLTERKLELETELS EAKKEVDSTQVKNKVEDVYYDFEYKLNQVRKKMEEVNSQL EKMDSLLHKLEGNTSGPIPYTAEIDELMSVLPFLKEELELENG TLSPKSIENLIDHIDELKNELASKQEKKNERNLNLIKKYEELCE QYKDDEEGLEEALWEEGIDVEEVNSAKKDISKPAPEIQKLTDL QEEQLRNHKESGVKLSSELEETLNSSVKMWKTKIDSPCQVISES SVKALVSKINSTRPELVKEKEQLPEQEESLSKEAKKAQEELIKI QEFSQFYSENSSAYMVIGLPPHHQVSLPLAVNGKRGLHPEAM LKKMHELVAGPEKKEFNLHTNNCSLTSIEVLSAGAQHDPLLH SIMGTRALGFFGTPQQVLENAKLTSKTINEGKKSNIFTPLVTAS PLDRALGYAMSIYMDPEASKAKQNAGLALGVLVGLAKTPGII IGSLLNPKQGFNDILNTLNLVYSRNSTGLKVGLTLMALPAMIV LAPLAAIQKGVEVIAETIAKPFKLIANLFKQKPESTDEITVSVGS KKVAEKEGSYSNTALAGLVNSKIKSKIDENTITVEFQKSPQKM IEEFESQLKENPGKVVVLSEKAHNAVLKFVSKSDDEALKQKF YDCCNQSVARSQKFAPKTRDEIDELVEEVTSTDKTELTTSPRQ EPSMSSTIDEEENIDSEHQIETGTESTMRI |
| VpdA | SEQ ID NO.: 40 | MKTKQEVSQQDKLKDSKSSTPLQTKETWFISDALNITFDPYDF SISVTEQAPMPYRIVFSGGGSRILAHIGALDELTRHGLKFTEFS GSSAGAMVAAFAYLGYNCSEIKQIISWFNEDKLLDSPLIFNFN NIKQIFNKGGLSSAKLMRQAANYVILKKVMDIISDEKFKTRFA KFQNFLEENIYRCPENITFQTLARIKEICPECELGEKLFITGTNL STQKHEVFSIDTTPSMALADAIIISANLPIAFERICYQGNVYSDG GISNNLPAHCFSEKGHKTTFLKHKDDVDFSVLALQFDNGLEE NALYSQNPIPKWSWLSNTFYSLITGHPNVTENWYEDLQILRRH AHQSILIKTPTIALTNLTISQDTKKALVESGRTAAKTYLELHEF YTDDYGNIRHNECLHEKFQKPEELLDYCVLHSHFELLKKIKQ AISCSQYLEKGYKHYLCELCDNLLPPQLKCPNEGSGTEQPEIK LEKDTIICEKNNNSGLTFSMTFFGVPSPLVKTLNQDSPELKIKL FTGLYPILIQNWQNLCPVSGISGILNSIRMSFVEISSTDTCIKTLI DKLNEIEIGHFLIFVFKAALKNYDKHDFILLLKNLKHLHHSIELI RNKPFHSDDRFYGQWSFEGHDPKRILEFIKSDDISGLMTILEDK KALPNNKPN |
| Lpg0969 | SEQ ID NO.: 41 | MVSLEHIQKLISECRKLGKDGLDNGTNGLIPELEIDVVPPSAFL GVGNNPAIFVNSKTYKLMRTTHEKWVENKTIVFKSYLLSQPA IKIIGAIVHETGHAFNVAAKIPNTEANACIFEIEVLMRLFQVKSP LLLGCTELDMQSYFKSRLTDYNKCVKDCQCLAEMVEFITHQF KLDEVSISEKENQIPLLSISNKWPGLFAKKQIAPDMDKLLTSPV TITPEVKILFYQLVKEHFHSPETEIKLDI |

TABLE 1-continued

| | | |
|---|---|---|
| Lpg1978 | SEQ ID NO.: 42 | MYKIYSYLGWRIDMKTENLPQAGQEAQIDKKIHFIWVGHIMP<br>QKNIQVVSEWAEKNPGYETIIWVDKKIAPAKELDLFILDMKSK<br>GITVKDINEEGVCRDSIRHELDQESPNYGMVSDMLRLNILAAE<br>GGIYLDSDILCSAPFPDEIYAPFGFLLSPWSQGANNTLCNDIILC<br>SKGNQIIQQLADAIEQSYIARDSFEFTHEYASMKETKGERIAKT<br>LGVTGPGFLFHQLKKMGILNDKSEMEAIHWELQDQRYLIDGS<br>VKEPDYFYVPQNNTNDASWVPSIKRPGIENMSFQERLENAVQ<br>LIAFDIQKTGLFNLDHYANELKVKQNSWCIAAETSPELKPDSY<br>LLIRPRDKTGEWTLYYVDEDKKLNPVTLPVIKGAIKLSEVSDP<br>LRKFHTLLSQVSDPVNPTAHELKQIGRALIELK<br>PRQDEWHCKNKWSGAEEIAQELWQRITSNETLRAQIKQCFTQ<br>FESLKPRVAELGLTRASGAGTEVEAHESTVKEQEIISQNTVGE<br>EGTKEKNSVQLASENSSDEKIKTAHDLIDEIIQDVIQLDGKLGL<br>LGGGNTRQLEDGRVINIPNGAAMIFDDYKKYKQGELTAESALE<br>SMIKIAKLSNQLNRHTFFNQRQPETGQFYKKVAAIDLQTTIAA<br>EYDNNHGLRI |
| YopE | SEQ ID NO.: 43 | MKISSFISTSLPLPTSVSGSSSVGEMSGRSVSQQTSDQYANNLA<br>GRTESPQGSSLASRIIERLSSVAHSVIGFIQRMFSEGSHKPVVTP<br>APTPAQMPSPTSFSDSIKQLAAETLPKYMQQLNSLDAEMLQK<br>NHDQFATGSGPLRGSITQCQGLMQFCGGELQAEASAILNTPV<br>CGIPFSQWGTIGGAASAYVASGVDLTQAANEIKGLAQQMQKL<br>LSLM |
| SptP | SEQ ID NO.: 44 | MLKYEERKLNNLTLSSFSKVGVSNDARLYIAKENTDKAYVAP<br>EKFSSKVLTWLGKMPLFKNTEVVQKHTENIRVQDQKILQTFL<br>HALTEKYGETAVNDALLMSRINMNKPLTQRLAVQITECVKA<br>ADEGFINLIKSKDNVGVRNAALVIKGGDTKVAEKNNDVGAES<br>KQPLLDIALKGLKRTLPQLEQMDGNSLRENFQEMASGNGPLR<br>SLMTNLQNLNKIPEAKQLNDYVTTLTNIQVGVARFSQWGTCG<br>GEVERWVDKASTHELTQAVKKIHVIAKELKNVTAELEKIEAG<br>APMPQTMSGPTLGLARFAVSSIPINQQTQVKLSDGMPVPVNTL<br>TFDGKPVALAGSYPKNTPDALEAHMKMLLEKECSCLVVLTSE<br>DQMQAKQLPPYFRGSYTFGEVHTNSQKVSSASQGEAIDQYN<br>MQLSCGEKRYTIPVLHVKNWPDHQPLPSTDQLEYLADRVKNS<br>NQNGAPGRSSSDKHLPMIHCLGGVGRTGTMAAALVLKDNPH<br>SNLEQVRADFRDSRNNRMLEDASQFVQLKAMQAQLLMTTAS |
| SopE2 | SEQ ID NO.: 45 | MTNITLSTQHYRIHRSDVEPVKEKTTEKDIFAKSITAVRNSFISL<br>STSLSDRFSLHQQTDIPTTHFHRGNASEGRAVLTSKTVKDFML<br>QKLNSLDIKGNASKDPAYARQTCEAILSAVYSNNKDQCCKLL<br>ISKGVSITPFLKEIGEAAQNAGLPGEIKNGVFTPGGAGANPFVV<br>PLIASASIKYPHMFINHNQQVSFKAYAEKIVMKEVTPLFNKGT<br>MPTPQQFQLTIENIANKYLQNAS |
| SopB/SigD | SEQ ID NO.: 46 | MQIQSFYHSASLKTQEAFKSLQKTLYNGMQILSGQGKAPAKA<br>PDARPEIIVLREPGATWGNYLQHQKASNHSLHNLYNLQRDLL<br>TVAATVLGKQDPVLTSMANQMELAKVKADRPATKQEEAAA<br>KALKKNLIELIAARTQQQDGLPAKEAHRFAAVAFRDAQVKQL<br>NNQPWQTIKNTLTHNGHHYTNTQLPAAEMKIGAKDIFPSAYE<br>GKGVCSWDTKNIHHANNLWMSTVSVHEDGKDKTLFCGIRHG<br>VLSPYHEKDPLLRHVGAENKAKEVLTAALFSKPELLNKALAG<br>EAVSLKLVSVGLLTASNIFGKEGTMVEDQMRAWQSLTQPGK<br>MIHLKIRNKDGDLQTVKIKPDVAAFNVGVNELALKLGFGLKA<br>SDSYNAEALHQLLGNDLRPEARPGGWVGEWLAQYPDNYEV<br>VNTLARQIKDIWKNNQHHKDGGEPYKLAQRLAMLAHEIDAV<br>PAWNCKSGKDRTGMMDSEIKREIISLHQTHMLSAPGSLPDSG<br>GQKIFQKVLLNSGNLEIQKQNTGGAGNKVMKNLSPEVLNLSY<br>QKRVGDENIWQSVKGISSLITS |
| SipA | SEQ ID NO.: 47 | MVTSVRTQPPVIMPGMQTEIKTQATNLAANLSAVRESATTTL<br>SGEIKGPQLEDFPALIKQASLDALFKCGKDAEALKEVFTNSNN<br>VAGKKAIMEFAGLFRSALNATSDSPEAKTLLMKVGAEYTAQI<br>IKDGLKEKSAFGPWLPETKKAEAKLENLEKQLLDIIKNNTGGE<br>LSKLSTNLVMQEVMPYIASCIEHNFGCTLDPLTRSNLTHLVDK<br>AAAKAVEALDMCHQKLTQEQGTSVGREARHLEMQTLIPLLL<br>RNVFAQIPADKLPDPKIPEPAAGPVPDGGKKAEPTGININIDS<br>SNHSVDNSKHINNSRSHVDNSQRHIDNSNHDNSRKTIDNSRTF<br>IDNSQRNGESHHSTNSSNVSHSHSRVDSTTHQTETAHSASTGA<br>IDHGIAGKIDVTAHATAEAVTNASSESKDGKVVTSEKGTTGET<br>TSFDEVDGVTSKSIIGKPVQATVHGVDDNKQQSQTAEIVNVK<br>PLASQLAGVENVKTDTLQSDTTVITGNKAGTTDNDNSQTDKT<br>GPFSGLKFKQNSFLSTVPSVTNMHSMHFDARETFLGVIRKALE<br>PDTSTPFPVRRAFDGLRAEILPNDTIKSAALKAQCSDIDKHPEL<br>KAKMETLKEVITHHPQKEKLAEIALQFAREAGLTRLKGETDY<br>VLSNVLDGLIGDGSWRAGPAYESYLNKPGVDRVITTVDGLH<br>MQR |
| YpkA | SEQ ID NO.: 48 | MKSVKIMGTMPPSISLAKAHERISQHWQNPVGELNIGGKRYRI<br>IDNQVLRLNPHSGFSLFREGVGKIFSGKMFNFSIARNLTDTLH |

TABLE 1-continued

| | | |
|---|---|---|
| | | AAQKTTSQELRSDIPNALSNLFGAKPQTELPLGWKGEPLSGAP<br>DLEGMRVAETDKFAEGESHISIIETKDKQRLVAKIERSIAEGHL<br>FAELEAYKHIYKTAGKHPNLANVHGMAVVPYGNRKEEALLM<br>DEVDGWRCSDTLRTLADSWKQGKINSEAYWGTIKFIAHRLLD<br>VTNHLAKAGVVHNDIKPGNVVFDRASGEPVVIDLGLHSRSGE<br>QPKGFTESFKAPELGVGNLGASEKSDVFLVVSTLLHCIEGFEK<br>NPEIKPNQGLRFITSEPAHVMDENGYPIHRPGIAGVETAYTRFI<br>TDILGVSADSRPDSNEARLHEFLSDGTIDEESAKQILKDTLTGE<br>MSPLSTDVRRITPKKLRELSDLLRTHLSSAATKQLDMGGVLSD<br>LDTMLVALDKAEREGGVDKDQLKSFNSLILKTYRVIEDYVKG<br>REGDTKNSSTEVSPYHRSNFMLSIVEPSLQRIQKHLDQTHSFSD<br>IGSLVRAHKHLETLLEVLVTLSQQGQPVSSETYGFLNRLAEAK<br>ITLSQQLNTLQQQQESAKAQLSILINRSGSWADVARQSLQRFD<br>STRPVVKFGTEQYTAIHRQMMAAHAAITLQEVSEFTDDMRNF<br>TVDSIPLLIQLGRSSLMDEHLVEQREKLRELTTIAERLNRLERE<br>WM |
| YopM | SEQ ID<br>NO.: 49 | MFINPRNVSNTFLQEPLRHSSNLTEMPVEAENVKSKTEYYNA<br>WSEWERNAPPGNGEQREMAVSRLRDCLDRQAHELELNNLGL<br>SSLPELPPHLESLVASCNSLTELPELPQSLKSLQVENNNLKALP<br>DLPPSLKKLHVRENDLTDLPELPQSLESLRVDNNNLKALSDLP<br>PSLEYLTASSNKLEELPELQNLPFLAAIYADNNLLETLPDLPPS<br>LKKLHVRENDLTDLPELPQSLESLQVDNNNLKALSDLPPSLEY<br>LTASSNKLEELPELQNLPFLAAIYADNNLLETLPDLPPHLEILV<br>ASYNSLTELPELPQSLKSLRVDNNNLKALSDLPPSLEYLTASS<br>NKLEELPELQNLPFLAAIYADNNLLETLPDLPPSLKKLHVREN<br>DLTDLPELPQSLTFLDVSDNNISGLSELPPNLYYLDASSNEIRSL<br>CDLPPSLVDLNVKSNQLSELPALPPHLERLIASFNYLAEVPELP<br>QNLKQLHVEQNALREFPDIPESLEELEMDSERVVDPYEFAHET<br>TDKLEDDVFE |
| Amatoxin | SEQ ID<br>NO.: 50 | MSDINATRLPIWGIGCNPCVGDDVTTLLTRGEALC |
| Phallacidin | SEQ ID<br>NO.: 51 | MSDINATRLPAWLVDCPCVGDDVNRLLTRGESLC |
| Killer<br>toxin<br>KP1 | SEQ ID<br>NO.: 52 | MIKPERSILTILIGILCLLAYVLANGEPHDGDNEWSSYCSDQGF<br>RRSDDGLVTTPDVGQESIGKNSINGSELVDYLQCLKVRLNGQ<br>KQVVSNDGWLLLLVQEPSVNVTQKAMSECNYNVSSGHKAGS<br>YIQVTNTPADYKVISRRGSYEGDQLPEDVKPYFGVQKTSDYR<br>PISKRINPNLTLRQLAYNFAALNMCSLWCNSCISRSCPYYIAEL<br>TVHVNNIHHGTVWLHHFCRNASPQGGNLYSTLTISHKDTAYY<br>VGTGWWKVRSTAATTNDVAGDWYPASWNQYWCGPHY |
| Killer<br>toxin<br>KP6 | SEQ ID<br>NO.: 53 | MLIFSVLMYLGLLLAGASALPNGLSPRNNAFCAGFGLSCKWE<br>CWCTAHGTGNELRYATAAGCGDHLSKSYYDARAGHCLFSD<br>DLRNQFYSHCSSLNNNMSCRSLSKRTIQDSATDTVDLGAELH<br>RDDPPPTASDIGKRGKRPRPVMCQCVDTTNGGVRLDAVTRA<br>ACSIDSFIDGYYTEKDGFCRAKYSWDLFTSGQFYQACLRYSH<br>AGTNCQPDPQYE |
| Killer<br>Toxin K1 | SEQ ID<br>NO.: 54 | MTKPTQVLVRSVSILFFITLLHLVVALNDVAGPAETAPVSLLP<br>REAPWYDKIWEVKDWLLQRATDGNWGKSITWGSFVASDAG<br>VVIFGINVCKNCVGERKDDISTDCGKQTLALLVSIFVAVTSGH<br>HLIWGGNRPVSQSDPNGATVARRDISTVADGDIPLDFSALNDI<br>LNEHGISILPANASQYVKRSDTAEHTTSFVVTNNYTSLHTDLI<br>HHGNGTYTTFTTPHIPAVAKRYVYPMCEHGIKASYCMALND<br>AMVSANGNLYGLAEKLFSEDEGQWETNYYKLYWSTGQWIM<br>SMKFIEESIDNANNDFEGCDTGH |
| Killer<br>Toxin<br>K28<br>(KHR) | SEQ ID<br>NO.: 55 | MGHLAILFSIIAVLNIATAVASSDSIYLKGHRVGQDIDSLYRVY<br>DNGTMYPVTFNEWLNDLTGMNDLATNNATILKRDSSDVSCV<br>TETCQYVDYHVDDEGVITIDISTYRIPVEWDSGSAGNASYGVS<br>KRDTKYETFCKKKICGINVSGFCNAYDFAVHAFDPGGSVYNP<br>VSGITDRIKEATKRDKTECLGYELDHVRIDPAVDWSISISTWK<br>QGSANCDTQASADSLKCAAQKALESEHNHQKTAFCIHLDNG<br>GSFNLDIRLISELSFSKYNPWALPCPKYKGSNSWQVVSDCFQ |
| Killer<br>Toxin<br>K28<br>(KHS) | SEQ ID<br>NO.: 56 | MPRFAIIFALLIAYSLFLSTLFTGSIPDRANTVTSNAPCQVVIWD<br>WIRTRRICNCCSRLCYSLLGRSNLSRTAKRGVCTIAGAVLATA<br>AVIVAAVLVGKSSGSATKRGLTKTISVLNHTIPFTDHILNGQTL<br>SNGTGSNFVTIGFSGYAVHATIKRASTTDIISWVIPESMEPTLA<br>RVASYVSSSSINLAAVPDTGGNASALSFQNAVQEFATSWVSM<br>TYDQSYGDLRNVANDEGGEEILILMRKRSYRISFQVIETGSTA<br>LLLRTRRVVSQLITMTYLVTVQARVGIQIGDIFQHYGCrIDNYV<br>MTSISVLRTLEDKAFHENKLLIVREPPNKSNQDANQSYRLRPF<br>SANDLIQNLKSVDIGFLAFCSFFDKYAHYPEIIMMKITIFISKGN<br>LWSIIYVIQARYVRKRVMKVRGQMPGGLLTNMESLLNIVSTP<br>NLNISEFHIQTHSMSQSKPMYFQKQCYSSQNNIIYIYNSIHITCG |

TABLE 1-continued

| | | |
|---|---|---|
| | | AVYVIVHDVRTPSVFVLIELRNCKPLKNSWCETTKTSPRDTKI<br>KKNEYNETVCRRAGALLDGRVRTIRFLMMRTHWSRVKGVSC<br>NTANRLSRFCNHVVSYYPSQNATIHLLPTSLRAESLEQQYTTR<br>PLSSSNNRFCCLKSIFINNCKKACESPSLVSCNLQQTAELLMVY<br>YLYICEACYVSRNHDLLSKQCMSTVRAVYVARMRLPKFRSTF<br>PCMPRLCWLVNGVVVV |
| Anthrax lethal factor endopeptidase | SEQ ID NO.: 57 | MHVKEKEKNKDENKRKDEERNKTQEEHLKEIMKHIVKIEVK<br>GEEAVKKEAAEKLLEKVPSDVLEMYKAIGGKIYIVDGDITKHI<br>SLEALSEDKKKIKDIYGKDALLHEHYVYAKEGYEPVLVIQSSE<br>DYVENTEKALNVYYEIGKILSRDILSKINQPYQKFLDVLNTIKN<br>ASDSDGQDLLFTNQLKEHPTDFSVEFLEQNSNEVQEVFAKAF<br>AYYIEPQHRDVLQLYAPEAFNYMDKFNEQEINLSLEELKDQR<br>MLSRYEKWEKIKQHYQHWSDSLSEEGRGLLKKLQIPIEPKKD<br>DIIHSLSQEEKELLKRIQIDSSDFLSTEEKEFLKKLQIDIRDSLSE<br>EEKELLNRIQVDSSNPLSEKEKEFLKKLKLDIQPYDINQRLQDT<br>GGLIDSPSINLDVRKQYKRDIQNIDALLHQSIGSTLYNKIYLYE<br>NMNINNLTATLGADLVDSTDNTKINRGIFNEFKKNFKYSISSN<br>YMIVDINERPALDNERLKWRIQLSPDTRAGYLENGKLILQRNI<br>GLEIKDVQIIKQSEKEYIRIDAKVVPKSKIDTKIQEAQLNINQE<br>WNKALGLPKYTKLITFNVHNRYASNIVESAYLILNEWKNNIQ<br>SDLIKKVTNYLVDGNGRFVFTDITLPNIAEQYTHQDEIYEQVH<br>SKGLYVPESRSILLHGPSKGVELRNDSEGFIHEFGHAVDDYAG<br>YLLDKNQSDLVTNSKKFIDIFKEEGSNLTSYGRTNEAEFFAEA<br>FRLMHSTDHAERLKVQKNAPKTFQFINDQIKFIINS |
| Shiga Toxin | SEQ ID NO.: 58 | MKCILLKWVLCLLLGFSSVSYSREFTIDFSTQQSYVSSLNSIRT<br>EISTPLEHISQGTTSVSVINHTPPGSYFAVDIRGLDVYQARFDH<br>LRLIIEQNNLYVAGFVNTATNTFYRFSDFAHISVPGVTTVSMT<br>TDSSYTTLQRVAALERSGMQISRHSLVSSYLALMEFSGNTMT<br>RDASRAVLRFVTVTAEALRFRQIQREFRQALSETAPVYTMTP<br>GDVDLTLNWGRISNVLPEYRGEDGVRVGRISFNNISAILGTVA<br>VILNCHHQGARSVRAVNEESQPECQITGDRPVIKINNTLWESN<br>TAAAFLNRKSQSLYTTGE |
| Ricin Toxin | SEQ ID NO.: 59 | MYAVATWLCFGSTSGWSFTLEDNNIFPKQYPIINFTTAGATVQ<br>SYTNFIRAVRGRLTTGADVRHDIPVLPNRVGLPINQRFILVELS<br>NHAELSVTLALDVTNAYVVGYRAGNSAYFFHPDNQEDAEAI<br>THLFTDVQNRYTFAFGGNYDRLEQLAGNLRENIELGNGPLEE<br>AISALYYYSTGGTQLPTLARSFIICIQMISEAARFQYIEGEMRTR<br>IRYNRRSAPDPSVITLENSWGRLSTAIQESNQGAFASPIQLQRR<br>NGSKFSVYDVSILIPIIALMVYRCAPPPSSQFSLLIRPVVPNFNA<br>DVCMDPEPIVRIVGRNGLCVDVRDGRFHNGNAIQLWPCKSNT<br>DANQLWTLKRDNTIRSNGKCLTTYGYSPGVYVMIYDCNTAA<br>TDATRWQIWDNGTIINPRSSLVLAATSGNSGTTLTVQTNIYAV<br>SQGWLPTNNTQPFVTTIVGLYGLCLQANSGQVWIEDCSSEKA<br>EQQWALYADGSIRPQQNRDNCLTSDSNIRETVVKILSCGPASS<br>GQRWMFKNDGTILNLYSGLVLDVRRSDPSLKQIILYPLHGDP<br>NQIWLPLF |

A cytotoxic reporter of the invention can be, for example, a ribosomally-encoded xenobiotic agent, a ribosomally-encoded poison, a ribosomally-encoded endogenous or exogenous gene that results in severe growth defects upon mild overexpression, a ribosomally-encoded recombinase that excises an essential gene for viability, or a limiting factor (or multiple factors) that can be involved in the synthesis of a toxic secondary metabolite.

The system of the invention can use the reconstitution of a transcription factor mediated by the interaction between a protein fused to an AD, for example, Dof1, and another protein fused to a DBD, for example, TetR.

Figure 7:
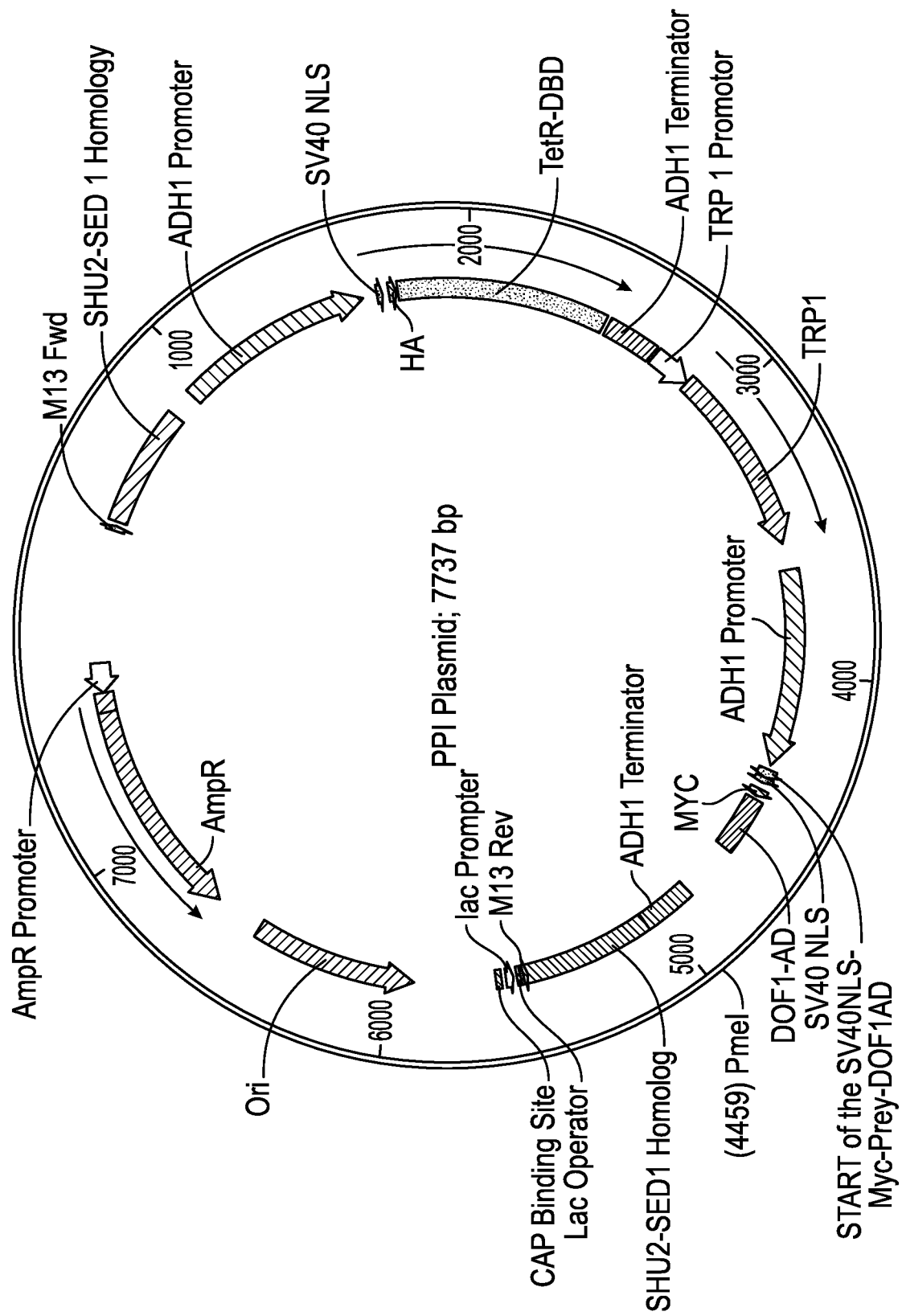
FIG. 7 is an illustrative example of a protein-protein integration plasmid.
Figure 9:
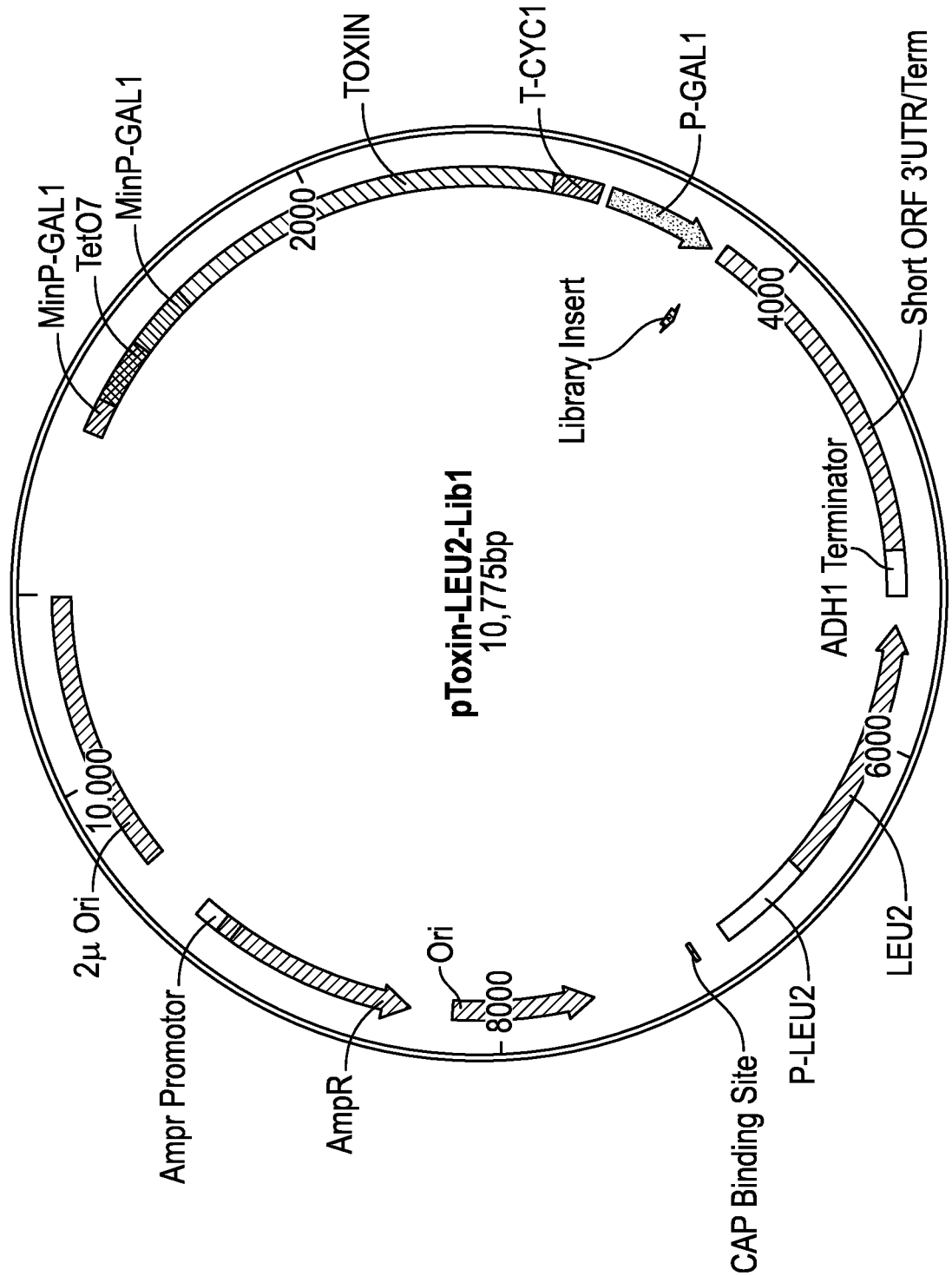
FIG. 9 is an illustrative example of a selection and library plasmid.
Figure 11:
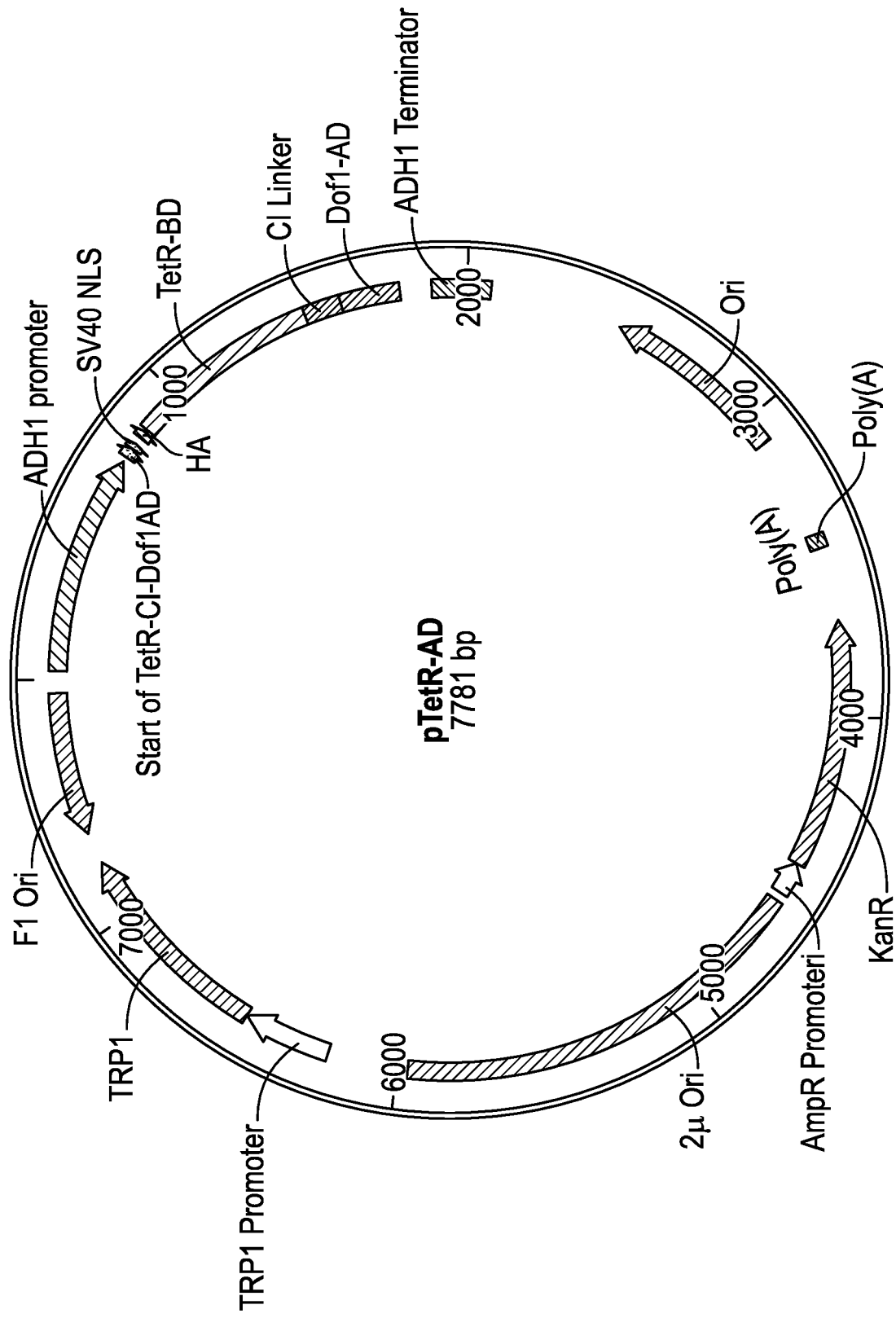
FIG. 11 is an illustrative example of a confirmation plasmid.

To identify peptides that can disrupt a PPI, a PPI integration plasmid (Plasmid 1; FIG. 7), a selection and library plasmid (Plasmid 2; FIG. 9), and a confirmation (Plasmid 3; FIG. 11) can be used.

Plasmid 1 can contain, for example, two restriction sites that enable the integration of two proteins that constitute the PPI of interest. The PPI of interest can involve a pair of domains having known importance for carcinogesis, such as p53-MDM2, RAS-RASRBD, and MYC-MAX. The PPI of interest can also involve the interaction of an oncogene (such as Cdk1, Cdk2, Cdk3, Cdk4, Cdk6, c-MYC, EGFR, HER2, K-Ras, PDGFR, Raf kinase, and VEGF) or a tumor suppressor (such as BRCA1, BRCA2, cyclin-dependent kinase inhibitor 1C, PTEN, p16, p27, p53, p73, and Retinoblastoma protein (pRb)) with a known cellular interaction partner. The PPI of interest can involve the interaction of a protein involved in the DNA repair pathway (such as ATM, ATRX, BRCA1, BRCA2, ERCC1, FANCB, FANCF, FEN1, HMGA1, HMGA1, MDC1, MGMT, MLH1, MSH2, MSH4, Mre11A, NBS1, NEIL1, PARP1, PARP2, PMS2, RAD51, RAD52, RAD54, RAD51AP1, WRN, and XPF) with another cellular factor.

When designating a DNA sequence, an N means any possible deoxynucleotide.

Plasmid 1 can encode for the fusion of an AD (such as Dof1) or another gene activating moiety and a DBD (such as TetR) to each protein driven by either a strong promoter and terminator (such as ADH1), or by an inducible promoter (such as GAL1). Other exemplary activation domains include those of VP16 and B42AD. Other exemplary DBDs include those of GAL4 or LexA. Each protein fusion can be tagged for subsequent biochemical experiments with, for example, a FLAG, HA, or His tag. Plasmid 1 can also include bacterial selection and propagation markers (i.e. ori and AmpR), and yeast replication and selection markers (i.e. TRP1 and CEN or 2 um). The plasmid can also be integrated into the genome at a specified locus. The sequence of Plasmid 1 can be:

(SEQ ID NO.: 63)
TCGCGCGTTTCGGTGATGACGGTGAAAACCTCTGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGGGGCTGGCTTAACTATGCGGCATCAGAGCAGAT

TGTACTGAGAGTGCACCATATGCGGTGTGAAATACCGCACAGATGCGTAAGGAGAAAATACCGCATCAGGCGCCATTCGCCAT

TCAGGCTGCGCAACTGTTGGGAAGGGCGATCGGTGCGGGCCTCTTCGCTATTACGCCAGCTGGCGAAAGGGGGATGTGCTGCA

AGGCGATTAAGTTGGGTAACGCCAGGGTTTTCCCAGTCACGACGTTGTAAAACGACGGCCAGTGAATTCGAGCTCGGTACCCG

TCTTCTGTCCCAGTTACCGAATCTAAGGGCACTACCACCAAAGAAACAGGTGTTACTACCAAACAAACCACAGCCAACCCAAG

TCTAACCGTCTCCACAGTCGTCCCAGTTTCATCCTCTGCTTCTTCTCATTCCGTTGTCATCAACAGTAACGGTGCTAACGTCG

TCGTTCCAGGTGCTTTAGGTTTGGCTGGTGTTGCTATGTTATTCTTATAAACGGTGGTGTTTGACACATCCGCCTTCTTAATG

CTTTCTTTCAGTATTATGTTATTTTTTGTTATTCGTTTTTCACTTCTAGGCTTTTTGACAGACTAGCCCCGTTATACCACCA

TCTTTGTGGGAAAGCCCCTAAATTGCCCTGAGCAGTATCGTTTCATGTCTAGTCTCTTTAAAGATGTTTCTTACACTTCTCCT

ATGCACATATATTAATTAAAGTCCAATGCTAGTAGAGAAGGGGGGTAACACCCCTCCGCGCTCTTTTCCGATTTTTTCTAAA

CCGTGGAATATTTCGGATATCCTTTTGTTGTTTCCGGGTGTACAATATGGACTTCCTCTTTTCTGGCAACCAAACCCATACAT

CGGGATTCCTATAATACCTTCGTTGGTCTCCCTAACATGTAGGTGGCGGAGGGGAGATATACAATAGAACAGATACCAGACAA

GACATAATGGGCTAAACAAGACTACACCAATTACACTGCCTCATTGATGGTGGTACATAACGAACTAATACTGTAGCCCTAGA

CTTGATAGCCATCATCATATCGAAGTTTCACTACCCTTTTTCCATTTGCCATCTATTGAAGTAATAATAGGCGCATGCAACTT

CTTTTCTTTTTTTTCTTTTCTCTCTCCCCGTTGTTGTCTCACCATATCCGCAATGACAAAAAAATGATGGAAGACACTAAA

GGAAAAAATTAACGACAAAGACAGCACCAACAGATGTCGTTGTTCCAGAGCTGATGAGGGGTATCTCGAAGCACACGAAACTT

TTTCCTTCCTTCATTCACGCACACTACTCTCTAATGAGCAACGGTATACGGCCTTCCTTCCAGTTACTTGAATTTGAAATAAA

AAAAAGTTTGCTGTCTTGCTATCAAGTATAAATAGACCTGCAATTATTAATCTTTTGTTTCCTCGTCATTGTTCTCGTTCCCT

TTCTTCCTTGTTTCTTTTTCTGCACAATATTTCAAGCTATACCAAGCATACAATCAACTCCAAGCTTTGCAAAGATGGGGTCA

AAGGCCGAGCTAATCCCAGAGCCCCCTAAAAAAAAGAGAAAGGTCGAGCTGGGAACTGCGGCAGAGTACCCGTATGATGTACC

GGACTATGCCGGAGGTATGTCTAGATTGGACAAGTCTAAGGTTATCAACTCTGCTTTGGAATTGTTGAACGAAGTTGGTATCG

AAGGTTTGACTACTAGAAAGTTGGCTCAAAAGTTGGGTGTTGAACAACCAACTTTGTACTGGCACGTTAAGAACAAGAGAGCT

TTGTTGGACGCTTTGGCTATCGAAATGTTGGACAGACACCACACTCACTTCTGTCCATTGGAAGGTGAATCTTGGCAAGACTT

CTTGAGAAACAACGCTAAGTCTTTCAGATGTGCTTTGTTGTCTCACAGAGACGGTGCTAAGGTTCACTTGGGTACTAGACCAA

CTGAAAAGCAATACGAAACTTTGGAAAACCAATTGGCTTTCTTGTGTCAACAAGGTTTCTCTTTGGAAAACGCTTTGTACGCT

TTGTCTGCTGTTGGTCACTTCACTTTGGGTTGTGTTTTGGAAGACCAAGAACACCAAGTTGCTAAGGAAGAAAGAGAAACTCC

AACTACTGACTCTATGCCACCATTGTTGAGACAAGCTATCGAATTGTTCGACCACCAAGGTGCTGAACCAGCTTTCTTGTTCG

GTTTGGAATTGATCATCTGTGGTTTGGAAAAGCAATTGAAGTGTGAATCTGGTTCTGGGCAACCATCTTTGAGATCTGAATAC

GAATACCCAGTTTTCTCTCACGTTCAAGCTGGTATGTTCTCTCCAGAATTGAGAACTTTCACTAAGGGTGACGCTGAAAGATG

GGTTTCTGGTCCAGGCGCGCCACTTCTAAATAAGCGAATTTCTTATGATTTATGATTTTTATTATTAAATAAGTTATAAAAAA

AATAAGTGTATACAAATTTTAAAGTGACTCTTAGGTTTTAAAACGAAAATTCTTATTCTTGAGTAACTCTTTCCTGTAGGTCA

GGTTGCTTTCTCAGGTATAGCATGAGGTCGCTCTTATTGACCACACCTCTACCGGCAGATCTGTACAATCTTGATCCGGAGCT

TTTCTTTTTTGCCGATTAAGAATTAATTCGGTCGAAAAAGAAAGGAGAGGGCCAAGAGGGAGGGCATTGGTGACTATTGA

GCACGTGAGTATACGTGATTAAGCACACAAAGGCAGCTTGGAGTATGTCTGTTATTAATTTCACAGGTAGTTCTGGTCCATTG

GTGAAAGTTTGCGGCTTGCAGAGCACAGAGGCCGCAGAATGTGCTCTAGATTCCGATGCTGACTTGCTGGGTATTATATGTGT

GCCCAATAGAAAGAGAACAATTGACCCGGTTATTGCAAGGAAATTTCAAGTCTTGTAAAAGCATATAAAAATAGTTCAGGCA

CTCCGAAATACTTGGTTGGCGTGTTTCGTAATCAACCTAAGGAGGATGTTTGGCTCTGGTCAATGATTACGGCATTGATATC

GTCCAACTGCATGGAGATGAGTCGTGGCAAGAATACCAAGAGTTCCTCGGTTTGCCAGTTATTAAAAGACTCGTATTTCCAAA

AGACTGCAACATACTACTCAGTGCAGCTTCACAGAAACCTCATTCGTTTATTCCCTTGTTTGATTCAGAAGCAGGTGGGACAG

-continued

```
GTGAACTTTTGGATTGGAACTCGATTTCTGACTGGGTTGGAAGGCAAGAGAGCCCCGAAAGCTTACATTTTATGTTAGCTGGT
GGACTGACGCCAGAAAATGTTGGTGATGCGCTTAGATTAAATGGCGTTATTGGTGTTGATGTAAGCGGAGGTGTGGAGACAAA
TGGTGTAAAAGACTCTAACAAAATAGCAAATTTCGTCAAAAATGCTAAGAAATAGGTTATTACTGAGTAGTATTTATTTAAGT
ATTGTTTGTGCACTTGCCTGCGGTGTGAAATACCGCACAGATGCGTAAGGAATATTTCGGATATCCTTTTGTTGTTTCCGGGT
GTACAATATGGACTTCCTCTTTTCTGGCAACCAAACCCATACATCGGGATTCCTATAATACCTTCGTTGGTCTCCCTAACATG
TAGGTGGCGGAGGGGAGATATACAATAGAACAGATACCAGACAAGACATAATGGGCTAAACAAGACTACACCAATTACACTGC
CTCATTGATGGTGGTACATAACGAACTAATACTGTAGCCCTAGACTTGATAGCCATCATCATATCGAAGTTTCACTACCCTTT
TTCCATTTGCCATCTATTGAAGTAATAATAGGCGCATGCAACTTCTTTTCTTTTTTTTCTTTTCTCTCTCCCCCGTTGTTGT
CTCACCATATCCGCAATGACAAAAAAATGATGGAAGACACTAAAGGAAAAAATTAACGACAAAGACAGCACCAACAGATGTCG
TTGTTCCAGAGCTGATGAGGGGTATCTCGAAGCACACGAAACTTTTTCCTTCCTTCATTCACGCACACTACTCTCTAATGAGC
AACGGTATACGGCCTTCCTTCCAGTTACTTGAATTTGAAATAAAAAAAAGTTTGCTGTCTTGCTATCAAGTATAAATAGACCT
GCAATTATTAATCTTTTGTTTCCTCGTCATTGTTCTCGTTCCCTTTCTTCCTTGTTTCTTTTTCTGCACAATATTTCAAGCTA
TACCAAGCATACAATCAACTCCAAGCTTTGCAAAGATGGGGTCAAAGGCCGAGCTAATCCCAGAGCCCCCTAAAAAAAAGAGA
AAGGTCGAGCTGGGAACTGCGGCAGAGGAGCAGAAGCTGATCTCAGAGGAGGACCTGTTTAAACCAGGAGGCGGTTCTGGTCC
AGGTACTGAAGACGCTGAAGCTGTTGCTTTGGGTTTGGGTTTGTCTGACTTCCCATCTGCTGGTAAGGCTGTTTTGGACGACG
AAGACTCTTTCGTTTGGCCAGCTGCTTCTTTCGACATGGGTGCTTGTTGGGCTGGTGCTGGTTTCGCTGACCCAGACCCAGCT
TGTATCTTCTTGAACTTGCCATGAGCCCATCTTTTTTTGGACCTAAATTCTTCATGAAAATATATTACGAGGGCTTATTCAG
AAGCTTTGGACTTCTTCGCCAGAGGTTTGGTCAAGTCTCCAATCAAGGTTGTCGGCTTGTCTACCTTGCCAGAAATTTACGAA
AAGATGGAAAAGGGTCAAATCGTTGGTAGATACGTTGTTGACACTTCTAAATAAGCGAATTTCTTATGATTTATGATTTTTAT
TATTAAATAAGTTATAAAAAAAATAAGTGTATACAAATTTTAAAGTGACTCTTAGGTTTTAAAACGAAAATTCTTATTCTTGA
GTAACTCTTTCCTGTAGGTCAGGTTGCTTTCTCAGGTATAGCATGAGGTCGCTCTTATTGACCACACCTCTACCGGCCGGTCG
AAATTCCCCTACCCTATGAACATATTCCATTTTGTAATTTCGTGTCGCGTTGCGTGTAAAACATCCTCTCATTCAAGACAGGG
TTTTCTAAAAGCAATAGGGGTAGTTTAATAATTCTTATATAATCATCATATACACTATTTTTAGTTCTTAATTCTTTAATACA
AACTTATTAATGTGCTCTCCATTGATCTCTTAATCAGGAGGCGATATATACCGGAAGCGGTGTACTTTTCTTCACCTCTTACT
CAACTATGTTGATGTGCAAGTTTAACCACTCGTCGATATTATCTATTGCTATAACGAAAACTTTATTCGAGTTCACAGTGAAA
AACTTCAGCACATTTATGGAAGATCTAAGCAAAATGGAGAACGCCAGTAGATGCGAACAACAAACTTTATCAAATTTGAAATA
CCACTGCTTTGATAAGCTATAGCTTGGCGTAATCATGGTCATAGCTGTTTCCTGTGTGAAATTGTTATCCGCTCACAATTCCA
CACAACATACGAGCCGGAAGCATAAAGTGTAAAGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTCGGCTGCGGCGAGCGGTATCAGCTCACTCAAAG
GCGGTAATACGGTTATCCACAGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGAACAGTATTTGGTATCTGCGCTCTGCTGAAGCC
AGTTACCTTCGGAAAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTAAATTAAAAATGAAGTTTTAAATC
AATCTAAAGTATATATGAGTAAACTTGGTCTGACAGTTACCAATGCTTAATCAGTGAGGCACCTATCTCAGCGATCTGTCTAT
```

```
TTCGTTCATCCATAGTTGCCTGACTCCCCGTCGTGTAGATAACTACGATACGGGAGGGCTTACCATCTGGCCCCAGTGCTGCA

ATGATACCGCGAGACCCACGCTCACCGGCTCCAGATTTATCAGCAATAAACCAGCCAGCCGGAAGGGCCGAGCGCAGAAGTGG

TCCTGCAACTTTATCCGCCTCCATCCAGTCTATTAATTGTTGCCGGGAAGCTAGAGTAAGTAGTTCGCCAGTTAATAGTTTGC

GCAACGTTGTTGCCATTGCTACAGGCATCGTGGTGTCACGCTCGTCGTTTGGTATGGCTTCATTCAGCTCCGGTTCCCAACGA

TCAAGGCGAGTTACATGATCCCCCATGTTGTGCAAAAAAGCGGTTAGCTCCTTCGGTCCTCCGATCGTTGTCAGAAGTAAGTT

GGCCGCAGTGTTATCACTCATGGTTATGGCAGCACTGCATAATTCTCTTACTGTCATGCCATCCGTAAGATGCTTTTCTGTGA

CTGGTGAGTACTCAACCAAGTCATTCTGAGAATAGTGTATGCGGCGACCGAGTTGCTCTTGCCCGGCGTCAATACGGGATAAT

ACCGCGCCACATAGCAGAACTTTAAAAGTGCTCATCATTGGAAAACGTTCTTCGGGGCGAAAACTCTCAAGGATCTTACCGCT

GTTGAGATCCAGTTCGATGTAACCCACTCGTGCACCCAACTGATCTTCAGCATCTTTTACTTTCACCAGCGTTTCTGGGTGAG

CAAAAACAGGAAGGCAAAATGCCGCAAAAAAGGGAATAAGGGCGACACGGAAATGTTGAATACTCATACTCTTCCTTTTTCAA

TATTATTGAAGCATTTATCAGGGTTATTGTCTCATGAGCGGATACATATTTGAATGTATTTAGAAAAATAAACAAATAGGGGT

TCCGCGCACATTTCCCCGAAAAGTGCCACCTGACGTCTAAGAAACCATTATTATCATGACATTAACCTATAAAAATAGGCGTA

TCACGAGGCCCTTTCGTC.
```

Plasmid 2 can include, for example, a restriction site for integration of a randomized peptide library (such as a randomized NNK 60-mer sequences) driven by a strong promoter (such as the ADH1 promoter) or an inducible promoter (such as the GAL1 promoter). The library can also initiate with a fixed sequence of, for example, Methionine Valine Asparagine (MVN; SEQ ID NO.: 66) or another combination of high-half-life N-end residues (see, for e.g., Varshavsky. Proc. Natl. Acad. Sci. USA. 93:12142-12149 (1996)) to maximize the half-life of the peptide, and terminate with the UTR of a short protein (such as sORF1). The peptide can also be tagged with a protein tag such as Myc. The peptide can also be the product of a ribosomally synthesized and post-translationally modified peptide (RiPP) whereby the core peptide is flanked by prepropeptide sequence comprising a leader peptide and recognition sequences which signal for the recruitment of maturation, cleavage, and/or modifying enzymes such as excision or cyclization enzymes including, for example, lanthipeptides maturation enzymes from *Lactococcus lactis* (LanB, LanC, LanM, LanP) patellamide biosynthesis factors from cyanobacteria (PatD, PatG), butelase 1 from *Clitoria ternatea*, and POPB from *Galerina marginata* or *Amanita bisporigera*.

Plasmid 2 can additionally encode for one or more of the agents outlined as 'death agents' (e.g. cytotoxic reporters) driven by a promoter which depends on the DBD present in the PPI integration plasmid, for example, the TetO sequence which can become bound by TetR. To ensure repression of the 'death agents,' Plasmid 2 can include a silencing construct such as a TetR'-Tup11 fusion driven by a strong promoter (such as ADH1) to bind the DBD and silence transcription in the presence of doxycycline. Plasmid 2 can include bacterial selection and propagation markers (i.e. ori and AmpR), and yeast replication and selection markers (i.e. LEU2 and CEN or 2 um). The sequence of Plasmid 2 can be:

(SEQ ID NO.: 64)
```
TGCATGCCTGCAGGTCGAGATCCGGGATCGAAGAAATGATGGTAAATGAAATAGGAAATCAAGGAGCATGAAGGCAAAAGACAA

ATATAAGGGTCGAACGAAAAATAAAGTGAAAAGTGTTGATATGATGTATTTGGCTTTGCGGCGCCGAAAAAACGAGTTTACGCA

ATTGCACAATCATGCTGACTCTGTGGCGGACCCGCGCTCTTGCCGGCCCGGCGATAACGCTGGGCGTGAGGCTGTGCCCGGCGG

AGTTTTTTGCGCCTGCATTTTCCAAGGTTTACCCTGCGCTAAGGGGCGAGATTGGAGAAGCAATAAGAATGCCGGTTGGGGTTG

CGATGATGACGACCACGACAACTGGTGTCATTATTTAAGTTGCCGAAAGAACCTGAGTGCATTTGCAACATGAGTATACTAGAA

GAATGAGCCAAGACTTGCGAGACGCGAGTTTGCCGGTGGTGCGAACAATAGAGCGACCATGACCTTGAAGGTGAGACGCGCATA

ACCGCTAGAGTACTTTGAAGAGGAAACAGCAATAGGGTTGCTACCAGTATAAATAGACAGGTACATACAACACTGGAAATGGTT

GTCTGTTTGAGTACGCTTTCAATTCATTTGGGTGTGCACTTTATTATGTTACAATATGGAAGGGAACTTTACACTTCTCCTATG

CACATATATTAATCATAAGTTGAATTCGACAGGTTATCAGCAACAACACAGTCATATCCATTCTCAATTAGCTCTACCACAGTG

TGTGAACCAATGTATCCAGCACCACCTGTAACCAAAACAATTTTACCTCGATCGAGTTTACCACTCCCTATCAGTGATAGAGAA

AAGTTAAAGTCGAGTTTACCACTCCCTATCAGTGATAGAGAACAGTCAAAGTCGAGTTTACCACTCCCTATCAGTGATAGAGAA

AAGTTAAAGTCGAGTTTACCACTCCCTATCAGTGATAGAGAAAAGTTAAAGTCGAGTTTACCACTCCCTATCAGTGATAGAGAA

CAGTCAAAGTCGAGTTTACCACTCCCTATCAGTGATAGAGAATTGTGAAAGTCGAGTTTACCACTCCCTATCAGTGATAGAGAA

AAGTCCAAGTCGAGCTCGGTACCCTATGGCATGCATGTGGATGATAATGCGATTAGTTTTTTAGCCTTATTTCTGGGGTAATTA
```

-continued

ATCAGCGAAGCGATGATTTTTGATCTATTAACAGATATATAAATGGAAAAGCTGCATAACCACTTTAACTAATACTTTCAACAT

TTTCAGTTTGTATTACTTCTTATTCAAATGTCATAAAAGTATCAACAAAAAATTGTTAATATACCTCTATACTTTAACGTCAAG

GAGAAAAAACTATAATGCAAAAATCTCATTCAGAAGAAGTGATTGTACCTGAGTTCAATTCTAGCGCAAAGGAATTACCAAGAC

CATGGCCGAAAAGTGCCCGAGCGGTGCTNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNN(TOXIN)TAATAGCATCATGTAATTAGTTATGTCACGCTTACATT

CACGCCCTCCCCCCACATCCGCTCTAACCGAAAAGGAAGGAGTTAGACAACCTGAAGTCTAGGTCCCTATTTATTTTTTTATAG

TTATGTTAGTATTAAGAACGTTATTTATATTTCAAATTTTTCTTTTTTTTCTGTACAGACGCGTGTACGCATGTAACATTATAC

TGAAAACCTTGCTTGAGAAGGTTTTGGGACGCTCGAAGGCTTTAATTTGATACGGATTAGAAGCCGCCGAGCGGGCGACAGCCC

TCCGACGGAAGACTCTCCTCCGTGCGTCCTCGTCTTCACCGGTCGCGTTCCTGAA

-continued

```
CCGGCCGGTCGAAATTCCCCTACCCTATGAACATATTCCATTTTGTAATTTCGTGTCGTTTCTATTATGAATTTCATTTATAA

GTTTATGTACAAATATCATAAAAAAAGAGAATCTTTTTAAGCAAGGATTTTCTTAACTTCTTCGGCGACAGCATCACCGACTTC

GGTGGTACTGTTGGAACCACCTAAATCACCAGTTCTGATACCTGCATCCAAAACCTTTTTAACTGCATCTTCAATGGCCTTACC

TTCTTCAGGCAAGTTCAATGACAATTTCAACATCATTGCAGCAGACAAGATAGTGGCGATAGGGTTGACCTTATTCTTTGGCAA

ATCTGGAGCAGAACCGTGGCATGGTTCGTACAAACCAAATGCGGTGTTCTTGTCTGGCAAAGAGGCCAAGGACGCAGATGGCAA

CAAACCCAAGGAACCTGGGATAACGGAGGCTTCATCGGAGATGATATCACCAAACATGTTGCTGGTGATTATAATACCATTTAG

GTGGGTTGGGTTCTTAACTAGGATCATGGCGGCAGAATCAATCAATTGATGTTGAACCTTCAATGTAGGAAATTCGTTCTTGAT

GGTTTCCTCCACAGTTTTTCTCCATAATCTTGAAGAGGCCAAAACATTAGCTTTATCCAAGGACCAAATAGGCAATGGTGGCTC

ATGTTGTAGGGCCATGAAAGCGGCCATTCTTGTGATTCTTTGCACTTCTGGAACGGTGTATTGTTCACTATCCCAAGCGACACC

ATCACCATCGTCTTCCTTTCTCTTACCAAAGTAAATACCTCCCACTAATTCTCTGACAACAACGAAGTCAGTACCTTTAGCAAA

TTGTGGCTTGATTGGAGATAAGTCTAAAAGAGAGTCGGATGCAAAGTTACATGGTCTTAAGTTGGCGTACAATTGAAGTTCTTT

ACGGATTTTTAGTAAACCTTGTTCAGGTCTAACACTACCTGTACCCCATTTAGGACCACCCACAGCACCTAACAAAACGGCATC

AGCCTTCTTGGAGGCTTCCAGCGCCTCATCTGGAAGTGGGACACCTGTAGCTTCGATAGCAGCACCACCAATTAAATGATTTTC

GAAATCGAACTTGACATTGGAACGAACATCAGAAATAGCTTTAAGAACCTTAATGGCTTCGGCTGTGATTTCTTGACCAACGTG

GTCACCTGGCAAAACGACGATCTTCTTAGGGGCAGACATTAGAATGGTATATCCTTGAAATATATATATATATTGCTGAAATGT

AAAAGGTAAGAAAAGTTAGAAAGTAAGACGATTGCTAACCACCTATTGGAAAAAACAATAGGTCCTTAAATAATATTGTCAACT

TCAAGTATTGTGATGCAAGCATTTAGTCATGAACGCTTCTCTATTCTATATGAAAAGCCGGTTCCGGCGCTCTCACCTTTCCTT

TTTCTCCCAATTTTTCAGTTGAAAAAGGTATATGCGTCAGGCGACCTCTGAAATTAACAAAAAATTTCCAGTCATCGAATTTGA

TTCTGTGCGATAGCGCCCCTGTGTGTTCTCGTTATGTTGAGGAAAAAAATAATGGTTGCTAAGAGATTCGAACTCTTGCATCTT

ACGATACCTGAGTATTCCCACAGTTGGGGGATCTCGACTCTAGCTAGAGGATCAATTCGTAATCATGTCATAGCTGTTTCCTGT

GTGAAATTGTTATCCGCTCACAATTCCACACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTCGTGCCAGCTGATAACTTCGTATAATGT

ATGCTATACGAAGTTATTAGGTCTGAAGAGGAGTTTACGTCCAGCCAAGCTAGCTTGGCTGCAGGTCGAGCGGCCGCGATCCGG

AACCCTTAATATAACTTCGTATAATGTATGCTATACGAAGTTATCAGCTGCATTAATGAATCGGCCAACGCGCGGGGAGAGGCG

GTTTGCGTATTGGGCGCTCTTCCGCTTCCTCGCTCACTGACTCGCTGCGCTCGGTCGTTCGGCTGCGGCGAGCGGTATCAGCTC

ACTCAAAGGCGGTAATACGGTTATCCACAGAATCAGGGGATAACGCAGGAAAGAACATGTGAGCAAAAGGCCAGCAAAAGGCCA

GGAACCGTAAAAAGGCCGCGTTGCTGGCGTTTTTCCATAGGCTCCGCCCCCCTGACGAGCATCACAAAAATCGACGCTCAAGTC

AGAGGTGGCGAAACCCGACAGGACTATAAAGATACCAGGCGTTTCCCCCTGGAAGCTCCCTCGTGCGCTCTCCTGTTCCGACCC

TGCCGCTTACCGGATACCTGTCCGCCTTTCTCCCTTCGGGAAGCGTGGCGCTTTCTCATAGCTCACGCTGTAGGTATCTCAGTT

CGGTGTAGGTCGTTCGCTCCAAGCTGGGCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTAACAGGATTAGCAGAGCGAGGTATGTAG

GCGGTGCTACAGAGTTCTTGAAGTGGTGGCCTAACTACGGCTACACTAGAAGAACAGTATTTGGTATCTGCGCTCTGCTGAAGC

CAGTTACCTTCGGAAAAAGAGTTGGTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAGGCACCTATCTCAGCGATCTGTCTATTTC

GTTCATCCATAGTTGCCTGACTCCCCGTCGTGTAGATAACTACGATACGGGAGGGCTTACCATCTGGCCCCAGTGCTGCAATGA

TACCGCGAGACCCACGCTCACCGGCTCCAGATTTATCAGCAATAAACCAGCCAGCCGGAAGGGCCGAGCGCAGAAGTGGTCCTG

CAACTTTATCCGCCTCCATCCAGTCTATTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATTCAGCTCCGGTTCCCAACGATCAAGGC
```

-continued

```
GAGTTACATGATCCCCCATGTTGTGCAAAAAAGCGGTTAGCTCCTTCGGTCCTCCGATCGTTGTCAGAAGTAAGTTGGCCGCAG

TGTTATCACTCATGGTTATGGCAGCACTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGGCGTCAATACGGGATAATACCGCGCCAC

ATAGCAGAACTTTAAAAGTGCTCATCATTGGAAAACGTTCTTCGGGGCGAAAACTCTCAAGGATCTTACCGCTGTTGAGATCCA

GTTCGATGTAACCCACTCGTGCACCCAACTGATCTTCAGCATCTTTTACTTTCACCAGCGTTTCTGGGTGAGCAAAAACAGGAA

GGCAAAATGCCGCAAAAAAGGGAATAAGGGCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAATAAACAAATAGGGGTTCCGCGCACATTTC

CCCGAAAAGTGCCACCTGACGTCTAAGAAACCATTATTATCATGACATTAACCTATAAAAATAGGCGTATCACGAGGCCCTTTC

GTCTCGCGCGTTTCGGTGATGACGGTGAAAACCTCTGACACATGCAGCTCCCGGAGACGGTCACAGCTTGTCTGTAAGCGGATG

CCGGGAGCAGACAAGCCCGTCAGGGCGCGTCAGCGGGTGTTGGCGGGTGTCGGGGCTGGCTTAACTATGCGGCATCAGAGCAGA

TTGTACTGAGAGTGCACCATAACGCATTTAAGCATAAACACGCACTATGCCGTTCTTCTCATGTATATATATATACAGGCAACA

CGCAGATATAGGTGCGACGTGAACAGTGAGCTGTATGTGCGCAGCTCGCGTTGCATTTTCGGAAGCGCTCGTTTTCGGAAACGC

TTTGAAGTTCCTATTCCGAAGTTCCTATTCTCTAGCTAGAAAGTATAGGAACTTCAGAGCGCTTTTGAAAACCAAAAGCGCTCT

GAAGACGCACTTTCAAAAAACCAAAAACGCACCGGACTGTAACGAGCTACTAAAATATTGCGAATACCGCTTCCACAAACATTG

CTCAAAAGTATCTCTTTGCTATATATCTCTGTGCTATATCCCTATATAACCTACCCATCCACCTTTCGCTCCTTGAACTTGCAT

CTAAACTCGACCTCTACATTTTTTATGTTTATCTCTAGTATTACTCTTTAGACAAAAAAATTGTAGTAAGAACTATTCATAGAG

TGAATCGAAAACAATACGAAATGTAAACATTTCCTATACGTAGTATATAGAGACAAAATAGAAGAAACCGTTCATAATTTTCT

GACCAATGAAGAATCATCAACGCTATCACTTTCTGTTCACAAAGTATGCGCAATCCACATCGGTATAGAATATAATCGGGGATG

CCTTTATCTTGAAAAAATGCACCCGCAGCTTCGCTAGTAATCAGTAAACGCGGGAAGTGGAGTCAGGCTTTTTTATGGAAGAG

AAAATAGACACCAAAGTAGCCTTCTTCTAACCTTAACGGACCTACAGTGCAAAAAGTTATCAAGAGACTGCATTATAGAGCGCA

CAAAGGAGAAAAAAAGTAATCTAAGATGCTTTGTTAGAAAAATAGCGCTCTCGGGATGCATTTTGTAGAACAAAAAAGAAGTA

TAGATTCTTTGTTGGTAAAATAGCGCTCTCGCGTTGCATTTCTGTTCTGTAAAAATGCAGCTCAGATTCTTTGTTTGAAAAATT

AGCGCTCTCGCGTTGCATTTTTGTTTTACAAAAATGAAGCACAGATTCTTCGTTGGTAAAATAGCGCTTTCGCGTTGCATTTCT

GTTCTGTAAAAATGCAGCTCAGATTCTTTGTTTGAAAAATTAGCGCTCTCGCGTTGCATTTTTGTTCTACAAAATGAAGCACAG

ATGCTTCGTTGCT.
```

Plasmid 3 can be used to confirm expression of the reporters and the successful construction of the strains. Plasmid 3 can include a direct fusion between the AD and DBD. Plasmid 3 can further include bacterial selection and propagation markers (i.e. ori and AmpR), and yeast replication and selection markers (i.e. TRP1 and CEN or 2 um). The sequence of Plasmid 3 can be:

(SEQ ID NO.: 65)
```
CGGTGCGGGCCTCTTCGCTATTACGCCAGATCCTTTGTTGTTTCCGGGTGTACAATATGGACTTCCTCTTTTCTGGCAACCAAACC

CATACATCGGGATTCCTATAATACCTTCGTTGGTCTCCCTAACATGTAGGTGGCGGAGGGGAGATATACAATAGAACAGATACCAGA

CAAGACATAATGGGCTAAACAAGACTACACCAATTACACTGCCTCATTGATGGTGGTACATAACGAACTAATACTGTAGCCCTAGAC

TTGATAGCCATCATCATATCGAAGTTTCACTACCCTTTTTCCATTTGCCATCTATTGAAGTAATAATAGGCGCATGCAACTTCTTTT

CTTTTTTTTCTTTTCTCTCTCCCCGTTGTTGTCTCACCATATCCGCAATGACAAAAAAATGATGGAAGACACTAAAGGAAAAAT

TAACGACAAAGACAGCACCAACAGATGTCGTTGTTCCAGAGCTGATGAGGGGTATCTCGAAGCACACGAAACTTTTTCCTTCCTTCA

TTCACGCACACTACTCTCTAATGAGCAACGGTATACGGCCTTCCTTCCAGTTACTTGAATTTGAAATAAAAAAAGTTTGCTGTCTT

GCTATCAAGTATAAATAGACCTGCAATTATTAATCTTTTGTTTCCTCGTCATTGTTCTCGTTCCCTTTCTTCCTTGTTTCTTTTTCT

GCACAATATTTCAAGCTATACCAAGCATACAATCAACTCCAAGCTTTGCAAAGATGGGGTCAAAGGCCGAGCTAATCCCAGAGCCCC
```

```
CTAAAAAAAAGAGAAAGGTCGAGCTGGGAACTGCGGCAGAGTACCCGTATGATGTACCGGACTATGCCGGAGGTATGTCTAGATTGG
ACAAGTCTAAGGTTATCAACTCTGCTTTGGAATTGTTGAACGAAGTTGGTATCGAAGGTTTGACTACTAGAAAGTTGGCTCAAAAGT
TGGGTGTTGAACAACCAACTTTGTACTGGCACGTTAAGAACAAGAGAGCTTTGTTGGACGCTTTGGCTATCGAAATGTTGGACAGAC
ACCACACTCACTTCTGTCCATTGGAAGGTGAATCTTGGCAAGACTTCTTGAGAAACAACGCTAAGTCTTTCAGATGTGCTTTGTTGT
CTCACAGAGACGGTGCTAAGGTTCACTTGGGTACTAGACCAACTGAAAAGCAATACGAAACTTTGGAAAACCAATTGGCTTTCTTGT
GTCAACAAGGTTTCTCTTTGGAAAACGCTTTGTACGCTTTGTCTGCTGTTGGTCACTTCACTTTGGGTTGTGTTTTGGAAGACCAAG
AACACCAAGTTGCTAAGGAAGAAAGAGAAACTCCAACTACTGACTCTATGCCACCATTGTTGAGACAAGCTATCGAATTGTTCGACC
ACCAAGGTGCTGAACCAGCTTTCTTGTTCGGTTTGGAATTGATCATCTGTGGTTTGGAAAAGCAATTGAAGTGTGAATCTGGTTCTG
GGCAACCATCTTTGAGATCTGAATACGAATACCCAGTTTTCTCTCACGTTCAAGCTGGTATGTTCTCTCCAGAATTGAGAACTTTCA
CTAAGGGTGACGCTGAAAGATGGGTTTCTGGTCCAGGTACTGAAGACGCTGAAGCTGTTGCTTTGGGTTTGGGTTTGTCTGACTTCC
CATCTGCTGGTAAGGCTGTTTTGGACGACGAAGACTCTTTCGTTTGGCCAGCTGCTTCTTTCGACATGGGTGCTTGTTGGGCTGGTG
CTGGTTTCGCTGACCCAGACCCAGCTTGTATCTTCTTGAACTTGCCATGAGCCCATCTTTTTTTGGACCTAAATTCTTCATGAAAA
TATATTACGAGGGCTTATTCAGAAGCTTTGGACTTCTTCGCTTGCAGCCAAGCTAATTCCGGGCGAATTTCTTATGATTTATGATTT
TTATTATTAAATAAGTTATAAAAAAAATAAGTGTATACAAATTTTAAAGTGACTCTTAGGTTTTAAAACGAAAATTCTTATTCTTGA
GTAACTCTTTCCTGTAGGTCAGGTTGCTTTCTCAGGTATAGCATGAGGTCGCTCTTATTGACCACACCTCTACCGGCATGCAAGCTT
GGCGTAATCATGGTCATAGCTGTTTCCTGTGTGAAATTGTTATCCGCTCACAATTCCACACAACATACGAGCCGGAAGCATAAAGTG
TAAAGCCTGGGGTGCCTAATGAGTGAGCTAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACTACGGCTACACTAGAAGAACAGTATTTGGTAT
CTGCGCTCTGCTGAAGCCAGTTACCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGATCCTTTTAAATTAAAAATGAAGTTT
TAAATCAATCTAAAGTATATATGAGTAACCTGAGGCTATGGCAGGGCCTGCCGCCCCGACGTTGGCTGCGAGCCCTGGGCCTTCACC
CGAACTTGGGGGGTGGGGTGGGGAAAAGGAAGAAACGCGGGCGTATTGGCCCCAATGGGGTCTCGGTGGGGTATCGACAGAGTGCCA
GCCCTGGGACCGAACCCCGCGTTTATGAACAAACGACCCAACACCGTGCGTTTTATTCTGTCTTTTTATTGCCGTCATAGCGCGGGT
TCCTTCCGGTATTGTCTCCTTCCGTGTTTCAGTTAGCCTCCCCCTAGGGTGGGCGAAGAACTCCAGCATGAGATCCCCGCGCTGGAG
GATCATCCAGCCGGCGTCCCGGAAAACGATTCCGAAGCCCAACCTTTCATAGAAGGCGGCGGTGGAATCGAAATCTCGTGATGGCAG
GTTGGGCGTCGCTTGGTCGGTCATTTCGAACCCCAGAGTCCCGCTCAGAAGAACTCGTCAAGAAGGCGATAGAAGGCGATGCGCTGC
GAATCGGGAGCGGCGATACCGTAAAGCACGAGGAAGCGGTCAGCCCATTCGCCGCCAAGCTCTTCAGCAATATCACGGGTAGCCAAC
GCTATGTCCTGATAGCGGTCCGCCACACCCAGCCGGCCACAGTCGATGAATCCAGAAAAGCGGCCATTTTCCACCATGATATTCGGC
AAGCAGGCATCGCCATGAGTCACGACGAGATCCTCGCCGTCGGGCATGCTCGCCTTGAGCCTGGCGAACAGTTCGGCTGGCGCGAGC
CCCTGATGCTCTTCGTCCAGATCATCCTGATCGACAAGACCGGCTTCCATCCGAGTACGTGCTCGCTCGATGCGATGTTTCGCTTGG
TGGTCGAATGGGCAGGTAGCCGGATCAAGCGTATGCAGCCGCCGCATTGCATCAGCCATGATGGATACTTTCTCGGCAGGAGCAAGG
TGAGATGACAGGAGATCCTGCCCCGGCACTTCGCCCAATAGCAGCCAGTCCCTTCCCGCTTCAGTGACAACGTCGAGCACAGCTGCG
CAAGGAACGCCCGTCGTGGCCAGCCACGATAGCCGCGCTGCCTCGTCTTGCAGTTCATTCAGGGCACCGGACAGGTCGGTCTTGACA
```

-continued

```
AAAAGAACCGGGCGCCCCTGCGCTGACAGCCGGAACACGGCGGCATCAGAGCAGCCGATTGTCTGTTGTGCCCAGTCATAGCCGAAT
AGCCTCTCCACCCAAGCGGCCGGAGAACCTGCGTGCAATCCATCTTGTTCAATCATACTCTTCCTTTTTCAATATTATTGAAGCATT
TATCAGGGTTATTGTCTCATGAGCGGATACATATTTGAATGTATTTAGAAAAATAAACAAATAGGGGTTCCGCGCACATTTCCCCGA
AAAGTGCCACCTGAACGAAGCATCTGTGCTTCATTTTGTAGAACAAAAATGCAACGCGAGAGCGCTAATTTTTCAAACAAAGAATCT
GAGCTGCATTTTTACAGAACAGAAATGCAACGCGAAAGCGCTATTTTACCAACGAAGAATCTGTGCTTCATTTTTGTAAAACAAAAA
TGCAACGCGAGAGCGCTAATTTTTCAAACAAAGAATCTGAGCTGCATTTTTACAGAACAGAAATGCAACGCGAGAGCGCTATTTTAC
CAACAAAGAATCTATACTTCTTTTTTGTTCTACAAAAATGCATCCCGAGAGCGCTATTTTTCTAACAAAGCATCTTAGATTACTTTT
TTTCTCCTTTGTGCGCTCTATAATGCAGTCTCTTGATAACTTTTTGCACTGTAGGTCCGTTAAGGTTAGAAGAAGGCTACTTTGGTG
TCTATTTTCTCTTCCATAAAAAAAGCCTGACTCCACTTCCCGCGTTTACTGATTACTAGCGAAGCTGCGGGTGCATTTTTTCAAGAT
AAAGGCATCCCCGATTATATTCTATACCGATGTGGATTGCGCATACTTTGTGAACAGAAAGTGATAGCGTTGATGATTCTTCATTGG
TCAGAAAATTATGAACGGTTTCTTCTATTTTGTCTCTATATACTACGTATAGGAAATGTTTACATTTTCGTATTGTTTTCGATTCAC
TCTATGAATAGTTCTTACTACAATTTTTTGTCTAAAGAGTAATACTAGAGATAAACATAAAAAATGTAGAGGTCGAGTTTAGATGC
AAGTTCAAGGAGCGAAAGGTGGATGGGTAGGTTATATAGGGATATAGCACAGAGATATATAGCAAAGAGATACTTTTGAGCAATGTT
TGTGGAAGCGGTATTCGCAATATTTTAGTAGCTCGTTACAGTCCGGTGCGTTTTTGGTTTTTTGAAAGTGCGTCTTCAGAGCGCTTT
TGGTTTTCAAAAGCGCTCTGAAGTTCCTATACTTTCTAGAGAATAGGAACTTCGGAATAGGAACTTCAAAGCGTTTCCGAAAACGAG
CGCTTCCGAAAATGCAACGCGAGCTGCGCACATACAGCTCACTGTTCACGTCGCACCTATATCTGCGTGTTGCCTGTATATATAT
ACATGAGAAGAACGGCATAGTGCGTGTTTATGCTTAAATGCGTACTTATATGCGTCTATTTATGTAGGATGAAAGGTAGTCTAGTAC
CTCCTGTGATATTATCCCATTCCATGCGGGGTATCGTATGCTTCCTTCAGCACTACCCTTTAGCTGTTCTATATGCTGCCACTCCTC
AATTGGATTAGTCTCATCCTTCAATGCTATCATTTCCTTTGATATTGGATCATACTAAGAAACCATTATTATCATGACATTAACCTA
TAAAAATAGGCGTATCACGAGGCCCTTTCGTCTCGCGCGTTTCGGTGATGACGGTGAAAACCTCTGACACATGCAGCTCCCGGAGAC
GGTCACAGCTTGTCTGTAAGCGGATGCCGGGAGCAGACAAGCCCGTCAGGGCGCGTCAGCGGGTGTTGGCGGGTGTCGGGGCTGGCT
TAACTATGCGGCATCAGAGCAGATTGTACTGAGAGTGCACCATAGATCAACGACATTACTATATATATAATATAGGAAGCATTTAAT
AGAACAGCATCGTAATATATGTGTACTTTGCAGTTATGACGCCAGATGGCAGTAGTGGAAGATATTCTTTATTGAAAAATAGCTTGT
CACCTTACGTACAATCTTGATCCGGAGCTTTTCTTTTTTTGCCGATTAAGAATTAATTCGGTCGAAAAAAGAAAAGGAGAGGGCCAA
GAGGGAGGGCATTGGTGACTATTGAGCACGTGAGTATACGTGATTAAGCACACAAAGGCAGCTTGGAGTATGTCTGTTATTAATTTC
ACAGGTAGTTCTGGTCCATTGGTGAAAGTTTGCGGCTTGCAGAGCACAGAGGCCGCAGAATGTGCTCTAGATTCCGATGCTGACTTG
CTGGGTATTATATGTGTGCCCAATAGAAAGAGAACAATTGACCCGGTTATTGCAAGGAAAATTTCAAGTCTTGTAAAAGCATATAAA
AATAGTTCAGGCACTCCGAAATACTTGGTTGGCGTGTTTCGTAATCAACCTAAGGAGGATGTTTTGGCTCTGGTCAATGATTACGGC
ATTGATATCGTCCAACTGCATGGAGATGAGTCGTGGCAAGAATACCAAGAGTTCCTCGGTTTGCCAGTTATTAAAAGACTCGTATTT
CCAAAAGACTGCAACATACTACTCAGTGCAGCTTCACAGAAACCTCATTCGTTTATTCCCTTGTTTGATTCAGAAGCAGGTGGGACA
GGTGAACTTTTGGATTGGAACTCGATTTCTGACTGGGTTGGAAGGCAAGAGAGCCCCGAAAGCTTACATTTTATGTTAGCTGGTGGA
CTGACGCCAGAAAATGTTGGTGATGCGCTTAGATTAAATGGCGTTATTGGTGTTGATGTAAGCGGAGGTGTGGAGACAAATGGTGTA
AAAGACTCTAACAAAATAGCAAATTTCGTCAAAAATGCTAAGAAATAGGTTATTACTGAGTAGTATTTATTTAAGTATTGTTTGTGC
ACTTGCCGATCTATGCGGTGTGAAATACCGCACAGATGCGTAAGGAGAAAATACCGCATCAGGAAATTGTAAGCGTTAATATTTTGT
TAAAATTCGCGTTAAATTTTTGTTAAATCAGCTCATTTTTTAACCAATAGGCCGAAATCGGCAAAATCCCTTATAAATCAAAGAAT
AGACCGAGATAGGGTTGAGTGTTGTTCCAGTTTGGAACAAGAGTCCACTATTAAAGAACGTGGACTCCAACGTCAAAGGGCGAAAAA
CCGTCTATCAGGGCGATGGCCCACTACGTGAACCATCACCCTAATCAAGTTTTTTGGGGTCGAGGTGCCGTAAAGCACTAAATCGGA
ACCCTAAAGGGAGCCCCCGATTTAGAGCTTGACGGGAAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCACACCCGCCGCGCTTAATGCGCCGCTACAGGGCGCGTCCA
TTCGCCATTCAGGCTGCGCAACTGTTGGGAAGGGCGAT.
```

The host cell used for identification of the peptide that disrupts a PPI can be *Saccharomyces cerevisiae* of either mating type or a diploid, and include the genomic integration of genetic reporters (such as ADE2, HIS3, and/or URA3) driven by the recognition sequence of the DBD used in Plasmid 1 (such as TetO). The host cell used for identification of the peptide that disrupts a PPI can also be another host cell as previously described herein, such as a bacterial cell (e.g. *E. coli, B. subtilis*) or a mammalian cell (e.g. immortalized primary cells or immortalized cell lines). The host cell can also express enzymes necessary for the cyclization and methylation of peptides (e.g. lanthipeptides maturation enzymes from *Lactococcus lactis* (LanB, LanC, LanM, LanP), patellamide biosynthesis factors from cyanobacteria (PatD, PatG), butelase 1 from *Clitoria ternatea*, or POPB from *Galerina marginata* or *Amanita bisporigera*. Exemplary POPs necessary for cyclization of peptides can also comprise any of the sequences outlined below in Table 2.

screen for protein-protein interactions that are inhibited by a defined agent. In some embodiments a library of variants of Plasmid 1 are provided, wherein a plurality of different short test polypeptide sequences for screening are represented. The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

Plasmids 1, 2, and 3 can be used in various permutations. In a first example, integration of Plasmid 1 into the genome of the host cell (as confirmed using Plasmid 3) can be followed by transformation of a library of Plasmid 2 with randomly encoded peptides using, for example, NNK or NNN codons.

In this first example, to perform a screen to identify a peptide that can disrupt a PPI, the host cell 1 can be

TABLE 2

| Species/Gene | Sequence Reference No | Amino Acid Sequence | | | |
|---|---|---|---|---|---|
| *Amanita bisporigera* POPB | GenBank HQ225841.1 | MPPTPWAPHS EENSNEVDEW YVKFSAPTLL QRGTRKVGEV VSHLGVDYFT KFTTITWTKD VGTTQLEDII ASKQNLLWVA GSLIYVKTNV LTQVKCVNKG FIGVASITNR RLSILRTTKL KSTKFDGTAP ILAVPNIRGG VKNKYAAPGK EGGVADLLKF VHNVPKDRVL PQNPHPLLIR SLGLEWKTVD | YPPTRRSDHV TTAQTAFTQG DSGHWYWFYN YFDPNVLSAD IYVRPTSSSL SKGFLYQRYP VQQDKENPDW EFDKDGVKPE NAPQYKVVTI YFVAIYKRNV EKQPHSFLTF NGLNADDFES AIQNGYGGFA GEFGGEWHKA VAITGASNGG NKFTGGMAWT PATLLMTNAG VDKSWLGHGF (SEQ ID NO: 83) | DVYQSASRGE YLDKNADRQK SGVQSQAVLY GTAIMGTCRF SQAPEAEGGD ARESLVAKDR TYGTDASEDG IPWRKVINEF DLSTGEPEIR KDEIYLYSKA SGFNTPGTIS TQVWYKSKDG ITADPFFSPI GRRETKGNTF FLVCGSVVRA SEYGNPFIKE DDRVVPMHSL GKTTDKHTKD | VPVPDPYQWL LEEKFRASKD RSKKPVLPDF SPSGEYFAYA GRLSDGVKWC DKDAMVCYHR KYIYLVVYKD GADYHVITNH DFIPEQKDAK GDQLSRLASD RYDFTAPDTQ TKVPMFIVRH MLTFMQTYGA DDFIAAAQFL PEGTFGAAVS DFDFVQALSP KFVANLQYNV AADKWSFVAQ |
| *Galerina marginata* POPB | GenBank JN827314.2 | MSSVTWAPGN EESTDEVDKW YAKFSAPTLL SNGDDNVGDV VSHLGGDYST KFSTIIWTKD VGTTQEEDII TSKKNLLWVA GSLVYIKTNL LAQVNCANEE FVGAASIANR RFSILRTTKV KSTKFDGTAA IFAVPSIRGG VKNKYAAPGK EGGVADLLKF VHNVRTDKVM PQNPHPLLIK ALGLELKTVE | YPSTRRSDHV TTAQADLAQS DDGHWYWFYN FFDPNVLATD IYIRSTSSPL SKGFLYQRYP VYQDNEHPEW ELNEDGVKSG NAPQYKVITI YFVAIYKRNV QKQTHFFLTL NELDPDDFES AIQYGYGGFA GEFGEEWHKG VAINGASNGG HKFTGGQAWI PATLITVNIG IDKSWLGHGM (SEQ ID NO: 84) | DTYQSASKGE YLDQNADIQK RGLQSQSVLY GSAGMVLCKF SQASAVQGTD ARERHEGTRS IYGADTSEDG IQWRKVVNEY DLSKDEPEIR KDEIYLYSKA SGFNTPGTIA TQVWYESKDG TSADPFFSPI GRRETKVNTF LLVMGSIVRA SEYGNPSIPE DGRVVPMHSF GKPTDKNVKD | VPVPDPYQWL LAEKFRASRN RSNEPALPDF SPDGKFFAYA GRLSDEVKWF DRNAMMCYHK KYLYLYQFKD VADYNVITNH DFIPEEKDAK GVQLTRLAPD RYDFTAPETQ TKIPMFIVRH ILTFLQTYGA DDFIAAAQFL PEGTFGAAVP EFDYIYPLSP KFIATLQHNV AADKWGFIAR |

Envisioned within the scope of this disclosure are kits comprising Plasmid 1, Plasmid 2, Plasmid 3, transfectable host cells compatible with Plasmids 1-3, or any combination thereof. In some embodiments, Plasmids 1 or 2 are provided already transfected into host cells. In some embodiments, kits according to this disclosure include selectable agents for use with host cells transfected with Plasmids 1-3. In some embodiments a library of variants of Plasmid 1 are provided, wherein more than a single pair of Y2H interactors are represented. Such a library can be used to, for example, propagated in selection media to ensure the presence of Plasmid 1 and that a faithful PPI is occurring (e.g. on media lacking Trp for yeast, or in media containing antibiotic for human or bacterial cells). This host cell can then be transformed with Plasmid 2, and immediately be transferred to selection media to ensure all components are present (i.e. on media lacking Trp and Leu for yeast, or antibiotics for bacterial or mammalian cells), and are inducing expression of any inducible component (e.g. with Gal, doxycycline, etc).

Figure 12:
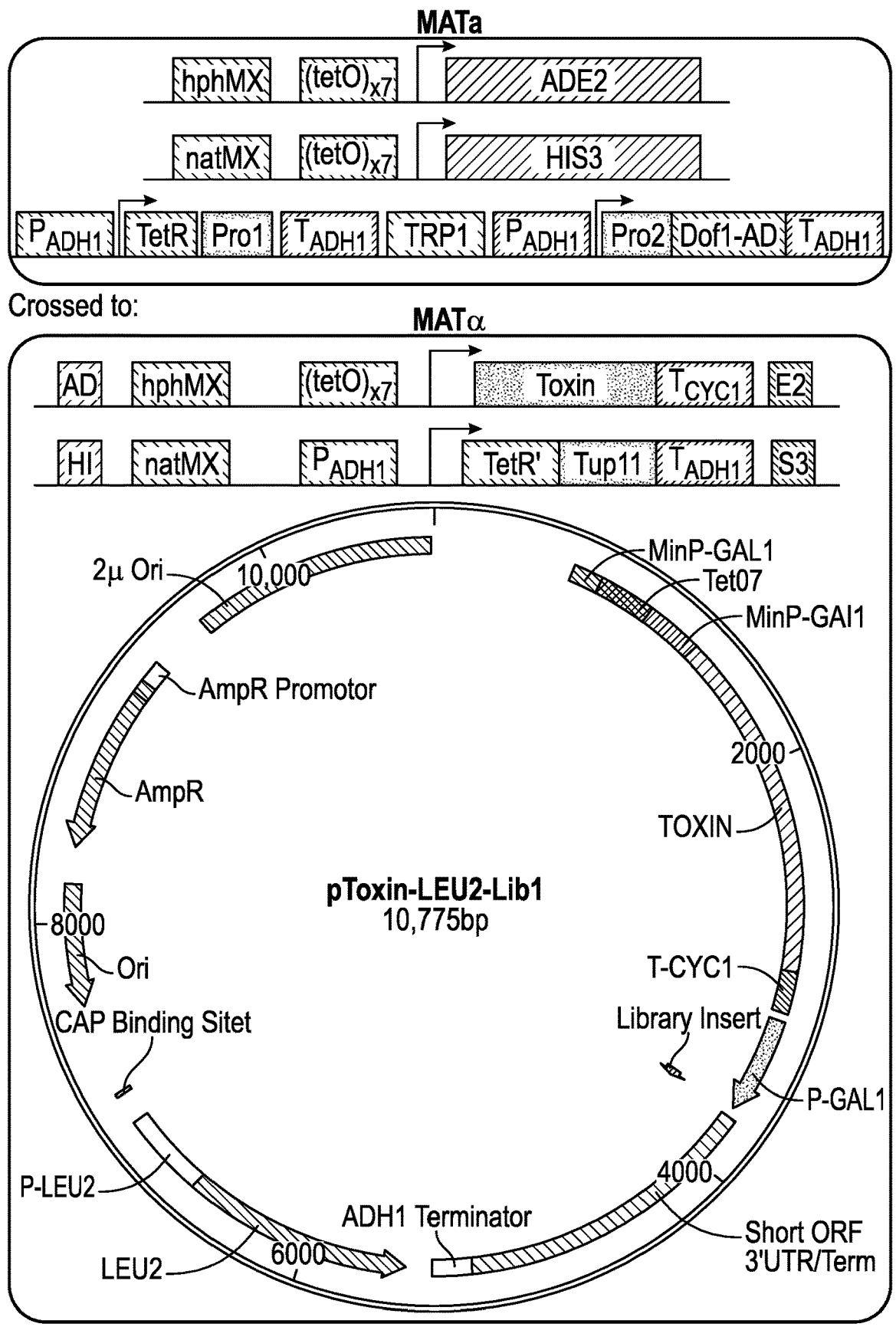
FIG. 12 is an illustrative example of a platform of the present disclosure to identify a compound that disrupts a protein-protein interaction.

In a second example, the plasmids can be used as a 'plug and play platform' utilizing the yeast mating type system (FIG. 12), where the 2 or more plasmids (or the genetic elements therein) can be introduced into the same cell by cell fusion or cell fusion followed by meiosis instead of transfection. This cell fusion involves two different yeast host cells bearing different genetic elements. In this method, yeast host cell 1 can be one of MATa or MATalpha and include an integration of Plasmid 1. This strain can be propagated on positive selection media to ensure a faithful PPI is present. Also in this method, the yeast host cell 2 is of the opposite mating type. This strain carries (or has integrated) the randomized peptide library and 'death agent' (e.g. cytotoxic reporter) plasmid (Plasmid 2). Yeast host cell 2 can be generated via large batch high efficiency transformation protocols which ensure a highly diversified library variation within the cell culture. Aliquots of this library batch can then be frozen to maintain consistency.

In this second example, the strains are mated in batch to result in a diploid strain that carries all the markers, the PPI, 'death agents' and peptide. This batch culture then can be propagated on solid medium that enables selection of all the system components (i.e. media lacking Leu and Trp), and inducing expression of any inducible component (i.e. with Gal).

Surviving colonies from limiting dilution experiments performed on host cells bearing both the Y2H and library/cytotoxic constructs (either introduced to the cell by transfection or mating) constitute colonies with a PPI that has been disrupted by a peptide and no longer triggers the death cascade triggered by the encoded 'death agents' (e.g. cytotoxic reporters). The peptide sequence can be obtained by DNA sequencing the peptide-encoding region of Plasmid 2 in each surviving colony.

To ensure that survival is due to inhibition of the PPI rather than stochastic chance or faulty gene expression, the inducible marker can be used to inactivate the production of either the PPI or the peptide and confirm specificity. For example, observation of cell survival only on media with galactose wherein all the components are expressed, and no survival on media without galactose when expression of the peptide is lost.

The plasmid can also be isolated and re-transformed into a fresh host cell to confirm specificity. Biochemical fractionation of the viable host cells which contains the PPI, peptide and 'death agent' followed by pull-down experiments can confirm an interaction between the peptide sequence and either PPI partner using the encoded tags (e.g. Myc-tag, HA-tag, His-tag).

Once enough surviving host cell colonies are sequenced, highly conserved sequence patterns can emerge and can be readily identified using a multiple-sequence alignment. Any such pattern can be used to 'anchor' residues within the library peptide insert sequence and permute the variable residues to generate diversity and achieve tighter binding. This can also be done using an algorithm developed for pattern recognition and library design. Upon convergence, the disrupting peptide pattern, as identified through sequencing, can be used to define a necessary and sufficient peptide disruptor sequence. Convergence is defined by the lack of retrieval of any new sequences in the last iteration relative to the penultimate one.

Compounds

Figure 22:
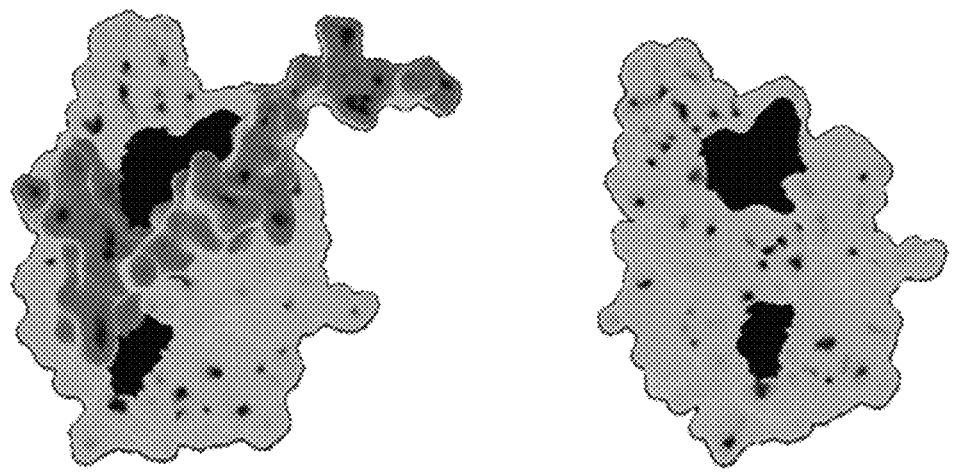
FIG. 22 shows a binding model of an exemplary RAD51 peptide according to the invention bound to RAD51 (as represented by pdb structure 1N0W). Critical residues identified for peptide binding are highlighted. The left panel shows a BRCA2 peptide bound on RAD51 (with the Compound interacting with the highlighted residues around the BRCA2 peptide), the right panel excludes this sequence of BRCA2 and highlights just the Compound interacting residues on RAD51.

Disclosed herein are non-naturally occurring compounds that can bind to a protein interface of RAD51 and inhibit the function of RAD51 in vitro or in cells. The protein interface can be a subregion of the ATPase domain of RAD51. The protein interface can be RAD51AP1's binding site on RAD51. The protein interface can be amino acid residues 190-218 of human RAD51. An exemplary model of a protein interface where non-naturally occurring compounds according to the invention can bind on RAD51 is presented in FIG. 22, wherein compound interacts with residues highlighted in black. Gray shows the binding of BRCA2 to RAD51.

In vitro, compounds as disclosed herein can inhibit RAD51 multimerization, RAD51 interaction with another known interacting partner of RAD51 (e.g. BRCA2 or RAD51AP1), or RAD51 chelation/binding of Ca2+ ions. The inhibition of interaction with another known interacting partner of RAD51 may be competitive or allosteric. Inhibition of RAD51 multimerization, RAD51 interaction with another known interacting partner of RAD51 (e.g. BRCA2 or RAD51AP1), or RAD51 chelation/binding of Ca2+ ions may be accompanied by inhibition of RAD51 ATPase activity. Inhibition of RAD51 multimerization, RAD51 interaction with another known interacting partner of RAD51 (e.g. BRCA2 or RAD51AP1), or RAD51 chelation/binding of Ca2+ ions may be without inhibition of RAD51 ATPase activity.

In cells, compounds as disclosed herein can inhibit assembly of RAD51 filaments on DNA. In cells, compounds as disclosed herein can inhibit DNA damage repair. In cells, compounds as disclosed herein can inhibit cellular homologous recombination. In cells, compounds as disclosed herein can result in sensitization to genotoxic chemotherapeutics of cancer cells. In cells, compounds as disclosed herein can reduce drug resistance to chemotherapeutic agents, either through inhibition of DNA damage repair, or through inducing cellular stress through increase in intracellular free calcium concentration. In cells that depend on RAD51 overexpression, compounds as disclosed herein can result in cell death. In cells, compounds as disclosed herein may cause death in cellular conditions depending on RAD51 overexpression. In some embodiments, cells can be cancer cells or cells of patients with inheritable benign proliferative disorders (e.g. Cowden's syndrome). Further, any of the compounds disclosed herein can be used in combination with, for example, immuno-oncology agents or PARP inhibitors, or other chemotherapeutics for the purpose of inducing cell death.

The compounds disclosed herein can be used in methods of treatment of a disorder or condition where cell growth inhibition occurs by downregulation of homologous recombination, or where there is overexpression of proteins involved in the DNA damage repair pathway. The compounds disclosed herein can be used in methods of treatment of a disorder or condition associated with aberrant RAD51 activity.

The interface of RAD51 that can be targeted by a compound of the invention can be important for the control of the activity of the BRCA1/2 homologous recombination DNA repair pathway. Blocking of this interface important for the control of the activity of the BRCA1/2 homologous recombination DNA repair pathway with the compounds disclosed herein can have clinical relevance for several therapeutic indications.

A compound disclosed herein can be used as a monotherapy for the treatment of, for example, intrahepatic cholangiocarcinoma (ICC), metastatic castration-resistant prostate cancer (mCRPC), and other cancers that display upregulation of effectors of the RAD51/BRCA2 DNA damage repair pathway.

ICC cells can depend on the BRCA2 pathway for survival and render subjects untreatable. The inactivation of the homologous recombination pathway through RAD51 disrupting compounds can lead to cell death. This cell death can be selective for cells that depend on the BRCA2 pathway such as ICC cells. An example of this kind of selectivity is demonstrated in FIG. 2, wherein both HeLa cells (cervical cancer cells) and SSP-25 cells (ICC-derived cells) are treated with compounds 1 and 5 and little cell death is generated in the HeLa cells compared to the SSP-25 cells upon compound treatment In castration-resistant prostate cancers that overexpress the BRCA2 pathway, the inactivation of BRCA2 via inhibition of RAD51 disrupting compounds disclosed herein can lead to cell death. Several cancers exhibit upregulation of the homologous recombination pathway, specifically of RAD51 and BRCA2, which can render the cancer cells resistant to genotoxic chemotherapy. Cancers that spontaneously overexpress the RAD51/BRCA2 pathway components include, for example, hepatocellular carcinoma, acute myeloid leukemia (AML), aggressive mantle cell lymphoma, ovarian cancer, and imatinib-resistant BCR/ABL cancers.

The mechanism of action of the compounds disclosed herein can involve, for example, dislodging a pair of calcium ions coordinated by the RAD51 polymer in an acute manner leading to an acute intracellular free calcium concentration increase. The increase in the intracellular free calcium concentration can lead to cell death. This mechanism of cell death can occur in cells overexpressing the RAD51 protein, and the cell death can be orders of magnitude higher than cells without RAD51 overexpression. The cell death in cells contacted with compounds disclosed herein that overexpress the RAD51 protein may be at least 3, at least 10, at least 50, or at least 100 times greater than in cells contacted with compounds disclosed herein that do not overexpress RAD51. The sequestering of calcium ions by the RAD51 filaments to, for example, micromolar levels and the subsequent acute release of the pool of calcium ions into the cytosol upon compound binding can result in cell death in cancers dependent on the RAD51/BRCA2 pathway such as ICC and mCRPC. Evidence for this sequestration/release mechanism can be seen in FIGS. 24 and 25, wherein the intracellular calcium chelators BAPTA-AM and Ruthenium red are able to counteract the cell-death inducing effects of compound 10, suggesting that the cell death mechanism of compound 10 involves the release of Ca2+ ions. This cell death can occur acutely in a few minutes and can be p53- and cell cycle-independent. An example of the rapidity of this cell death can be seen in FIGS. 13 and 14, where administration of compound (arrows) causes rapid cell death (decrease in cell index).

The mechanism of action of the compounds disclosed herein in cell death can involve inactivation of the recombination pathway through RAD51 alongside increases in cellular free calcium concentration. The mechanism of action of the compounds in cell death can involve increases in cellular free calcium concentration without inhibition of the recombination pathway through RAD51. The mechanism of action of the compounds in cell death can involve inhibition of RAD51 ATPase activity alongside increases in cellular free calcium concentration. The mechanism of action of the compounds in cell death can involve increases in cellular free calcium concentration without inhibition RAD51 ATPase activity.

The compounds can also be used in the treatment of rare and orphan diseases including, for example, Bloom's syndrome, Fanconi Anemia, Werner's syndrome, and Nijmegen Breakage Syndrome, which can display an increase in homologous recombination in their patients' cells. Downregulation of recombination by administration of RAD51 disrupting compounds as disclosed herein to individuals' cells can reverse the DNA damage hypersensitivity of the cells. Downregulation of recombination by contact of the RAD51 disrupting compounds as disclosed herein to the cells can reverse the DNA damage hypersensitivity of the cells. An example of this phenomenon can be seen in FIG. 6, where compound 5 is able to rescue the hypersensitivity of a Bloom's cell line (GM08505) to a genotoxic stress (etoposide).

Figure 26:
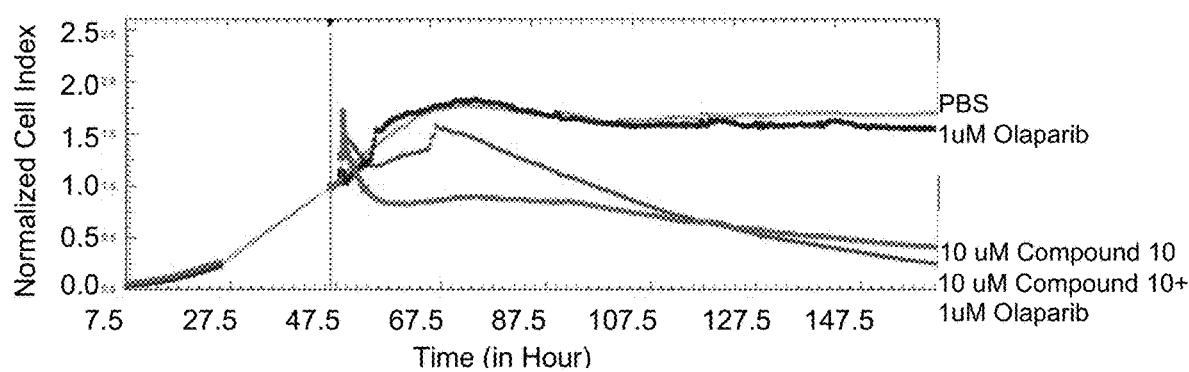
FIG. 26 shows an xCELLigence cell death assay on SSP-25 cells, wherein compound 10 or olaparib are added alone or in combination, demonstrating that the combination of compound 10 and olaparib enhances cell death relative to compound 10 or olaparib alone.

The compounds can also be used in combination with other therapeutic agents including, for example, immuno-oncology agents, PARP inhibitors, and canonical chemotherapeutics. For example, metastatic melanoma patients who are responsive to anti-PD1 therapy can be highly enriched for somatic mutations in the BRCA2 gene within the patient tumors. This correlation can indicate that inactivation of the BRCA2 pathway sensitizes cells to anti-PD1 immunotherapy. The anti-PD1 agents can be, for example, nivolumab, pembrolizumab, or pidilizumab. An example of synergy of compounds as described herein with other therapeutic agents targeting the BRCA pathway can be seen in FIG. 26, where co-administration of compound 10 and Olaparib (a PARP inhibitor) cause enhanced cell death relative to either alone.

PARP inhibitors can exhibit potent and selective activity against BRCA1 and BRCA2 mutated breast, ovarian, and other cancers. The use of a RAD51-disrupting compound can mimic the effects of a BRCA2 mutation and can potentially render a wider array of cancers treatable by PARP inhibitors. The PARP inhibitors can be, for example, olaparib, veliparib, niraparib, talazoparib, rucaparib, and CEP-9722.

A compound disclosed herein can be used in combination with other chemotherapeutic agents. The chemotherapeutic agents can include, for example, anti-PD1 agents, pembrolizumab, melphalan, doxorubicin, adrianmycin, etoposide, camptothecins, mitomycin C, cisplatin, oxaliplatin, carboplatin, or gemcitabine.

The compounds can be, for example, small molecules, biologics, antibodies, peptidomimetics, or peptides. The compound may be a peptide.

The compounds disclosed herein can harbor a cell penetration entity (CPP) or a protein transduction domain (PTD) to facilitate entry into the target cell. Protein transduction can refer to the delivery of peptides, proteins, and other molecules across cytoplasmic membranes into cells. The compounds can include at least one cell-penetration peptide (CPP) signal sequence. Examples of CPPs include HIV-TAT (GRKKRRQRRRPPQ; SEQ ID NO.: 13), R8 (RRRRRRRR; SEQ ID NO.: 14), MAP (KLALKLALKA-LKAALKLA; SEQ ID NO.: 15), transportan (GWTLN-SAGYLLGKINLKALAALAKKIL; SEQ ID NO.: 16), pegelin (RGGRLSYSRRRFSTSTGR; SEQ ID NO.: 17), penetrin (RQIKIWFQNRRMKWKK; SEQ ID NO.: 18), cFΦR4 (cyclic heptapeptide cyclo(FΦRrRrK) where Φ is 1-2-naphthylalanine linked via an isopeptide bond between the epsilon amino of the lysine to the carboxyl group of the terminal glycine in the peptide sequence, see Qian et al. Biochemistry. 2014 Jun. 24; 53(24):4034-46.), and derivatives or combinations thereof. A comparison of various compounds according to the invention with various cell-penetrating peptides can be seen in FIG. 18, wherein analogous sequences are tested with various different cell-penetrating peptides and demonstrate similar cellular activity against SSP25 cells.

Any of the peptide compounds referred to herein can be N-terminally (e.g. alpha-amine) acetylated, C-terminally amidated, or backbone N-methylated. Any of the compounds referred to herein can be modified to include a 5FAM (Fluorescein amidite) label linked via a 6 carbon chain to the epsilon amino group of a lysine residue. Examples of compounds according to the invention that encompass various amino acid chemical modifications and display activity against SSP25 cells can be seen in FIG. 17.

The peptides disclosed herein can also be stabilized by conversion to peptidomimetic entities. A peptidomimetic can be a polymer encompassing amino acid residues joined together through amide bonds. Such stabilization approaches can include, for example, cyclization to macrocycles, lactam esterification, N-methylation of the backbone residues, hydrocarbon stapling, and combinations thereof.

The peptides disclosed herein can be stabilized or modified by conversion to "retro-inverso" entities. Retro-inverso peptides are linear peptides whose amino acid sequence is reversed and the alpha-carbon-center chirality of the amino acid subunits is inverted as well. Such a modification is known to increase stability of peptides when the original peptide is an (L)-peptide.

A compound of the invention can have, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues. In some embodiments, a compound of the invention is not an antibody. In some embodiments, a compound of the invention is an antibody or a functional binding fragment/derivative thereof (e.g. a Fab fragment or an ScFv). A compound of the invention can contain a RAD51 interacting motif with the following consensus sequence: R-L-G-L/M/V-S-R-R/L/K-R/F/V (SEQ ID NO.: 19).

A compound of the invention can comprise a sequence according to any one of the formulas in Table 3 below, or an invert thereof:

TABLE 3

| Formula 1 | [T/K/R/Q]$_{1-3}$-[L/I/V/F/M/W/Y]-[R/G/S]-[L/I/V/F/M/W/Y] (formula I) (SEQ ID NO.: 70) |
|---|---|
| Formula II | [R/K]-[L]-[G]-[M/V]-(formula II) (SEQ ID NO.: 71) |
| Formula III | [R]-[L]-[G]-[V]-[M/V]-[L/I/V/F/M/A/W/Y] (formula III) (SEQ ID NO.: 72) |
| Formula IV | [T/K/R/Q]$_{1-2}$-[R]-[L]-[G]-[V]-[M/V]-[L/I/V/F/M/A/W/Y] (formula IV) (SEQ ID NO.: 73) |

Any of the polypeptides encompassed by formula I, II, III, or IV can include one or more, 2 or more, 3 or more, 4 or more, 5 or more, 6 or more non-naturally occurring amino acids or (D)-amino acids. In some embodiments, the entire peptide is composed of D-amino acids or non-naturally occurring amino acids.

Thus, in some embodiments, the present disclosure contemplates a compound comprising Formula I, II, III or IV, wherein any one or more of the amino acids are optionally non-natural amino acids or (D)-amino acids.

A compound of the invention can comprise an amino acid sequence according to any of the SEQ IDs in Table 4 below:

TABLE 4

Compounds and amino acid sequences they contain

| Compound 1 | SEQ ID NO.: 1 | KQSLRLGLSRLARVKRLHPGARRRRRRRR |
|---|---|---|
| Compound 2 | SEQ ID NO.: 2 | KQSLRLGQSRLARVKRLHPGARRRRRRRR |
| Compound 3 | SEQ ID NO.: 3 | KQSLRLGLSRLARVKRLHPGARRRRRRRR |
| Compound 4 | SEQ ID NO.: 4 | KQSNLRLGLSRLARVKRLHPGCCRRRRRRRR |
| Compound 5 | SEQ ID NO.: 5 | KRRRRRRRKRLGVRLRVSRML |
| Compound 6 | SEQ ID NO.: 6 | KRRRRRRRKRLGQRLRQSRML |
| Compound 7 | SEQ ID NO.: 7 | KRRRRRRRRLGMSRRF |
| Compound 9 | SEQ ID NO.: 8 | KRRRRRRRKRLGLRLGVSRRV |
| Compound 10 | SEQ ID NO.: 9 | LMRSVRLRVGLRKRRRRRRR |
| Compound 11 | SEQ ID NO.: 10 | KRRRRRRRSLRLGLSRLARVKRLHPG |
| Compound 13 | SEQ ID NO.: 11 | RRRRRRRRKRLGVRLRVSRML |
| Compound 14 | SEQ ID NO.: 12 | RQKIWFQNRRMKWKKRLGVRLRVSRML |
| Compound 19 | SEQ ID NO.: 13 | A(R8)KRLGVR(S5)RVSRML |
| Compound 25 | SEQ ID NO.: 14 | LMRSVRLRVGLRKAG |

(R8) refers to the non-natural amino acid D-2-(7'-octenyl)alanine, and (S5) refers to the non-natural amino acid 2-(4'-pentenyl)alanine Any of SEQ ID NO: 1-11 or 66-69 can include one or more, 2 or more, 3 or more, 4 or more, 5 or more, 6 or more non-naturally occurring amino acids or (D)-amino acids. In some embodiments, the entire peptide described in Table 4 is composed of (D)-amino acids or non-naturally occurring amino acids.

Exemplary compounds of the disclosure are provided below in Table 5:

TABLE 5

Compound 1  Ac-K(C6_5FAM)-QSLRLGLSRLARVKRLHPGARRRRRRRR-NH2
            (SEQ ID NO: 85)

TABLE 5-continued

```
Compound 2   Ac-K(C6_5FAM)-QSLRLGQSRLARVKRLHPGARRRRRRRR-NH2
             (SEQ ID NO: 86)

Compound 4   Ac-K(C6_5FAM)-QS-NMe-LRLGLSR-NMe-LAR-NMe-VKRLHPGC-NH2-
             InterDimer-Ac-CRRRRRRRR-NH2 (SEQ ID NOS 87 and 88)

Compound 5   Ac-K(C6_5FAM)-RRRRRRRKRLGVRLRVSRML-NH2 (SEQ ID NO: 89)

Compound 6   Ac-K(C6_5FAM)-RRRRRRRKRLGQRLRQSRML-NH2 (SEQ ID NO: 90)

Compound 7   Ac-K(C6_5FAM)-RRRRRRRRLGMSRRF-NH2 (SEQ ID NO: 91)

Compound 9   Ac-K(C6_5FAM)-RRRRRRRKRLGLRLGVSRRV-NH2 (SEQ ID NO: 92)

Compound 10  Ac-lmrsvrlrvGlrkrrrrrrr-NH2

Compound 11  Ac-K(C6_5FAM)-RRRRRRRSLRLGLSRLARVKRLHPG-NH2 (SEQ ID NO: 93)

Compound 13  Ac-RRRRRRRKRLGVRLRVSRML-NH2 (SEQ ID NO: 94)

Compound 14  Ac-RQKIWFQNRRMKWKKRLGVRLRVSRML-NH2 (SEQ ID NO: 95)

Compound 19  Ac-A(R8)KRLGVR(S5)RVSRML-NH2 (SEQ ID NO: 96)

Compound 25  Ac-lmrsvrlrvGlrkaG:::(cFφR4)
```

K(C6_5FAM) -> refers to a 5FAM (Fluorescein amidite) label linked via a 6 carbon chain to the epsilon amino group of a lysine.
Ac -> refers to alpha amine acetylation
NH2 -> refers to amidation of the carboxy terminal
R8 and S5 -> refer to a i + 7 hydrocarbon staple between R8, which is D-2-(7'-octenyl)alanine, and S5, which is 2-(4'-pentenyl)alanine
cFφR4 -> refers to cyclic heptapeptide cyclo(FφRrRrK) where φ is 1-2-naphthylalanine linked via an isopeptide bond between the epsilon amino of the lysine to the carboxyl group of the terminal glycine in the peptide sequence
For the purposes of Table 5, lower case letters indicate (D)-amino acids while upper case letters indicate (L)-amino acids The compounds disclosed herein can also include, for example, non-binding, negative control peptides that harbor point mutations. The negative control peptides would not disrupt the interaction between RAD51 and BRCA2, and can be used as experimental controls.

A compound disclosed herein can inhibit a protein-protein interaction by, for example, competitive or allosteric inhibition. A compound herein can bind a cellular target that is associated with, for example, the DNA damage repair pathway. The binding can cause a decrease in the deleterious effects of the mutated gene in the DNA damage repair pathway.

A compound disclosed herein can target the interaction between RAD51 and BRCA2 or RAD51AP1. The compound can inhibit the interaction between RAD51 and RAD51AP1.

The compound can be tested on cell lines that harbor resistant mutations, are programmed to become resistant to drugs or apoptosis, or have mutations specific to the DNA damage repair pathway. Cell lines that can be tested in a method disclosed herein include, for example, HEK-293T, H1299, HCT-116, MCF-7, U2OS, U251, U87, T98G, human GBM, A549 NSCLC, H1993, H2073, MES-SA, MES-SA/Dx5, HT1080, HeLa, Saos-2, IMR90, SSP-25, PC3, LnCAP, Calu3, NciH1975, MDA_MB_231, A375, and mouse embryonic fibroblasts (MEFs). An example of this testing can be seen in FIG. 20, wherein compound 10 is tested on a panel of cell lines and displays IC50s in the 10^-7 to 10^-5 range, suggesting that a wide variety of cancer cells may be sensitive to RAD51 perturbation by compounds disclosed here.

A compound disclosed herein can bind to a subregion of human RAD51. Human RAD51 can comprise the sequence:

(SEQ ID NO.: 82)
MAMQMQLEANADTSVEEESFGPQPISRLEQCGINANDVKKLEEAGFHTVE

AVAYAPKKELINIKGISEAKADKILAEAAKLVPMGFTTATEFHQRRSEII

QITTGSKELDKLLQGGIETGSITEMFGEFRTGKTQICHTLAVTCQLPIDR

GGGEGKAMYIDTEGTFRPERLLAVAERYGLSGSDVLDNVAYARAFNTDHQ

TQLLYQASAMMVESRYALLIVDSATALYRTDYSGRGELSARQMHLARFLR

MLLRLADEFGVAVVITNQVVAQVDGAAMFAADPKKPIGGNIIAHASTTRL

YLRKGRGETRICKIYDSPCLPEAEAMFAINADGVGDAKD.

A compound as disclosed herein can also interact with a subregion of a sequence at least 80 or at least 90 percent identical to human RAD51 (e.g. SEQ ID NO.: 82). A compound as disclosed herein can bind to RAD51AP1's binding site on RAD51. A compound as disclosed herein can bind within a subregion of human RAD51 (e.g. SEQ ID NO.: 82), wherein the subregion is amino acids 190-339 of human RAD51 (e.g. SEQ ID NO.: 82). A compound as disclosed herein can interact with a subregion of human RAD51 (e.g. SEQ ID NO.: 82), wherein the subregion is amino acids 190-218 of human RAD51 (e.g. SEQ ID NO.: 82). A compound as disclosed herein can interact with at least one of residues 202, 205, and 206 of human RAD51 (e.g. SEQ ID NO.: 82). A compound as disclosed herein can interact with at least two of residues 202, 205, and 206 of human RAD51 (e.g. SEQ ID NO.: 82). A compound as disclosed herein can interact with all three of residues 202, 205, and 206 of human RAD51 (e.g. SEQ ID NO.: 82). A compound as disclosed herein can interact with residue 187 of human RAD51 (e.g. SEQ ID NO.: 82). A compound as disclosed herein can interact with at least one of residues 187, 202, 205, and 206 of human RAD51 (e.g. SEQ ID NO.: 82). A compound as disclosed herein can interact with at least two of residues 187, 202, 205, and 206 of human RAD51 (e.g. SEQ ID NO.: 82). A compound as disclosed herein can interact with at least three of residues 187, 202, 205, and 206 of human RAD51 (e.g. SEQ ID NO.: 82). A compound as disclosed herein can interact with all four of residues 187, 202, 205, and 206 of human RAD51 (e.g. SEQ ID NO.: 82). An illustration of these residues can be found in FIG. 23, where sequences alignments are clustered based on their ability to bind or not bind an exemplary peptide according to the invention (SEQ ID NO.: 5), and mutation of residues 187, 202, 205, and 206 correlates with binding ability.

Amino Acids.

Any of the compounds described herein can be include hydrophilic amino acids, hydrophobic amino acids, charged amino acids, uncharged amino acids, acidic amino acids, basic amino acids, neutral amino acids, aromatic amino acids, aliphatic amino acids, natural amino acids, non-natural amino acids, synthetic amino acids, artificial amino acids, capped amino acids, genetically-encoded amino acids, non-genetically encoded amino acids, and amino acid analogues, homologues, and congeners.

The peptides and polypeptides herein can include one or more D-amino acids or non-naturally occurring amino acids or all D-amino acids or non-naturally occurring amino acids. The peptides and polypeptides herein can be inverted and include one or more D-amino acids or non-naturally occurring amino acids, or all D-amino acids or non-naturally occurring amino acids.

Amino acids herein can be designated using their one letter or three letter abbreviation. IUPAC designation is provided below:

| Abbreviation | | Amino acid name |
|---|---|---|
| Ala | A | Alanine |
| Arg | R | Arginine |
| Asn | N | Asparagine |
| Asp | D | Aspartic acid (Aspartate) |
| Cys | C | Cysteine |
| Gln | Q | Glutamine |
| Glu | E | Glutamic acid (Glutamate) |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |
| Asx | B | Aspartic acid or Asparagine |
| Glx | Z | Glutamine or Glutamic acid. |

A non-natural amino acid used in compounds described herein can be, for example, an amino acid that is prepared chemically or expressed by tRNA synthetase technology. A non-limiting example of an achiral amino acid that can be used in compounds described herein is glycine (G, Gly). Non-limiting examples of L-enantiomeric and D-enantiomeric amino acids that can be used in compounds described herein are: alanine (A, Ala); arginine (R, Arg); asparagine (N, Asn); aspartic acid (D, Asp); cysteine (C, Cys); glutamic acid (E, Glu); glutamine (Q, Gln); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val). In some embodiments, conservative or non-conservative substitutions of amino acids are possible of any compounds described herein.

Any of the compounds described herein can be modified by conservative amino acid substitution. Conservative amino acid substitutions involve the substitution of an amino acid with a chemically similar amino acid. Conservative substitution tables providing functionally similar amino acids are available from a variety of references (see, for e.g., Creighton, Proteins: Structures and Molecular Properties (W H Freeman & Co.; $2^{nd}$ edition (December 1993)). The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine(S), Threonine (T); and
8) Cysteine (C), Methionine (M)

Non-natural amino acids can be substituted for natural/canonical amino acids in any of the compounds described herein, particularly when the non-natural amino acids have similar chemical properties (e.g. hydrophobicity, hydrophilicity). Non-natural amino acids are amino acids that are not one of the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) or pyrolysine or selenocysteine; other terms that may be used synonymously with the term "non-natural amino acid" are "non-naturally encoded amino acid, "unnatural amino acid," "non-naturally-occurring amino acid," and variously hyphenated and non-hyphenated versions thereof. The term "non-natural amino acid" includes, but is not limited to, amino acids that occur naturally by modification of a naturally encoded amino acid (including but not limited to, the 20 common amino acids or pyrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

Non-natural amino acids include amino acid analogs. Amino acid analogs are compounds that have the same basic chemical structure as a naturally occurring amino acid, i.e., a central carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Peptide Synthesis

Compounds as described herein can be synthetic peptides. Synthetic peptides were synthesized following standard solid-phase peptide synthesis protocols. The identity and purity of the peptides were confirmed and determined by RP-HPLC, MS/MS, and peptide content analysis. The trifluoroacetic acid (TFA) was exchanged for a non-toxic salt form (e.g. acetate or HCl) and the purity of the peptides was at least 95% before use in experiments.

Pharmaceutically-Acceptable Salts.

The invention provides the use of pharmaceutically-acceptable salts of any therapeutic compound disclosed herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Purity of Compounds.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the invention can be applied topically to the skin, or a body cavity, for example, oral, vaginal, bladder, cranial, spinal, thoracic, or pelvic cavity of a subject. In some embodiments, the compounds of the invention can be applied to an accessible body cavity.

Compounds disclosed herein can increase cell death or inhibit cell growth in a cell by, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold greater than when the cell is not exposed to the compound.

Compounds disclosed herein can increase free calcium concentration in a cell by, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, or about 20-fold. Compounds disclosed herein can increase free calcium concentration in a cell by, for example, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold.

Compounds disclosed herein can display $GI_{50}$ values that are, for example, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 15 nM, about 20 nM, about 25 nM, about 30 nM, about 35 nM, about 40 nM, about 45 nM, about 50 nM, about 60 nM, about 70 nM, about 80 nM, about 90 nM, about 100 nM, about 110 nM, about 120 nM, about 130 nM, about 140 nM, about 150 nM, about 200 nM, about 250 nM, about 300 nM, about 350 nM, about 400 nM, about 450 nM, about 500 nm, about 600 nM, about 700 nM, about 800 nM, about 900 nM, about 1 µM, about 1.5 µM, about 2 µM, about 2.5 µM, about 3 µM, about 3.5 µM, about 4 µM, about 4.5 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, about 50 µM, about 60 µM, about 70 µM, about 80 µM, about 90 µM, about 100 µM, about 150 µM, about 200 µM, about 300 µM, about 400 µM, about 500 µM, about 600 µM, about 700 µM, about 800 µM, about 900 µM, or about 1 mM.

Compounds disclosed herein can be used to treat cancer in a subject. A compound disclosed herein can, for example, slow the proliferation of cancer cells, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

FIGS. 19 and 20 provide data showing suggestive cancer-related indications and administration methods for compounds according to the invention. FIG. 19 displays the activity of compound 10 in a xenograft model using A549 (a non-small cell lung cancer derived cell line), wherein compound 10 exhibits significant effects on tumor volume after only a few days of treatment. FIG. 20 shows the activity of compound 10 against various immortalized cell lines derived from cancer indications as described above, suggesting the efficacy of compounds related to 10 for various cancer indications.

Cholangiocarcinoma, with an incidence of about 1-2 cases per 100,000, is a rare cancer characterized by mutated epithelial cells, which originate in the bile ducts. Cholangiocarcinoma can be characterized as intrahepatic, perihilar, or distal bile duct cancer. Intrahepatic cholangiocarcinoma is a form of a cholangiocarcinoma that occurs within the bile ducts of the liver. The cancer in the bile duct can lead to the blockage of bile ducts and the accumulation of bilirubin. The major symptoms of cholangiocarcinoma include, for example, abnormal liver function tests, abdominal discomfort, jaundice, weight loss, pruritus, fever, loss of appetite, and changes in color of stool or urine.

Risk factors for cholangiocarcinoma include, for example, chronic inflammation or dysfunction of the bile ducts. Dysfunction of the bile ducts can manifest as, for example, primary sclerosing cholangitis, bile duct stones, choledochal cysts, liver fluke infections, polycystic liver disease, Caroli syndrome, cirrhosis, hepatitis B infection, or hepatitis C infection. Mutations in BRCA1/BRCA2 can also cause cholangiocarcinoma. Liver flukes are parasites that are commonly found in Asian countries in raw or poorly cooked fish. Other risk factors for cholangiocarcinoma include, for example, inflammatory bowel disease, age, obesity, exposure to thorium dioxide, diabetes, smoking, pancreatitis, HIV infection, asbestos exposure, or radon exposure.

Treatment for cholangiocarcinoma can include, for example, curative surgery, palliative surgery, laparoscopic procedures, external beam radiation therapy, three-dimensional conformal radiation therapy, intensity-modulated radiation therapy, stereotactic body radiotherapy, brachytherapy, 5-fluorouracil (5-FU), gemcitabine, cisplatin, capecitabine, or oxaliplatin.

In metastatic castration-resistant prostate cancer (CRPC), despite castrate levels of androgens, the androgen receptor (AR) remains active and drives cancer progression. The major symptoms of early stage prostate cancer include, for example, difficulty urinating, painful urination, frequent urination, hematuria, or pelvic pain. Prostate cancer often metastasizes to the bone and lymph nodes.

Hormone-dependent prostate cancer can become resistant to treatment after one to three years of therapy. Treatment for CRPC, includes, for example, anti-mitotic chemotherapeutics, docetaxel, cabazitaxel, bevacizumab, thalidomide, prednisone, sipuleucel-T, abiraterone, enzalutamide, or any combination thereof.

Pancreatic cancer arises when cells in the pancreas begin to multiply out of control and form a mass, which can metastasize to other parts of the body. The major symptoms of pancreatic cancer include, for example, upper abdominal pain, back pain, jaundice, loss of appetite, weight loss, and blood clots. Exocrine cancer can be, for example, pancreatic adenocarcinoma, acinar cell carcinoma, cystadenocarcinoma, pancreatoblastoma, adenosquamous carcinoma, signet ring cell carcinoma, hepatoid carcinoma, colloid carcinoma and pancreatic mucinous cystic neoplasm. Pancreatic neuroendocrine tumors (PanNETs) can arise elsewhere in the pancreas.

Treatment of pancreatic cancer can include, for example, surgical removal of the pancreas or the affected region of the pancreas, chemotherapy, 5-fluorouracil, gemcitabine, erlotinib, nab-paclitaxel, folic acid, irinotecan, oxaliplatin, FOLFIRINOX regimen, octreotide, lanreotide, everolimus, sunitinib, radiation therapy, or any combination thereof.

Small-cell carcinoma arises in the lungs, and can be highly malignant. Small-cell carcinoma is a neuroendocrine carcinoma that can exhibit aggressive behavior, rapid growth, early spread to distant sites, sensitivity to chemotherapy and radiation, and frequent association with distinct paraneoplastic syndromes, including, for example, hypercalcemia, Eaton-lambert syndrome, or syndrome of inappropriate diuretic hormone. Symptoms of small-cell carcinoma can include, for example, cough, dyspnea, weight loss, and frailty. Treatment for small-cell carcinoma can include, for example, cyclophosphamide, cisplatin, doxorubicin, etoposide, vincristine, paclitaxel, radiation therapy, or any combination thereof.

Compounds disclosed herein can be used to treat Bloom's syndrome in a subject. Bloom's syndrome is a rare autosomal recessive genetic disorder caused by a mutation in the BIM gene, which encodes for a DNA helicase enzyme. Cells for subjects afflicted with Bloom's syndrome exhibit marked chromosomal instability leading to increased sensitivity to UV radiation and higher risk for cancer. The features of Bloom's syndrome include, for example, unusually small stature, sparse fat tissue, high-pitched voice, long and narrow face, prominent nose, prominent ears, sun sensitivity, skin rash upon exposure to the sun, hypopigmentation, hyperpigmentation, reduced fertility in women, infertility in men, increased risk for diabetes, and chronic obstructive pulmonary disease, mild immune system abnormalities, and a shortened life expectancy.

Subjects can be, for example, elderly adults, adults, adolescents, pre-adolescents, children, toddlers, infants, and non-human animals. In some embodiments, a subject is a patient.

Pharmaceutical Compositions

A pharmaceutical composition disclosed herein can be used, for example, before, during, or after treatment of a subject with another pharmaceutical agent.

A pharmaceutical composition disclosed herein can be a combination of any pharmaceutical compounds disclosed herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino) propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremophor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds disclosed herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound disclosed herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds disclosed herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound disclosed herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents disclosed herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions disclosed herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound disclosed herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound disclosed herein can be present in a composition in an amount of about 1 µg, about 10 µg, about 100 µg, about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A therapeutically-effective amount of the compound can be, for example, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 15 nM, about 20 nM, about 25 nM, about 30 nM, about 35 nM, about 40 nM, about 45 nM, about 50 nM, about 60 nM, about 70 nM, about 80 nM, about 90 nM, about 100 nM, about 110 nM, about 120 nM, about 130 nM, about 140 nM, about 150 nM, about 200 nM, about 250 nM, about 300 nM, about 350 nM, about 400 nM, about 450 nM, about 500 nm, about 600 nM, about 700 nM, about 800 nM, about 900 nM, about 1 µM, about 1.5 µM, about 2 µM, about 2.5 µM, about 3 µM, about 3.5 µM, about 4 µM, about 4.5 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, about 50 µM, about 60 µM, about 70 µM, about 80 µM, about 90 µM, about 100 µM, about 150 µM, about 200 µM, about 300 µM, about 400 µM, about 500 µM, about 600 µM, about 700 µM, about 800 µM, about 900 µM, or about 1 mM.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

EXAMPLES

Example 1: Method for Identifying Protein-Protein Interaction Disruptor

To achieve stabilization of short peptides the terminator sequence and untranslated region (UTR) or a short protein (such as sORF1) was used. The N-end rule of protein stability to begin the peptide sequence with residues that minimize proteolysis (such as Met, Gly, Ala, Ser, Thr, Val, or Pro) was used.

The PPI integration plasmid (Plasmid 1; FIG. 7) contained two restriction sites to enable the integration of two proteins that constituted the PPI of interest. The plasmid encoded for the fusion of an AD (such as Dof1; FIG. 8 (bottom)) and a DBD (such as TetR; FIG. 8 (top)) to each protein driven by either a strong promoter and terminator (such as ADH1), or by an inducible promoter (such as GAL1). Each protein fusion sequence was tagged with either FLAG or HA. The plasmid further included bacterial selection and propagation markers (i.e. ori and AmpR), and yeast replication and selection markers (i.e. TRP1 and CEN or 2 um). The plasmid also had sites for integration into the genome at a specified locus.

Figure 10:
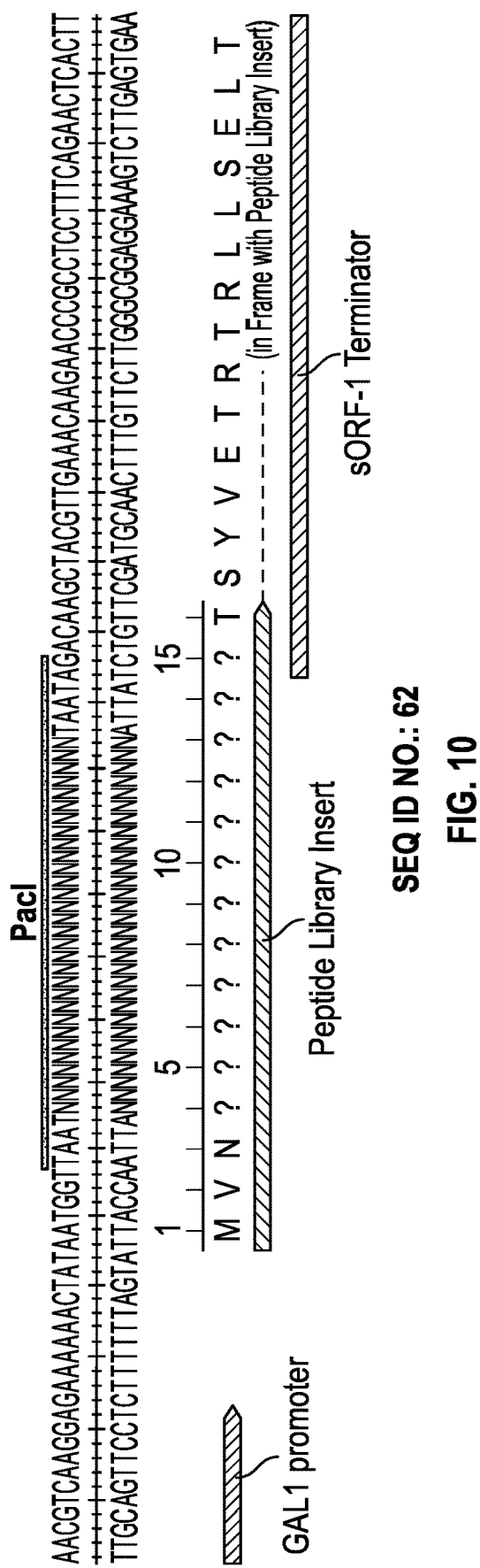
FIG. 10 is a sequence for the selection and library plasmid (FIG. 10 discloses the top nucleotide sequence as SEQ ID NO: 62 and the coded protein as SEQ ID NO: 99)

The selection and library plasmid (FIG. 9) included a restriction site for integration of a randomized peptide library (i.e. randomized NNK 60-mer sequences) driven by a strong promoter (such as the ADH1 promoter) or an inducible promoter (such as the GAL1 promoter). The initiation sequence of the selection and library plasmid was a fixed sequence of Methionine Valine Asparagine (MVN) to maximize the half-life of the peptide, and terminated with the UTR of a short protein (sORF1); (FIG. 10; SEQ ID NO.: 62). The peptide was also tagged with a Myc tag.

The selection and library plasmid additionally encoded for one or more of the agents outlined as 'death agents' (e.g. cytotoxic reporters) driven by a promoter, which depends on the DBD present in the PPI integration plasmid (FIG. 7). The TetO sequence in the selection and library plasmid can become bound by TetR in the PPI integration plasmid. The random library was inserted at the PacI site right in between the GAL1 promoter and the sORF-1 terminator.

To ensure repression of the 'death agents,' the selection and library plasmid included a silencing construct, TetR'-Tup11 fusion driven by a strong promoter (ADH1) to bind the DBD and silence transcription in the presence of doxycycline.

The selection and library plasmid further included bacterial selection and propagation markers (ori and AmpR), and yeast replication and selection markers (LEU2 and CEN or 2 um) (FIG. 9).

The confirmation plasmid (FIG. 11) was used to confirm expression of the reporters and the successful construction of the strains. It includes a direct fusion between the AD and DBD. The confirmation plasmid included bacterial selection and propagation markers (i.e. ori and AmpR), and yeast replication and selection markers (i.e. TRP1 and CEN or 2 um). The confirmation plasmid is used to confirm proper promoter integration in the background strain, for example, integration of TetO7 promoter before the ADE2 gene. Transformation with the confirmation plasmid allows for the activation of ADE2 only if the promoter is properly integrated.

The yeast background strain that was used for the experiment was *Saccharomyces cerevisiae* of either mating type or a diploid, and included the genomic integration of genetic reporters (such as ADE2, HIS3, and/or URA3) driven by the recognition sequence of the DBD used in the PPI Integration Plasmid (FIG. 7), such as TetO.

The background strain also expressed the enzymes necessary for the cyclization and methylation of peptides (e.g. lanthipeptides maturation enzymes from *Lactococcus lactis* (LanB, LanC, LanM, LanP), patellamide biosynthesis factors from cyanobacteria (PatD, PatG), butelase 1 from *Clitoria ternatea*, and GmPOPB from *Galerina marginata*).

The screen was performed using two methods. In the first method, the parental strain was propagated on selection media to ensure the presence of the PPI Integration plasmid, and that a faithful protein-protein interaction occurred, which was confirmed via use of the confirmation plasmid. The strain was cultured on media lacking Trp to ensure selection of colonies where the desired interaction occurred. The strain was then transformed with the selection and library plasmid, and immediately plated on selection media to ensure all components are present (i.e. on media lacking Trp and Leu) and inducing expression of any inducible component (i.e. with Gal).

In the second method, the strains were mated in batch to result in a diploid strain, which carried all the markers, the PPI, the 'death agents,' and the peptide. This batch culture was then propagated on solid medium, which enabled selection of all the system components (i.e. media lacking Leu and Trp) and induced expression of any inducible component (i.e. with Gal).

Surviving colonies from either option described above constituted colonies with a PPI that had been disrupted by a peptide and no longer triggered the death cascade triggered by the encoded 'death agents'.

The peptide sequence that was able to disrupt the PPI was obtained by DNA sequencing the peptide-encoding region of the selection and library plasmid in each surviving colony.

To confirm specificity, the inducible marker was used to inactivate the production of either the PPI or the peptide and confirm specificity. For example, observation of cell survival only on media with Galactose wherein all the components are expressed, and no survival on media without Galactose when expression of the peptide is lost. The plasmid was then isolated and re-transformed into a fresh parental strain to confirm specificity.

Biochemical fractionation of the viable strain that contained the PPI, peptide and 'death agent', followed by pull-down experiments confirmed an interaction between the peptide sequence and either PPI partner using the encoded tags.

Example 2: Treatment of SSP-25 Cells (Cholangiocarcinoma) with Compounds Disclosed Herein To assess the growth inhibitory properties of compounds disclosed herein, 5 μM or 10 μM of compounds 1, 3, and 5 were tested against a water mock treatment for growth inhibition of SSP-25 cells using an MTT assay after 48 hours of cell growth. FIG. 1 shows that compounds 1 and 3 had a dose-dependent effect on the growth of SSP-25, while compound 5 had the strongest inhibitory effect, regardless of concentration.

Figure 13:
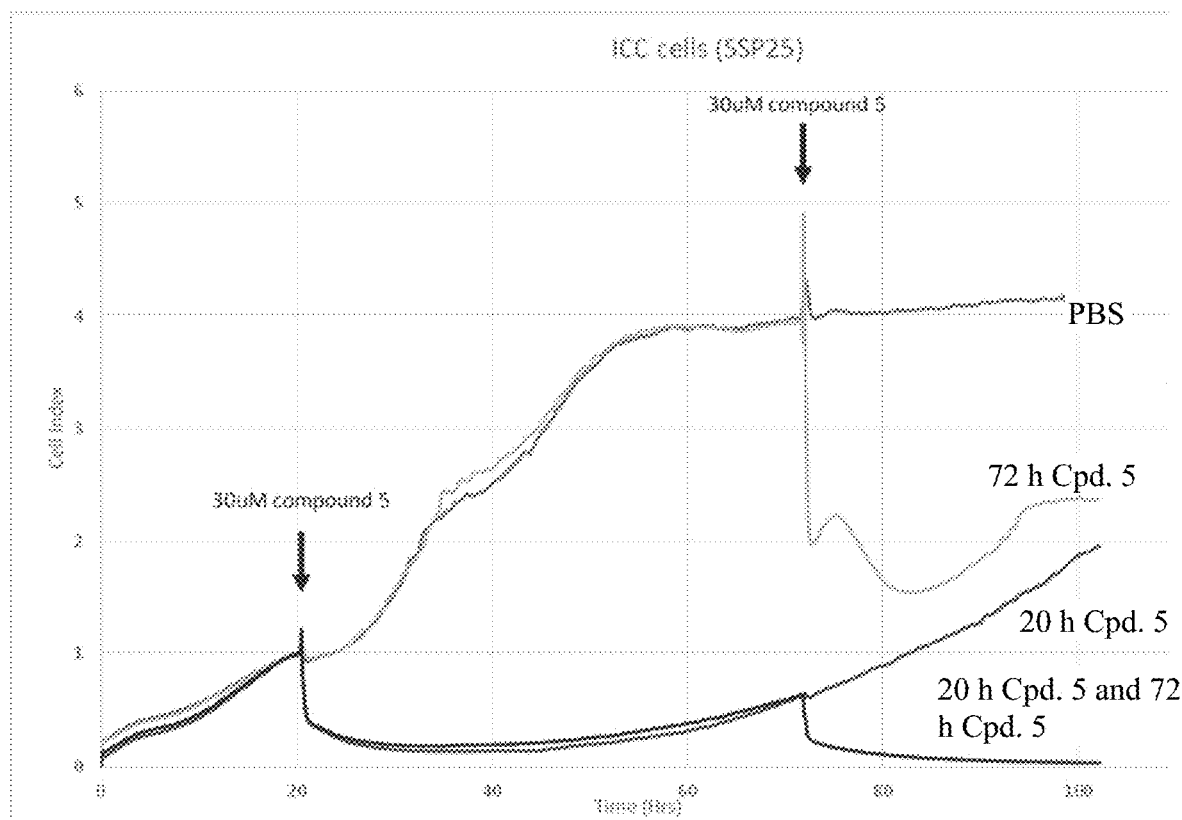
FIG. 13 shows cell killing of SSP-25 cells using Compound 5 using the xCELLigence assay. The vertical arrows indicate the times of compound administration, and the cell index (Y-axis) represents cell viability.

FIG. 13 shows the results of compound 5 treatment displaying acute cell death kinetics in SSP-25 cells as measured by an xCELLigence™ instrument. First, 5,000 SSP-25 cells were plated, and adherence and growth was measured for 20 hours using live measurements of current impedance through the plate using the xCELLigence™ instrument. At the 20 hour mark, 30 μM of compound 5 or a PBS control was added to the SSP-25 cells, which were cultured in 100 μM RPMI media with 10% FBS. Acute death kinetics were observed in real time and the cells were allowed to keep growing. At 72 hours, 30 μM more of compound 5 was added to both a pre-treated well and to a well previously treated with PBS only. FIG. 13 shows that resulting cell growth after initial treatment was not due to resistance, but to insufficient dosing of the compound. Further, singly-dosed cells continued to recover, which indicated reduced general cytotoxicity of the compound in the media or the lysed cells. This result supported the idea that an acute treatment with a dose above a certain threshold can be needed to activate the rapid killing mechanism due to increased calcium concentration. Additionally, treatment with compound 5 of previously untreated cells grown in PBS after 72 hours demonstrated the efficacy of compound 5 in acidified media.

Example 3: Treatment of PC3 Cells (mCRPC Cells) with Compounds Disclosed Herein

Figure 14:
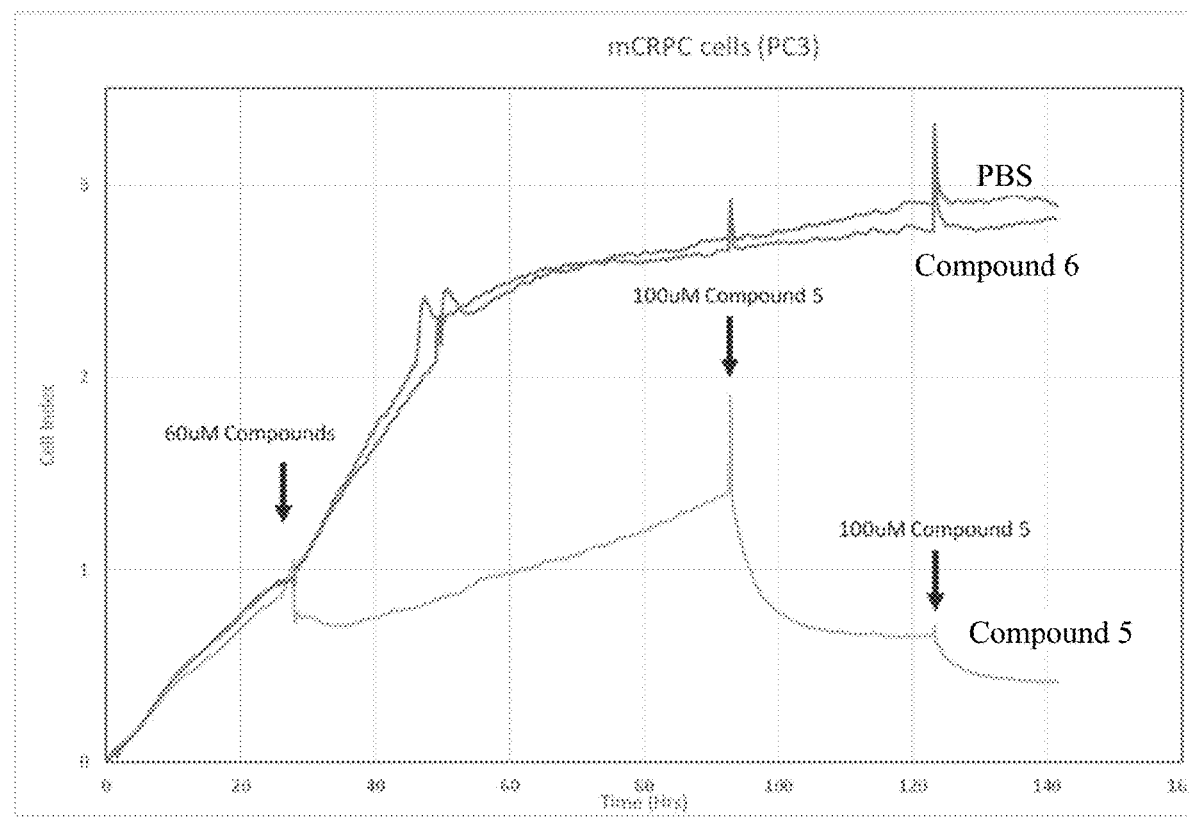
FIG. 14 compares cell killing of PC3 cells using Compounds 5 and 6 using the xCELLigence assay.

FIG. 14 shows the results of compound 5 treatment displaying acute cell death kinetics in mCRPC cells as measured by an xCELLigence™ instrument. First, 5,000 PC3 cells were plated, and adherence and growth was measured for 24 hours using live measurements of current impedance through the plate using the xCELLigence™ instrument. At the 24 hour mark, 60 μM of compound 5, 60 μM of compound 6, or a PBS control was added to the PC3 cells grown in 100 μM DMEM with 10% FBS. Acute death kinetics were observed in real time and the cells were allowed to keep growing. At 84 hours, 100 μM more of compound 5 was added to the pre-treated cells. This was repeated again at the 124 hour mark. This regimen was successful in eliminating over 75% of the PC3 cells compared to the compound 6 and PBS controls.

FIG. 14 showed that compound 5, but not compound 6, was highly potent against PC3 cells. Furthermore, increased dosing was more effective in killing PC3 cells in a rapid way, but at higher concentrations than required for killing of SSP-25 cells, indicating either altered compound uptake kinetics or altered threshold required to trigger the acute cell death due to increased intracellular calcium concentrations.

Example 4: Selective Killing of Cells

Figure 2:
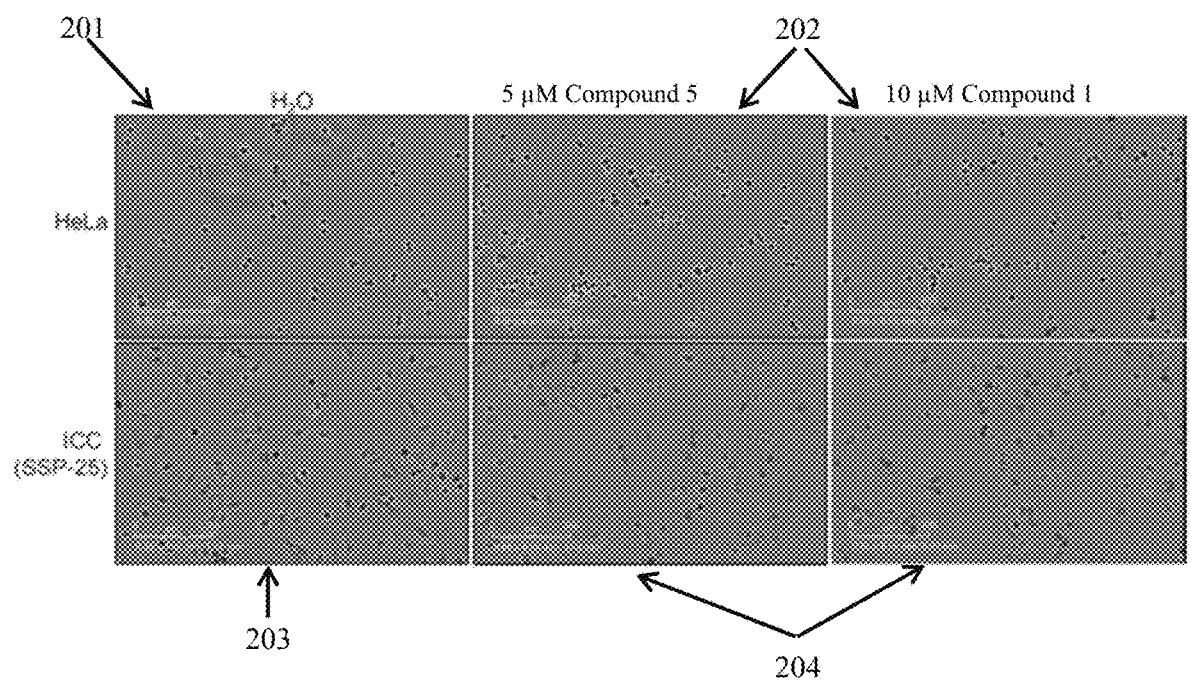
FIG. 2 depicts the effect of Compounds 1 and 5 on SSP-25 and HeLa cells.

To assess the specificity of compounds disclosed herein in targeting cancers with mutations in the BRCA2 pathway, compounds 1 and 5 were tested against HeLa (human cervical cancer) and SSP-25 cells (cholangiocarcinoma cell line) (FIG. 2). To measure killing of the cells by compounds 1 and 5, a cell stain (CytoTox Red™) was used, which can be measured spectrophotometrically, and is indicative of cell viability. First, 5,000 cells were incubated in 96-well culture plates overnight. The media (RPMI with 10% FBS) was removed and replaced with serum free media (RPMI) containing 125 nM CytoTox Red™. FITC-labeled compounds 5 and 1 were added to concentrations of 5 μM and 10 μM, respectively, and imaging commenced using an IncuCyte™ instrument using 15 minute time points. 2× serum-containing media was added after one hour incubation, and the cells were imaged every 2 hours. To detect CytoTox Red™ the following parameters were used: Excitation Wavelength: 585 nm; Passband: [565,605] nm and Emission Wavelength: 635 nm; Passband: [625, 705] nm. To detect compounds 5 and 1 using the FITC label, the following parameters were used: Excitation Wavelength: 460 nm; Passband: [440,480] nm and Emission Wavelength: 524 nm; Passband: [504,544] nm was used.

FIG. 2 provides an image of the stained cells, which prior to treatment show little staining in both the HeLa (201) and SSP-25 (203) cell populations. After treatment with compounds 1 or 5, there was little cell death in the HeLa cells (202), while the compounds showed greatest efficacy in the SSP-25 cells as compared to placebo treatment with PBS (204), as indicated by the lighter gray staining of the cells (204). Both the HeLa and SSP-25 cells showed efficient uptake of the compounds as indicated by the light gray staining of the cells.

Figure 3:
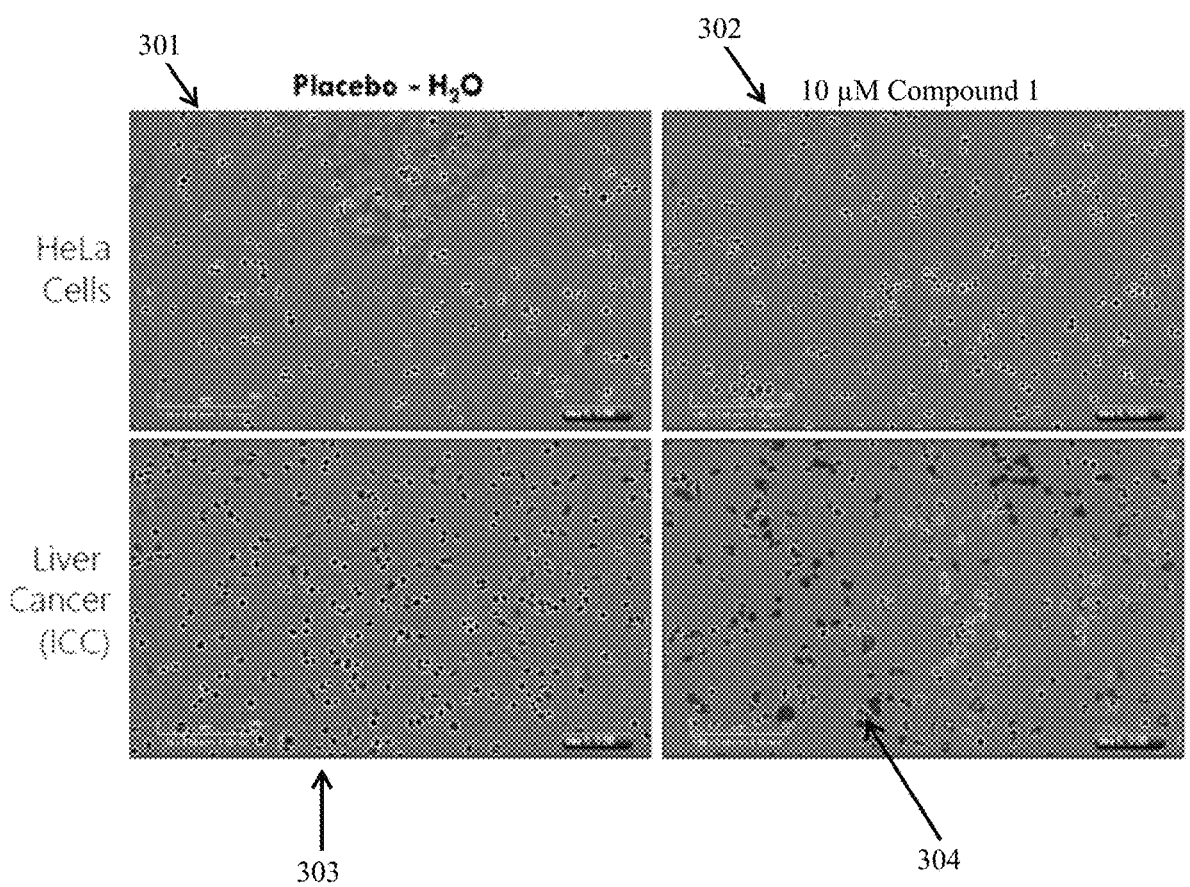
FIG. 3 depicts the effect of Compound 1 on SSP-25 and HeLa cells.

The same viability assay as above was repeated using 10 μM of compound 1. FIG. 3 displays the results of the experiment, and shows that compound 1 was specific to the SSP-25 cells as compared to a placebo treatment of PBS.

FIG. 3 provides an image of the stained cells, which prior to treatment show little staining in both the HeLa (301) and SSP-25 (302) cell populations. After treatment with compound 1, there is little cell death in the HeLa cells (303), while the liver cancer cells showed show the greatest staining (304), as indicated by the dark gray staining (304).

Example 5: Specificity of the Compounds to RAD51

Figure 4:
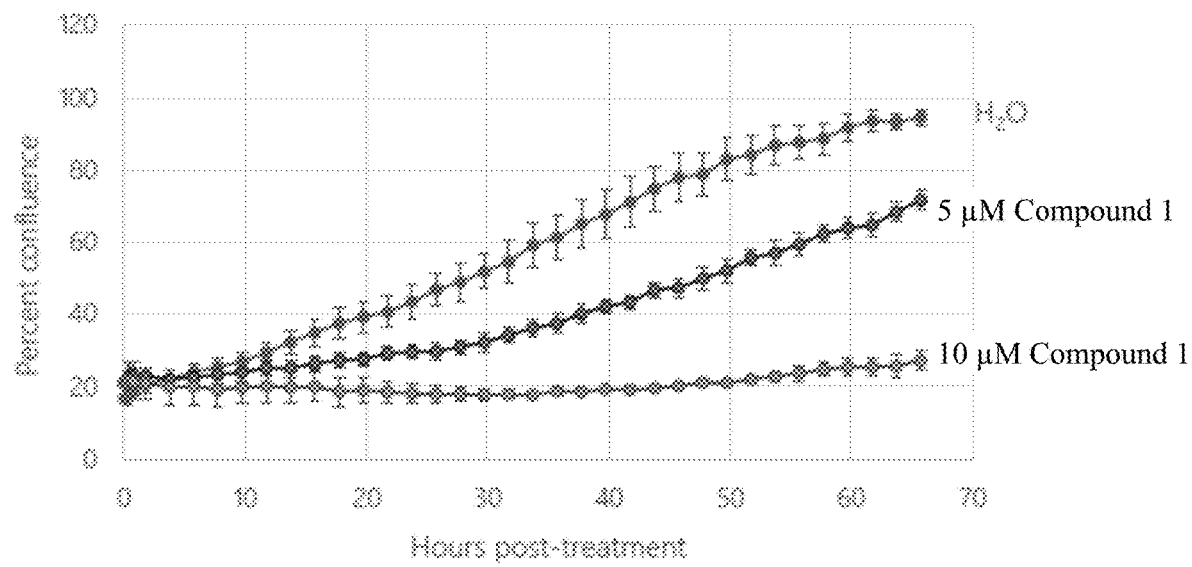
FIG. 4 depicts the effect of Compound 1 on SSP-25 cells.

A growth assay was performed using SSP-25 cells with 5 μM or 10 μM of compound 1. FIG. 4 shows that treatment with compound decreased the percent confluence of the cells over the tested time period as compared to treatment with PBS. The experimental protocol described in Example 3 was used for the growth assay.

Figure 5:
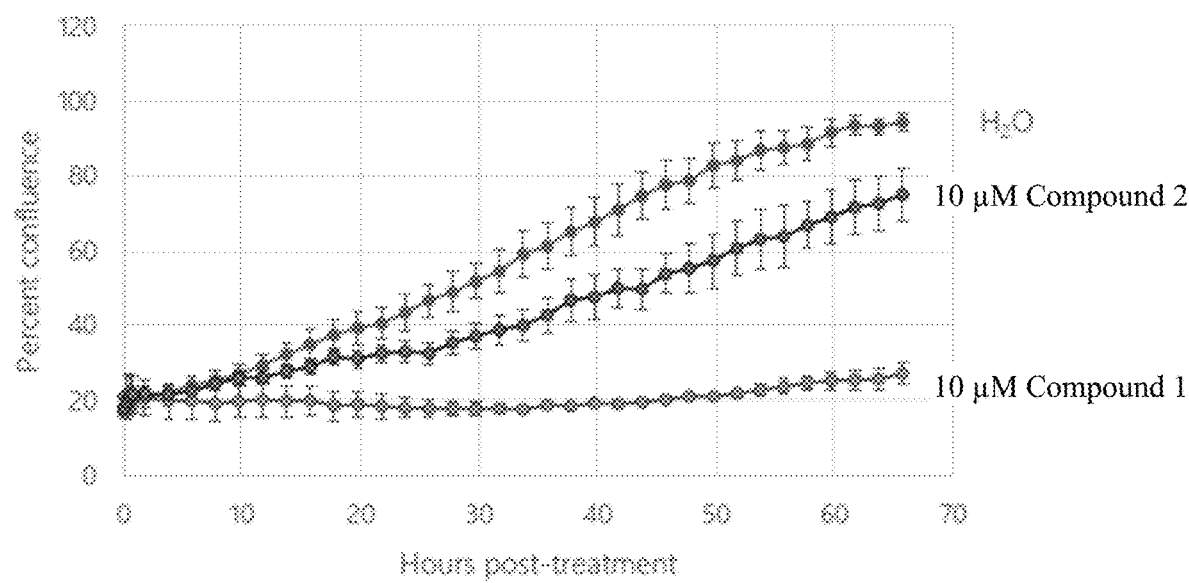
FIG. 5 depicts the effect of Compounds 1 and 2 on SSP-25 cells.

The same growth assay was repeated using 10 μM of compound 1 and compound 2. Compound 2 contains a single substitution within the core consensus sequence, which interrupts the binding of compound 2 to RAD51. Thus, as shown in FIG. 5, compound 2 was not able to decrease the growth of the SSP-25 cells to the same extent as compound 1, indicating the specificity of compound 1 to RAD51.

Example 6: Counteracting Increased Sensitivity to Stress in Bloom's Cells

Figure 6:
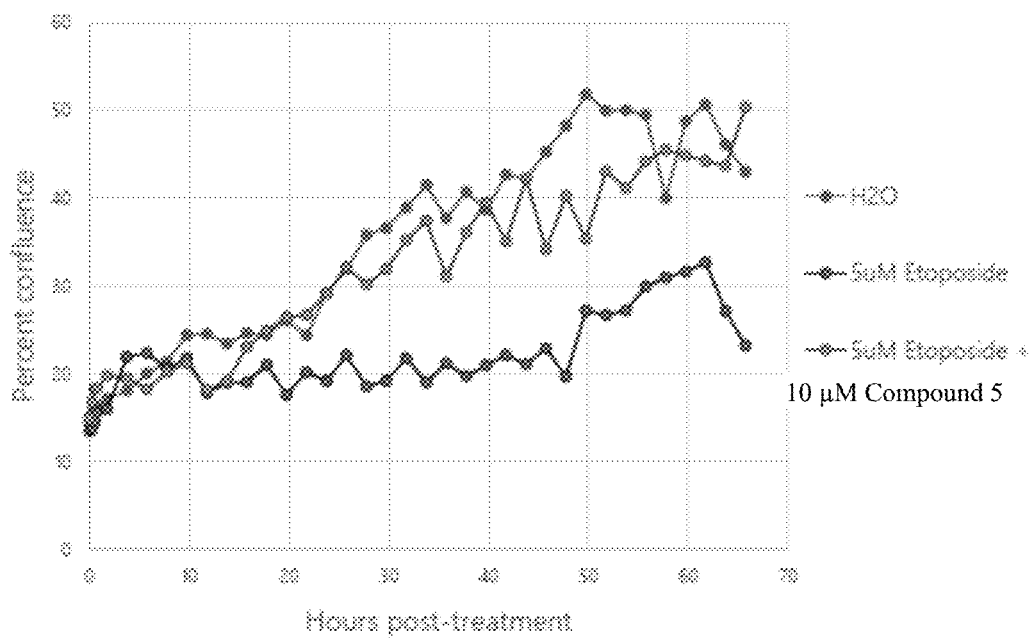
FIG. 6 depicts the effect of etoposide and Compound 1 on GM08505 cells.

To assess the ability of compounds disclosed herein to rescue the drug-sensitivity of Bloom's Syndrome patient cells, GM08505, Blm cells were treated with PBS, 5 μM etoposide, or 5 μM etoposide and 10 μM compound 5. FIG. 6 shows that the growth of the Blm cells was affected by 5 μM etoposide treatment. However, treatment with PBS or the combination of etoposide and compound 5 was comparable, indicating suppression of cell growth defects induced by etoposide using compound 5 as measured by the percent confluence of the cells during the time period tested.

Example 7: General Peptide Preparation and Optimization for Cellular Activity

Synthetic peptide compounds (compounds 1, 3, 4, 5, 7, 9, 10, 11, 13, 14, 19, and 25; see Table 5 and FIG. 17) were prepared with a diversity of modifications, amino acid stereoisomers, non-natural amino acids, and cell-penetrating peptides according to the consensus RAD51 binding sequence identified by the method of Example 1. Peptides were synthesized following standard solid-phase peptide synthesis protocols. The identity and purity of the peptides were confirmed and determined by RP-HPLC, MS/MS, and peptide content analysis. The trifluoroacetic acid (TFA) was exchanged for a non-toxic salt form (e.g. acetate or HCl) and the purity of the peptides was at least 95% before use in experiments.

Figure 15:
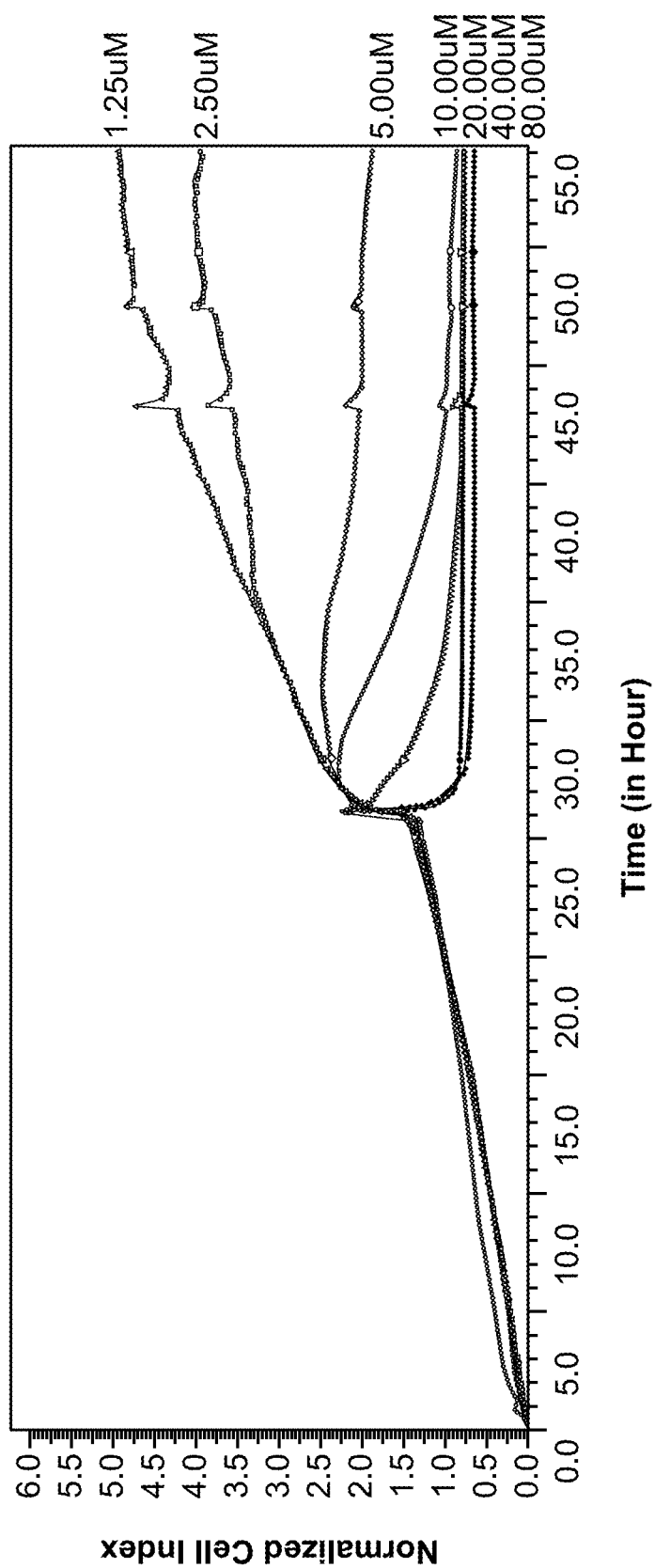
FIG. 15 shows cell killing of A549 cells by Compound 10 using an xCELLigence assay. The vertical line indicates the time of compound administration, and the cell index (Y-axis) represents cell viability
Figure 16:
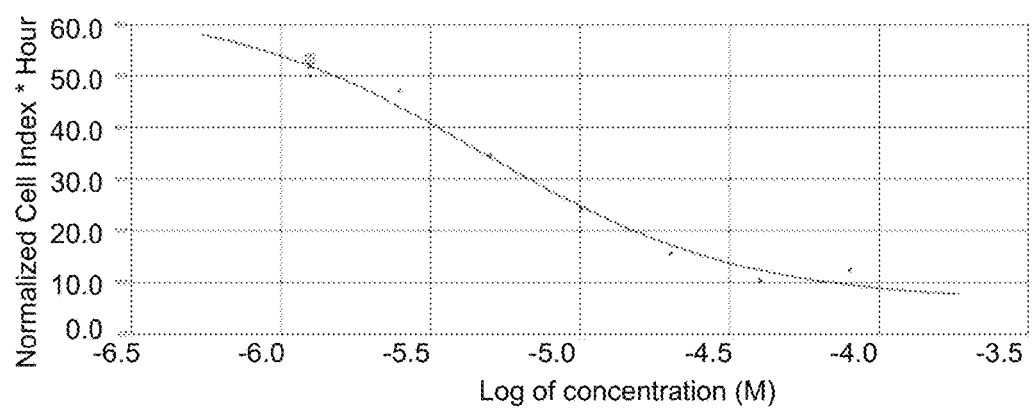
FIG. 16 shows an example of a curve fit to calculate the IC50 for compound 10 based on the data show in in FIG. 15.

To optimize cellular activity, compounds were tested in xCELLigence cell death assays against various cell lines. An example of the workflow used is shown using A549 cells and compound 10 in FIGS. 15 and 16. FIG. 15 shows an exemplary xCELLigence treatment experiment, where the vertical line indicates the time of compound administration, and the cell index (Y-axis) represents cell viability. Data from xCELLigence traces at different compound concentrations from FIG. 15 was then used to generate a dose-response curve, which was then subjected to nonlinear regression using a sigmoidal dose-response model to generate IC50s and R2 values for cell death for each compound/cell line combination (FIG. 16).

An example of an optimization experiment is shown in FIG. 17, where compounds 1, 3, 4, 5, 7, 9, 10, 11, 13, 14, 19, and 25 were tested against SSP-25 cells. The cell death IC50s of the compounds varied from the $10^{-4}$ M to the $10^{-6}$ M range. An analysis of analogous peptides with different cell-penetrating peptides sequences incorporated into them (FIG. 18) demonstrated that the cellular activity is largely agnostic to which cell-penetrating peptide is chosen (as compounds 5, 13, 14, 10, and 25 all have similar IC50 values).

Example 8: Mapping of Binding Site of RAD51-Binding Peptides Using Mutational Analysis in Y2H Assay RAD51-binding peptides were tested for ability to bind RAD51 of several different species using a "conventional" Y2H assay, where interaction between the two-hybrid pair drove expression of ADE2 and HIS genes. In this Y2H assay the two-hybrid pair was RAD51 and the compound 5 peptide sequence (SEQ ID NO.: 5), so that cells having the interaction would survive (+) and cells not having the interaction would die (−) on selective media (−ADE, −HIS). While peptides successfully bound to *H. sapiens, P. pastoris*, and *S. pombe* RAD51, they did not bind to *S. cerevisiae* RAD51, indicating a sequence divergence between *cerevisiae* and human that precludes binding of the peptide. A subset of this data is summarized in Table 6.

TABLE 6

| SEQ ID NO.: 5 binding to diverse species orthologs of RAD51 | |
|---|---|
| Species | Compound 5 Sequence Binding |
| *H.sapiens* Rad51 | + |
| *G.gallus* Rad51 | + |
| *D.rerio* Rad51 | + |
| *S.pombe* Rad51 | + |
| *K.pastoris* Rad51 | + |
| *C.albicans* Rad51 | + |
| *K.lactis* Rad51 | − |
| *S.cerevisiae* Rad51 | − |

Based on sequence comparisons of *S. cerevisiae* and *H. sapiens* RAD51, multiple *cerevisiae-sapiens* hybrid constructs of RAD51 were constructed and tested for their ability to bind RAD51-binding peptide in the same RAD51/SEQ ID NO.: 5 hybrid system described above. The RAD51 peptides only successfully bound a construct containing at least residues 190-339 of human RAD51, and did not bind a construct that included residues 218-339 of human RAD51, indicating the binding site lay somewhere in the 190-218 region. The data is summarized in Table 7.

TABLE 7

| RAD51 peptide binding to RAD51 hybrid constructs | |
|---|---|
| Constructs | SEQ ID NO.: 5 Binding |
| *S.cerevisiae* Rad51 (1-226) + *H.sapiens* Rad51 (168-339) | + |
| *S.cerevisiae* Rad51 (1-250) + *H.sapiens* Rad51 (190-339) | + |
| *S.cerevisiae* Rad51 (1-278) + *H.sapiens* Rad51 (218-339) | − |

Figure 23:
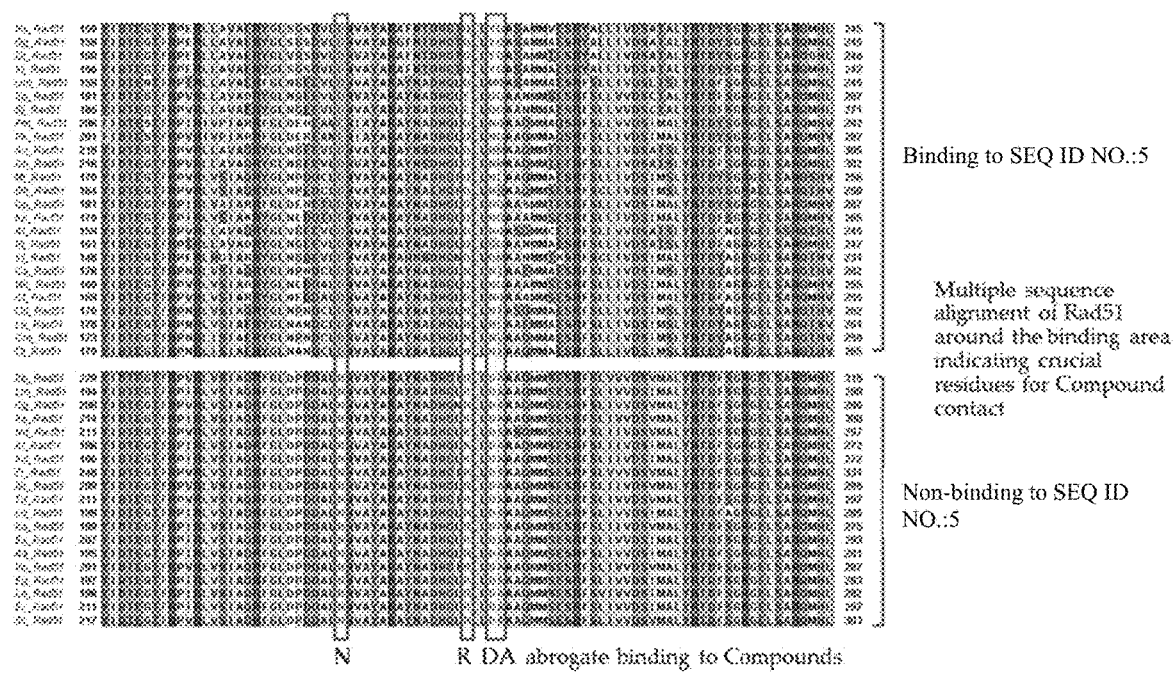
FIG. 23 shows a sequence alignment of RAD51 derived from various different species, grouped according to whether RAD51-interacting peptides according to the invention do or do not bind to SEQ ID NO.: 5 as assessed by a Y2H assay using a RAD51/SEQ ID NO.: 5 pair. Highlighted are variant residues that appear to account for the difference in binding.

The ability of peptides to bind human RAD51 with various mutations was then tested by Y2H assay. The mutations encompassed both mutations described in the literature known to affect binding of RAD51 interaction partners such as BRCA2 and RAD51-AP1, and residues identified by a broader sequence alignment analysis of RAD51 species orthologs that do/do not bind SEQ ID NO.: 5 (FIG. 23, see residues "R", "D" and "A" boxed). While mutations affecting BRCA2 binding had no effect on peptide binding, mutations that affected RAD51-AP1 binding did disrupt peptide binding. As these mutations were at residues 202, 205, and 206, they were consistent with the previous fusion data showing binding somewhere in the 190-218 region, and indicated the peptide SEQ ID NO.: 5 contacts at least residues 202, 205, and 206 of RAD51.

TABLE 8

RAD51 peptide binding to human RAD51 bearing protein-protein interaction-disrupting mutations

| Construct | BRCA2 | Rad51 | Rad51-AP1 | SEQ ID NO.: 5 |
|---|---|---|---|---|
| Rad51 (F86E; A89E) | + | − | + | + |
| Rad51 (A190L; A192L) | − | − | + | + |
| Rad51 (S208L; A209E; M210A) | − | − | + | + |
| Rad51 (S208E; A209D) | − | + | + | + |
| Rad51 (Q202R, Y205D, Q206A) | + | + | − | − |

(+) denotes a successful interaction between the two Y2H baits,
(−) denotes a lack of interaction
"BRCA2"denotes residues 1517-1551 of human BRCA2 used as Y2H bait.
"RAD51AP1" denotes residues 245-352 of human RAD51AP1 (GenBank AAH16330.1) used as Y2H bait.
"SEQ ID NO.: 5" denotes SEQ ID NO.: 5 used as Y2H bait.

It should be noted that the sequence alignment of FIG. 23 also indicates that residue 187 relative to human RAD51 is variant between orthologs that do/do not bind compounds, suggesting residue 187 of human RAD51 additionally plays a role in compound binding.

Example 9: RAD51-Binding Peptide Interaction with Calcium Binding to RAD51

To test the interaction between calcium binding and peptide binding to RAD51, the Kds of active (Compound 5, 10) peptides for RAD51 were tested by a microscale thermophoresis assay, and the Kd of compound 5 was additionally performed in the presence of 1 mM calcium.

Microscale thermophoresis was performed as previously described (see, for e.g. Jerabek-Willemsen, M., Wienken, C. J., Braun, D., Baaske, P. & Duhr, S. Molecular interaction studies using microscale thermophoresis. Assay Drug Dev. Technol. 9, 342-353 (2011)). The affinity of the Compound was measured using the Monolith NT.115 from Nanotemper Technologies. Rad51 was fluorescently labelled according to the manufacturer's protocol and the labelled protein used for each assay was about 500 nM. A solution of unlabelled peptide was diluted for appropriate serial concentration gradient. The samples were loaded into silica capillaries (Polymicro Technologies). Measurements were performed at room temperature in buffer containing PBS, 0.1% Tween 20, 0.5 mM ATP, 2.5 uM ssDNA, with 1 mM CaCl2 (when mentioned). Measurements were done using 12% LED power and 60% MST power. The assays were repeated three times for each affinity measurement. Data analyses were performed using Nanotemper Analysis software and OriginPro 8.0 software provided by the manufacturer.

| Peptide | Buffer conditions | Kd (nM) |
|---|---|---|
| Compound 5 | PBS + 1 mM $Ca^{2+}$ | 28.87 |
| Compound 5 | PBS | 8.37 |
| Compound 10 | PBS | 8.55 |

The microscale thermophoresis data is summarized in Table 9. Both active peptides (5 and 10) bound with a Kd approximately 8 nanomolar. However, when the in vitro concentration of calcium (Ca2+) in the RAD51 binding assay was increased to from 0 to 1 mM, the Kd increased 3.4-fold, indicating that there is allosteric communication between the calcium binding sites and the peptide binding interface on RAD51.

Example 10: Compound Efficacy in an Athymic Xenograft Mouse Model of Cancer

Female athymic nu/nu mice (6-8 weeks old) were purchased from Simonsen labs (n=12) and were housed at the Murigenics vivarium in Vallejo. The mice were acclimated to the setting of the vivarium for 5 days and maintained on a standard chow diet; 12:12 dark/light cycle; and group housed (3 mice per cage) in hepa-filtered cages. After acclimation, each mouse was injected subcutaneously (lower left abdominal flank) with 5×10^6 A549 (ATCC: CCL-185) cells mixed with 1:1 (v/v) with Matrigel solution. When the tumors reached a volume of ~100 mm3, the mice were divided into separate treatment groups for the desired treatments. Experiments using both intra-tumoral (IT) and intraperitoneal (IP) administration were performed and the data are reported in FIG. 19.

Experiment 1: Intra-Tumoral (IT) Dosing

Mice prepared as described above were divided into 4 groups:
  Group 1: were not treated with anything (n=3)
  Group 2: received an intra-tumoral injection of 50 microliters of Phosphate Buffered Saline (mock) (n=3)
  Group 3: received an intra-tumoral injection of 50 microliters of 10 mg/ml compound 10 in Phosphate Buffered Saline (n=3)
  Group 4: received an intra-tumoral injection of 50 microliters of 20 mg/ml compound 10 in Phosphate Buffered Saline (n=3)

The 50 microliter injections were carried out with a (30 g needle). The injections were administered on day zero and then again on day 3. The length (L) and the width (W) of the tumor mass was measured with a Vernier caliper and the tumor volume (V) was calculated as V=(L×W^2)/2. The relative tumor volume of each tumor mass on each measurement day was normalized against the initial volume of the same mass on day zero right before initiation of injections. Measurements were performed on days 0, 3, and 6, and the data is summarized in FIG. 19, which shows measurable decreases in tumor size as early as day 3.

Experiment 2: Intra-Peritoneal (IP) Dosing

Mice prepared as described above were divided into 2 groups:
  Group 1: received an intra-peritoneal injection of 125 microliters of Phosphate Buffered Saline (mock) (n=2)
  Group 2: received an intra-peritoneal injection of 125 microliters of 3 mg/ml compound 10 in Phosphate Buffered Saline (n=3)

The injections were carried out with a 30 g needle. The injections were administered on day seven. The length (L)

and the width (W) of the tumor mass was measured with a Vernier caliper and the tumor volume (V) was calculated as V=(LxW^2)/2. The relative tumor volume of each tumor mass on each measurement day was normalized against the initial volume of the same mass on day zero right before initiation of injections. Measurements were performed through days 0-10, with IP dosing on day 7, and the data is summarized in FIG. 19, which shows measurable decreases in tumor size as early as 3 days after injection (day 10).

Example 11: Intracellular Ca2+ Chelation Suppresses the Cytotoxicity of Compound 10 in SSP-25 Cells To further investigate the hypothesis that peptide binding to RAD51 in cells causes cell death via increases in intracellular free calcium levels, compound 10 alone and in combination with two different intracellular calcium chelators (1,2-Bis(2-aminophenoxy)ethane-N,N,N',N'-tetraacetic acid tetrakis(acetoxymethyl ester) aka "BAPTA-AM", and ammoniated ruthenium oxychloride aka "ruthenium red") was tested in an xCELLigence™ cell death assay as in Example 3. The intracellular calcium chelators alone were also evaluated on the cells. In both cases, administration of calcium chelators rescues cell death, suggesting that the RAD51 binding compounds herein kill cells as a result of a rise in intracellular free Ca2+ ions, and that counteracting the rise in intracellular free Ca2+ ions prevents cell death due to the RAD51 binding compounds.

FIG. 23 demonstrates that addition of 10 μM BAPTA-AM to cells treated with 10 μM compound 10 rescues cell death relative to compound alone (see curves in FIG. 23, where the curve representing the BAPTA-AM+compound combination is roughly equivalent to PBS alone, while the curves representing compound 10 alone displays significant cell death).

Figure 24:
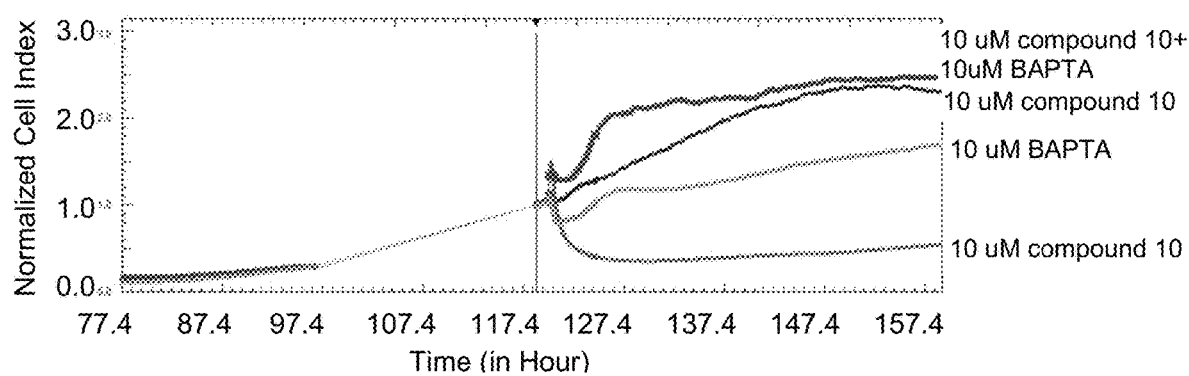
FIG. 24 shows an xCELLigence cell death assay on SSP-25 cells, wherein compound 10 is added alone or combined with the calcium chelator BAPTA-AM, demonstrating that addition of BAPTA-AM rescues cell death due to compound 10.

FIG. 24 demonstrates that addition of 40 μM Ruthenium red to cells treated with 10 μM compound 10 rescues cell death relative to compound alone (see curves in FIG. 24, where the curve representing the ruthenium red+compound combination is roughly equivalent to PBS alone, while the curve representing compound alone displays significant cell death).

Example 12: Olaparib Synergy with Compound 10 on SSP-25 Cells

To further investigate the hypothesis that peptide binding to RAD51 causes defective DNA repair and thus synergizes with other agents that target DNA repair, compound 10 or the poly ADP ribose polymerase (PARP) inhibitor Olaparib (AZD-2281, Lynparza, 4-[4-Fluoro-3-[(4-methoxypiperidin-1-yl)carbonyl]benzyl]phthalazin-1(2H)-one, 4-[[4-Fluoro-3-[(4-methoxy-1-piperidinyl)carbonyl]phenyl]methyl]-1(2H)-phthalazinone) alone or in combination were tested in an xCELLigence™ cell death assay as in Example 3.

Figure 25:
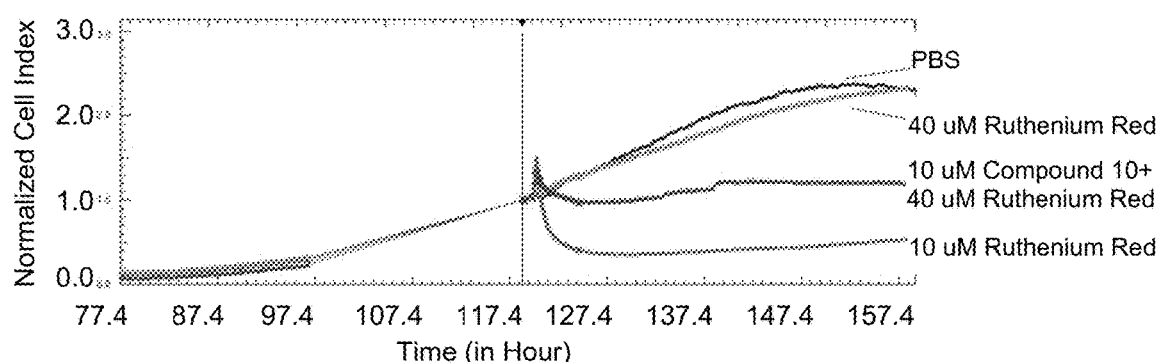
FIG. 25 shows an xCELLigence cell death assay on SSP-25 cells, wherein compound 10 is added alone or combined with the calcium chelator ruthenium red, demonstrating that addition of ruthenium red rescues cell death due to compound 10.

FIG. 25 demonstrates that addition of 1 μM Olaparib to cells treated with 10 μM compound 10 enhances cell death relative to compound alone or Olaparib alone (see curves in FIG. 25, where the curve representing the olaparib+compound combination displays enhanced cell death relative to the other curves).

Embodiments

The following non-limiting embodiments provide illustrative examples of the invention, but do not limit the scope of the invention.

Embodiment 1. A method of treating a condition, the method comprising administering to a subject in need thereof a therapeutically effective amount of a polypeptide that binds to a eukaryotic recombinase in a cell, wherein the binding of the polypeptide to the eukaryotic recombinase inhibits binding of the eukaryotic recombinase to a protein in the cell, wherein the inhibition of binding of the eukaryotic recombinase to the protein decreases or inhibits deoxyribonucleic acid (DNA) damage repair in the cell as compared to a cell that is not exposed to the polypeptide.

Embodiment 2. The method of embodiment 1, wherein the eukaryotic recombinase is RAD51.

Embodiment 3. The method of any one of embodiments 1-2, wherein the polypeptide is not an antibody.

Embodiment 4. The method of any one of embodiments 1-3, wherein the protein is BRCA2.

Embodiment 5. The method of any one of embodiments 1-3, wherein the protein is RAD51AP1.

Embodiment 6. The method of any one of embodiments 1-5, wherein the inhibition of binding of the eukaryotic recombinase to the protein occurs via competitive inhibition between the polypeptide and the protein.

Embodiment 7. The method of any one of embodiments 1-5, wherein the inhibition of binding of the eukaryotic recombinase to the protein occurs via allosteric inhibition of the binding of the eukaryotic recombinase to the protein.

Embodiment 8. The method of any one of embodiments 1-7, wherein the binding of the polypeptide to the eukaryotic recombinase in the cell decreases proliferation of the cell.

Embodiment 9. The method of any one of embodiments 1-7, wherein the binding of the polypeptide to the eukaryotic recombinase in the cell induces death of the cell.

Embodiment 10. The method of embodiment 9, wherein the cell death is apoptotic cell death.

Embodiment 11. The method of any one of embodiments 1-10, further comprising a decrease of homologous recombination in the cell.

Embodiment 12. The method of any one of embodiments 1-11, wherein the decrease or inhibition of DNA damage repair in the cell sensitizes the cell to a chemotherapeutic.

Embodiment 13. The method of any one of embodiments 1-12, wherein the polypeptide is from 4 to 70 amino acids in length.

Embodiment 14. The method of any one of embodiments 1-13, wherein the polypeptide is from 15 to 30 amino acids in length.

Embodiment 15. The method of any one of embodiments 1-14, wherein the polypeptide comprises a cell penetration peptide signal sequence.

Embodiment 16. The method of any one of embodiments 1-15, wherein the polypeptide comprises a RAD51 interacting motif, wherein the RAD51 interacting motif is SEQ ID NO.: 19.

Embodiment 17. The method of any one of embodiments 1-16, wherein the polypeptide comprises a protein transduction domain.

Embodiment 18. The method of any one of embodiments 1-17, wherein the polypeptide is SEQ ID NO.: 1.

Embodiment 19. The method of any one of embodiments 1-17, wherein the polypeptide is SEQ ID NO.: 3.

Embodiment 20. The method of any one of embodiments 1-17, wherein the polypeptide is SEQ ID NO.: 5.

Embodiment 21. The method of any one of embodiments 1-20, further comprising administration of a chemotherapeutic.

Embodiment 22. The method of embodiment 21, wherein the chemotherapeutic is an anti-PD1 agent.

Embodiment 23. The method of embodiment 21, wherein the chemotherapeutic is a PARP inhibitor.

Embodiment 24. The method of any one of embodiments 1-23, wherein the condition is cancer.

Embodiment 25. The method of any one of embodiments 1-24, wherein the condition is intrahepatic cholangiocarcinoma.

Embodiment 26. The method of any one of embodiments 1-24, wherein the condition is castration-resistant prostate cancer.

Embodiment 27. The method of any one of embodiments 1-23, wherein the condition is Bloom's Syndrome.

Embodiment 28. The method of any one of embodiments 1-27, wherein the administration is oral.

Embodiment 29. The method of any one of embodiments 1-27, wherein the administration is subcutaneous.

Embodiment 30. The method of any one of embodiments 1-27, wherein the administration is intravenous.

Embodiment 31. The method of any one of embodiments 1-30, wherein the therapeutically effective amount is from about 5 µM to about 1 mM.

Embodiment 32. The method of any one of embodiments 1-31, wherein the subject is human.

Embodiment 33. The method of any one of embodiments 1-32, wherein the cell exhibits an increase in calcium concentration upon binding of the polypeptide to the eukaryotic recombinase.

Embodiment 34. The method of embodiment 33, wherein the increase in calcium concentration induces death of the cell.

Embodiment 35. A method of inducing death in a cell, the method comprising contacting the cell with a polypeptide, wherein the polypeptide binds to a eukaryotic recombinase in the cell, wherein the binding of the polypeptide to the eukaryotic recombinase inhibits binding of the eukaryotic recombinase to a protein in the cell, wherein the inhibition of binding of the eukaryotic recombinase to the protein decreases or inhibits deoxyribonucleic acid (DNA) damage repair in the cell, wherein the inhibition of binding of the eukaryotic recombinase to the protein induces death in the cell as compared to a cell that is not contacted with the polypeptide.

Embodiment 36. A method of reducing drug resistance in a cell, the method comprising contacting the cell with a polypeptide, wherein the polypeptide binds to a eukaryotic recombinase in the cell, wherein the binding of the polypeptide to the eukaryotic recombinase inhibits binding of the eukaryotic recombinase to a protein in the cell, wherein the inhibition of binding of the eukaryotic recombinase to the protein decreases or inhibits deoxyribonucleic acid (DNA) damage repair in the cell, wherein the inhibition of binding of the eukaryotic recombinase reduces drug resistance of the cell as compared to a cell that is not contacted with the polypeptide.

What is claimed is:

1. A method for screening for inhibitors of a protein interaction between a first test protein and a second test protein, the method comprising:
   expressing, in a plurality of host cells, a first fusion protein comprising a first test protein and a DNA-binding moiety; and
   expressing, in each of the plurality of host cells, a second fusion protein comprising the second test protein and a gene-activating moiety,
   wherein each of the plurality of host cells comprises a plurality of heterologous polynucleotide sequences that each encode a different cytotoxic agent, wherein expression of each of the heterologous polynucleotide sequences that each encode a different cytotoxic agent is under the control of a promoter that has selective affinity for the DNA-binding moiety, wherein interaction between the first test protein and the second test protein causes the gene-activating moiety to activate expression of each of the different cytotoxic agents encoded by each of the plurality of heterologous polynucleotide sequences;
   wherein the DNA-binding moiety is a LexA, cI, Glucocorticoid receptor, TetR, or Ume6 DNA binding moiety;
   wherein the gene activating moiety is a GAL4, B42, or Dof1 gene activating moiety;
   wherein the plurality of different cytotoxic agents are selected from the group consisting of: a ribosomally-encoded xenobiotic agent, a ribosomally-encoded poison, a ribosomally-encoded recombinase that excises an essential gene for viability, and any combination thereof.

2. The method of claim 1, wherein the plurality of different cytotoxic agents are selected from the group consisting of: Cholera toxin, SpvB toxin, CARDS toxin, SpyA Toxin, HopU1, ChelT toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Ricin Toxin, and any combination thereof.

3. The method of claim 1, wherein the plurality of host cells are eukaryotic.

4. The method of claim 1, wherein the plurality of different cytotoxic agents are prokaryotic toxins.

5. The method of claim 1, wherein the plurality of host cells are fungal cells.

6. The method of claim 1, further comprising expressing, in each of the plurality of host cells, a randomized peptide.

7. The method of claim 6, wherein the randomized polypeptide comprises a polypeptide of 60 or fewer amino acids in length.

8. The method of claim 6, wherein an N-terminal stabilization sequence is attached to the randomized polypeptide.

* * * * *